(12) United States Patent
Brossmer et al.

(10) Patent No.: US 9,260,467 B2
(45) Date of Patent: Feb. 16, 2016

(54) SIALIC ACID DIMERS

(71) Applicants: Reinhard Brossmer, Heidelberg (DE); Horst Prescher, Basel (CH)

(72) Inventors: Reinhard Brossmer, Heidelberg (DE); Horst Prescher, Basel (CH)

( * ) Notice: Subject to any disclaimer, the term of this patent is extended or adjusted under 35 U.S.C. 154(b) by 10 days.

(21) Appl. No.: 14/369,493

(22) PCT Filed: Dec. 21, 2012

(86) PCT No.: PCT/EP2012/005360
§ 371 (c)(1),
(2) Date: Jun. 27, 2014

(87) PCT Pub. No.: WO2013/097942
PCT Pub. Date: Jul. 4, 2013

(65) Prior Publication Data
US 2015/0005245 A1   Jan. 1, 2015

(30) Foreign Application Priority Data

Dec. 30, 2011 (EP) .................... 11196220

(51) Int. Cl.

| | | |
|---|---|---|
| *A01N 43/04* | (2006.01) | |
| *A61K 31/715* | (2006.01) | |
| *C07H 19/056* | (2006.01) | |
| *A61K 31/7012* | (2006.01) | |
| *A61K 31/7004* | (2006.01) | |
| *A61K 31/7016* | (2006.01) | |
| *A61K 31/7008* | (2006.01) | |
| *C07H 15/04* | (2006.01) | |
| *C07H 15/10* | (2006.01) | |
| *C07H 15/18* | (2006.01) | |
| *C07H 15/12* | (2006.01) | |
| *C07H 15/26* | (2006.01) | |

(52) U.S. Cl.
CPC .......... *C07H 19/056* (2013.01); *A61K 31/7004* (2013.01); *A61K 31/7008* (2013.01); *A61K 31/7012* (2013.01); *A61K 31/7016* (2013.01); *C07H 15/04* (2013.01); *C07H 15/10* (2013.01); *C07H 15/12* (2013.01); *C07H 15/18* (2013.01); *C07H 15/26* (2013.01)

(58) Field of Classification Search
None
See application file for complete search history.

(56) References Cited

U.S. PATENT DOCUMENTS 7,820,714 B2   10/2010   Kelm et al.

OTHER PUBLICATIONS

Abdu-Allah et al. Bioorganic & Medicinal Chemistry Letters (2009), vol. 19, pp. 5573-5575.*
International Preliminary Report on Patentability for PCT/EP2012/005360 dated Jul. 1, 2014.
Collins, et al., "High-affinity ligand probes of CD22 overcome the threshold set by eis ligands to allow for binding, endocytosis, and killing of B cells", Journal of Immunology, American Association of Immunologists, vol. 177, No. 5, Sep. 1, 2006, pp. 2994-3003.
Hajjaj Abdu-Allah, et al., Design and Synthesis of a Multivalent Heterobifunctional CD22 Ligand as a Potential Immunomodulator, Synthesis, vol. 2011, No. 18, Sep. 1, 2011, pp. 2968-2974.

* cited by examiner

*Primary Examiner* — Patrick Lewis

(57) ABSTRACT

Sialic acid derivatives of the formula (I)

(I)

$$A^1-Y^1-N(R^8)-CH(R^7)-...-Z^1-...-D-...-Z^1-...-CH(R^7)-N(R^8)-Y^2-A^2$$

in which the symbols have the definitions stated in the description are suitable as medicaments, more particularly for diseases whose course is influenced by Siglec ligands.

12 Claims, 1 Drawing Sheet

SIALIC ACID DIMERS

PRIORITY CLAIM

This application is a national stage application PCT/EP2012/005360, filed Dec. 21, 2012, the entire contents and disclosures of which are hereby incorporated by reference.

The invention relates to derivatives of sialic acid, processes for preparing them, their use, especially as active pharmaceutical ingredients, and pharmaceutical active ingredient compositions which comprise such compounds.

"Sialic acids" is the generic term for a large family of unbranched sugars having a parent structure comprising nine carbon atoms, all of which are derivatives of neuramic acid (Neu) or of keto-deoxy-nonulosonic acid (KDN).

Sialic acids play multivarious roles in mammals and in the human body (Schauer (2004) Zoology, 107, 49-64; Varki (2008) Trends in Mol Med, 14, 8, 351-360). Furthermore, they are utilized by many pathogens in order, for example, to achieve efficient infection or in order to evade the immune system of the host (Glycoconjugate J. 2006, vol. 23, issue 1-2, all articles). Many such functions are regulated via proteins which recognize sialic acid (Lehmann et al. (2006) Cell. Mol. Life. Sci. 63, 1331-1354). Through binding artificial ligands, especially through modified sialic acids, to these proteins, it is possible to achieve a therapeutically advantageous effect.

One subgroup of such proteins are the Siglecs (Sialic acid recognizing immunoglobulin like lectins). They are lectins of the Ig type, which are characterized by an N-terminal V-set domain, which allows specific recognition of sialic acids. A review of the types of Siglec proteins hitherto disclosed, and diseases potentially treatable using Siglec ligands, is given in Trends in Pharmacological Sciences 2009, 30 (5), 240-248 and references therein. Within this subgroup, CD22 (Siglec-2) has a strong influence on the development and regulation of the B-cells and on their influence on the immune system. Ligands for Siglec-2 may be used in particular with clinical pictures in connection with B-cells (Tedder et al (2005) Advances in Immunology 88, 1-50).

It is known from WO 03/000709, for example, that certain monomeric derivatives of sialic acid act as ligands for Siglecs (sialic acid-binding Ig-like lectins) proteins, and have potential suitability as medicaments.

Moreover, antibodies and polymeric sialic acids have already been developed as ligands with therapeutic suitability for Siglecs (Courtney et al (2009) PNAS 106, 8, 2500-505; Collins et al. (2006) Journal of Immunology 177, 2994-3003). Because of the increased number of ligands, the polymers described lead to a sharp increase in affinity, and at the same time have the advantage of being able to bind to a plurality of binding pockets. In these polymeric ligands, galactose-containing trisaccharides were utilized, so making them potential ligands for the asialoglycoprotein receptor and for galectines (Steirer et al. (2009) J. Biol. Chem. 284, 6, 3777-3783). The polymers have the disadvantage, moreover, of a very high molar mass, and of an undefinable and non-uniform size and composition.

Despite the fact that the known Siglec ligands already have a high affinity for certain Siglec proteins, there is still a broad room for improvements, in particular with regard to affinity, selectivity and definability of the therapeutically active molecule, but also in relation to pharmacological tolerance and administration forms, and to stability in plasma and liver.

It is an object of the invention to provide compounds with which advantages are achieved within parts at least of the stated areas.

It has been found that certain dimeric sialic acid derivatives, with a nitrogen substituted in the 9-position, are especially suitable as Siglec ligands, more particularly for Siglec-2 (CD22). Through the combination of the divalency and of the substitution in the 9-position, an unexpectedly high affinity was obtained.

The invention accordingly provides a sialic acid derivative of the formula (I),

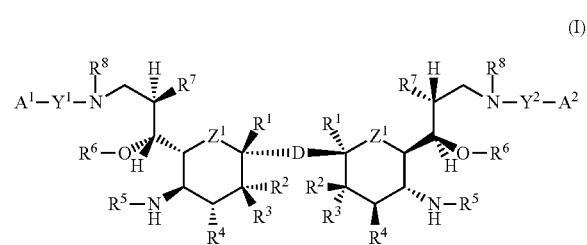

(I)

where the symbols have the following definitions:

$A^1$, $A^2$ are identically or differently a group $D^1$-[$Y^3$-$D^2$-]$_m$~;

$D^1$, $D^2$ are identically or differently a mono- or polycylic aromatic, partially unsaturated or saturated $C_3$-$C_{14}$ hydrocarbon radical or an aromatic, partially unsaturated or saturated three- to eight-membered heterocyclic radical, the stated radicals being unsubstituted or substituted one or more times by a group $X^1$;

$X^1$ is identically or differently halogen, cyano, nitro, hydroxyl, mercapto, amino, carboxyl, hydroxylamino, azido, $B(OH)_2$, SO, $SO_3M$, $OSO_3M$, $SO_2NH_2$, $SO_2CF_3$, $PO_3M$, $OPO_3M$, cyanomethyl, alkyl, haloalkyl, alkenyl, alkynyl, alkyloxy, haloalkyloxy, alkenyloxy, alkynyloxy, alkylthio, alkylamino, dialkylamino, trialkylamino, formyl, alkylcarbonyl, alkylsulphonyl, alkylsulphoxyl, alkylaminosulphoxyl, dialkylaminosulphoxyl, alkyloxycarbonyl, alkylcarbonyloxy, aminocarbonyl, aminothiocarbonyl, alkylaminocarbonyl, alkylcarbonylamino, dialkylaminocarbonyl, alkylaminothiocarbonyl, oxo (=O), thioxo (=S), $C_1$-$C_8$ alkylimino (=N—$C_1$-$C_8$ alkyl), $C_1$-$C_8$ alkyloximino (=N—O—$C_1$-$C_8$ alkyl), the alkyl groups in these radicals containing 1 to 8 carbon atoms, and the stated alkenyl or alkynyl groups in these radicals containing 2 to 8 carbon atoms;

$Y^1$, $Y^2$ are identically or differently ~($C_1$-$C_4$ alkyl)-, ~($C_1$-$C_4$ haloalkyl)-, ~($C_1$-$C_4$ alkyl)-(CO)—, ~C(O)—, ~$CH_2$—C(O)—, ~CH=CH—C(O)—, ~C≡C—C(O)—, ~S(O)$_2$—, ~$CH_2$—S(O)$_2$—, ~$NR^x$—C(O)—, ~CH(CF$_3$)—, ~$NR^x$-3-cyclobutene-1,2-dione-4-, ~$CH_2$—$NR^x$-3-cyclobutene-1,2-dione-4-, ~$NR^x$-3-2,5-thiadiazole 1-oxide-4-, ~$NR^x$-3-2,5-thiadiazole 1,1-dioxide-4-, where ~ denotes the bond to the group A, or $Y^1$, $Y^2$ form, independently of one another, together with the nitrogen to which they are bonded, and with the group $R^8$, a group ~4-1H-(1,2,3)triazol-1-yl-, ~5-1H-(1,2,3)triazol-1-yl-, ~$CH_2$-4-1H-(1,2,3)triazol-1-yl- or —$CH_2$-5-1H-(1,2,3)triazol-1-yl-, where ~ denotes the bond to the group A;

$Y^3$ is a bond, O, S, S(O), S(O)$_2$, $CH_2$, C(O), $CR_2^x$; or $NR^x$;

m is 0, 1 or 2;

$Z^1$ is O, S, $CH_2$ or $NR^x$;

D is a group $Z^2$-$T^1$-$Y^4$-$A^3$-$Y^5$-$T^2$-$Z^2$;

$Z^2$ is identically or differently —O~, —S~, —$NR^x$~, —NH—C(O)~, —$CH_2$~, —$CF_2$~, —CH(OH)~, —N($R^x$)—O~, —O—$NR^x$~, —O—N=CH—, ~4-1H-

(1,2,3)triazol-1-yl-, or ~-5-1H-(1,2,3)triazol-1-yl-, where ~ denotes the bond to the group T;

$T^1$, $T^2$ are identically or differently a straight-chain or branched alkanediyl group having 1 to 30 C atoms, where
  (i) optionally one or more non-terminal $CH_2$ groups are replaced by —O—, —S—, —S(O)—, —S(O)$_2$—, —S$^+$(CH$_3$)—, —P(O$_2$)— and/or —NR$^x$—, and/or
  (ii) optionally one or more H atoms are replaced by F, Cl, OR$^x$, OSO$_3$M, (=O), (=S), carboxyl, NH$_2$, NHR$^z$ and/or NHR$^y$, and/or
  (iii) optionally one or more non-terminal —CH$_2$—CH$_2$— groups are replaced by -5-1H-(1,2,3)triazol-1-yl-, —CR$^x$=CR$^x$— and/or —C≡C—, and/or
  (iv) optionally a non-terminal —CH$_2$CH$_2$CH$_2$— group is replaced by -4-1H-(1,2,3)triazol-1-yl- and/or —O—N=CH—, and/or
  (v) optionally a non-terminal —CH$_2$CH$_2$CH$_2$CH$_2$— group is replaced by phenyl-1,4-diyl;

$Y^4$, $Y^5$ are identically or differently a bond, O, S, NR$^x$, S(O), S(O)$_2$, C(O), ~C(O)—NR$^x$—, ~NR$^x$—C(O)~, ~C(O)—O—, ~O—C(O)—, ~NR$^x$—CO—NR$^x$—, ~NR$^x$—S(O)$_2$—, ~S(O)$_2$—NR$^x$—, ~CH$_2$—NR$^x$—C(O)—, ~CH$_2$—C(O)—NR$^x$—, ~CH$_2$—NR$^x$—, ~CH(CF$_3$)—NR$^x$—, ~CH=N—O— or ~O—N=CH—, where ~ denotes the bond to group A;

$A^3$ is
  a) $C_1$-$C_8$ alkanediyl, $C_2$-$C_8$ alkenediyl, $C_2$-$C_8$ alkynediyl, $C_4$-$C_8$ alkadienediyl, optionally two or more CH$_2$ groups in the stated groups being replaced by O, S, S(O), S(O)$_2$, NR$^x$ and/or C(O), and optionally one or more H atoms in the stated groups being replaced by a group $X^2$,
  b) a group $A^4$-[$Z^3$-$A^5$]$_n$,
  c) 1,1'-ferrocenediyl, 1,1'-cobaltocenediyl, 1,1'-ruthenocene or dichloroplatinumdiaminodiyl;

$A^4$, $A^5$ are identically or differently a saturated, partially unsaturated or aromatic, mono- or polycyclic hydrocarbon radical having 3 to 14 C atoms, or a three- to eight-membered aromatic, partially unsaturated or saturated mono- or polycyclic heterocyclic radical, the stated groups being each optionally substituted by one or more groups $X^2$;

$Z^3$ is a bond, O, S, S(O), S(O)$_2$, NR$^x$, C(O) or CR$_2^x$;

$X^2$ is identically or differently fluoro, chloro, bromo, nitro, hydroxylamino, B(OH)$_2$, SO$_3$M, OSO$_3$M, SO$_2$NH$_2$, PO$_3$M, OPO$_3$M, alkyl, haloalkyl, alkyloxy, haloalkyloxy, alkylthio, alkylamino, dialkylamino, trialkylamino, alkylcarbonyl, alkylsulphonyl, alkylsulphoxyl, alkylaminosulphoxyl, dialkylaminosulphoxyl, alkyloxycarbonyl, alkylcarbonyloxy, aminocarbonyl, alkylaminocarbonyl, alkylcarbonylamino, dialkylaminocarbonyl, alkylaminothiocarbonyl, $C_1$-$C_4$ alkylimino (=N—$C_1$-$C_4$ alkyl), $C_1$-$C_4$ alkyloximino (=N—O—$C_1$-$C_4$ alkyl), the alkyl groups in these radicals containing 1 to 4 carbon atoms, and the groups haloalkyl and haloalkyloxy containing the halogens F and/or Cl;

n is 0, 1;

$R^1$ is identically C(O)OM, O—PO$_3$M$_2$, O—SO$_3$M, SO$_3$M, C(O)—NH—S(O)$_2$—R$^x$, PO$_3$M$_2$ or C(O)NOM;

$R^2$, $R^3$ are identically or differently H or F;

$R^4$, $R^7$ are identically or differently H, OH, OR$^z$, OC(O)NHR$^y$ or NR$^x$;

$R^6$ is identically or differently H or R$^z$;

$R^5$ is identically or differently H, R$^x$, R$_2^x$, C(O)H, C(O)CH$_2$OH or C(O)-haloalkyl;

$R^8$ is identically or differently R$^x$;

M is H, $C_1$-$C_6$ alkyl or a cation;

$R^x$ is identically or differently H, R$^y$ or R$^z$;

$R^y$ is identically or differently $C_1$-$C_6$ alkyl, phenyl or benzyl, and $R^z$ is identically or differently —C(O)—$C_1$-$C_6$ alkyl, —C(O) phenyl or —C(O)—$C_1$-$C_4$ alkyl-phenyl, and also its pharmacologically tolerated salts, metabolites and prodrugs.

Likewise provided by the invention is a pharmaceutical preparation comprising at least one sialic acid derivative of the formula (I), or a pharmacologically tolerated salt or prodrug thereof, and a pharmacologically tolerated carrier.

Additionally provided by the invention, moreover, is a sialic acid derivative of the formula (I), or a pharmacologically tolerated salt or prodrug thereof, as medicament. By way of example, modifications to individual substituents in pharmacologically active molecules, to form prodrug forms, are described in Nature Drug Discovery Reviews, 2008, 7, 255-270 and in Hydrolysis in Drug and Prodrug Metabolism, Wiley-VCH, 2003, Bernard Testa and Joachim M. Mayer.

The invention also provides a sialic acid derivative of the formula (I), or a pharmacologically tolerated salt or prodrug thereof, for the treatment or prevention of allergies, autoimmune diseases, chronic inflammations, paraplegia, multiple sclerosis, cancer, viral diseases, for example AIDS, bacterial diseases, for example streptococci, parasitic diseases, for example Chagas disease, diseases where the immune response is disrupted in the context of B cell activation, such as Common Variable Immunodeficiency (CVID) and IgA deficiency, in diseases of the haematopoietic organs and of the blood, and also in cancer, for example lymphomas and myelomas, and for regulating the immune system, for example in the case of vaccinations.

Additionally provided by the invention is a sialic acid derivative of the formula (I), or a to pharmacologically tolerated salt or prodrug thereof, for use in the production of a medicament for regulating the immune system, for example in the case of vaccinations, and also for the treatment of allergies, autoimmune diseases, chronic inflammations, paraplegia, multiple sclerosis, cancer, viral diseases, for example AIDS, bacterial diseases, for example streptococci, parasitic diseases, for example Chagas disease, diseases where the immune response is disrupted in the context of B cell activation, such as Common Variable Immunodeficiency (CVID) and IgA deficiency, in diseases of the haematopoietic organs and of the blood, and also in cancer, for example lymphomas and myelomas.

Likewise provided with the invention is a method for regulating the immune system, for example in the case of vaccinations, and also for the treatment of diseases whose course or activity may be influenced by the Siglec ligands, more particularly from the group of allergies, autoimmune diseases, chronic inflammations, paraplegia, multiple sclerosis, cancer, viral diseases, for example AIDS, bacterial diseases, for example streptococci, parasitic diseases, for example Chagas disease, diseases where the immune response is disrupted in the context of B cell activation, such as Common Variable Immunodeficiency (CVID) and IgA deficiency, in diseases of the haematopoietic organs and of the blood, and also in cancer, for example lymphomas and myelomas, wherein a person affected by the disease is administered a preferably therapeutically effective amount of a sialic acid derivative of the formula (I) or of a pharmacologically tolerated salt or prodrug thereof.

Figure 1:
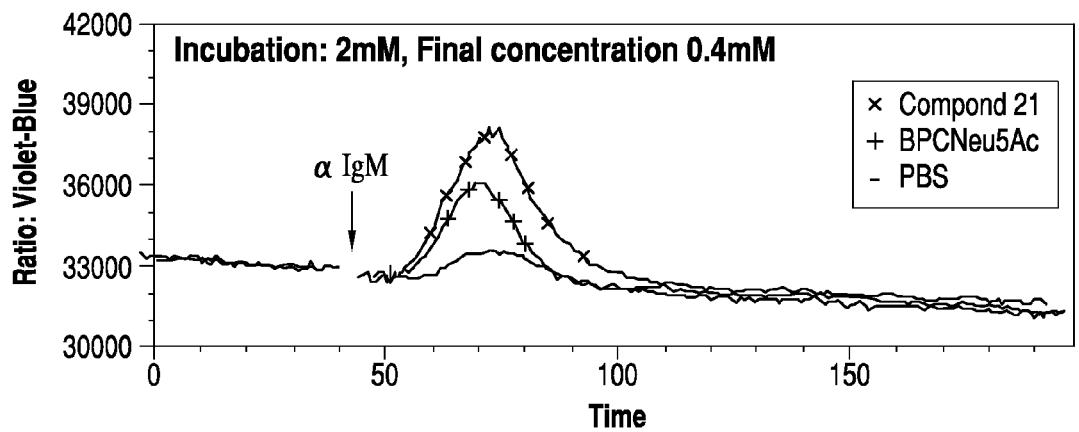
FIG. 1 is a graph showing the calcium flux of exemplary compound 21 in comparison to BPC Neu5Ac at a final concentration of 0.4 mM.

By virtue of the divalency, the sialic acid derivatives of the formula (I) are able to bind simultaneously to two binding pockets or two proteins. In an affinity assay, they exhibit a significantly altered behaviour to monomers. The substitution in the 9-position increases the affinity to an unexpectedly great extent. They exhibit a high activity as Siglec ligands and have, in contrast to polymers, an unambiguous and definable structure in each case. Apart from sialic acid, moreover, they contain no other carbohydrates, and can be modified in a simple way to form prodrugs. The compounds are prepared without use of cell cultures or enzymes, thus enabling their preparation on an industrial scale.

The term "sialic acid derivative of the formula (I)" encompasses all stereoisomeric forms of the compound of the formula (I), especially E/Z or cis/trans isomers in the case of substituted double bonds or rings, and also stereoisomers resulting from the centres of chirality in the compounds of the formula (I), especially enantiomers and diastereoisomers in pure form or in the form of mixtures of any composition, with the individual centres of chirality present in each case in the (S)- or (R)-form.

The individual stereoisomers may be prepared, for example, by enrichment of the isomeric mixtures in accordance with customary techniques, such as chromatography or crystallization, or by use of isomerically pure starting materials. The enrichment of the isomers may take place at the stage of the reactants, intermediates or end products of the formula (I). The isomers encompassed in accordance with the invention also include all tautomeric forms of compounds (I), and all mesomorphous forms.

Furthermore, the term "sialic acid derivatives of the formula (I)" encompasses pharmacologically tolerated salts of the compounds (I), including internal salts (zwitterions).

Furthermore, the term "sialic acid derivatives of the formula (I)" encompasses pharmacologically active metabolites of the compounds (I). In particular, the term "metabolites" encompasses cleavage products generated by enzymes that occur in vivo, such as esterases, amidases and other enzymes.

Generally speaking, the salts contemplated are the salts of those cations, or the acid addition salts of those acids, whose cations, or anions, do not adversely affect the pharmacological activity of the compounds (I).

Contemplated as cations more particularly are ions of the alkali metals, preferably lithium, sodium and potassium, of the alkaline earth metals, preferably calcium and magnesium, and of the transition metals, preferably manganese, copper, zinc and iron, and also ammonium, in which case, if desired, one to four hydrogen atoms may be replaced by $R^Y$, preferably ammonium, dimethylammonium, diisopropylammonium, tetramethylammonium, triethylammonium, tetrabutylammonium, 2-(2-hydroxyeth-1-oxy)eth-1-ylammonium, di-(2-hydroxyeth-1-yl)ammonium, trimethylbenzylammonium, and also phosphonium ions, sulphonium ions, preferably tri($C_1$-$C_4$-alkyl)sulphonium and sulphoxonium ions, preferably tri($C_1$-$C_4$-alkyl)sulphoxonium. Preferred are Na, Li, K, Ca, Mg and ammonium (optionally substituted); particularly preferred are Na, Li and K; especially preferred is Na.

Anions of pharmacologically tolerated acid addition salts are, for example, chloride, bromide, fluoride, hydrogensulphate, sulphate, dihydrogenphosphate, hydrogen-phosphate, nitrate, hydrogencarbonate, carbonate, hexafluorosilicate, hexafluorophosphate, benzoate, the anions of $C_1$-$C_4$ alkanoic acids, preferably formate, acetate, propionate and butyrate, and of other organic acids, such as pivalic acid, maleic acid, succinic acid, pimelic acid, fumaric acid, malic acid, sulphaminic acid, phenylpropionate acid, gluconic acid, ascorbic acid, nicotinic acid, citric acid and adipic acid.

Furthermore, the term "sialic acid derivative of the formula (I)" encompasses solvates, for example hydrates or adducts with alcohols, and also all crystal modifications.

Unless otherwise indicated, symbols which are used more than once may have the same or different definitions independently of one another.

The terms used in the definitions of the symbols indicated in the formula (I) are as follows:

halogen (halo): fluorine (fluoro), chlorine (chloro), bromine (bromo) and iodine (iodo); alkyl: saturated, straight-chain, branched or cyclic hydrocarbon radicals having for example 1 to 8 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1,1-dimethylpropyl, 1-ethylpropyl, hexyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-methylpentyl, 2-methylpentyl, 3-methylpentyl, 4-methylpentyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, cyclopropyl, cyclobutyl, 1-methylcyclopropyl, 2-methylcyclopropyl, cyclopentyl, 2,2-dimethylcyclopropyl, 2,3-dimethylcyclopropyl, cyclohexyl and cyclooctyl;

haloalkyl: straight-chain, branched or cyclic alkyl groups having for example 1 to 6 carbon atoms (as specified above), some or all of the hydrogen atoms in these groups having been replaced by halogen atoms: such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1-fluoro-1-methyl-ethyl, 1-fluorocyclopropyl, heptafluoropropyl or nonafluorobutyl;

alkenyl: unsaturated, straight-chain or branched hydrocarbon radicals having for example 2 to 8 carbon atoms and one or two double bonds in any position (including all E and Z stereoisomers), e.g. $C_2$-$C_6$ alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1- butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl or but-1,3-enyl;

alkynyl: straight-chain or branched hydrocarbon groups having 2 to 8 carbon atoms and one or two triple bonds in any position, e.g. $C_2$-$C_6$ alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkyloxy: alkyloxy groups with a saturated, straight-chain, branched or cyclic alkyl radical, this radical being from the above-stated group of the alkyls, and containing 1 to 6 carbon atoms;

haloalkyloxy: haloalkyloxy groups with a straight-chain, branched or cyclic haloalkyl radical, this radical being from the above-stated group of the haloalkyls, and containing 1 to 6 carbon atoms;

alkenyloxy: alkenyloxy groups with an unsaturated, straight-chain or branched alkenyl radical, this radical being from the above-stated group of the alkenyls, and containing 1 to 6 carbon atoms;

alkynyloxy: alkynyloxy groups with a straight-chain or branched alkynyl radical, this radical being from the above-stated group of the alkenyls, and containing 1 to 6 carbon atoms;

alkylthio: alkylthio groups with a saturated, straight-chain, branched or cyclic alkyl radical, this radical being from the above-stated group of the alkyls, and containing 1 to 4 carbon atoms;

alkylamino: alkylamino groups with a saturated, straight-chain, branched or cyclic alkyl radical, this radical being from the above-stated group of the alkyls, and containing 1 to 4 carbon atoms;

dialkylamino: dialkylamino groups with saturated, straight-chain, branched or cyclic alkyl radicals, these radicals being, identically or differently, from the above-stated group of the alkyls, and containing 1 to 4 carbon atoms;

trialkylamino: trialkylamino groups with saturated, straight-chain, branched or cyclic alkyl radicals, these radicals being, identically or differently, from the above-stated group of the alkyls, and containing 1 to 4 carbon atoms;

alkylcarbonyl: alkylcarbonyl groups with a saturated, straight-chain, branched or cyclic alkyl radical, this radical being from the above-stated group of the alkyls, and containing 1 to 5 carbon atoms;

alkylsulphonyl: alkylsulphonyl groups with a saturated, straight-chain, branched or cyclic alkyl radical, this radical being from the above-stated group of the alkyls, and containing 1 to 4 carbon atoms;

alkylsulphoxyl: alkylsulphoxyl groups with a saturated, straight-chain, branched or cyclic alkyl radical, this radical being from the above-stated group of the alkyls, and containing 1 to 6 carbon atoms;

alkylaminosulphoxyl: alkylaminosulphoxyl groups with a saturated, straight-chain, branched or cyclic alkyl radical, this radical being from the above-stated group of the alkyls, and containing 1 to 6 carbon atoms;

dialkylaminosulphoxyl: dialkylaminosulphoxyl groups with a saturated, straight-chain, branched or cyclic alkyl radical, this radical being from the above-stated group of the alkyls, and containing 1 to 6 carbon atoms;

alkyloxycarbonyl: alkyloxycarbonyl groups with a saturated, straight-chain, branched or cyclic alkyl radical, this radical being from the above-stated group of the alkyls, and containing 1 to 8 carbon atoms;

alkylcarbonyloxy: alkylcarbonyloxy groups with a saturated, straight-chain, branched or cyclic alkyl radical, this radical being from the above-stated group of the alkyls, and containing 1 to 8 carbon atoms;

alkylaminocarbonyl: alkylaminocarbonyl groups with a saturated, straight-chain, branched or cyclic alkyl radical, this radical being from the above-stated group of the alkyls, and containing 1 to 8 carbon atoms;

dialkylaminocarbonyl: dialkylaminocarbonyl groups with a saturated, straight-chain, branched or cyclic alkyl radical, this radical being from the above-stated group of the alkyls, and containing 1 to 8 carbon atoms;

alkylaminothiocarbonyl: alkylaminothiocarbonyl groups with a saturated, straight-chain, branched or cyclic alkyl radical, this radical being from the above-stated group of the alkyls, and containing 1 to 8 carbon atoms; alkylimino, alkylimino groups with a saturated, straight-chain, branched or cyclic alkyl radical, this radical being from the above-stated group of the alkyls, and containing 1 to 8 carbon atoms;

alkyloximino: alkyloximino groups with a saturated, straight-chain, branched or cyclic alkyl radical, this radical being from the above-stated group of the alkyls, and containing 1 to 8 carbon atoms;

alkylcarbonylamino: alkylcarbonylamino groups with a saturated, straight-chain, branched or cyclic alkyl radical, this radical being from the above-stated group of the alkyls, and containing 1 to 8 carbon atoms;

alkanediyl for radical $A^3$: saturated, straight-chain or branched alkanediyl group having for example 1 to 8 carbon atoms, such as methane-1,1-diyl, ethane-1,2-diyl, propane-1,3-diyl, butane-1,4-diyl, pentane-1,5-diyl, hexane-1,6-diyl, heptane-1,7-diyl or octane-1,8-diyl;

alkanediyl for radical $T^1$ and $T^2$: saturated, straight-chain or branched alkanediyl group having for example 1 to 21 carbon atoms, such as methane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl, octadecane-1,18-diyl, nonadecane-1,19-diyl, eicosane-1,20-diyl or heneicosane-1,21-diyl;

alkenediyl (e.g. for radical $A^3$): unsaturated, straight-chain or branched alkenediyl groups (including all E and Z stereoisomers) having for example 2 to 8 carbon atoms, such as ethene-1,1-diyl, prop-2-ene-1,3-diyl, but-2-ene-1,4-diyl, 3,4-dimethylbut-2-ene-1,4-diyl, pent-2-ene-1,5-diyl, hex-3-ene-1,6-diyl and oct-4-ene-1,8-diyl alkynediyl (e.g. for $A^3$): unsaturated, straight-chain or branched alkynediyl groups having for example 2 to 8 carbon atoms, such as ethyne-1,1-diyl, prop-2-yne-1,3-diyl, but-2-yne-1,4-diyl, pent-2-yne-1,5-diyl, hex-3-yne-1,6-diyl, oct-4-yne-1,8-diyl;

alkadienediyl (e.g. for $A^3$): unsaturated, straight-chain or branched alkadienediyl group (including all E and Z stereoisomers) having for example 4 to 8 carbon atoms, such as but-1,3-diene-1,4-diyl, 3,4-dimethylbut-1,3-diene-1,4-diyl and hex-2,4-diene-1,6-diyl.

Mono- or polycyclic, aromatic, partially unsaturated or saturated $C_3$-$C_{14}$ hydrocarbon radical for $A^4$ and $A^5$ denotes, for example:
a) identically or differently, $C_6$-$C_{14}$ aryldiyl, more particularly phenylene-1,4-diyl, phenylene-1,3-diyl, phenylene-1,2-diyl, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, biphenylene-1,2-diyl, biphenylene-1,3-diyl, biphenylene-1,4-diyl, biphenylene-1,5-diyl, biphenylene-1,6-diyl, biphenylene-1,7-diyl, biphenylene-1,8-diyl, biphenylene-2,3-diyl, biphenylene-2,6-diyl, biphenylene-2,7-diyl, anthracene-1,2-diyl, anthracene-1,3-diyl, anthracene-1,4-diyl, anthracene-1,5-diyl, anthracene-1,6-diyl, anthracene-1,7-diyl, anthracene-1,8-diyl, anthracene-1,9-diyl, anthracene-1,10-diyl, anthracene-2,3-diyl, anthracene-2,6-diyl, anthracene-2,7-diyl, anthracene-2,9-diyl, anthracene-2,10-diyl, anthracene-9,10-diyl, indene-4,7-diyl, s-indacene-4,8-diyl, fluorene-1,4-diyl, phenanthrene-1,4-diyl, indenediyl, s-indacenediyl, fluorenediyl or phenanthrenediyl, 1,2,3,4-tetrahydronaphth-2,6-diyl, trans-1,2,3,4-tetrahydronaphth-1,4-diyl, 1,2,3,4-tetrahydronaphth-5,8-diyl and 2,3-dihydroindene-4,7-diyl;
b) $C_3$-$C_{14}$-cycloalkenediyl or $C_5$-$C_{14}$-cycloalkadienediyl, more particularly cycloprop-1-ene-1,2-diyl, cyclobut-1-ene-1,2-diyl, cyclopent-1-ene-1,3-diyl, cyclohex-1-ene-1,4-diyl, cyclopenta-1,3,-diene-1,3-diyl, cyclohexa-1,3-diene-1,3-diyl and cyclohexa-1,3-diene-1,4-diyl;
c) $C_3$-$C_8$-cycloalkyldiyl or for example cyclopropane-1,2-diyl, more particularly trans-cyclobutane-1,2-diyl, trans-cyclobutane-1-3-diyl, cis-cyclopentane-1,3-diyl, cis-cyclopentane-1,3-diyl, cis-cyclohexane-1,4-diyl, trans-cyclohexan-1,4-diyl, cis-cyclohexane-1,3-diyl, trans-cyclohexane-1,3-diyl, trans-cycloheptane-1,3-diyl and trans-cycloheptane-1,4-diyl.

Three- to eight-membered saturated, partially unsaturated or aromatic heterocyclic radical for $A^4$, $A^5$ denotes, for example:
a) non-aromatic, saturated or partially unsaturated 5- or 6-membered heterocyclodiyl, containing one to three nitrogen atoms and/or one oxygen or sulphur atom or one or two oxygen and/or sulphur atoms, more particularly trans-tetrahydrofuran-2,5-diyl, trans-tetrahydrofuran-2,4-diyl, cis-tetrahydrofuran-2,5-diyl, trans-tetrahydrothiene-2,5-diyl, trans-pyrrolidine-2,5-diyl, isoxazolidin-2,4-diyl, isoxazolidine-2,5-diyl, isothiazolidine-2,4-diyl, isothiazolidine-2,5-diyl, pyrazolidine-1,3,diyl, trans-oxazolidine-2,4-diyl, trans-thiazolidine-2,5-diyl, imidazolidine-1,3-diyl, trans-imidazolidine-2,4-diyl, pyrroline-1,3-diyl, trans-pyrroline-2,4-diyl, trans-pyrroline-2,5-diyl, piperidine-1,4-diyl, trans-piperidine-2,5-diyl, dioxane-2,5-diyl, trans-tetrahydropyrane-2,5-diyl, trans-hexahydropyridazine-3,6-diyl, hexahydro-pyridazine-1,4-diyl, trans-hexahydropyrimidine-2,5-diyl, hexahydropyrimidine-1,3-diyl, hexahydropyrimidine-1,4-diyl, piperazine-1,4-diyl, trans-piperazine-2,5-diyl and piperazine-1,3-diyl;
b) 5-membered heteroaryldiyl, containing one to four nitrogen atoms or one to three nitrogen atoms and/or one sulphur or oxygen atom, more particularly furan-2,4-diyl, furan-2,5-diyl, thiophene-2,4-diyl, thiophene-2,5-diyl, pyrrole-2,4-diyl, pyrrole-2,5-diyl, pyrazole-1,3-diyl, oxazole-2,4-diyl, oxazole-2,5-diyl, 1,3,4-oxadiazole-2,5-diyl, 1,2,4-oxadiazole-3,5-diyl, 1,2,4-thiadiazole-3,5-diyl, 1,3,4-thiadiazole-2,5-diyl, thiazole-2,4-diyl, thiazole-2,5-diyl, imidazole-2,4-diyl, 2H-tetrazole-2,5-diyl, 1H(1,2,4) triazole-2,5-diyl, 1H-(1,2,3)triazole-1,4-diyl, and 1H-(1,2,3)triazole-1,5-diyl;
c) 6-membered heteroaryldiyl, containing one to three or one to four nitrogen atoms, more particularly pyridine-2,5-diyl, pyridine-2,4-diyl, pyridazine-2,5-diyl, pyrimidine-2,5-diyl, pyrimidine-2,4-diyl, pyrazine-2,5-diyl and tetrazine-2,5-diyl.

Polycyclic aromatic, partially unsaturated or saturated heterocyclic radical for $A^4$, $A^5$ denotes, for example:
1-benzofuran-4,7-diyl, 1-benzofuran-2,7-diyl, 2-benzofuran-4,7-diyl, 2-benzofuran-3,6-diyl, chromene-5,8-diyl, chromene-3,7-diyl, xanthene-1,4-diyl, xanthene-2,6-diyl, indazole-4,7-diyl, purine-2,8-diyl, 4H-quinolizine-6,9-diyl, 3-isoquinoline-1,4-diyl, phthalazine-1,4-diyl, 1,8-naphthyridine-2,6-diyl, quinoxaline-2,6-diyl, quinazoline-5,8-diyl, cinnoline-5,8-diyl, pteridine-2,6-diyl, indolizine-2,6-diyl, indolizine-5,8-diyl, indole-4,7-diyl, indole-2,5-diyl, indole-3,6-diyl, isoindole-4,7-diyl, isoindole-2,5-diyl, carbazole-1,4-diyl, acridine-1,4-diyl, phenoxazine-1,4-diyl, benzoxazole-4,7-diyl, benzothiazole-4,7-diyl, benzoimidazole-4,7-diyl, 1H-benzotriazole-4,7-diyl and benzothiophene-1,4-diyl.

Mono- or polycyclic, aromatic, partially unsaturated or saturated $C_3$-$C_{14}$ hydrocarbon radical for $D^2$ denotes, for example:
a) identically or differently $C_6$-$C_{14}$ aryldiyl, more particularly phenylene-1,4-diyl, phenylene-1,3-diyl, phenylene-1,2-diyl, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, biphenylene-1,2-diyl, biphenylene-1,3-diyl, biphenylene-1,4-diyl, biphenylene-1,5-diyl, biphenylene-1,6-diyl, biphenylene-1,7-diyl, biphenylene-1,8-diyl, biphenylene-2,3-diyl, biphenylene-2,6-diyl, biphenylene-2,7-diyl, anthracene-1,2-diyl, anthracene-1,3-diyl, anthracene-1,4-diyl, anthracene-1,5-diyl, anthracene-1,6-diyl, anthracene-1,7-diyl, anthracene-1,8-diyl, anthracene-1,9-diyl, anthracene-1,10-diyl, anthracene-2,3-diyl, anthracene-2,6-diyl, anthracene-2,7-diyl, anthracene-2,9-diyl, anthracene-2,10-diyl, anthracene-9,10-diyl, indene-4,7-diyl, s-indacene-4,8-diyl, fluorene-1,4-diyl, phenanthrene-1,4-diyl and indene-4,7-diyl;
b) $C_3$-$C_{14}$-cycloalkenyldiyl or $C_5$-$C_{14}$-cycloalkadiendiyl, more particularly cyclopropene-1,2-diyl, cyclobutene-1,2-diyl, cyclopentene-1,3-diyl, cyclohexene-1,4-diyl, cycloheptene-1,4-diyl, cyclopentadiene-1,3-diyl and cyclohexa-1,3-diene-1,4-diyl;
c) $C_3$-$C_8$-cycloalkyldiyl, more particularly trans-cyclopropane-1,2-diyl, cyclopropane-1,1-diyl, trans-cyclobutane-1,3-diyl, cis-cyclobutane-1,3-diyl, trans-cyclopentane-1,3-diyl, cis-cyclohexane-1,4-diyl, trans-cyclohexane-1,4-diyl, trans-cycloheptane-1,4-diyl and trans-cyclooctane-1,5-diyl.

Three- to eight-membered saturated, partially unsaturated or aromatic heterocyclic radical for $D^2$ denotes, for example:
a) non-aromatic, saturated or partially unsaturated 5- or 6-membered heterocyclodiyl, containing one to three nitrogen atoms and/or one oxygen or sulphur atom or one or two oxygen and/or sulphur atoms, more particularly trans-tetrahydrofuran-2,5-diyl, trans-tetrahydrofuran-2,4-diyl, cis-tetrahydrofuran-2,5-diyl, trans-tetrahydrothiene-2,5-diyl, trans-tetrahydrothiene-2,4-diyl, trans-pyrrolidine-2,5-diyl, trans-pyrrolidine-2,4-diyl, isoxazolidin-2,4- diyl, isoxazolidine-2,5-diyl, isothiazolidine-2,4-diyl, isothiazolidine-2,5-diyl, pyrazolidine-1,3,diyl, trans-oxazolidine-2,4-diyl, trans-thiazolidine-2,5-diyl, imidazolidine-1,3-diyl, trans-imidazolidine-2,4-diyl, pyrroline-1,3-diyl, trans-pyrroline-2,4-diyl, trans-pyrroline-2,5-diyl, trans-piperidine-2,5-diyl, piperidine-1,4-diyl, trans-dioxane-2,5-diyl, trans-tetrahydropyrane-2,5-diyl, trans-hexahydropyridazine-3,6-diyl, trans-hexahydro-pyridazine-1,4-diyl, trans-hexahydropyrimidine-2,5-diyl, hexahydropyrimidine-1,3-diyl, hexahydropyrimidine-1,4-diyl, piperazine-1,4-diyl, trans-piperazine-2,5-diyl and piperazine-1,3-diyl;

b) 5-membered heteroaryldiyl, containing one to four nitrogen atoms or one to three nitrogen atoms and/or one sulphur or oxygen atom, more particularly furan-2,4-diyl, furan-2,5-diyl, thiophene-2,4-diyl, thiophene-2,5-diyl, pyrrole-2,4-diyl, pyrrole-2,5-diyl, pyrazole-1,3-diyl, oxazole-2,4-diyl, oxazole-2,5-diyl, 1,3,4-oxadiazole-2,5-diyl, 1,2,4-oxadiazole-3,5-diyl, 1,2,4-thiadiazole-3,5-diyl, 1,3,4-thiadiazole-2,5-diyl, isooxazole-3,5-diyl, thiazole-2,4-diyl, thiazole-2,5-diyl, isothiazole-3,5-diyl, imidazole-2,4-diyl, 2H-tetrazole-2,5-diyl, 1H(1,2,4)triazole-2,5-diyl, 1H-(1,2,3)triazole-1,4-diyl, and 1H-(1,2,3)triazole-1,5-diyl;

c) 6-membered heteroaryldiyl, containing one to three or one to four nitrogen atoms, more particularly pyridine-2,5-diyl, pyridine-2,4-diyl, pyridine-2,3-diyl, pyridazine-3,6-diyl, pyrimidine-2,5-diyl, pyrimidine-2,6-diyl, pyrazine-2,5-diyl and tetrazine-3,5-diyl.

Polycyclic aromatic, partially unsaturated or saturated heterocyclic radical for $D^2$ denotes, for example:

1-benzofuran-4,7-diyl, 1-benzofuran-2,7-diyl, 2-benzofuran-4,7-diyl, 2-benzofuran-3,6-diyl, chromene-5,8-diyl, chromene-3,7-diyl, xanthene-1,4-diyl, xanthene-2,6-diyl, indazole-4,7-diyl, purine-2,8-diyl, 4H-quinolizine-6,9-diyl, 3-isoquinoline-1,4-diyl, phthalazine-1,4-diyl, 1,8-naphthyridine-2,6-diyl, quinoxaline-2,6-diyl, quinazoline-5,8-diyl, cinnoline-5,8-diyl, pteridine-2,6-diyl, indolizine-2,6-diyl, indole-4,7-diyl, indole-2,5-diyl, indole-3,6-diyl, isoindole-4,7-diyl, isoindole-2,5-diyl, carbazole-1,4-diyl, acridine-1,4-diyl, phenoxazine-1,4-diyl, benzoxazole-4,7-diyl, benzothiazole-4,7-diyl, benzoimidazole-4,7-diyl, 1H-benzotriazole-4,7-diyl and benzothiophenediyl.

Mono- or polycyclic, aromatic, partially unsaturated or saturated $C_3$-$C_{14}$ hydrocarbon radicals for $D^1$ denotes, for example:

a) $C_6$-$C_{14}$-aryl, more particularly phenyl, 1-naphthyl, 2-naphthyl, 1-biphenylene, 2-biphenylene, 1-pyrenyl, 1-anthracenyl, 2-anthracenyl, 9-anthracenyl, 4-indenyl, 2-fluorenyl, 3-fluorenyl, 9-fluorenyl and 3-phenanthrenyl;

b) $C_3$-$C_{14}$-cycloalkenyl or $C_5$-$C_{14}$-cycloalkadienyl, more particularly cyclopropenyl, cyclobutenyl, cyclopentenyl, cyclohexenyl, cycloheptenyl, cyclooctenyl, cyclopentadien-1-yl, cyclohexadien-1-yl and cyclooctadien-1-yl;

c) $C_3$-$C_8$-cycloalkyl, more particularly cyclopropyl, cyclobutyl, cyclopentyl, cyclohexyl, cycloheptyl, adamantan-1-yl, cuban-1-yl, bicyclo[4.4.0]decan-2-yl and cyclooctyl.

Three- to eight-membered saturated, partially unsaturated or aromatic heterocyclic radical for $D^1$ denotes, for example:

a) non-aromatic, saturated or partially unsaturated 4-, 5-, 6- or 7-membered heterocyclyl, containing one to four nitrogen atoms and/or one oxygen or sulphur atom or one or two oxygen and/or sulphur atoms, more particularly 1-aza-2-oxocyclobut-1-yl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 4,5-dihydro-1,3-oxazol-2-yl, 4,5-dihydro-1,3-oxazol-4-yl, 4,5-dihydro-1,3-oxazol-5-yl, 4,5-dihydro-1,3-thiazol-2-yl, 4,5-dihydro-1,3-thiazol-4-yl, 4,5-dihydro-1,3-thiazol-5-yl, 4,5-dihydro-4H-1,3-oxazin-2-yl, 4,5-dihydro-4H-1,3-thiazin-2-yl, 4,5,6,7-tetrahydro-1,3-oxazepin-2-yl, 4,5,6,7-tetrahydro-1,3-thiazepin-2-yl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 1-piperidinyl, 2-piperidinyl, 3-piperidinyl, 4-piperidinyl, 4-morpholinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 5H-tetrazol-5-yl, 1H-tetrazol-5-yl, 2H-tetrazol-5-yl, 1-piperazinyl and 2-piperazinyl;

b) 5-membered heteroaryl, containing one to four nitrogen atoms or one to three nitrogen atoms and/or one sulphur or oxygen atom: more particularly 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-isoxazolyl, 4-isooxazolyl, 5-isooxazolyl, 2-thiazolyl, 4-thiazolyl, 5-thiazolyl, 2-isothiazolyl, 4-isothiazolyl, 5-isothiazolyl, 2-imidazolyl, 4-imidazolyl, 1,2,5-thiadiazol-3-yl, 1,2,4-thiadiazol-3-yl, 1,2,4-thiadiazol-5-yl, 1,2,5-oxadiazol-3-yl, 1,2,4-oxadiazol-3-yl, 1,2,4-oxadiazol-5-yl, 1,2,3-thiadiazol-4-yl, 1,2,3-thiadiazol-5-yl, 1,2,3,4-thiatriazol-5-yl, 1H-(1,2,3)triazol-1-yl, 1H-(1,2,3)triazol-4-yl, 1H-(1,2,3)triazol-5-yl, 1H-(1,3,4)triazol-1-yl and 1H-(1,3,4)triazol-2-yl;

c) 6-membered heteroaryl, containing one to three or one to four nitrogen atoms: more particularly 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl;

d) 1,2-di-carba-closo-dodecaboran-1-yl, 1,7-di-carba-closo-dodecaboran-1-yl or 1,12-di-carba-closo-dodecaboran-1-yl.

Polycyclic aromatic, partially unsaturated or saturated heterocyclic radical for $D^1$ denotes, for example:

1-benzofuran-2-yl, 1-benzofuran-3-yl, 1-benzofuran-5-yl, 1-benzofuran-6-yl, 1-benzofuran-7-yl, 2-benzofuran-1-yl, 2-benzofuran-3-yl, 2-benzofuran-4-yl, 2-benzofuran-5-yl, 2-benzofuran-6-yl, 2-benzofuran-7-yl, 2H-chromen-3-yl, 2H-chromen-4-yl, 2H-chromen-5-yl, 2H-chromen-6-yl, 2H-chromen-7-yl, 2H-chromen-8-yl, xanthen-1-yl, xanthen-4-yl, xanthen-9-yl, indazol-1-yl, indazol-3-yl, indazol-4-yl, indazol-5-yl, indazol-6-yl, indazol-7-yl, purin-2-yl, purin-6-yl, purin-7-yl, purin-8-yl, quinolin-2-yl, quinolin-3-yl, quinolin-4-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, phthalazin-1-yl, phthalazin-3-yl, phthalazin-5-yl, phthalazin-6-yl, 1,8-naphthyridin-2-yl, 1,8-naphthyridin-3-yl, 1,8-naphthyridin-4-yl, 1,8-naphthyridin-6-yl, 1,8-naphthyridin-7-yl, quinoxalin-2-yl, quinoxalin-5-yl, quinoxalin-6-yl, quinazolin-4-yl, quinazolin-6-yl, cinnolin-3-yl, cinnolin-4-yl, cinnolin-6-yl, pteridin-2-yl, pteridin-4-yl, pteridin-6-yl, pteridin-7-yl, indolizin-1-yl, indol-1-yl, indol-2-yl, indol-3-yl, indol-5-yl, indol-6-yl, indol-7-yl, indol-8-yl, isoindol-1-yl, isoindol-2-yl, isoindol-4-yl, isoindol-5-yl, carbazol-9-yl, acridin-9-yl, phenoxazin-10-yl, 1-benzothiophen-2-yl, 1-benzothiophen-3-yl, 1-benzothiophen-5-yl, 1-benzothiophen-6-yl, 1-benzothiophen-7-yl, 1-benzothiophen-8-yl, benzimidazol-1-yl, benzimidazol-2-yl, benzimidazol-5-yl, benzimidazol-6-yl, benzimidazol-7- yl, benzimidazol-8-yl, 1H-benzotriazol-1-yl, 1H-benzotriazol-5-yl, 1H-benzotriazol-6-yl, 1H-benzotriazol-7-yl, 1H-benzotriazol-8-yl, 4H-3,1-benzoxazin-2-yl, 4H-2-benzopyran-2-yl, 2H-isoquinolin-3-yl, benzothiazol-2-yl, benzothiazol-5-yl, benzothiazol-6-yl, benzothiazol-7-yl, benzothiazol-8-yl, benzoxazol-2-yl, benzoxazol-5-yl, benzoxazol-6-yl, benzoxazol-7-yl or benzoxazol-8-yl.

The stated linear or cyclic hydrocarbon radicals and heterocycles may be unsubstituted or substituted, the substituents being selected preferably from the group $X^2$. Preferred, independently of the respective chain size or ring size, are 1, 2, 3 or 4 substituents; in the case of halogen substituents, preference is also given to substitution up to the maximum possible number (persubstitution).

The symbols in the formula (I) advantageously have the following definitions:

$A^1, A^2$ are advantageously, identically or differently, a group $D^1$-$[Y^3$-$D^2$-$]_m$-;

$D^1$ is advantageously, identically or differently, a) $C_6$-$C_{14}$-aryl, more particularly phenyl, 1-naphthyl, 2-naphthyl, 1-biphenylene, 2-biphenylene, 1-pyrenyl, 1-anthracenyl, 2-fluorenyl, 3-fluorenyl, 9-fluorenyl or 3-phenanthrenyl, or, b) $C_3$-$C_{14}$-cycloalkenyl or $C_5$-$C_{14}$-cycloalkadienyl, more particularly cyclopropenyl, cyclobutenyl, cyclopentenyl, cyclohexenyl, cycloheptenyl or cyclooctenyl;

c) $C_3$-$C_8$-cycloalkyl, more particularly cyclopropyl, cyclobutyl, cyclopentyl or cyclohexyl or, d) non-aromatic, saturated or partially unsaturated 5- or 6-membered heterocyclyl, containing one to three nitrogen atoms and/or one oxygen or sulphur atom or one or two oxygen and/or sulphur atoms, more particularly 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 2-piperidinyl, 3-piperidinyl, 4-piperidinyl, 4-morpholinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydro-pyrimidinyl, 1-piperazinyl or 2-piperazinyl or, e) 5-membered heteroaryl, containing one to four nitrogen atoms or one to three nitrogen atoms and/or one sulphur or oxygen atom, more particularly 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1H-tetrazol-5-yl, 1H-(1,2,3)-triazol-1-yl, 1H-(1,2,3)-triazol-4-yl, 1H-(1,2,3)-triazol-5-yl or 1H-(1,3,4)-triazol-2-yl or, f) 6-membered heteroaryl, containing one to four nitrogen atoms, more particularly 2-pyridinyl, 3-pyridinyl, 4-pyridinyl, 3-pyridazinyl, 4-pyridazinyl, 2-pyrimidinyl, 4-pyrimidinyl, 5-pyrimidinyl or 2-pyrazinyl, or, g) polycyclic heterocyclic radical, more particularly 1-benzofuran-2-yl, 1-benzofuran-3-yl, 1-benzofuran-5-yl, 1-benzofuran-6-yl, 1-benzofuran-7-yl, 2-benzofuran-5-yl, 2-benzofuran-6-yl, 2H-chromen-3-yl, 2H-chromen-4-yl, 2H-chromen-5-yl, 2H-chromen-6-yl, 2H-chromen-7-yl, indazol-7-yl, purin-8-yl, isoquinolin-3-yl, phthalazin-1-yl, 1,8-naphthyridin-2-yl, quinoxalin-2-yl, quinazolin-2-yl, cinnolin-3-yl, pteridin-2-yl, indol-1-yl, isoindol-2-yl, carbozol-9-yl, acridin-9-yl, 1-benzothiophen-2-yl, benzimidazol-2-yl, benzothiazol-2-yl or benzoxazol-2-yl, the stated groups being unsubstituted or substituted by one or more groups $X^1$.

$D^2$ is advantageously, identically or differently, a) $C_6$-$C_{14}$-aryldiyl, more particularly phenylene-1,4-diyl, phenylene-1,3-diyl, phenylene-1,2-diyl, naphthalene-1,4-diyl, naphthalene-1,5-diyl, anthracene-9,10-diyl or indene-4,7-diyl;

b) $C_3$-$C_8$-cycloalkyldiyl, more particularly cyclopropanediyl, trans-cyclobutane-1,3-diyl, trans-cyclopentane-1,3-diyl and trans-cyclohexane-1,4-diyl, c) non-aromatic, saturated or partially unsaturated 5- or 6-membered heterocyclodiyl, containing one to three nitrogen atoms and/or one oxygen or sulphur atom or one or two oxygen and/or sulphur atoms, more particularly tetrahydrofuran-2,5-diyl, tetrahydrofuran-2,4-diyl, piperidine-1,4-diyl, imidazolidine-1,3-diyl or piperazine-1,4-diyl;

d) 5-membered heteroaryldiyl, containing one to four nitrogen atoms and or one to three nitrogen atoms and/or one sulphur or oxygen atom, more particularly furan-2,4-diyl, furan-2,5-diyl, thiophene-2,4-diyl, thiophene-2,5-diyl, pyrrole-2,4-diyl, pyrrole-2,5-diyl, 1H(1,2,4)-triazole-2,5-diyl, 1H(1,2,3)-triazole-1,4-diyl or 1H(1,2,3)-triazole-1,5-diyl, e) 6-membered heteroaryldiyl, containing one to four nitrogen atoms, more particularly pyridine-2,5-diyl, pyridine-2,4-diyl, pyridine-2,3-diyl, pyridazine-3,6-diyl, pyrimidine-2,5-diyl, pyrimidine-2,6-diyl, pyrazine-2,5-diyl or tetrazine-3,5-diyl, the stated groups being unsubstituted or substituted by one or more groups $X^1$.

$X^1$ is advantageously, identically or differently, F, Cl, Br, I, cyano, nitro, hydroxyl, mercapto, amino, carboxyl, hydroxylamino, azido, $SO_3M$, $OSO_3M$, $SO_2NH_2$, $OPO_3M$, alkyl, haloalkyl, alkenyl, alkynyl, alkyloxy, haloalkyloxy, alkenyloxy, alkynyloxy, alkylthio, alkylamino, dialkylamino, trialkylamino, formyl, alkylcarbonyl, alkylsulphonyl, alkylsulphoxyl, aminocarbonyl, alkylaminocarbonyl, alkylcarbonylamino, oxo (=O), thioxo (=S), the alkyl groups in these radicals containing 1 to 8 carbon atoms, and the stated alkenyl or alkynyl groups in these radicals containing 2 to 8 carbon atoms.

$Y^1, Y^2$ are advantageously, identically or differently, ~$CH_2$—, ~$CH_2CH_2$—, ~$CH_2CH_2CH_2$—, ~C(O)—, ~$CH_2$C(O)—, ~$CH_2CH_2$C(O)—, ~$CH_2CH_2CH_2$C(O)—, ~CH=CH—C(O)—, ~C≡C—C(O)—, ~S(O)$_2$—, ~$CH_2$S(O)$_2$—, ~NH—C(O)—, ~$NR^x$-3-cyclobutene-1,2-dione-4-, ~$CH_2$—$NR^x$-3-cyclobutene-1,2-dione-4-, ~$NR^x$-3-2,5-thiadiazole 1 1-dioxide-4-9 where ~ denotes the bond to the group A or $Y^1, Y^2$ form, independently of one another, together with the nitrogen to which they are bonded, and with the group $R^8$, a group ~4-1H-(1,2,3)triazol-1-yl-, ~5-1H-(1,2,3)triazol-1-yl-, ~$CH_2$-4-1H-(1,2,3)triazol-1-yl- or ~$CH_2$-5-1H-(1,2,3)triazol-1-yl-, where ~ denotes the bond to the group A.

$Y^3$ is advantageously a bond O, S(O), S(O$_2$), $CH_2$, C(O) or $NR^x$.

m is advantageously 0, 1 or 2.

$Z^1$ is advantageously O, S or $CH_2$.

D is advantageously a group $Z^2$-$T^1$-$Y^4$-$A^3$-$Y^5$-$T^2$-$Z^2$.

$Z^2$ is advantageously, identically or differently, —O~, —S~, —$NR^x$~, —NHC(O)~, —$CH_2$~, —O—$NR^x$~ or ~4-1H-(1,2,3)triazol-1-yl-, where ~ denotes the bond to the group T.

$T^1$, $T^2$ are advantageously, identically or differently, a straight-chain or branched alkanediyl group having 4 to 30 C atoms, where
- (i) optionally one or more non-terminal $CH_2$ groups are replaced by —O—, —S—, —S(O)—, —S(O)$_2$—, —P(O$_2$)— and/or —NR$^x$—, and/or
- (ii) optionally one or more H atoms are replaced by F, Cl, OR$^x$, —OSO$_3$M, (=O), carboxyl, NH$_2$, NHR$^Y$ and/or NHR$^Z$, and/or
- (iii) optionally a non-terminal —CH$_2$—CH$_2$— group is replaced by -5-1H-(1,2,3)triazol-1-yl-, and/or
- (iv) optionally a non-terminal —CH$_2$CH$_2$CH$_2$— group is replaced by -4-1H-(1,2,3)triazol-1-yl- or —O—N=CH—.

$Y^4$, $Y^5$ are advantageously, identically or differently, O, NR$^x$, S(O), S(O)$_2$, C(O), ~NR$^x$—C(O)—, ~C(O)—NR$^x$—, ~NR$^x$—CO—NR$^x$—, ~NR$^x$—S(O)$_2$—, ~S(O)$_2$—NR$^x$—, ~CH$_2$—NR$^x$—C(O)—, ~CH$_2$—C(O)—NR$^x$— or ~CH$_2$—NR$^x$—, where ~ denotes the bond to group A.

$A^3$ is advantageously
- a) $C_1$-$C_8$ alkanediyl, $C_2$-$C_8$ alkenediyl, $C_2$-$C_8$ alkyndiyl, $C_4$-$C_8$ alkadienediyl, 1, 2, 3 or 4 CH$_2$ groups in the stated groups being optionally replaced by O, S(O), S(O)$_2$, NR$^x$ and/or S, and one or more H atoms in the stated groups being optionally replaced by F or Cl,
- b) a group $A^4$-[$Z^3$-$A^5$]$_n$,
- c) 1,1'-ferrocenediyl, 1,1'-cobaltocenediyl, 1,1'-ruthenocene or dichloroplatinumdiaminodiyl.

$A^4$, $A^5$ are advantageously, identically or differently,
- a) $C_6$-$C_{14}$-aryldiyl, more particularly phenylene-1,4-diyl, phenylene-1,3-diyl, phenylene-1,2-diyl, naphthalene-1,4-diyl, naphthalene-1,5-diyl, naphthalene-2,6-diyl, naphthalene-2,7-diyl, biphenylene-1,4-diyl, biphenylene-2,6-diyl, anthracene-1,4-diyl, anthracene-9,10-diyl, indene-4,7-diyl, s-indacene-4,8-diyl, fluorene-1,4-diyl or phenanthrene-1,4-diyl;
- b) $C_3$-$C_8$-cycloalkyldiyl, more particularly trans-cyclopropane-1,2-diyl, trans-cyclobutane-1,2-diyl, trans-cyclobutane-1-3-diyl, trans-cyclohexane-1,4-diyl or trans-cyclohexane-1,3-diyl;
- c) non-aromatic, saturated or partially unsaturated 5- or 6-membered heterocyclodiyl, containing one to three nitrogen atoms and/or one oxygen or sulphur atom or one or two oxygen and/or sulphur atoms, more particularly piperazine-1,4-diyl, tetrahydrofuran-2,5-diyl or tetrahydrofuran-2,4-diyl;
- d) 5-membered heteroaryldiyl, containing one to four nitrogen atoms or one to three nitrogen atoms and/or one sulphur or oxygen atom, more particularly furan-2,4-diyl, furan-2,5-diyl, thiophene-2,4-diyl, thiophene-2,5-diyl, pyrrole-2,5-diyl, pyrrole-2,5-diyl, pyrazole-1,3-diyl, oxazole-2,4-diyl, oxazole-2,5-diyl, 1,3,4-oxadiazole-2,5-diyl, 1,2,4-oxadiazole-3,5-diyl, 1,2,4-thiadiazole-3,5-diyl, 1,3,4-thiadiazole-2,5-diyl, thiazole-2,4-diyl, thiazole-2,5-diyl, imidazole-2,4-diyl, 2H-tetrazole-2,5-diyl, 1H-(1,2,4)triazole-2,5-diyl, 1H-(1,2,3)triazole-1,4-diyl or 1H-(1,2,3)triazole-1,5-diyl;
- e) 6-membered heteroaryldiyl, containing one to three or one to four nitrogen atoms, more particularly pyridine-2,5-diyl, pyridine-2,4-diyl, pyridazine-2,5-diyl, pyrimidine-2,5-diyl, pyrimidine-2,4-diyl, pyrazine-2,5-diyl or tetrazine-2,5-diyl;
- f) polycyclic heterocyclyl from the group of 1-benzofuran-4,7-diyl, 2-benzofuran-4,7-diyl or xanthene-1,4-diyl, the stated radicals being unsubstituted or substituted by one or more groups $X^2$.

$Z^3$ is advantageously a bond, O, S(O), S(O)$_2$ or C(O).

$X^2$ is advantageously, identically or differently, fluoro, chloro, bromo, nitro, hydroxylamino, SO$_3$M, OSO$_3$M, SO$_2$NH$_2$, PO$_3$M, OPO$_3$M, alkyl, haloalkyl, alkyloxy, haloalkyloxy, alkylamino, dialkylamino, trialkylamino, alkylcarbonyl, alkylsulphonyl, alkylsulphoxyl, alkylaminosulphoxyl, dialkylaminosulphoxyl, alkyloxycarbonyl, alkylcarbonyloxy, aminocarbonyl, alkylaminocarbonyl, alkylcarbonylamino, dialkylaminocarbonyl, $C_1$-$C_4$ alkylimino (=N—$C_1$-$C_4$ alkyl), $C_1$-$C_4$ alkyloximino (=N—O—$C_1$-$C_4$ alkyl), the alkyl groups in these radicals containing 1 to 4 carbon atoms, and the groups haloalkyl and haloalkyloxy containing the halogens F and/or Cl.

n is advantageously 0 or 1.

$R^1$ is advantageously, identically, C(O)OM, SO$_3$M, C(O)—NH—S(O)$_2$—R$^x$, PO$_3$M$_2$ or C(O)NOM.

$R^2$, $R^3$ are advantageously, identically or differently, H or F.

$R^4$, $R^7$ are advantageously, identically or differently, H, OH, OR$^z$, OC(O)NHR$^y$ or NR$^x$.

$R^6$ is advantageously, identically or differently, H or R$^z$.

$R^5$ is advantageously, identically or differently, H, R$^x$, C(O) CH$_2$OH, C(O)-haloalkyl or C(O)H.

$R^8$ is advantageously, identically or differently, R$^x$.

M is advantageously H, $C_1$-$C_4$ alkyl or a cation from the group of the alkali metals, alkaline earth metals, manganese, copper, zinc, iron and optionally substituted ammonium.

$R^x$ is advantageously, identically or differently, H, R$^y$ or R$^z$.

$R^y$ is advantageously, identically or differently, $C_1$-$C_4$ alkyl, more particularly methyl, ethyl, 1-methylethyl, propyl, 1-methylpropyl, 1,1-dimethylpropyl, butyl, phenyl or benzyl.

$R^z$ is advantageously, identically or differently, —C(O)—$C_1$-$C_6$ alkyl, —C(O)-phenyl, —C(O)—$C_1$-$C_4$ alkyl-phenyl, more particularly methylcarbonyl, ethylcarbonyl, propylcarbonyl, 1-methylethylcarbonyl, 1,1-dimethylethylcarbonyl, 1-methylpropylcarbonyl, 2-methylpropylcarbonyl, 1,1-dimethylpropylcarbonyl, butylcarbonyl, pentylcarbonyl or benzylcarbonyl.

The meanings of the definitions of the symbols as indicated in the formula (I) are advantageously as follows:

halogen (halo): fluorine (fluoro), chlorine (chloro) and bromine (bromo);

alkyl: saturated, straight-chain, branched or cyclic hydrocarbon radicals having for example 1 to 7 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1,1-dimethylpropyl, 1-ethylpropyl, hexyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-methylpentyl, 2-methylpentyl, 3-methylpentyl, 4-methylpentyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, cyclopropyl, cyclobutyl, 1-methylcyclopropyl, 2-methylcyclopropyl, cyclopentyl, 2,2-dimethylcyclopropyl, 2,3-dimethylcyclopropyl and cyclohexyl;

haloalkyl: straight-chain, branched or cyclic alkyl groups having for example 1 to 5 carbon atoms (as specified above), some or all of the hydrogen atoms in these groups having been replaced by halogen atoms: such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1-fluoro-1-methylethyl, 1-fluorocyclopropyl, heptafluoropropyl or nonafluorobutyl;

alkenyl: unsaturated, straight-chain or branched hydrocarbon radicals having for example 2 to 4 carbon atoms and one or two double bonds in any position (including all E and Z stereoisomers) e.g. $C_2$-$C_6$ alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl or but-1,3-enyl;

alkynyl: straight-chain or branched hydrocarbon groups having 2 to 4 carbon atoms and one or two triple bonds in any position, e.g. $C_2$-$C_6$ alkynyl such as ethynyl, 1-propynyl, 2-propynyl, 1-butynyl, 2-butynyl, 3-butynyl, 1-methyl-2-propynyl;

alkyloxy: alkyloxy groups with a saturated, straight-chain, branched or cyclic alkyl radical, this radical being from the above-stated group of the alkyls, and containing 1 to 4 carbon atoms;

haloalkyloxy: haloalkyloxy groups with a straight-chain, branched or cyclic haloalkyl radical, this radical being from the above-stated group of the haloalkyls, and containing 1 to 4 carbon atoms;

alkenyloxy: alkenyloxy groups with an unsaturated, straight-chain or branched alkenyl radical, this radical being from the above-stated group of the alkenyls, and containing 1 to 4 carbon atoms;

alkynyloxy: alkynyloxy groups with a straight-chain or branched alkynyl radical, this radical being from the above-stated group of the alkenyls, and containing 1 to 4 carbon atoms;

alkylthio: alkylthio groups with a saturated, straight-chain, branched or cyclic alkyl radical, this radical being from the above-stated group of the alkyls, and containing 1 to 4 carbon atoms;

alkylamino: alkylamino groups with a saturated, straight-chain, branched or cyclic alkyl radical, this radical being from the above-stated group of the alkyls, and containing 1 to 4 carbon atoms;

dialkylamino: dialkylamino groups with saturated, straight-chain, branched or cyclic alkyl radicals, these radicals being, identically or differently, from the above-stated group of the alkyls, and containing 1 to 4 carbon atoms;

trialkylamino: trialkylamino groups with saturated, straight-chain, branched or cyclic alkyl radicals, these radicals being, identically or differently, from the above-stated group of the alkyls, and containing 1 to 4 carbon atoms;

alkylcarbonyl: alkylcarbonyl groups with a saturated, straight-chain, branched or cyclic alkyl radical, this radical being from the above-stated group of the alkyls, and containing 1 to 4 carbon atoms;

alkylsulphonyl: alkylsulphonyl groups with a saturated, straight-chain, branched or cyclic alkyl radical, this radical being from the above-stated group of the alkyls, and containing 1 to 4 carbon atoms;

alkylsulphoxyl: alkylsulphoxyl groups with a saturated, straight-chain, branched or cyclic alkyl radical, this radical being from the above-stated group of the alkyls, and containing 1 to 4 carbon atoms;

alkylaminosulphoxyl: alkylaminosulphoxyl groups with a saturated, straight-chain, branched or cyclic alkyl radical, this radical being from the above-stated group of the alkyls, and containing 1 to 4 carbon atoms;

dialkylaminosulphoxyl: dialkylaminosulphoxyl groups with a saturated, straight-chain, branched or cyclic alkyl radical, this radical being from the above-stated group of the alkyls, and containing 1 to 4 carbon atoms;

alkyloxycarbonyl: alkyloxycarbonyl groups with a saturated, straight-chain, branched or cyclic alkyl radical, this radical being from the above-stated group of the alkyls, and containing 1 to 4 carbon atoms;

alkylcarbonyloxy: alkylcarbonyloxy groups with a saturated, straight-chain, branched or cyclic alkyl radical, this radical being from the above-stated group of the alkyls, and containing 1 to 8 carbon atoms;

alkylaminocarbonyl: alkylaminocarbonyl groups with a saturated, straight-chain, branched or cyclic alkyl radical, this radical being from the above-stated group of the alkyls, and containing 1 to 4 carbon atoms;

dialkylaminocarbonyl: dialkylaminocarbonyl groups with a saturated, straight-chain, branched or cyclic alkyl radical, this radical being from the above-stated group of the alkyls, and containing 1 to 4 carbon atoms;

alkylaminothiocarbonyl: alkylaminothiocarbonyl groups with a saturated, straight-chain, branched or cyclic alkyl radical, this radical being from the above-stated group of the alkyls, and containing 1 to 4 carbon atoms;

alkylimino: alkylimino groups with a saturated, straight-chain, branched or cyclic alkyl radical, this radical being from the above-stated group of the alkyls, and containing 1 to 4 carbon atoms;

alkyloximino: alkyloximino groups with a saturated, straight-chain, branched or cyclic alkyl radical, this radical being from the above-stated group of the alkyls, and containing 1 to 4 carbon atoms;

alkylcarbonylamino: alkylcarbonylamino groups with a saturated, straight-chain, branched or cyclic alkyl radical, this radical being from the above-stated group of the alkyls, and containing 1 to 4 carbon atoms;

alkanediyl for radical $A^3$ denotes: saturated, straight-chain or branched alkanediyl group having for example 1 to 6 carbon atoms, such as methane-1,1-diyl, ethane-1,2-diyl, propane-1,3-diyl, butane-1,4-diyl, pentane-1,5-diyl and hexane-1,6-diyl; alkanediyl for radical $T^1$ and $T^2$ denotes: saturated, straight-chain or branched alkanediyl group having for example 1 to 21 carbon atoms, such as methane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl, octadecane-1,18-diyl, nonadecane-1,19-diyl, eicosane-1,20-diyl or heneicosane-1,21-diyl;

alkenediyl (e.g. for radical $A^3$): unsaturated, straight-chain or branched alkenediyl groups (including all E and Z stereoisomers) having for example 2 to 6 carbon atoms, such as ethene-1,1-diyl, prop-2-ene-1,3-diyl, but-2-ene-1,4-diyl, 3,4-dimethylbut-2-ene-1,4-diyl, pent-2-ene-1,5-diyl and hex-3-ene-1,6-diyl; alkynediyl (e.g. for radical $A^3$): unsaturated, straight-chain or branched alkynediyl groups having for example 2 to 6 carbon atoms, such as ethyne-1,1-diyl, prop-2-yne-1,3-diyl, but-2-yne-1,4-diyl, pent-2-yne-1,5-diyl and hex-3-yne-1,6-diyl;

alkadienediyl (e.g. for radical $A^3$): unsaturated, straight-chain or branched alkadienediyl group (including all E and Z stereoisomers) having for example 4 to 6 carbon atoms, such as but-1,3-diene-1,4-diyl, 3,4-dimethylbut-1,3-diene-1,4-diyl and hex-2,4-diene-1,6-diyl.

Advantageously compounds of the formula (I) are those for which all symbols, definitions and indices have the advantageous meanings.

The symbols and indices in the formula (I) preferably have the following definitions:

$A^1$, $A^2$ are preferably, identically or differently, a group $D^1$-$[Y^3$-$D^2$-$]_m$-.

$D^1$ is preferably, identically or differently,
  a) $C_6$-$C_{12}$ aryl, more particularly phenyl, 1-naphthyl, 2-naphthyl, 2-biphenylene and also 2-fluoroenyl, 3-fluoroenyl or 2-phenanthrenyl;
  b) $C_3$-$C_6$ cycloalkyl, more particularly cyclopropyl, cyclobutyl, cyclopentyl or cyclohexyl;
  c) non-aromatic, saturated or partially unsaturated 5- or 6-membered heterocyclyl, containing one to three nitrogen atoms and/or one oxygen or sulphur atom or one or two oxygen and/or sulphur atoms, more particularly 2-piperidinyl, 3-piperidinyl, 4-piperidinyl, 1,3-dioxan-5-yl, 4-tetrahydropyranyl, 3-hexahydropyridazinyl, 4-hexahydropyridazinyl, 2-hexahydropyrimidinyl, 4-hexahydropyrimidinyl, 5-hexahydropyrimidinyl, 1-piperazinyl, 2-piperazinyl or 4-morpholinyl;
  d) 5-membered heteroaryl, containing one to four nitrogen atoms or one to three nitrogen atoms and/or one sulphur or oxygen atom, more particularly 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,3-triazol-1-yl, 1,2,3-triazol-4-yl, 1,2,3-triazol-5-yl or 1,3,4-triazol-2-yl;
  e) 6-membered heteroaryldiyl, containing one to three nitrogen atoms, more particularly 2-pyridinyl, 3-pyridinyl, 4-pyridinyl, 3-pyridazinyl, 4-pyridazinyl, 2-pyrimidinyl, 4-pyrimidinyl, 5-pyrimidinyl or 2-pyrazinyl;
  f) polycyclic heterocyclic radicals, more particularly 1-benzofuran-2-yl, 1-benzofuran-5-yl, 1-benzofuran-6-yl, 2-benzofuran-5-yl, 2-benzofuran-6-yl, 2H-chromen-3-yl, 2H-chromen-6-yl, 2H-chromen-7-yl, indolyl, 1-benzothiophen-2-yl or benzimidazolyl,
  the stated groups being unsubstituted or substituted by one or more groups $X^1$.

$D^2$ is preferably, identically or differently,
  a) $C_6$-$C_{12}$ aryldiyl, more particularly phenylene-1,4-diyl, phenylene-1,3-diyl, naphthalene-1,4-diyl;
  b) $C_5$-$C_6$ cycloalkyldiyl, more particularly trans-cyclobutan-1,3-diyl or trans-cyclohexane-1,4-diyl;
  c) 5-membered heteroaryldiyl, containing one to four nitrogen atoms or one to three nitrogen atoms and/or one sulphur or oxygen atom, more particularly furan-2,5-diyl, thiophene-2,4-diyl, thiophene-2,5-diyl, 1H(1,2,3)-triazole-1,4-diyl or pyrrole-2,5-diyl;
  d) 6-membered heteroaryldiyl, containing one to four nitrogen atoms, more particularly pyridine-2,5-diyl, pyridine-2,4-diyl, pyridazine-3,6-diyl, pyrimidine-2,5-diyl, pyrimidine-2,6-diyl, pyrazine-2,5-diyl and tetrazine-3,5-diyl;
  the stated groups being unsubstituted or substituted by a group $X^1$.
    $X^1$ is preferably, identically or differently, F, Cl, Br, I, cyano, nitro, hydroxyl, amino, carboxyl, hydroxylamino, azido, $SO_3M$, $SO_2NH_2$, alkyl, haloalkyl, alkynyl, alkyloxy, haloalkyloxy, alkynyloxy, alkylamino, dialkylamino, trialkylamino, alkylcarbonyl, alkylsulphonyl, alkylsulphoxyl, aminocarbonyl, alkylaminocarbonyl, alkylcarbonylamino or oxo (=O), the alkyl groups in these radicals containing 1 to 6 carbon atoms, and the stated alkynyl groups in these radicals containing 2, 4 or 6 carbon atoms.

$Y^1$, $Y^2$ are preferably, identically or differently, ~$CH_2$—, ~$C(O)$—, ~$CH_2C(O)$—, ~$CH_2CH_2$—$C(O)$—, ~$CH$=$CH$—$C(O)$—, ~$C$≡$C$—$C(O)$—, ~$CH_2$—$NR^x$-3-cyclobutene-1,2-dione-4-, ~$S(O)_2$—, ~$CH_2S(O)_2$— or ~$NH$—$C(O)$—, where ~ denotes the bond to the group A, or $Y^1$, $Y^2$ form, independently of one another, together with the nitrogen to which they are bonded, and with the group $R^8$, a group ~4-1H-(1,2,3)triazol-1-yl- or ~5-1H-(1,2,3)triazol-1-yl-, where ~ denotes the bond to the group A.

$Y^3$ is preferably a bond, O, $S(O_2)$, $CH_2$ or $C(O)$.

m is preferably 0, 1 or 2.

$Z^1$ is preferably O or S.

D is preferably a group $Z^2$-$T^1$-$Y^4$-$A^3$-$Y^5$-$T^2$-$Z^2$.

$Z^2$ is preferably identically O, S, ~4-1H-(1,2,3)triazol-1-yl-, —NH—C(O)~ or $CH_2$, where ~ denotes the bond to the group T.

$T^1$, $T^2$ are preferably, identically or differently, a straight-chain or branched alkanediyl group having 4 to 30 C atoms, where
  (i) optionally one or more non-terminal $CH_2$ groups are replaced by —O—, —S—, —S(O)—, —$S(O)_2$— and/or —$NR^x$— and/or
  (ii) optionally one or more H atoms are replaced by fluoro, chloro, (=O), carboxyl, $NH_2$ or $NHR^z$, and/or
  (iv) optionally a non-terminal —$CH_2CH_2CH_2$— group is replaced by -4-1H-(1,2,3)triazol-1-yl-.

$Y^4$, $Y^5$ are preferably, identically or differently, O, $NR^x$, ~$NR^x$—$C(O)$—, ~$C(O)$—$NR^x$—, ~$NR^x$—CO—$NR^x$—, ~$NR^x$—$S(O)_2$—, ~$S(O)_2$—$NR^x$—, ~$CH_2$—$NR^x$—$C(O)$—, ~$CH_2$—$C(O)$—$NR^x$— or ~$CH_2$—$NR^x$—, where ~ denotes the bond to group A.

$A^3$ is preferably
  a) $C_1$-$C_6$ alkanediyl, $C_2$-$C_4$ alkenediyl, $C_2$-$C_4$ alkynediyl or $C_2$-$C_4$ alkadienediyl, 1, 2 or 3 $CH_2$— groups in the stated groups being optionally replaced by O and/or S, and one or more H atoms in the stated groups being optionally replaced by F or Cl,
  b) a group $A^4$-$[Z^3$-$A^5]_n$ or
  c) 1,1'-ferrocenediyl.

$A^4$, $A^5$ are preferably, identically or differently,
  a) $C_6$-$C_{10}$-aryldiyl, more particularly phenylene-1,4-diyl, phenylene-1,3-diyl, phenylene-1,2-diyl or naphthalene-1,4-diyl;
  b) $C_5$-$C_6$-cycloalkyldiyl, more particularly trans-cyclobutane-1,3-diyl or trans-cyclohexane-1,4-diyl;
  c) thiophene-2,5-diyl, furan-2,5-diyl, piperazine-1,4-diyl, 1H-(1,2,3)triazole-1,4-diyl, pyridine-2,5-diyl, pyridine-2,4-diyl, pyridazine-2,5-diyl, pyrimidine-2,5-diyl, pyrimidine-2,4-diyl, pyrazine-2,5-diyl or tetrazine-2,5-diyl;
  the stated radicals being unsubstituted or substituted by one or more groups $X^2$.

$Z^3$ is preferably a bond or O.

$X^2$ is preferably, identically or differently, fluoro, chloro, bromo, nitro, $SO_3M$, $SO_2NH_2$, $PO_3M$, alkyl, haloalkyl, alkyloxy, haloalkyloxy, alkylamino, dialkylamino, trialkylamino, alkylcarbonyl, alkylsulphoxyl, alkylaminosulphoxyl, dialkylaminosulphoxyl, alkyloxycarbonyl, alkylcarbonyloxy, aminocarbonyl, alkylaminocarbonyl, alkylcarbonylamino, the alkyl groups in these radicals containing 1 to 4 carbon atoms, and the groups haloalkyl and haloalkyloxy containing the halogens F and/or Cl.

n is preferably 0 or 1.

$R^1$ is preferably identical and is C(O)OM, $SO_3M$, $PO_3M_2$ or C(O)NOM.

$R^2$, $R^3$ are preferably identically H.

$R^4$, $R^7$ are preferably identically OH or $OR^z$, $R^6$ is preferably identically H or $R^z$.

$R^5$ is preferably identically $R^x$, $C(O)CH_2OH$ or C(O)-haloalkyl.

$R^8$ is preferably, identically or differently, $R^x$.

M is preferably H, methyl, ethyl or a cation from the group of the alkali metals, alkaline earth metals and optionally substituted ammonium.

$R^x$ is preferably, identically or differently, H, $R^y$ or $R^z$.

$R^y$ is preferably, identically or differently, methyl, ethyl, 1-methylethyl, propyl, 1-methylpropyl, 1,1-dimethylpropyl or benzyl.

$R^z$ is preferably, identically or differently, methylcarbonyl, ethylcarbonyl, propylcarbonyl, 1-methylethylcarbonyl, 1,1-dimethylethylcarbonyl or phenylcarbonyl.

The meanings of the definitions of the symbols as specified in the formula (I) are preferably as follows:

alkyl: saturated, straight-chain, branched or cyclic hydrocarbon radicals having for example 1 to 5 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1,1-dimethylpropyl, 1-ethylpropyl, cyclopropyl, cyclobutyl, 1-methylcyclopropyl, 2-methylcyclopropyl, cyclopentyl, 2,2-dimethylcyclopropyl and 2,3-dimethylcyclopropyl;

haloalkyl: straight-chain, branched or cyclic alkyl groups having for example 1 to 4 carbon atoms (as specified above), some or all of the hydrogen atoms in these groups being replaced by halogen atoms: such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1-fluoro-1-methyl-ethyl, 1-fluorocyclopropyl, heptafluoropropyl or nonafluorobutyl;

alkynyl: straight-chain or branched hydrocarbon groups having 2 to 3 carbon atoms and one triple bond, such as ethynyl, 1-propynyl and 2-propynyl;

alkyloxy: alkyloxy groups with a saturated, straight-chain, branched or cyclic alkyl radical, this radical being from the above-stated group of the alkyls, and containing 1 to 3 carbon atoms;

Haloalkyloxy: haloalkyloxy groups with a straight-chain, branched or cyclic haloalkyl radical, this radical being from the above-stated group of the haloalkyls, and containing 1 to 3 carbon atoms;

alkynyloxy: alkynyloxy groups with a straight-chain or branched alkynyl radical, this radical being from the above-stated group of the alkynyls, and containing 1 to 3 carbon atoms;

alkylamino: alkylamino groups with a saturated, straight-chain, branched or cyclic alkyl radical, this radical being from the above-stated group of the alkyls, and containing 1 to 3 carbon atoms;

dialkylamino: dialkylamino groups with saturated, straight-chain, branched or cyclic alkyl radicals, these radicals, identically or differently, being from the above-stated group of the alkyls, and containing 1 to 3 carbon atoms;

trialkylamino: trialkylamino groups with saturated, straight-chain, branched or cyclic alkyl radicals, these radicals, identically or differently, being from the above-stated group of the alkyls, and containing 1 to 3 carbon atoms;

alkylcarbonyl: alkylcarbonyl groups with a saturated, straight-chain, branched or cyclic alkyl radical, this radical being from the above-stated group of the alkyls and containing 1 to 3 carbon atoms;

alkylsulphonyl: alkylsulphonyl groups with a saturated, straight-chain, branched or cyclic alkyl radical, this radical being from the above-stated group of the alkyls and containing 1 to 3 carbon atoms;

alkylsulphoxyl: alkylsulphoxyl groups with a saturated, straight-chain, branched or cyclic alkyl radical, this radical being from the above-stated group of the alkyls and containing 1 to 3 carbon atoms;

alkylaminocarbonyl: alkylaminocarbonyl groups with a saturated, straight-chain, branched or cyclic alkyl radical, this radical being from the above-stated group of the alkyls and containing 1 to 4 carbon atoms;

alkylcarbonylamino: alkylcarbonylamino groups with a saturated, straight-chain, branched or cyclic alkyl radical, this radical being from the above-stated group of the alkyls and containing 1 to 4 carbon atoms;

alkanediyl for radical $A^3$ denotes: saturated, straight-chain or branched alkanediyl group having for example 1 to 6 carbon atoms, such as methane-1,1-diyl, ethane-1,2-diyl, propane-1,3-diyl, butane-1,4-diyl, pentane-1,5-diyl and hexane-1,6-diyl;

alkanediyl for radical $T^1$ and $T^2$ denotes: saturated, straight-chain or branched alkanediyl group having for example 2 to 21 carbon atoms, such as ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl, octadecane-1,18-diyl, nonadecane-1,19-diyl, eicosane-1,20-diyl or heneicosane-1,21-diyl;

alkenediyl (e.g. for radical $A^3$): unsaturated, straight-chain or branched alkenediyl groups (including all E and Z stereoisomers) having for example 2 to 4 carbon atoms, such as ethene-1,1-diyl, prop-2-ene-1,3-diyl and but-2-ene-1,4-diyl;

alkynediyl (e.g. for radical $A^3$): unsaturated, straight-chain or branched alkenediyl groups having for example 2 to 4 carbon atoms, such as ethyne-1,1-diyl, prop-2-yne-1,3-diyl and but-2-yne-1,4-diyl;

alkadienediyl (e.g. for radical $A^3$): unsaturated, straight-chain or branched alkadienediyl group (including all E and Z stereoisomers) having for example 4 to 6 carbon atoms, such as but-1,3-diene-1,4-diyl, 3,4-dimethylbut-1,3-diene-1,4-diyl and hex-2,4-diene-1,6-diyl.

Preferred compounds of the formula (I) are those in which all of the symbols, definitions and indices have the preferred meanings.

The symbols and indices in the formula (I) more preferably have the following definitions:

$A^1$, $A^2$ are more preferably, identically or differently, a group $D^1$-$[Y^3$-$D^2$-$]_m$-.

$D^1$ is more preferably, identically or differently,
phenyl, 1-naphthyl, 2-naphthyl, 2-biphenylene, 2-fluoroenyl, 3-fluoroenyl, 2-phenanthrenyl, cyclopropyl, cyclobutyl, cyclopentyl, cyclohexyl, 2-piperidinyl, 3-piperidinyl, 4-piperidinyl, 1,3-dioxan-5-yl, 4-tetrahydropyranyl, 3-hexahydropyridazinyl, 4-hexahydropyridazinyl, 2-hexahydropyrimidinyl, 4-hexahydropyrimidinyl, 5-hexahydropyrimidinyl, 1-piperazinyl, 2-piperazinyl, 4-morpholinyl, 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,3-triazol-1-yl, 1,2,3-triazol-4-yl, 1,2,3-triazol-5-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1-benzofuran-2-yl, 1-benzofuran-5-yl, 1-benzofuran-6-yl, 2-benzofuran-5-yl, 2-benzofuran-6-yl, 2H-chromen-3-yl, 2H-chromen-6-yl, 2H-chromen-7-yl, indol-2-yl, 1-benzothiophen-2-yl or benzimidazol-2-yl, the stated groups being unsubstituted or substituted by one or more groups $X^1$.

$D^2$ is more preferably, identically or differently,
phenylene-1,4-diyl, phenylene-1,3-diyl biphenyl-4,4'-diyl, naphthalene-1,4-diyl, trans-cyclohexane-1,4-diyl, furan-2,5-diyl, thiophene-2,4-diyl, thiophene-2,5-diyl, 1H(1,2,3)-triazole-1,4-diyl or pyrrole-2,5-diyl, pyridine-2,5-diyl, pyridine-2,4-diyl, pyridazine-3,6-diyl, pyrimidine-2,5-diyl, pyrimidine-2,6-diyl, pyrazine-2,5-diyl or tetrazine-3,5-diyl, the stated groups being unsubstituted or substituted by one or more groups $X^1$.

$X^1$ is more preferably, identically or differently, F, Cl, Br, I, cyano, nitro, hydroxyl, amino, carboxyl, azido, $SO_3M$, $SO_2NH_2$, alkyl, haloalkyl, alkyloxy, haloalkyloxy, alkylamino, dialkylamino, trialkylamino, alkylcarbonyl, alkylsulphoxyl, aminocarbonyl, alkylaminocarbonyl, alkylcarbonylamino, oxo (=O), the alkyl groups in these radicals having 1 to 6 carbon atoms.

$Y^1$, $Y^2$ are more preferably identically or differently ~CH$_2$—, ~C(O)—, ~CH$_2$—C(O)—, ~CH$_2$CH$_2$C(O)—, ~CH═CH—C(O)—, ~C≡C—C(O)—, ~NH—C(O)—, ~CH$_2$—NR$^x$-3-cyclobutene-1,2-dione-4-, —S(O)$_2$— or —CH$_2$S(O)$_2$—, where ~ denotes the bond to the group A, or $Y^1$, $Y^2$ form, independently of one another, together with the nitrogen to which they are bonded, and with the group $R^8$, a group ~4-1H-(1,2,3)triazol-1-yl-, where ~ a denotes the bond to the group A.

$Y^3$ is more preferably a bond, O, S(O$_2$), CH$_2$ or C(O).

m is more preferably 0, 1 or 2.

$Z^1$ is more preferably O.

D is more preferably a group $Z^2$-$T^1$-$Y^4$-$A^3$-$Y^5$-$T^2$-$Z^2$.

$Z^2$ is more preferably identically O, S, ~4-1H-(1,2,3)triazol-1-yl-, —NH—C(O)~ or CH$_2$, where ~ a denotes the bond to the group T.

$T^1$, $T^2$ are more preferably, identically or differently, a straight-chain or branched alkanediyl group having 4 to 20 C atoms, where
(i) optionally one or more non-terminal CH$_2$ groups are replaced by —S—, —S(O)—, —S(O)$_2$—, and/or —NR$^x$—, and/or
(ii) optionally one or more H atoms are replaced by fluoro, chloro, (=O), carboxyl, NH$_2$, or NHR$^z$, and/or
(iv) optionally a non-terminal —CH$_2$CH$_2$CH$_2$— group is replaced by -4-1H-(1,2,3)triazol-1-yl-.

$Y^4$, $Y^5$ are more preferably, identically or differently, —NR$^x$—C(O)—, ~C(O)—NR$^x$—, ~NR$^x$—S(O)$_2$, ~NR$^x$—, ~CH$_2$NR$^x$, ~NR$^x$C(O)NR$^x$—, ~CH$_2$NR$^x$C(O)—, ~CH$_2$C(O)NR$^x$— or ~S(O)$_2$—NR$^x$—, where ~ a denotes the bond to group A.

$A^3$ is more preferably
a) $C_1$-$C_6$ alkanediyl, $C_2$-$C_4$-alkynediyl, one or more H atoms in the stated groups being optionally replaced by F or Cl, or
b) a group $A^4$.

$A^4$ is more preferably identically
phenylene-1,4-diyl, biphenyl-4,4'-diyl, naphthalene-1,4-diyl, trans-cyclohexane-1,4-diyl, thiophene-2,5-diyl or 1H-(1,2,3)triazole-1,4-diyl, pyridine-2,5-diyl, pyridine-2,4-diyl, pyridazine-2,5-diyl, pyrimidine-2,5-diyl, pyrimidine-2,4-diyl, pyrazine-2,5-diyl or tetrazine-2,5-diyl, the stated radicals being unsubstituted or substituted by a group $X^2$.

$X^2$ is more preferably, identically or differently, fluoro, chloro, bromo, nitro, $SO_3M$, alkyl, haloalkyl, alkyloxy, haloalkyloxy, alkylamino, dialkylamino, trialkylamino, alkylcarbonyl, alkylsulphoxyl, alkylcarbonyloxy, aminocarbonyl, alkylaminocarbonyl, alkylcarbonyl-amino, the alkyl groups in these radicals containing 1 to 4 carbon atoms, and the groups haloalkyl and haloalkyloxy containing the halogens F and/or Cl.

$R^1$ is more preferably identical and is C(O)OM or C(O)NOM.

$R^2$, $R^3$ are more preferably identically H.

$R^4$, $R^7$ are more preferably identically OH or Ole.

$R^6$ is more preferably identically H or $R^z$.

$R^5$ is more preferably identically $R^x$, C(O)CH$_2$OH or C(O)-haloalkyl.

$R^8$ is more preferably, identically or differently, $R^x$.

M is more preferably H, methyl, ethyl or a cation from the group Li, Na, K, Ca, Mg and optionally substituted ammonium.

$R^x$ is more preferably, identically or differently, H, $R^y$ or $R^z$.

$R^y$ is more preferably, identically or differently, methyl, ethyl, 1-methylethyl, propyl, 1-methylpropyl, 1,1-dimethylpropyl or benzyl.

$R^z$ is more preferably, identically or differently, methylcarbonyl, ethylcarbonyl, propylcarbonyl, 1-methylethylcarbonyl, 1,1-dimethylethylcarbonyl or phenylcarbonyl.

The meanings of the definitions of the symbols as specified in the formula (I) are more preferably as follows:

alkyl: saturated, straight-chain, branched or cyclic hydrocarbon radicals having for example 1 to 4 carbon atoms, such as methyl, ethyl, propyl, 1-methylethyl, butyl, 1-methylpropyl, 2-methylpropyl, 1,1-dimethylethyl, cyclopropyl, cyclobutyl, 1-methylcyclopropyl, 2-methylcyclopropyl;

haloalkyl: straight-chain, branched or cyclic alkyl groups having for example 1 to 3 carbon atoms (as specified above), some or all of the hydrogen atoms in these groups being replaced by halogen atoms: such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2,2,2-trichloroethyl, pentafluoroethyl, 1-fluoro-1-methyl-ethyl, 1-fluorocyclopropyl and heptafluoropropyl;

alkynyl: straight-chain or branched hydrocarbon groups having 2 to 3 carbon atoms and one triple bond, such as ethynyl, 1-propynyl and 2-propynyl;

alkyloxy: alkyloxy groups with a saturated, straight-chain, branched or cyclic alkyl radical, this radical being from the above-stated group of the alkyls, and containing 1 to 3 carbon atoms;

haloalkyloxy: haloalkyloxy groups with a straight-chain, branched or cyclic haloalkyl radical, this radical being from the above-stated group of the haloalkyls, and containing 1 to 2 carbon atoms;

alkylamino: alkylamino groups with a saturated, straight-chain, branched or cyclic alkyl radical, this radical being from the above-stated group of the alkyls, and containing 1 to 3 carbon atoms;

dialkylamino: dialkylamino groups with saturated, straight-chain, branched or cyclic alkyl radicals, these radicals being, identically or differently, from the above-stated group of the alkyls, and containing 1 to 2 carbon atoms;

trialkylamino: trialkylamino groups with saturated, straight-chain, branched or cyclic alkyl radicals, these radicals being, identically or differently, from the above-stated group of the alkyls, and containing 1 to 2 carbon atoms;

alkylcarbonyl: alkylcarbonyl groups with a saturated, straight-chain, branched or cyclic alkyl radical, this radical being from the above-stated group of the alkyls, and containing 1 to 2 carbon atoms;

alkylsulphoxyl: alkylsulphoxyl groups with a saturated, straight-chain, branched or cyclic alkyl radical, this radical being from the above-stated group of the alkyls, and containing 1 to 2 carbon atoms;

alkylaminocarbonyl: alkylaminocarbonyl groups with a saturated, straight-chain, branched or cyclic alkyl radical, this radical being from the above-stated group of the alkyls, and containing 1 to 3 carbon atoms;

alkylcarbonylamino: alkylcarbonylamino groups with a saturated, straight-chain, branched or cyclic alkyl radical, this radical being from the above-stated group of the alkyls, and containing 1 to 3 carbon atoms;

alkanediyl for radical $A^3$ denotes: saturated, straight-chain or branched alkanediyl group having for example 1 to 6 carbon atoms, such as methane-1,1-diyl, ethane-1,2-diyl, propane-1,3-diyl, butane-1,4-diyl, pentane-1,5-diyl and hexane-1,6-diyl;

alkanediyl for radical $T^1$ and $T^2$ denotes: saturated, straight-chain or branched alkanediyl group having for example 2 to 21 carbon atoms, such as ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl, octadecane-1,18-diyl, nonadecane-1,19-diyl, eicosane-1,20-diyl or heneicosane-1,21-diyl;

alkynediyl (e.g. for radical $A^3$): unsaturated, straight-chain or branched alkyndiyl groups having for example 2 to 3 carbon atoms, such as ethyne-1,1-diyl, prop-2-yne-1,3-diyl.

More preferred compounds of the formula (I) are those in which all of the symbols and indices have the more preferred definitions.

The meanings of the symbols and indices in the formula (I) are very preferably as follows:

$A^1$, $A^2$ are very preferably identically a group $D^1$-$[Y^3$-$D^2]_m$-.

$D^1$ is very preferably identically phenyl, 2-naphtyl, cyclohexyl, 2-fluoroenyl, 2-furanyl, 2-benzothiophenyl, 2-thienyl, 3-thienyl, 2-pyridinyl, 3-pyridinyl, 4-pyridinyl, 3-pyridazinyl, 4-pyridazinyl, 2-pyrimidinyl, 4-pyrimidinyl, 5-pyrimidinyl or 2-pyrazinyl, the stated groups being unsubstituted or substituted by a group $X^1$.

$D^2$ is very preferably identically phenylene-1,4-diyl, naphthalene-1,4-diyl, thiophene-2,5-diyl, pyridine-2,5-diyl, pyridazine-3,6-diyl, pyrimidine-2,5-diyl or pyrazine-2,5-diyl, the stated groups being unsubstituted or substituted by a group $X^1$.

$X^1$ is very preferably identically F, Cl, Br, nitro, hydroxyl, carboxyl, alkyl, haloalkyl, alkyloxy, haloalkyloxy, alkylamino, dialkylamino, trialkylamino, alkylcarbonyl, alkylsulphoxyl, aminocarbonyl, alkylaminocarbonyl, alkylcarbonylamino, the alkyl groups in these radicals containing 1 to 4 carbon atoms.

$Y^1$, $Y^2$ are very preferably identically ~CH$_2$—, ~C(O)—, ~CH$_2$—C(O)—, ~C≡C—C(O)—, ~CH=CH—C(O)—, ~CH$_2$—NR$^x$-3-cyclobutene-1,2-dion-4- or ~S(O)$_2$—, where ~ denotes the bond to the group A, or $Y^1$, $Y^2$ form, independently of one another, together with the nitrogen to which they are bonded, and with the group $R^8$, a group ~4-1H-(1,2,3)triazol-1-yl-, where ~ denotes the bond to the group A.

$Y^3$ is very preferably a bond or O.

m is very preferably 0 or 1.

$Z^1$ is very preferably O.

D is very preferably a group $Z^2$-T1-$Y^4$-$A^3$-$Y^5$-$T^2$-$Z^2$.

$Z^2$ is very preferably identically O, ~4-1H-(1,2,3)triazol-1-yl-, —NH—C(O)~ or CH$_2$, where ~ denotes the bond to the group T.

$T^1$, $T^2$ are very preferably, identically or differently, a straight-chain alkanediyl group having 4 to 10 C atoms, where
  (i) optionally one or more non-terminal CH$_2$ groups are replaced by —S— and/or —NH—, and/or
  (ii) optionally one or more H atoms are replaced by F, Cl, carboxyl, NH$_2$, or (=O).

$Y^4$, $Y^5$ are very preferably identically ~NR$^x$—C(O)—, ~NR$^x$—, ~CH$_2$NR$^x$—, —NR$^x$C(O)NR$^x$—, ~CH$_2$NR$^x$C(O)—, ~CH$_2$C(O)NR$^x$— or ~C(O)—NR$^x$—, where ~ denotes the bond to group A.

$A^3$ is very preferably
  a) $C_1$-$C_6$ alkanediyl, one or more H atoms in the stated groups being optionally replaced by F or Cl, or
  b) a group $A^4$.

$A^4$ is very preferably identically phenylene-1,4-diyl, biphenyl-4,4'-diyl, naphthalene-1,4-diyl, pyridine-2,5-diyl, pyridazine-2,5-diyl, pyrimidine-2,5-diyl, pyrazine-2,5-diyl, tetrazine-2,5-diyl, ethyne-1,2-diyl, thiophene-2,5-diyl, cyclohex-1,4-diyl or -3-cyclobutene-1,2-dione-4-; the stated radicals being unsubstituted or substituted by a group $X^2$.

$X^2$ is very preferably identically fluoro, chloro, bromo, nitro, SO$_3$M, alkyl, haloalkyl, alkyloxy, haloalkyloxy, alkylamino, dialkylamino, trialkylamino, alkylsulphoxyl, alkylcarbonyloxy, the alkyl groups in these radicals containing 1 to 4 carbon atoms, and the groups haloalkyl and haloalkyloxy containing the halogens F and/or Cl.

$R^1$ is very preferably identical and is C(O)OM.

$R^2$, $R^3$ are very preferably identically H.

$R^4$, $R^7$ are very preferably identically OH or OR$^z$.

$R^6$ is very preferably identically H or R$^z$.

$R^5$ is very preferably identically R$^x$, C(O)CH$_2$OH or C(O)-haloalkyl.

$R^8$ is very preferably identically R$^x$.

M is very preferably H, methyl, ethyl or a cation from the group Li, Na and K.

$R^x$ is very preferably, identically or differently H, R$^y$ or R$^z$.

$R^y$ is very preferably, identically or differently, methyl or ethyl.

$R^z$ is very preferably identically methylcarbonyl, ethylcarbonyl or 1-methylethylcarbonyl.

The meanings of the definitions of the symbols as specified in the formula (I) are very preferably as follows:

alkyl: saturated, straight-chain, branched or cyclic hydrocarbon radicals having for example 1 to 4 carbon atoms, such as methyl, ethyl, propyl, 1-methylethyl, butyl, 1-methylpropyl, 2-methylpropyl, 1,1-dimethylethyl, cyclopropyl, cyclobutyl, 1-methylcyclopropyl, 2-methylcyclopropyl;

haloalkyl: straight-chain, branched or cyclic alkyl groups having for example 1 to 3 carbon atoms (as specified above), some or all of the hydrogen atoms in these groups being replaced by halogen atoms: such as chloromethyl, dichloromethyl, trichloromethyl, fluoromethyl, difluoromethyl, trifluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2,2,2-trichloroethyl, pentafluoroethyl, 1-fluoro-1-methylethyl, 1-fluorocyclopropyl and heptafluoropropyl;

alkyloxy: alkyloxy groups with a saturated, straight-chain, branched or cyclic alkyl radical, this radical being from the above-stated group of the alkyls, and containing 1 to 2 carbon atoms;

haloalkyloxy: haloalkyloxy groups with a straight-chain, branched or cyclic haloalkyl radical, this radical being from the above-stated group of the haloalkyls, and containing 1 to 2 carbon atoms;

alkylamino: alkylamino groups with a saturated, straight-chain, branched or cyclic alkyl radical, this radical being from the above-stated group of the alkyls, and containing 1 to 2 carbon atoms;

dialkylamino: dialkylamino groups with saturated, straight-chain, branched or cyclic alkyl radicals, these radicals being, identically or differently, from the above-stated group of the alkyls, and containing 1 to 2 carbon atoms;

trialkylamino: trialkylamino groups with saturated, straight-chain, branched or cyclic alkyl radicals, these radicals being, identically or differently, from the above-stated group of the alkyls, and containing 1 to 2 carbon atoms;

alkylcarbonyl: alkylcarbonyl groups with a saturated, straight-chain, branched or cyclic alkyl radical, this radical being from the above-stated group of the alkyls, and containing 1 to 2 carbon atoms;

alkylsulphoxyl: alkylsulphoxyl groups with a saturated, straight-chain, branched or cyclic alkyl radical, this radical being from the above-stated group of the alkyls, and containing 1 to 2 carbon atoms;

alkylaminocarbonyl: alkylaminocarbonyl groups with a saturated, straight-chain, branched or cyclic alkyl radical, this radical being from the above-stated group of the alkyls, and containing 1 to 2 carbon atoms;

alkylcarbonylamino: alkylcarbonylamino groups with a saturated, straight-chain, branched or cyclic alkyl radical, this radical being from the above-stated group of the alkyls, and containing 1 to 2 carbon atoms;

alkanediyl for radical $A^3$ denotes: saturated, straight-chain or branched alkanediyl group having for example 1 to 6 carbon atoms, such as methane-1,1-diyl, ethane-1,2-diyl, propane-1,3-diyl, butane-1,4-diyl, pentane-1,5-diyl and hexane-1,6-diyl;

alkanediyl for radical $T^1$ and $T^2$ denotes: saturated, straight-chain or branched alkanediyl group having for example 2 to 21 carbon atoms, such as ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl, octadecane-1,18-diyl, nonadecane-1,19-diyl, eicosane-1,20-diyl or heneicosane-1,21-diyl.

Very preferred compounds of the formula (I) are those in which all of the symbols, definitions and indices have the very preferred meanings.

The meanings of the symbols and indices in the formula (I) are extremely preferably as follows:

$A^1$, $A^2$ are extremely preferably identically a group $D^1$-[$Y^3$-$D^2$-]$_m$-.

$D^1$ is extremely preferably identically
phenyl, cyclohexyl, naphth-2-yl, fluoren-2-yl, furan-2-yl, benzothiophen-2-yl, thien-2-yl, thien-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl or pyrazin-2-yl, the stated groups being unsubstituted or substituted by a group $X^1$.

$D^2$ is extremely preferably identically
phenylene-1,4-diyl, naphthalene-1,4-diyl, thiophene-2,5-diyl, pyridine-2,5-diyl, pyridazine-3,6-diyl, pyrimidine-2,5-diyl or pyrazine-2,5-diyl, the stated groups being unsubstituted or substituted by a group $X^1$.

$X^1$ is extremely preferably identically F, Cl, nitro, hydroxyl, carboxyl, alkyl, haloalkyl, alkyloxy, haloalkyloxy, alkylamino, dialkylamino, trialkylamino, alkylsulphoxyl, aminocarbonyl, alkylaminocarbonyl, alkylcarbonylamino, the alkyl groups in these radicals containing 1 to 3 carbon atoms.

$Y^1$, $Y^2$ are extremely preferably identically $\sim$CH$_2$—, $\sim$C(O)—, $\sim$CH$_2$—C(O)—, $\sim$C≡C—C(O)—, $\sim$CH=CH—C(O)—, $\sim$CH$_2$—NR$^x$-3-cyclobutene-1,2-dione-4- or $\sim$S(O)$_{2-9}$ where $\sim$ denotes the bond to the group A, or $Y^1$, $Y^2$ Y form, independently of one another, together with the nitrogen to which they are bonded, and with the group $R^8$, a group $\sim$4-1H-(1,2,3)triazol-1-yl-, where $\sim$ denotes the bond to the group A.

$Y^3$ is extremely preferably a bond.

m is extremely preferably 0 or 1.

$Z^1$ is extremely preferably O.

D is extremely preferably a group $Z^2$-$T^1$-$Y^4$-$A^3$-$Y^5$-$T^2$-$Z^2$.

$Z^2$ is extremely preferably identically O, CH$_2$ or $\sim$4-1H-(1,2,3)triazol-1-yl-, where $\sim$ denotes the bond to the group T.

$T^1$, $T^2$ are extremely preferably, identically or differently, a straight-chain alkanediyl group having 4 to 6 C atoms, where
(i) optionally one or more non-terminal CH$_2$ groups are replaced by —S—, and/or NH, and/or
(ii) optionally one or more H atoms are replaced by F, Cl, carboxyl, NH$_2$, or (=O).

$Y^4$, $Y^5$ are extremely preferably, identically or differently, $\sim$C(O)—NR$^x$—, $\sim$NR$^x$—, $\sim$CH$_2$NR$^x$—, $\sim$NHC(O)NH—, $\sim$CH$_2$NHC(O)—, $\sim$CH$_2$C(O)NH— or $\sim$NR$^x$—C(O)—, where $\sim$ denotes the bond to group A.

$A^3$ is extremely preferably
a) $C_1$-$C_6$ alkanediyl, one or more H atoms in the stated groups being optionally replaced by F or Cl, or
b) a group $A^4$.

$A^4$ is extremely preferably identically phenylene-1,4-diyl, biphenyl-4,4'-diyl, naphthalene-1,4-diyl, pyridine-2,5-diyl, pyridazine-2,5-diyl, pyrimidine-2,5-diyl, pyrazine-2,5-diyl, tetrazine-2,5-diyl, ethyne-1,2-diyl, thiophene-2,5-diyl, cyclohex-1,4-diyl or -3-cyclobutene-1,2-dione-4-;

the stated radicals being unsubstituted or substituted by a group $X^2$.

$X^2$ is extremely preferably identically fluoro, chloro, bromo, nitro, SO$_3$M, alkyl, haloalkyl, alkyloxy, haloalkyloxy, alkylamino, dialkylamino, trialkylamino, alkylsulphoxyl, alkylcarbonyloxy, the alkyl groups in these radicals containing 1 to 3 carbon atoms, and the groups haloalkyl and haloalkyloxy containing the halogens F and/or Cl.

$R^1$ is extremely preferably C(O)OM.

$R^2$, $R^3$ are extremely preferably identically H.

$R^4$, $R^7$ are extremely preferably identically OH or $OR^z$.

$R^6$ is extremely preferably identically H or Rz.

$R^5$ is extremely preferably identically $R^x$, $C(O)CH_2OH$ or C(O)-haloalkyl.

$R^8$ is extremely preferably identically H.

M is extremely preferably H, methyl or a cation from the group Li, Na and K.

Rx is extremely preferably, identically or differently, H, $R^y$ or $R^z$.

$R^y$ is extremely preferably, identically or differently, methyl or ethyl.

$R^z$ is extremely preferably identically methylcarbonyl, ethylcarbonyl or 1-methylethylcarbonyl.

The meanings of the definitions of the symbols specified in the formula (I) are extremely preferably as follows:

alkyl: saturated, straight-chain, branched or cyclic hydrocarbon radicals having for example 1 to 3 carbon atoms, such as methyl, ethyl, propyl, 1-methylethyl or cyclopropyl;

haloalkyl: straight-chain, branched or cyclic alkyl groups having for example 1 to 2 carbon atoms (as specified above), some or all of the hydrogen atoms in these groups being replaced by halogen atoms: such as chloromethyl, dichloromethyl, trichloromethyl, fluoromethyl, difluoromethyl, trifluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2,2,2-trichloroethyl or pentafluoroethyl;

alkyloxy: alkyloxy groups with a saturated, straight-chain, branched or cyclic alkyl radical, this radical being from the above-stated group of the alkyls, and containing 1 to 2 carbon atoms;

haloalkyloxy: haloalkyloxy groups with a straight-chain, branched or cyclic haloalkyl radical, this radical being from the above-stated group of the haloalkyls, and containing 1 to 2 carbon atoms;

alkylamino: alkylamino groups with a saturated, straight-chain, branched or cyclic alkyl radical, this radical being from the above-stated group of the alkyls, and containing 1 to 2 carbon atoms;

dialkylamino: dialkylamino groups with saturated, straight-chain, branched or cyclic alkyl radicals, these radicals being, identically or differently, from the above-stated group of the alkyls, and containing 1 to 2 carbon atoms;

trialkylamino: trialkylamino groups with saturated, straight-chain, branched or cyclic alkyl radicals, these radicals being, identically or differently, from the above-stated group of the alkyls, and containing 1 to 2 carbon atoms;

alkylsulphoxyl: alkylsulphoxyl groups with a saturated, straight-chain, branched or cyclic alkyl radical, this radical being from the above-stated group of the alkyls, and containing 1 to 2 carbon atoms;

alkylaminocarbonyl: alkylaminocarbonyl groups with a saturated, straight-chain, branched or cyclic alkyl radical, this radical being from the above-stated group of the alkyls, and containing 1 to 2 carbon atoms;

alkylcarbonylamino: alkylcarbonylamino groups with a saturated, straight-chain, branched or cyclic alkyl radical, this radical being from the above-stated group of the alkyls, and containing 1 to 2 carbon atoms;

alkanediyl for radical $A^3$ denotes: saturated, straight-chain or branched alkanediyl group having for example 1 to 6 carbon atoms, such as methane-1,1-diyl, ethane-1,2-diyl, propane-1,3-diyl, butane-1,4-diyl, pentane-1,5-diyl and hexane-1,6-diyl;

alkanediyl for radical $T^1$ and $T^2$ denotes: saturated, straight-chain or branched alkanediyl group having for example 4 to 21 carbon atoms, such as butane-1,4-diyl, pentane-1,5-diyl, hexane-1,6-diyl, hexadecane-1,16-diyl or heneicosane-1,21-diyl.

Extremely preferred compounds of the formula (I) are those in which all of the symbols, definitions and indices have the extremely preferred meanings.

The meanings of the symbols and indices in the formula (I) are especially preferably as follows:

$A^1$, $A^2$ are especially preferably identically a group $D^1$-[$Y^3$-$D^2$-]$_m$.

$D^1$ is especially preferably identically phenyl, pyridin-2-yl, fluoren-2-yl, cyclohexyl, naphth-2-yl, benzothiophen-2-yl, furan-2-yl, thien-2-yl or thien-3-yl, the stated groups being unsubstituted or substituted by a group $X^1$.

$D^2$ is especially preferably identically phenylene-1,4-diyl or thiophene-2,5-diyl, the stated groups being unsubstituted or substituted by a group $X^1$.

$X^1$ is especially preferably identically F, chloro, nitro, hydroxyl, carboxyl, methyl, trifluoromethyl, methyloxy.

$Y^1$, $Y^2$ are especially preferably identically ~C(O)—, ~$CH_2$—, ~C≡C—C(O)—, ~CH=CH—C(O)—, ~$S(O)_2$—, ~$CH_2$—NH-3-cyclobutene-1,2-dione-4- or ~$CH_2$—C(O)—, where ~ denotes the bond to the group A, or $Y^1$, $Y^2$ form, independently of one another, together with the nitrogen to which they are bonded, and with the group $R^8$, a group ~4-1H-(1,2,3)triazol-1-yl-, where ~ denotes the bond to the group A.

$Y^3$ is especially preferably a bond.

m is especially preferably 0 or 1.

$Z^1$ is especially preferably O.

D is especially preferably a group $Z^2$-T1-$Y^4$-$A^3$-$Y^5T^2$-$Z^2$.

$Z^2$ is especially preferably identically O, $CH_2$, ~CONH— or ~4-1H-(1,2,3)triazol-1-yl-, where ~ denotes the bond to the group T.

$T^1$, $T^2$ are especially preferably, identically or differently, ~$CH_2CH_2CH_2SCH_2CH_2$—, ~$CH_2CH_2CH_2S(O)CH_2CH_2$—, ~$CH_2C(O)NHCH_2CH_2CH_2$—, ~$CH_2$-4-(1H-(1,2,3)triazole)-1-$CH_2CH_2$—, butane-1,4-diyl, pentane-1,5-diyl or hexane-1,6-diyl, where ~ denotes the bond to the group $Z^2$.

$Y^4$, $Y^5$ are especially preferably identically ~C(O)—NH—, ~NH—, ~$CH_2$NH—, ~NHC(O)NH—, ~$CH_2$NHC(O)—, ~$CH_2$C(O)NH— or ~NH—C(O)—, where denotes the bond to group A.

$A^3$ is especially preferably methanediyl, ethane-1,2-diyl, butane-1,4-diyl, hexane-1,6-diyl, -3-cyclobutene-1,2-dione-4-, thiophene-2,5-diyl, cyclohexane-1,4-diyl, phenylene-1,4-diyl, naphthalene-1,4-diyl, ethyne-1,2-diyl, biphenyl-4,4'-diyl or pyridine-2,5-diyl, the stated radicals being unsubstituted or substituted by one or more groups $X^2$.

$X^2$ is especially preferably identically bromo, nitro, methyl or pentyloxy.
$R^1$ is especially preferably C(O)ONa.
$R^2$, $R^3$ are especially preferably identically H.
$R^4$, $R^7$ are especially preferably identically OH.
$R^6$ is especially preferably identically H.
$R^5$ is especially preferably identically C(O)CH$_3$, C(O)CH$_2$F or C(O)CH$_2$OH.
$R^8$ is especially preferably identically H.

Especially preferred compounds of the formula (I) are those in which all of the symbols and indices have the especially preferred definitions.

Further-preferred sialic acid derivatives of the formula (I) are those of the formulae (Ia)-(Ik), where the symbols have the preferences and definitions as indicated in the formula (I).

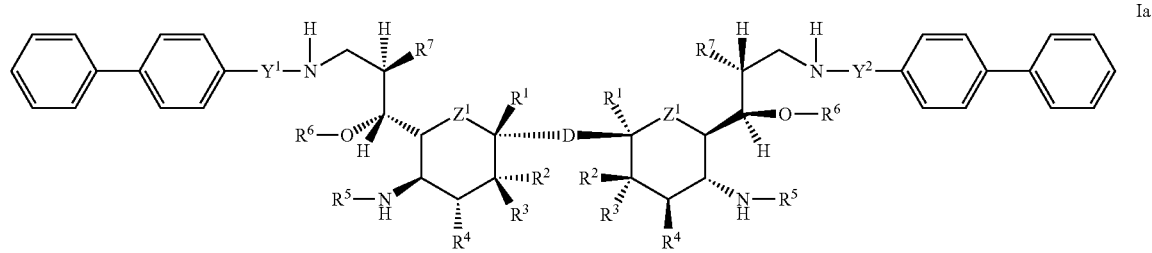

Ia

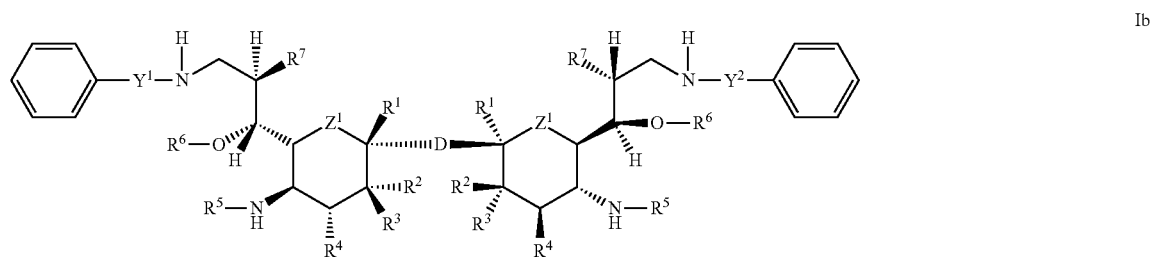

Ib

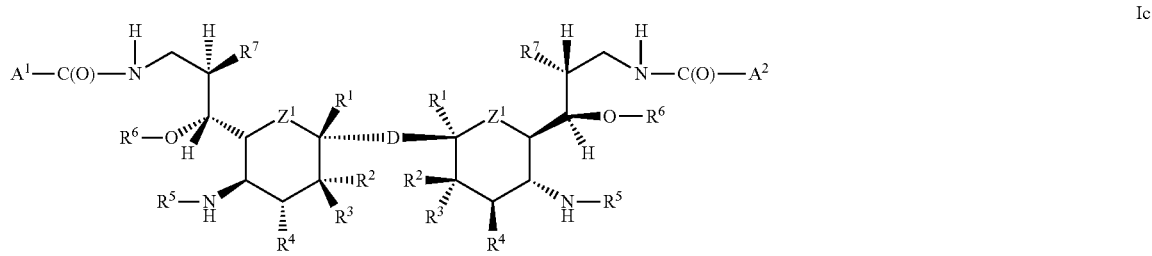

Ic

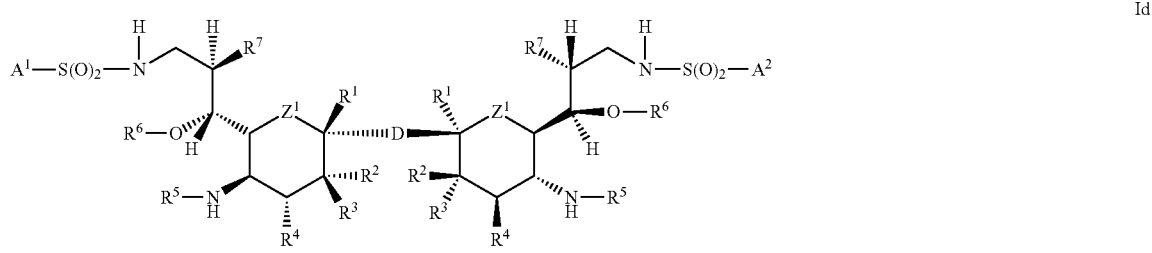

Id

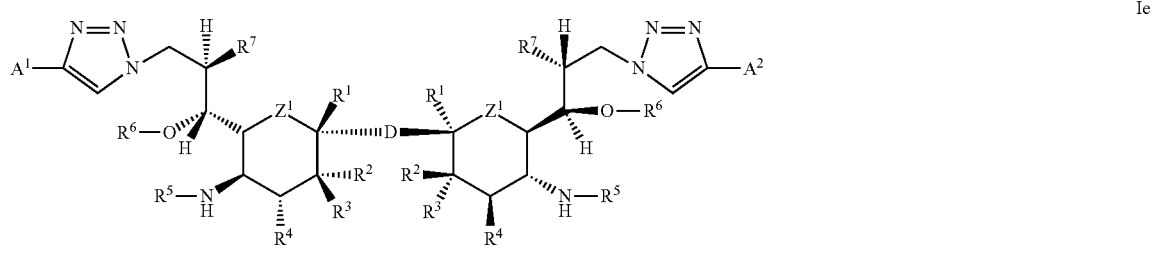

Ie

-continued
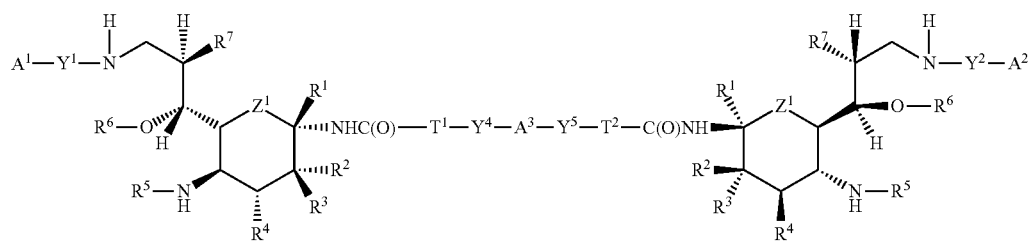
If
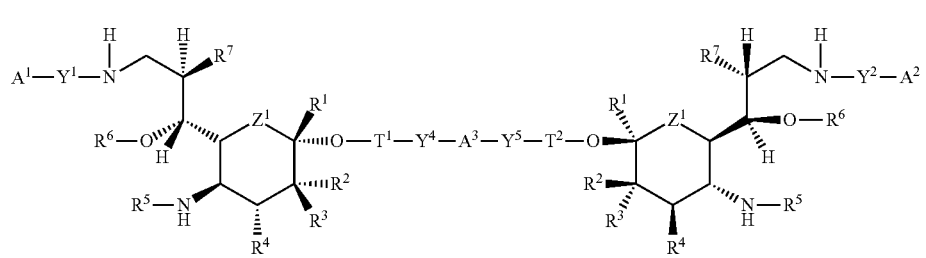
Ig
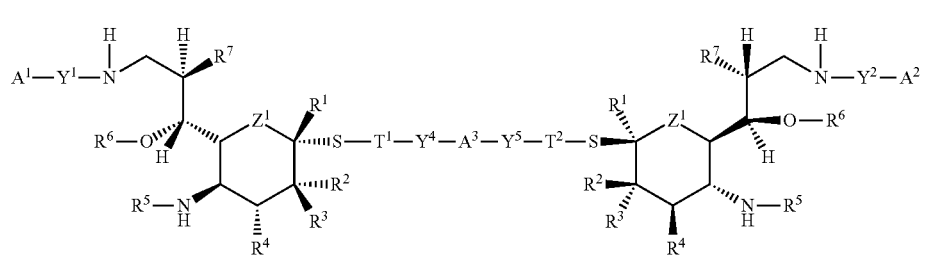
Ih
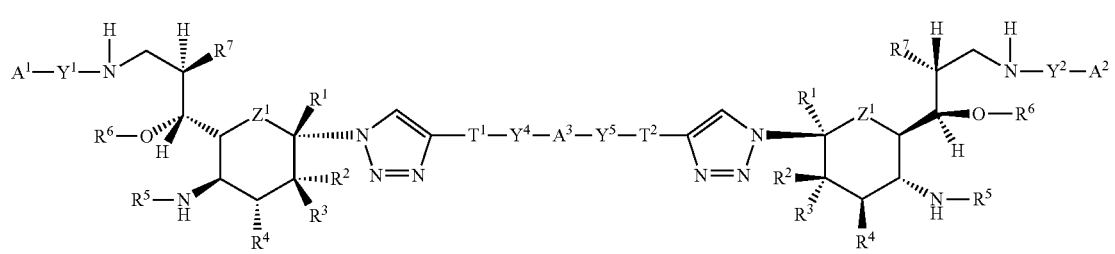
Ii
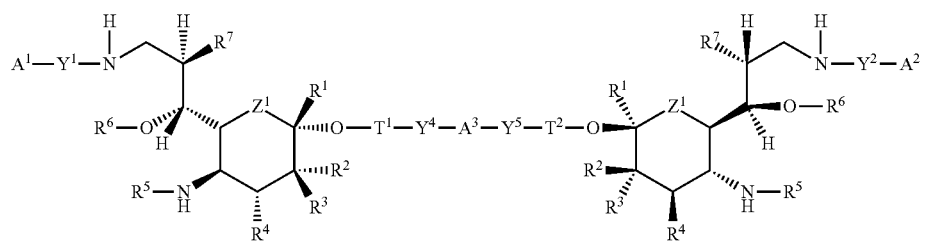
Ij
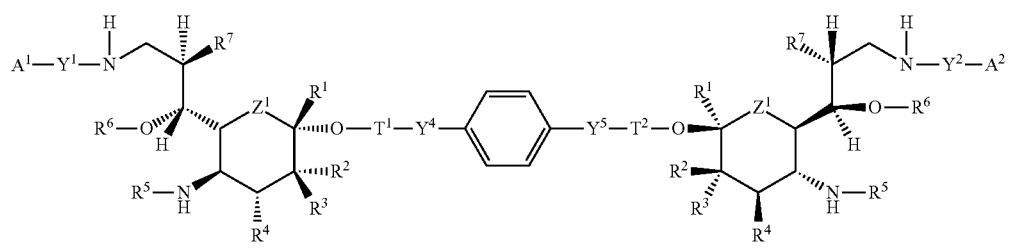
Ik Particularly preferred are also sialic acid derivatives of the formulae (Iaa)-(Iac), where the symbols have the definitions indicated in the formula (I):
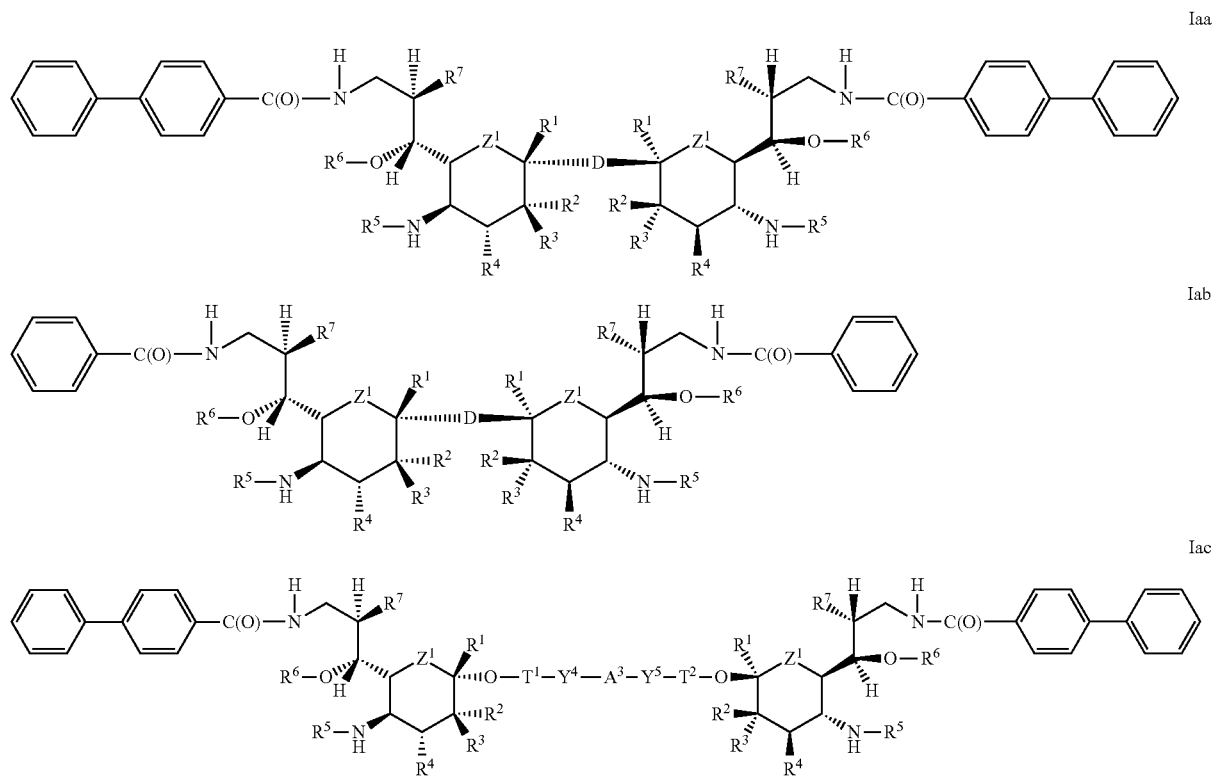
Also particularly preferred are sialic acid derivatives of the formulae (Iad)-(Iag), where the symbols have the definitions indicated in the formula (I):
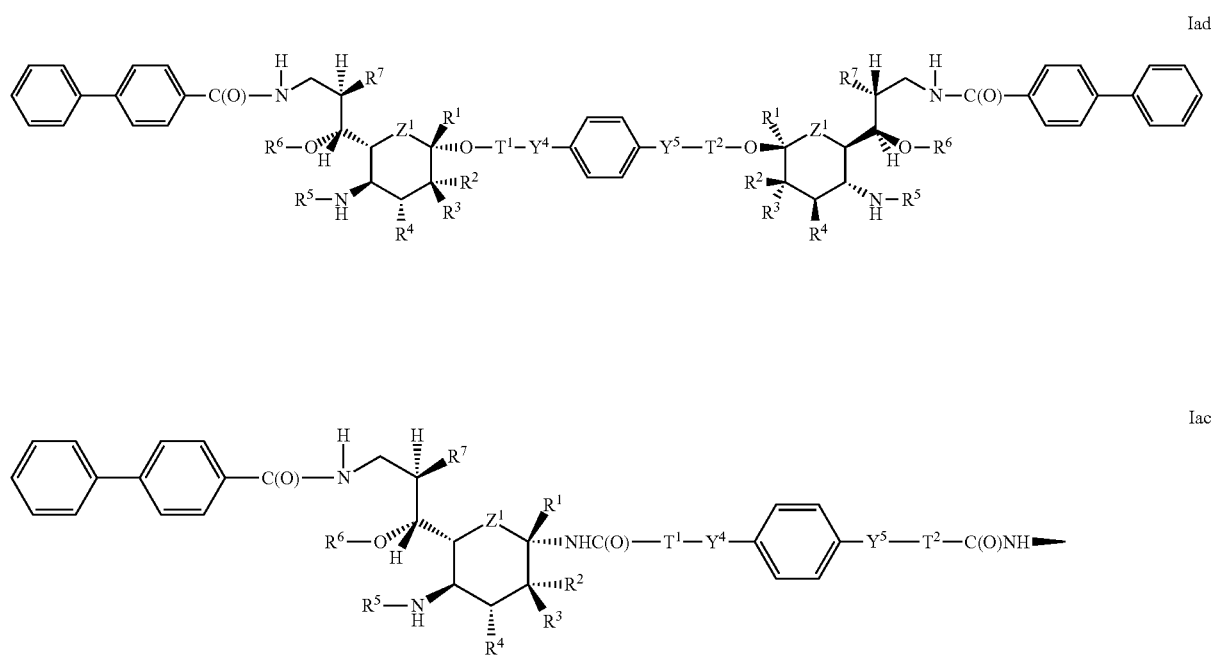

-continued
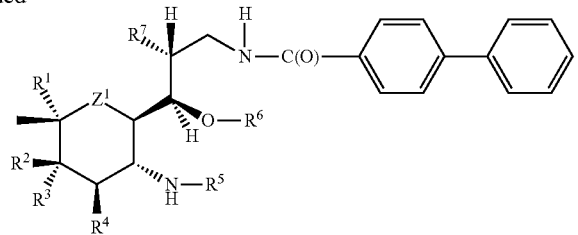
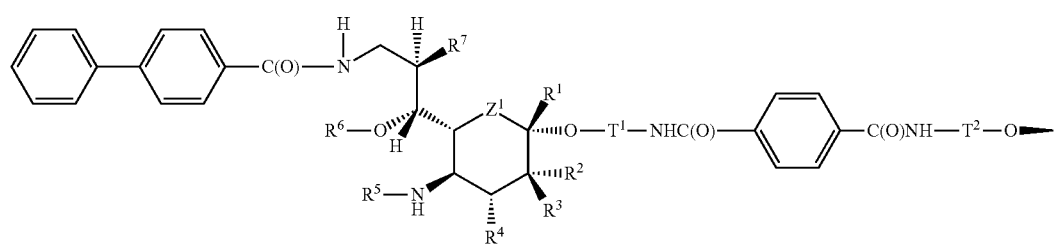
Iaf
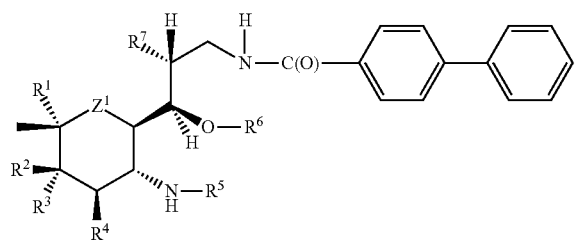
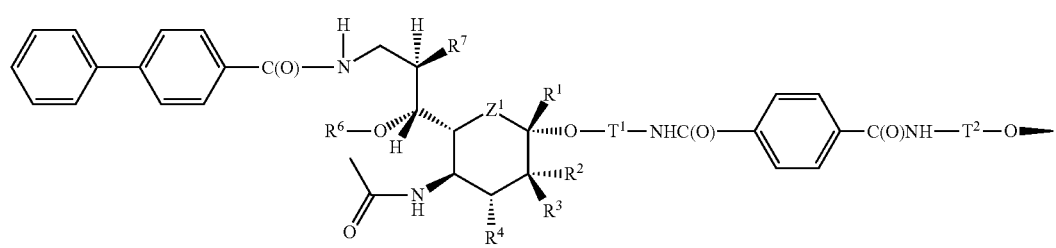
Iag
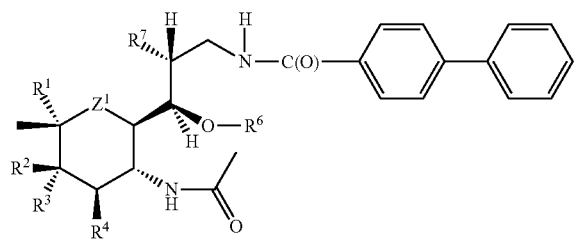

The sialic acid derivatives (I) of the invention are obtainable employing synthesis processes that are known in principle. The compounds are obtained preferably in accordance with the preparation processes of the invention, elucidated in more detail below, more particularly with synthesis Schemes I-XX:

Monomeric starting compounds may be prepared, for example, in accordance with synthesis Schemes I to XIV.

Scheme I

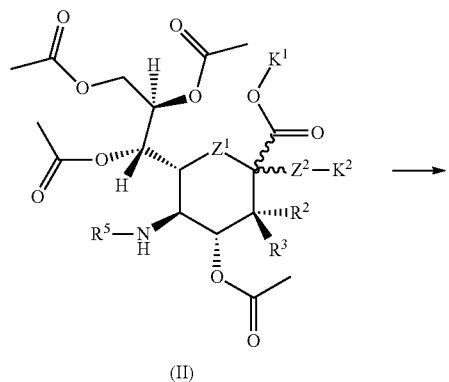

(II)

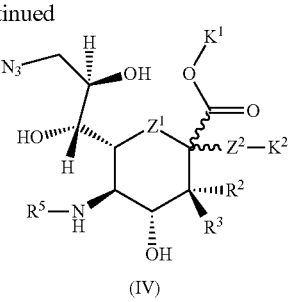

(IV)

$K^1$ is alkyl, more particularly $C_1$-$C_6$ alkyl
$K^2$ is any radical, e.g.: alkyl, alkenyl, alkynyl, aryl, protected aminoalkyl Compounds of the formula (IV) can be prepared by introducing an azido group from the compounds of the formula (III) (Scheme II). The introduction of azido groups is described for example in Angewandte Chemie 2005, 117, 5320-5374 and Chem Rev 1988, 88 (2), 297-368.

For example, compounds 4, 5, 96, 105, 112 and 118 were prepared.

Scheme III

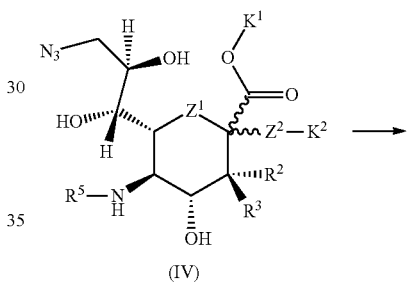

(III)

(IV)

$K^1$ is alkyl, more particularly $C_1$-$C_6$ alkyl
$K^2$ is e.g.: alkenyl, alkynyl, protected aminoalkyl Compounds of the formula (III) can be prepared by eliminating the O-acetyl groups from compounds of the formula (II) (Scheme I). Eliminations of O-acetyl groups are described for example in "Protecting Groups" Philip J Kocienski, 3rd Edition, Thieme 2005 and in "Carbohydrates: Best synthetic methods" H.M.I. Osborn, Academic Press 2003.

For example, compound 100 was prepared.

Scheme II

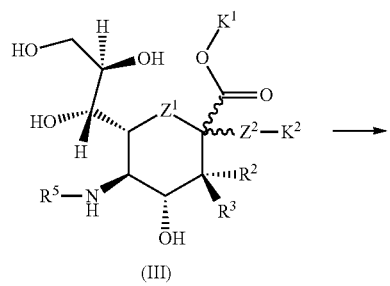

(III)

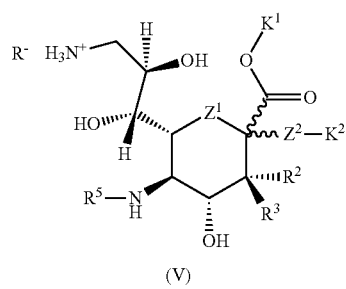

(V)

$K^1$ is alkyl, more particularly $C_1$-$C_6$ alkyl
$K^2$ is e.g.: alkyl, alkenyl, alkynyl, aryl, protected aminoalkyl Compounds of the formula V can be prepared by reducing the azido group from the compounds of the formula (IV) (Scheme III). The reduction of azido groups is described for example in Angewandte Chemie 2005, 117, 5320-5374 and Chem Rev 1988, 88 (2), 297-368.

For example, compounds 6, 7, 97, 107, 113 and 119 were prepared.

Scheme IV

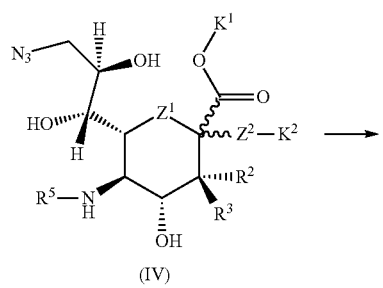

(IV)

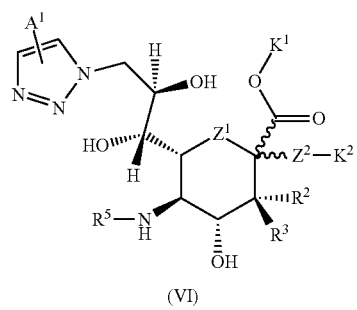

(VI)

$K^1$ is alkyl, more particularly $C_1$-$C_6$ alkyl
$K^2$ is e.g.: alkyl, alkenyl, alkynyl, aryl, protected aminoalkyl Compounds of the formula (VI) can be prepared by formation of a triazole ring from compounds of the formula (IV) (Scheme IV). Reactions of azides to triazoles are described for example in Angewandte Chemie 2005, 117, 5320-5374 and Medicinal Research Reviews 2008, 28, 278-308. For example, compound 93 was prepared.

Scheme V

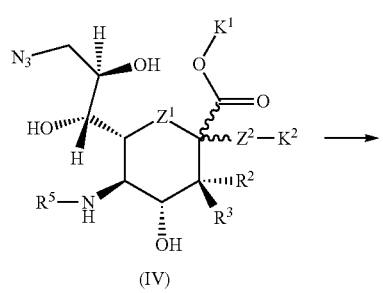

(IV)

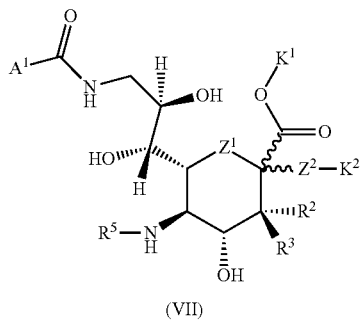

(VII)

$K^1$ is alkyl, more particularly $C_1$-$C_6$ alkyl
$K^2$ is e.g.: alkyl, alkenyl, alkynyl, aryl, protected aminoalkyl Compounds of the formula (VII) can be prepared by formation of an amide bond from compounds of the formula (IV) (Scheme V). Reactions of azides to amides are described for example in Angewandte Chemie 2005, 117, 5320-5374; Chem Rev 1988, 88 (2), 297-368; J. Am. Chem. Soc. 2003, 125, 7754-7755 and Carbohydrate Res. 2008, 343, 1636-1643.

For example, compound 9 was prepared.

Scheme VI

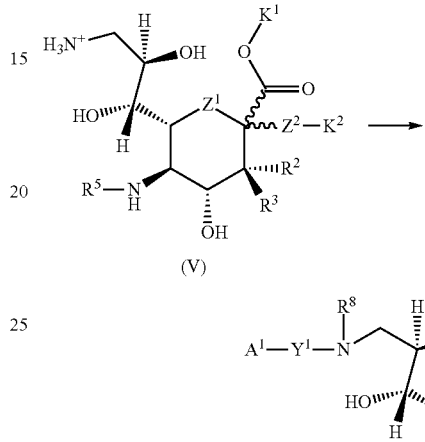

(V)

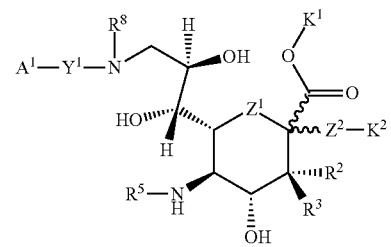

(VIII)

$K^1$ is alkyl, more particularly $C_1$-$C_6$ alkyl
$K^2$ is e.g.: alkyl, alkenyl, alkynyl, aryl, protected aminoalkyl Compounds of the formula (VIII) can also be prepared by formation of an amide bond from compounds of the formula (V) (Scheme VI). Reactions of amines to amides are described for example in Tetrahedron 2005, 61, 10827-10852.

For example, compounds 11, 42, 60, 99, 309, 419, 1049 and 1070 were prepared. Alternatively, a protecting group for the amino group can also be introduced into compound of the formula (V). Corresponding protecting groups are described for example in Chem. Rev. 2009, 109, 2455-2504 and in "Protecting Groups" Philip J Kocienski, 3rd Edition, Thieme 2005.

For example, compound 59 was prepared.

Scheme VII

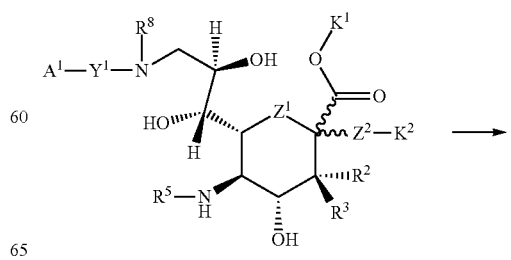

(VIII)

43
-continued

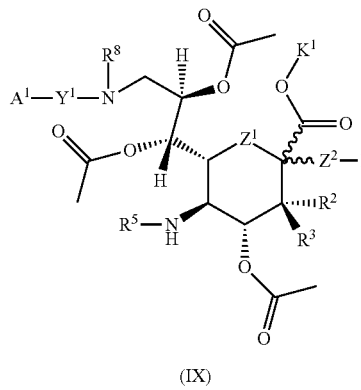

(IX)

K¹ is alkyl, more particularly C₁-C₆ alkyl
K² is any radical, e.g.: alkyl, alkenyl, alkynyl, aryl, protected aminoalkyl Compounds of the formula (IX) can be prepared by acetylation of the hydroxyl groups from compounds of the formula (VIII) (Scheme VII). Acetylations of hydroxyl groups are described for example in "Protecting Groups" Philip J. Kocienski, 3rd Edition, Thieme 2005 and in "Carbohydrates: Best synthetic methods" H.M.I. Osborn, Academic Press 2003.

For example, compounds 86 and 99 were prepared.

Scheme VIII

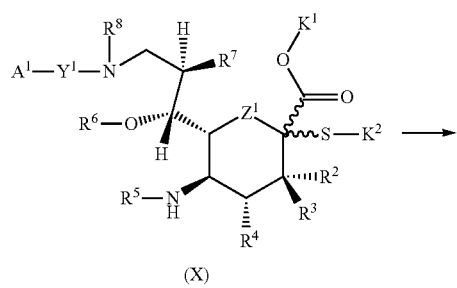

(X)

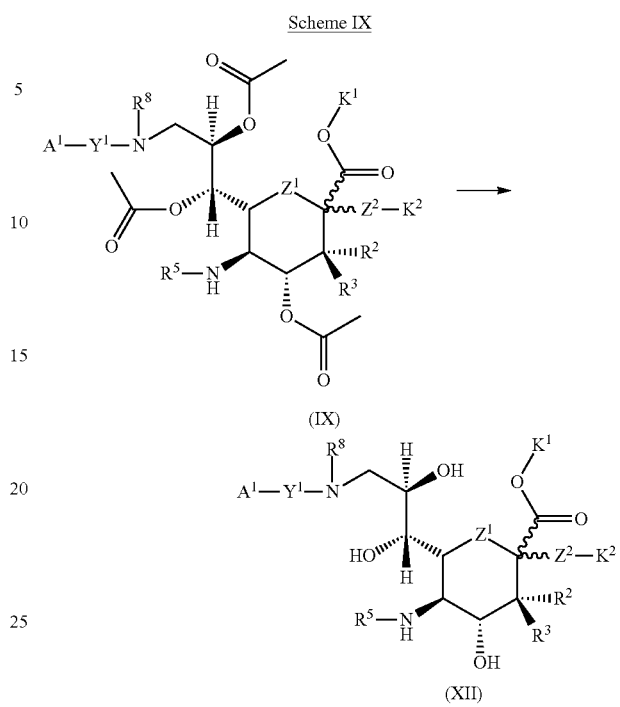

K¹ is alkyl, more particularly C₁-C₆ alkyl
K² is e.g.: alkyl, aryl
K³ is e.g. protected amine, carboxylic acid, alkene, alkyne Compounds of the formula (XI) can be prepared by reacting the compounds of the formula (X) with alcohols (Scheme VIII). Such reactions are described for example in "Carbohydrates: Best synthetic methods" H.M.I. Osborn, Academic Press 2003.

44

For example, compound 100 was prepared.

Compounds of the formula (XII) can be prepared by eliminating the O-acetyl groups from compounds of the formula (IX) (Scheme IX). The elimination of O-acetyl groups is described for example in "Protecting Groups" Philip J. Kocienski, 3rd Edition, Thieme 2005 and in "Carbohydrates: Best synthetic methods" H.M.I. Osborn, Academic Press 2003.

For example, compound 100 was prepared.

Compounds of the formula (XIV) can be prepared by deprotecting the amino group from the compound (XIII) (Scheme X). Protecting groups and reactions for deprotecting amino groups are described for example in "Protecting Groups" Philip J Kocienski, 3rd Edition, Thieme 2005 and Chem. Rev. 2009, 109, 2455-2504.

For example, compounds 101, 109 and 115 were prepared.

Scheme XI

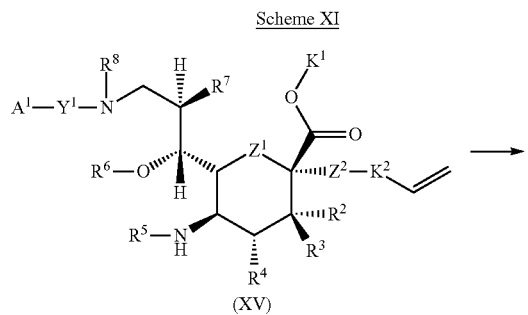

(XV)

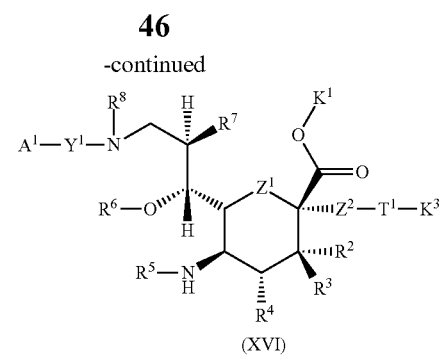

(XVI)

$K^1$ is alkyl, more particularly $C_1$-$C_6$ alkyl
$K^2$ is an alkanediyl, aryldiyl
$K^3$ is e.g.: protected amine, carboxyl, hydroxyl Compounds of the formula (XVI) can be prepared by reacting a terminal triple bond in compounds of the formula (XVII) with an azide (Scheme XII). The reaction of alkynes with azides is described for example in Angewandte Chemie 2005, 117, 5320-5374 and Medicinal Research Reviews 2008, 28, 278-308.

For example, compound 124 was prepared.

Scheme XIII

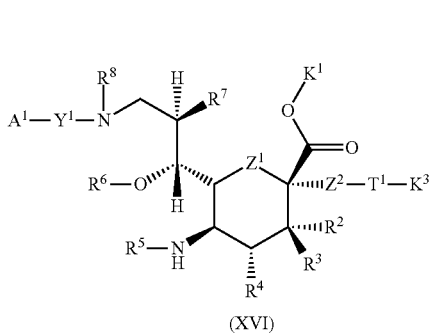

(XVI)

$K^1$ is alkyl or cation, more particularly $C_1$-$C_6$ alkyl, Li, Na or K
$K^2$ is alkanediyl, aryldiyl
$K^3$ is e.g.: amino, carboxyl, hydroxyl Compounds of the formula (XVI) can be prepared from compounds (XV) by reaction of the terminal double bond with a reactive group (Scheme XI). Reactions of double bond are described for example in J. Org. Chem. 2000, 65, 958-963.

For example, compounds 10, 11, 18, 50, 56, 60, 94, 121, 138 and 144 were prepared.

Scheme XII

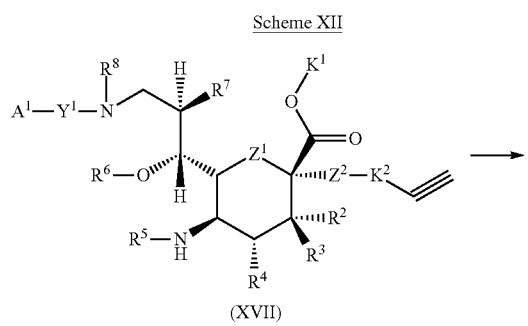

(XVII)

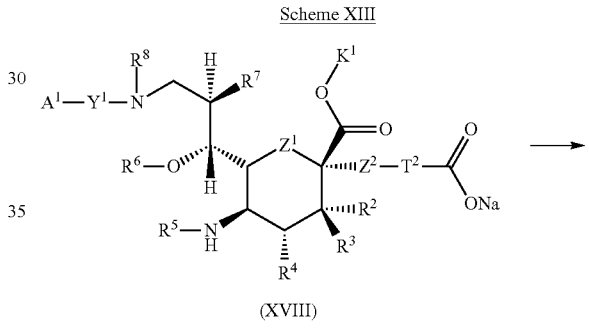

(XVIII)

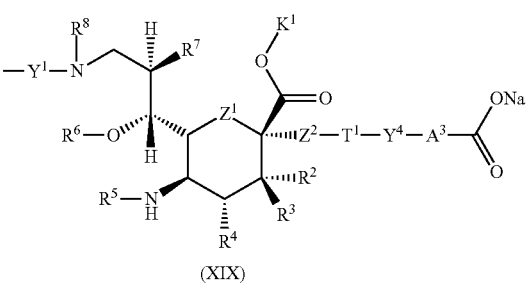

(XIX)

$K^1$ is alkyl, more particularly $C_1$-$C_6$ alkyl

Compounds of the formula (XIX) can be prepared by reacting the carboxyl group in compounds of the formula (XVIII) with an amine (Scheme XIII). Reactions of carboxylic acids with amines are described for example in Tetrahedron 2005, 61, 10827-10852 and Chem. Eur. J. 2009, 15, 9404-9416.

For example, compound 53 was prepared.

Scheme XIV

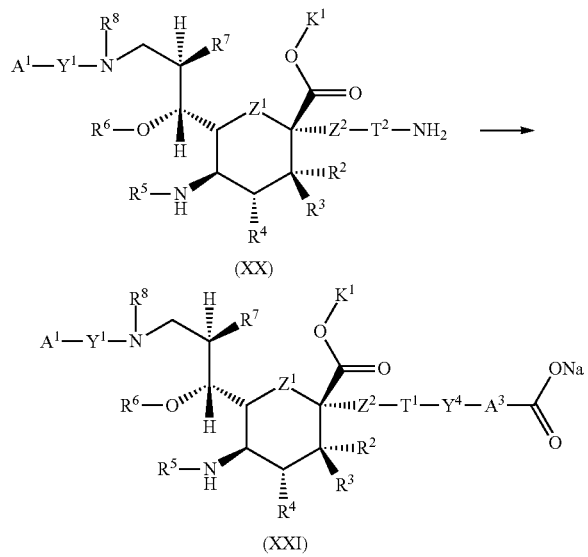

$K^1$ is alkyl, more particularly $C_1$-$C_6$ alkyl

Compounds of the formula (XXI) can be prepared by reacting the amine in compounds of the formula (XX) with a reactive group (Scheme XIV). Reactions of reactive groups to with amines are described for example in Tetrahedron 2005, 61, 10827-10852 and Chem. Eur. J. 2009, 15, 9404-9416.

For example, compound 91 was prepared.

The preparation of dimeric starting compounds is indicated for example in Schemes XV and XVI.

Scheme XV

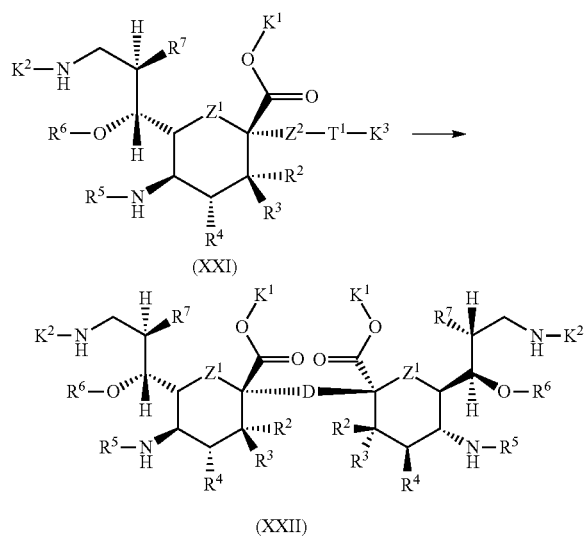

$K^1$ is alkyl, more particularly $C_1$-$C_6$ alkyl
$K^2$ is a protecting group, more particularly Fmoc
$K^3$ is amino or carboxyl Compounds of the formula (XXII) can be prepared by reacting a diamine/dicarboxylic acid with the carboxyl/amino groups of compounds of the formula (XXI), to form two amide bonds (Scheme XV). Reactions for the formation of amide bonds are described for example in Tetrahedron 2005, 61, 10827-10852 and Chem. Eur. J. 2009, 15, 9404-9416.

For example, compounds 61 and 126 were prepared.

Scheme XVI

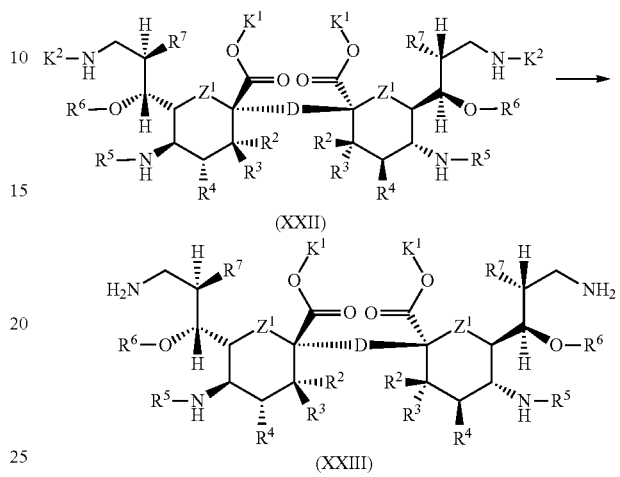

$K^1$ is alkyl, more particularly $C_1$-$C_6$ alkyl
$K^2$ is a protecting group
$K^3$ is alkyl or a cation, more particularly $C_1$-$C_6$ alkyl, Li or Na Compounds of the formula (XXIII) can be prepared by partial or complete elimination of the protecting groups from compounds of the formula (XXII) (Scheme XVI). Protecting groups and their elimination are described for example in "Protecting Groups" Philip J Kocienski, 3rd Edition, Thieme 2005 and Chem. Rev. 2009, 109, 2455-2504.

For example, compound 130 was prepared.

The preparation of sialic acid derivatives of the formula (I) is described for example in Schemes XVII to XX.

Scheme XVII

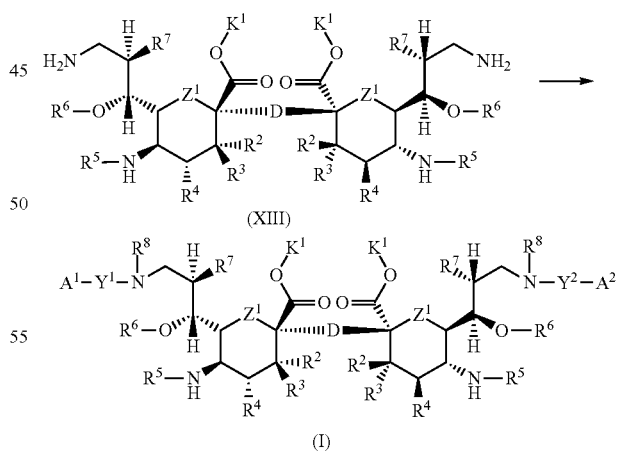

$K^1$ is alkyl or cation, more particularly $C_1$-$C_6$ alkyl, Na or Li

Compounds of the formula (I) can be prepared by reacting the amino groups of compounds of the formula (XXIII) with reactive compounds (Scheme XVII). Reactions of amines with reactive groups are described for example in Tetrahedron 2005, 61, 10827-10852 and Chem. Eur. J. 2009, 15, 9404-

9416. Alternatively, the compounds can also be prepared through the use of coupling reagents. Suitable coupling reagents and their reactions are described for example in Tetrahedron 2005, 61, 10827-10852 and Chem. Eur. J. 2009, 15, 9404-9416. The elimination of protecting groups that may be subsequently necessary is described for example in "Protecting Groups" Philip J. Kocienski, 3rd Edition, Thieme 2005 and Chem. Rev. 2009, 109, 2455-2504.

For example, compounds 62 to 73, 84, 85, 110, 116, 127, 128, 129, 131, 134, 139 and 145 were prepared.

Scheme XVIII

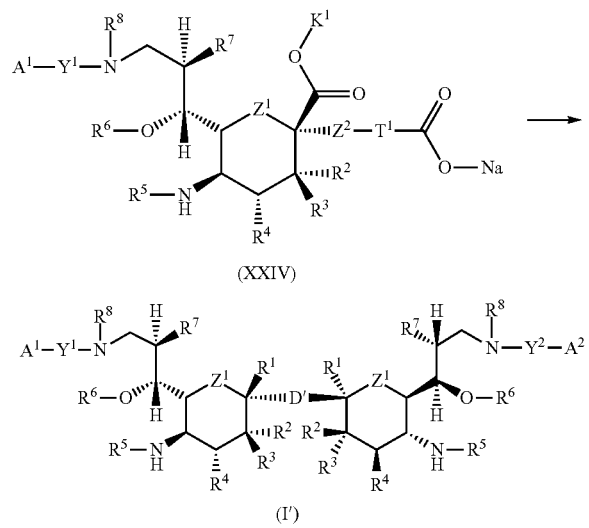

$K^1$ is alkyl, more particularly $C_1$-$C_6$ alkyl $D' = Z^2 - T^1 - C(O)NR^x - A^3 - NR^x - C(O) - T^2 - Z^2$ Compounds of the formula (I') can be prepared by reacting the carboxyl group in compounds of the formula (XXIV) with diamines (Scheme XVIII). The reaction may be implemented through the use of coupling reagents or activation of the carboxyl group. Coupling reagents and the activation of carboxylic acids are described for example in Tetrahedron 2005, 61, 10827-10852 and Chem. Eur. J. 2009, 15, 9404-9416. The elimination of protecting groups that may be subsequently necessary is described for example in "Protecting Groups" Philip J. Kocienski, 3rd Edition, Thieme 2005 and Chem. Rev. 2009, 109, 2455-2504.

For example, compounds 39 to 45 and 90 were prepared.

Scheme XIX

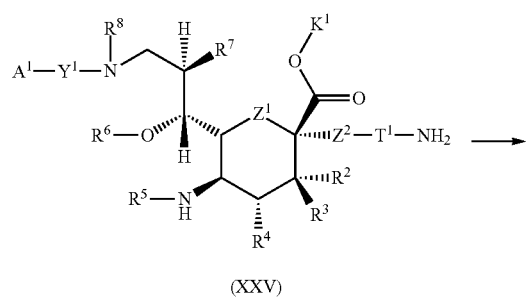

(XXV)

-continued

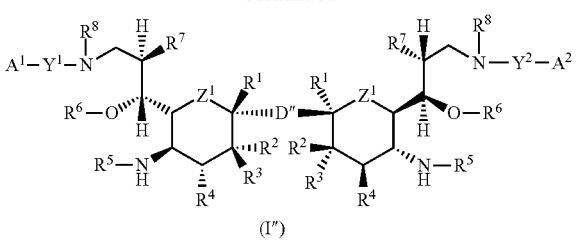

(I'')

$K^1$ is alkyl, more particularly methyl $D'' = Z^2 - T^1 - Y^4 - A^3 - Y^5 - T^2 - Z^2$ and $Y^6 = NR^x$, $-NR^x - C(O)\sim$, $-NR^x - C(O) - NR^x\sim$ or $NR^x - S(O)_2\sim$ Compounds of the formula (I'') can be prepared by reacting the amino group in compounds of the formula (XXV) with divalent reactive compounds (Scheme XIX). Reactions of amines with reactive compounds are described for example in Tetrahedron 2005, 61, 10827-10852 and Chem. Eur. J. 2009, 15, 9404-9416. The reaction can also be carried out through the use of coupling reagents or through in situ activations of a divalent compound. Coupling reagents and their reactions are described in Tetrahedron 2005, 61, 10827-10852 and Chem. Eur. J. 2009, 15, 9404-9416. The elimination of protecting groups that may be subsequently necessary is described for example in "Protecting Groups" Philip J. Kocienski, 3rd Edition, Thieme 2005 and Chem. Rev. 2009, 109, 2455-2504.

For example, compounds 19 to 32, 49, 51, 52, 57, 58, 95, 102, 122, 125, 140 and 149 were prepared.

Scheme XX

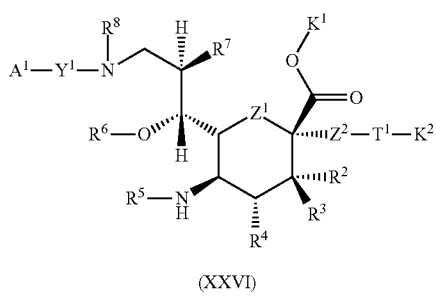

(XXVI)

+

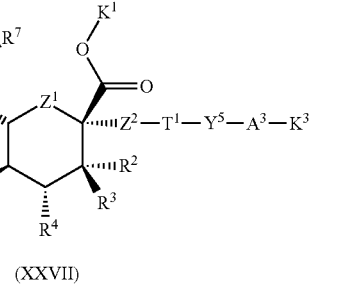

(XXVII)

-continued

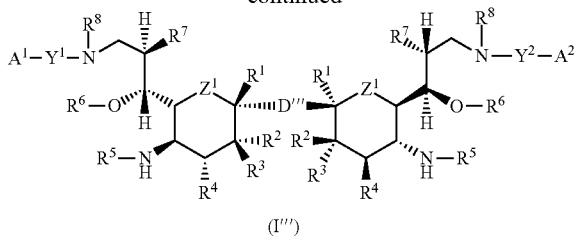

(I''')

$K^1$ is alkyl, more particularly $C_1$-$C_6$ alkyl
$K^2$ is an amino group/carboxyl group
$K^3$ is a carboxyl group/amino group
$D''' = Z^2 — T^1 — Y^7 — A^3 — Y^5 — T^2 — Z^2$ and
$Y^7$ is $—NR^x—C(O)$~ or $—C(O)—NR^x$~

Possibly asymmetric compounds of the formula (I'') can be prepared by reacting the amino/carboxyl group in compounds of the formula (XXVI) with the amino/carboxyl group of compounds of the formula (XXVII) (Scheme XX). The reaction may take place through the use of coupling reagents or by activation of the carboxylic acid. Amide formations, coupling reagents and activations are described for example in Tetrahedron 2005, 61, 10827-10852 and Chem. Eur. J. 2009, 15, 9404-9416. Any subsequent possible elimination of protecting groups is described for example in "Protecting Groups" Philip J. Kocienski, 3rd Edition, Thieme 2005 and Chem. Rev. 2009, 109, 2455-2504.

For example, compounds 22, 54 and 103 were prepared.

The sialic acid derivatives of the formula (I) are suitable as pharmacologically active compounds and active ingredients for medicament preparations. They act as Siglec ligands, more particularly of Siglec-2 (CD22), Siglec-4 (MAG), Siglec-7, for the regulation of the immune system, more particularly as an auxiliary in vaccinations, and also for the treatment of diseases whose course or activity can be influenced by the Siglec ligands, more particularly allergies, autoimmune diseases, chronic inflammations, paraplegia, multiple sclerosis, cancer, viral diseases, for example AIDS, and also in bacterial diseases, for example streptococci, parasitic diseases, for example Chagas disease, diseases in which the immune response is disrupted in the context of B cell activation, such as Common Variable Immunodeficiency (CVID) and IgA deficiency, in diseases of the haematopoietic organs and of the blood, and also in cancer, for example lymphomas and myelomas. Preferred indications are allergies, autoimmune diseases and CVID.

Treatment in the sense of the invention denotes a therapeutic treatment, both for curing and also for the alleviation of symptoms, and also a preventive treatment.

The sialic acid derivatives may be used in combination with other pharmacologically active substances, more particularly those which boost the activity of the compounds of the invention.

The invention also provides a method for treating a Siglec-mediated disease, more particularly from the group of allergies, autoimmune diseases, chronic inflammations, paraplegia, multiple sclerosis, cancer, viral diseases, for examples AIDS, diseases in which the immune response is disrupted in the context of B cell activation, such as Common Viable Immunodeficiency (CVID) and IgA deficiency, by administering a person affected by the disease a preferably therapeutically effective amount of a sialic acid derivative of the formula (I).

Further provided by the invention is a sialic acid derivative of the formula (I) or a pharmacologically tolerated salt thereof as medicament, more particularly for the treatment of Siglec-mediated diseases, such as those described above.

The invention provides, furthermore, a sialic acid derivative of the formula (I) or a pharmacologically tolerated salt thereof for use in a method for treating Siglec-mediated diseases, more particularly those described above.

Additionally provided by the invention is a sialic acid derivative of the formula (I) for use in the production of a medicament for the treatment of Siglec-mediated diseases, more particularly those described above.

Likewise provided by the invention is a pharmaceutical preparation (i.e. medicament) comprising at least one sialic acid derivative of the formula (I), or a pharmacologically tolerated salt thereof, and a pharmacologically tolerated carrier.

The dose that is necessary to achieve a corresponding activity in treatment or prophylaxis is commonly dependent on the compound to be administered, the patient, the nature and severity of the disease or condition, and the nature and frequency of administration, and is within the discretion of the physician to be treated. In the case of intravenous administration, the dose may appropriately be in the range from 0.1 to 1000 mg, preferably 0.5 to 500 mg, and for oral administration in the range from 1 to 1000 mg, preferably 10 to 500 mg, in each case one or more times daily. For this purpose, the compounds of the formula I according to the invention, optionally in combination with other active substances, may be processed together with one or more inert customary excipients and/or diluents, as for example with corn starch, lactose, cane sugar, microcrystalline cellulose, manganese stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into customary pharmaceutical preparations such as tablets, film tablets, capsules, powders, solutions, suspensions or suppositories.

The sialic acid derivatives (I) according to the invention may be administered by any conventional method, including orally and parentally, by means of subcutaneous or intramuscular injections, for example.

The sialic acid derivatives (I) may also be used for purposes other than those specified, for example as diagnostic agents, as for example in methods for determining the activity of Siglec ligands, as biochemical probes, or as intermediates for the preparation of further compounds, more particularly of pharmacologically active compounds.

The invention is illustrated, but not restricted, by the examples.
EXAMPLES
A. Synthesis Examples are Represented in Schemes 1 to 18
Scheme 1
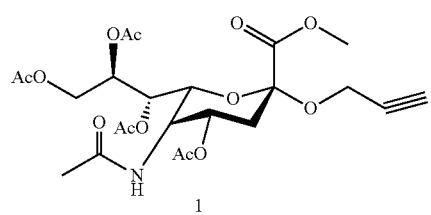
1
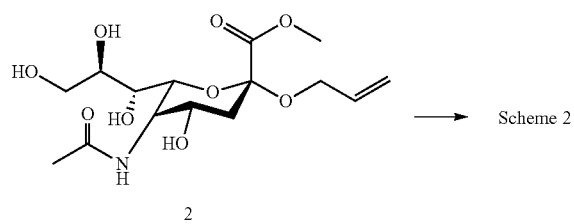
2 → Scheme 2
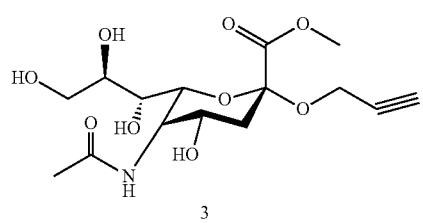
3
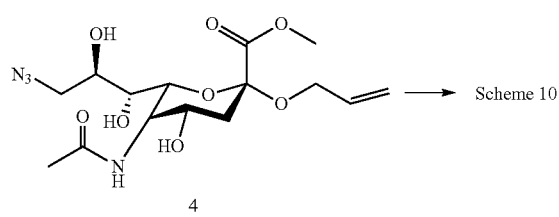
4 → Scheme 10
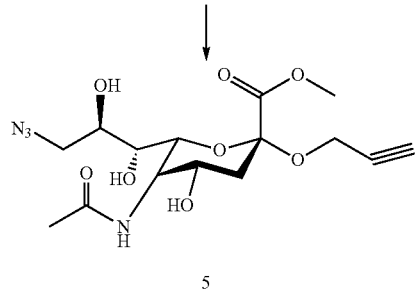
5
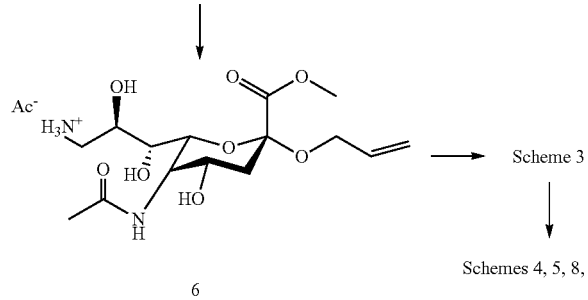
6 → Scheme 3
→ Schemes 4, 5, 8, 9
→ Scheme 6, 7
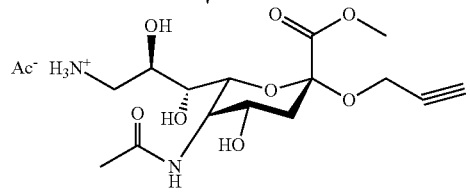
7
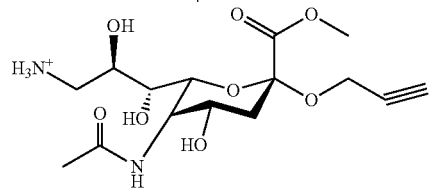
135
↓ Scheme 14
↓ Scheme 16

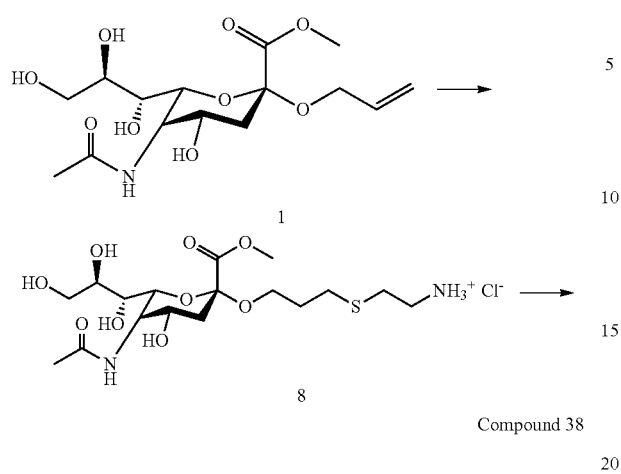

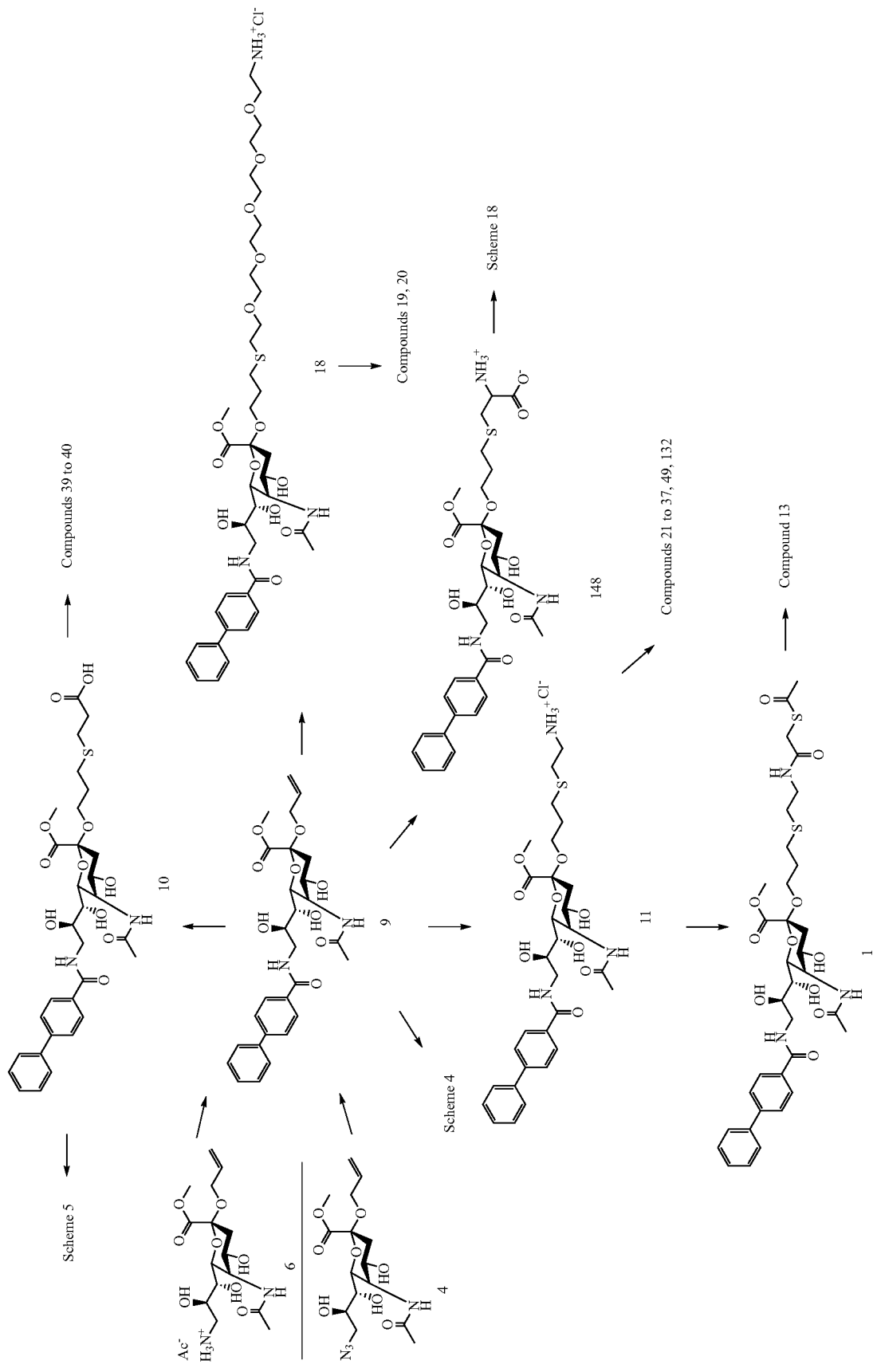

Scheme 4
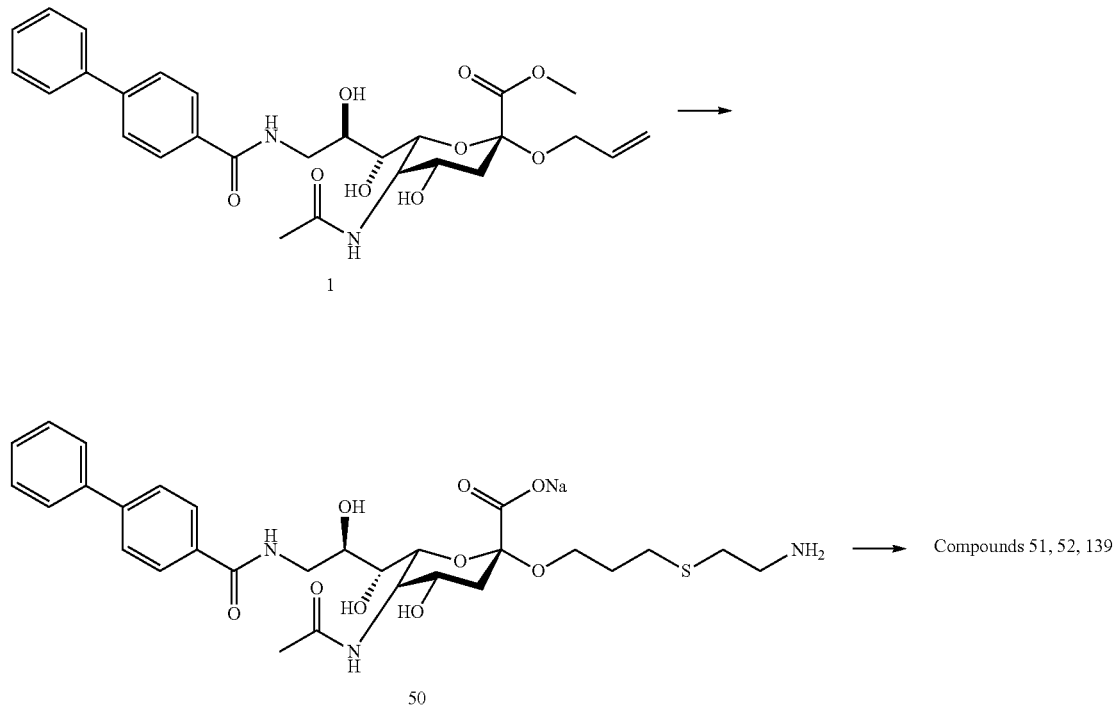
Scheme 5
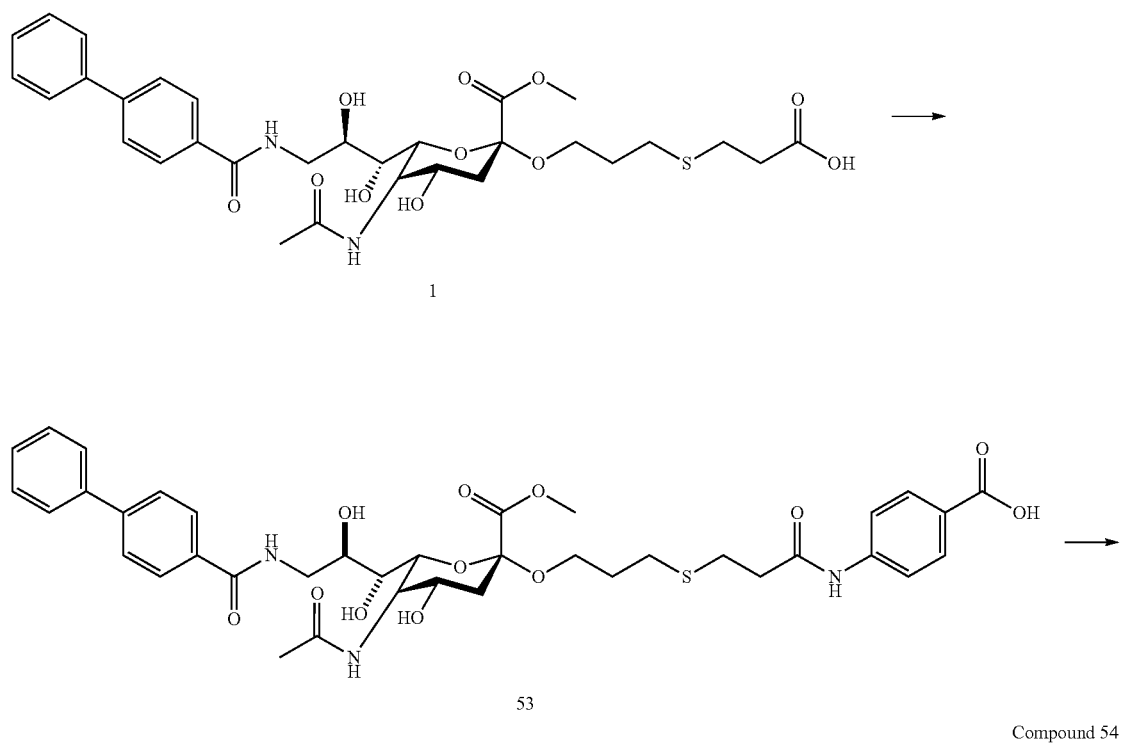

Scheme 6
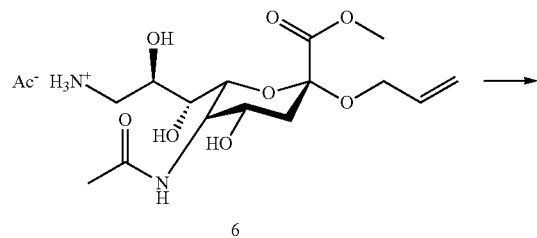
6
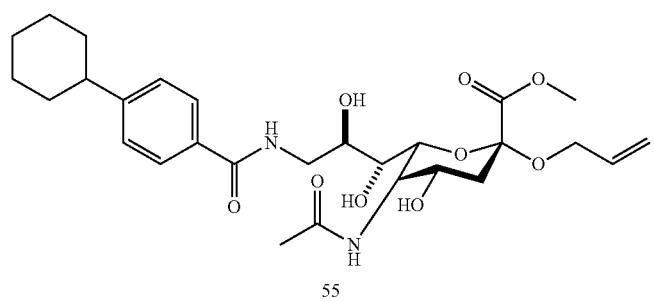
55
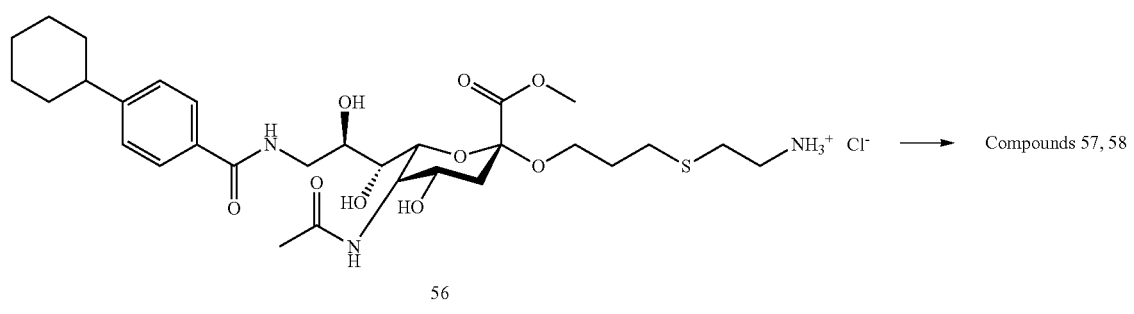
56 → Compounds 57, 58

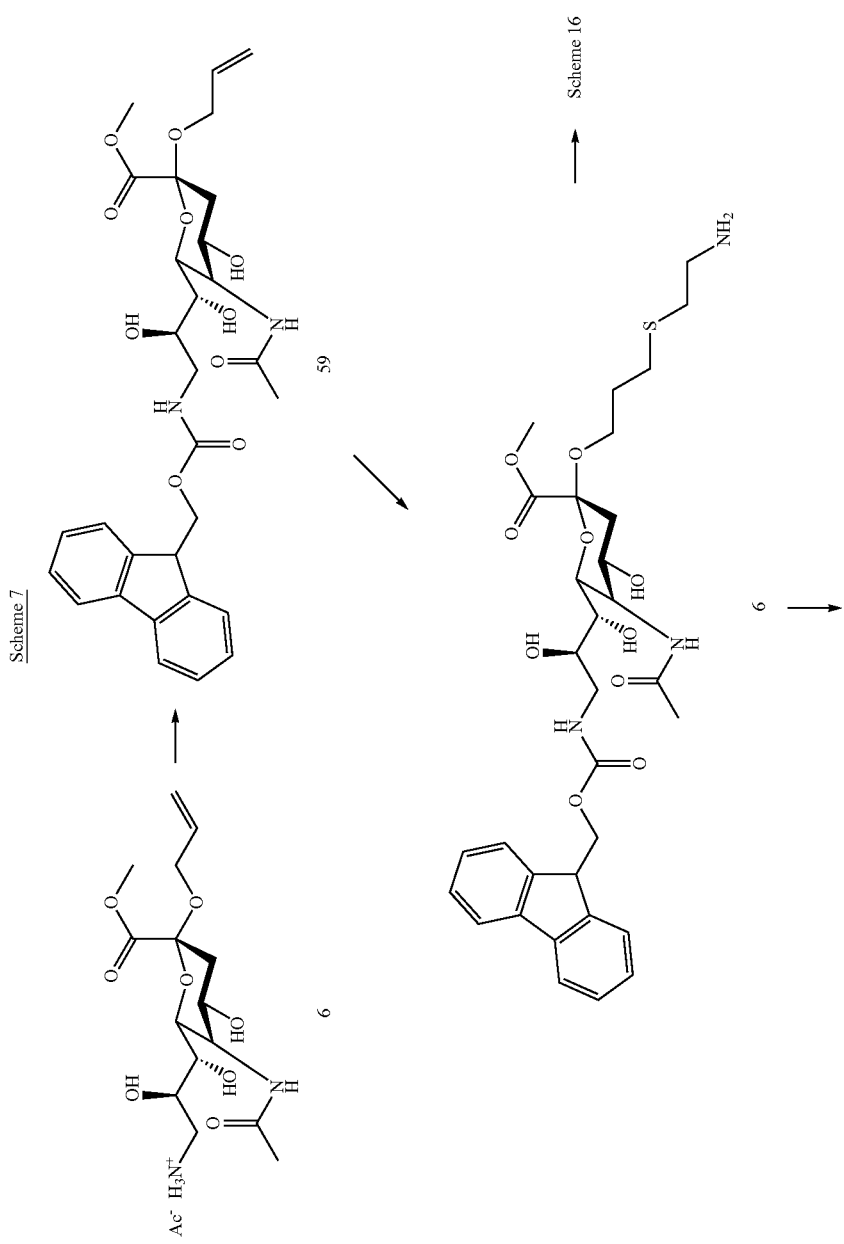

-continued
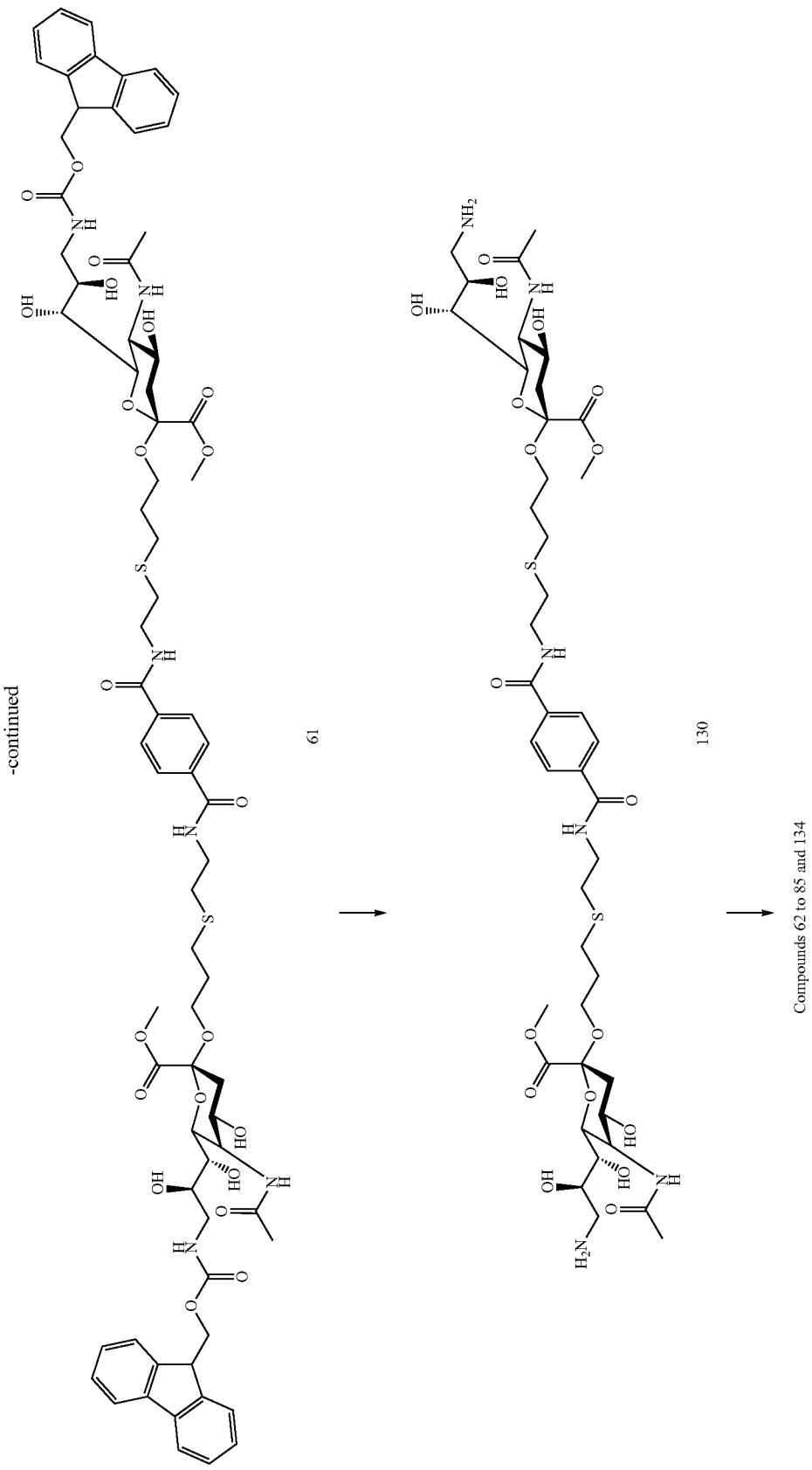
Compounds 62 to 85 and 134

Scheme 8
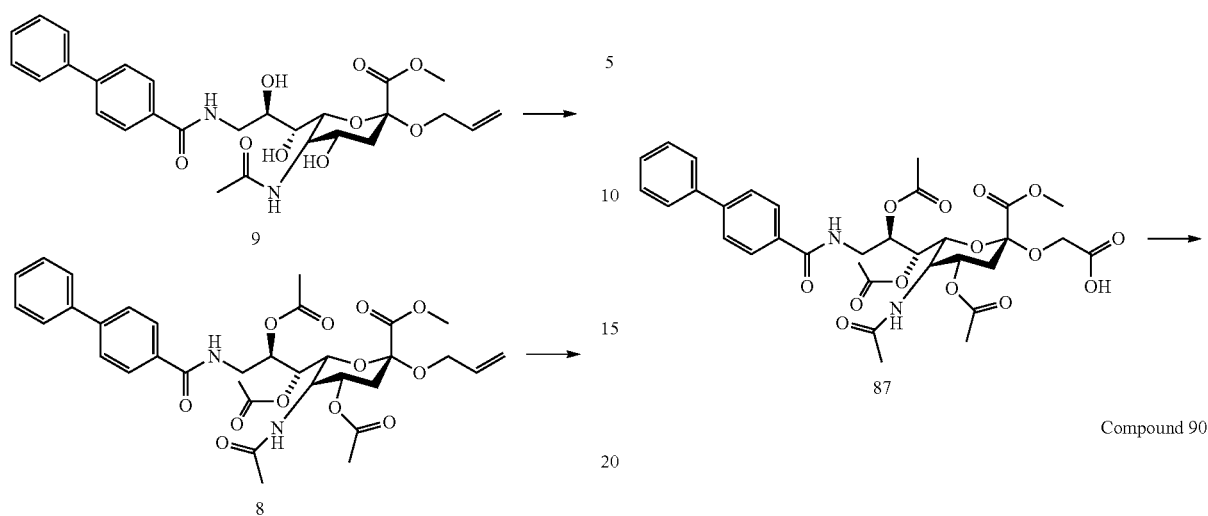
Scheme 9
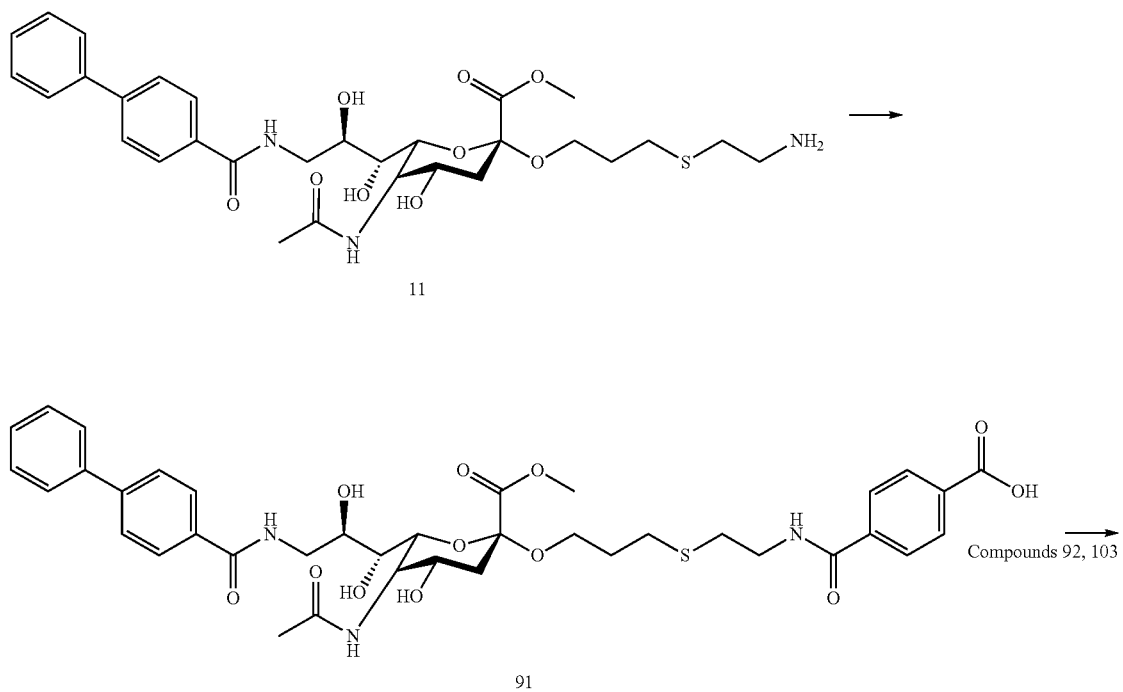
Scheme 10
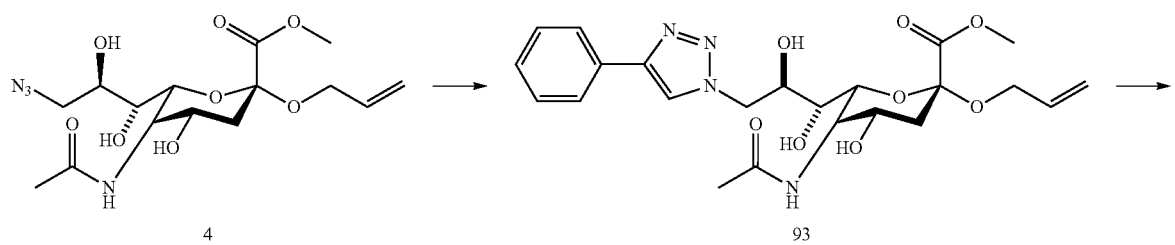

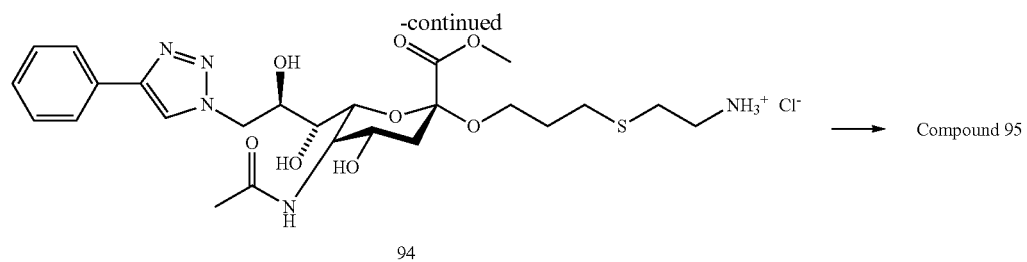

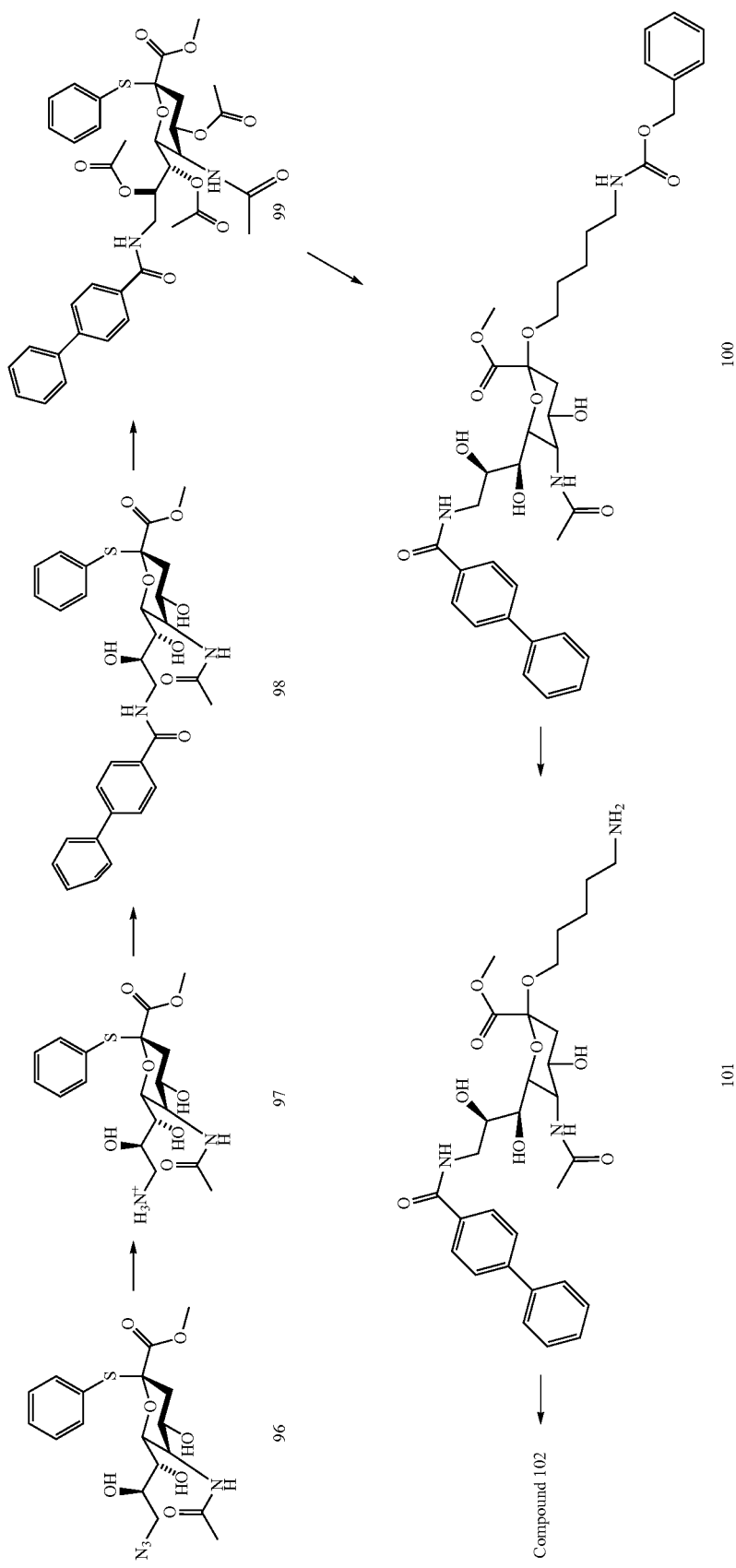

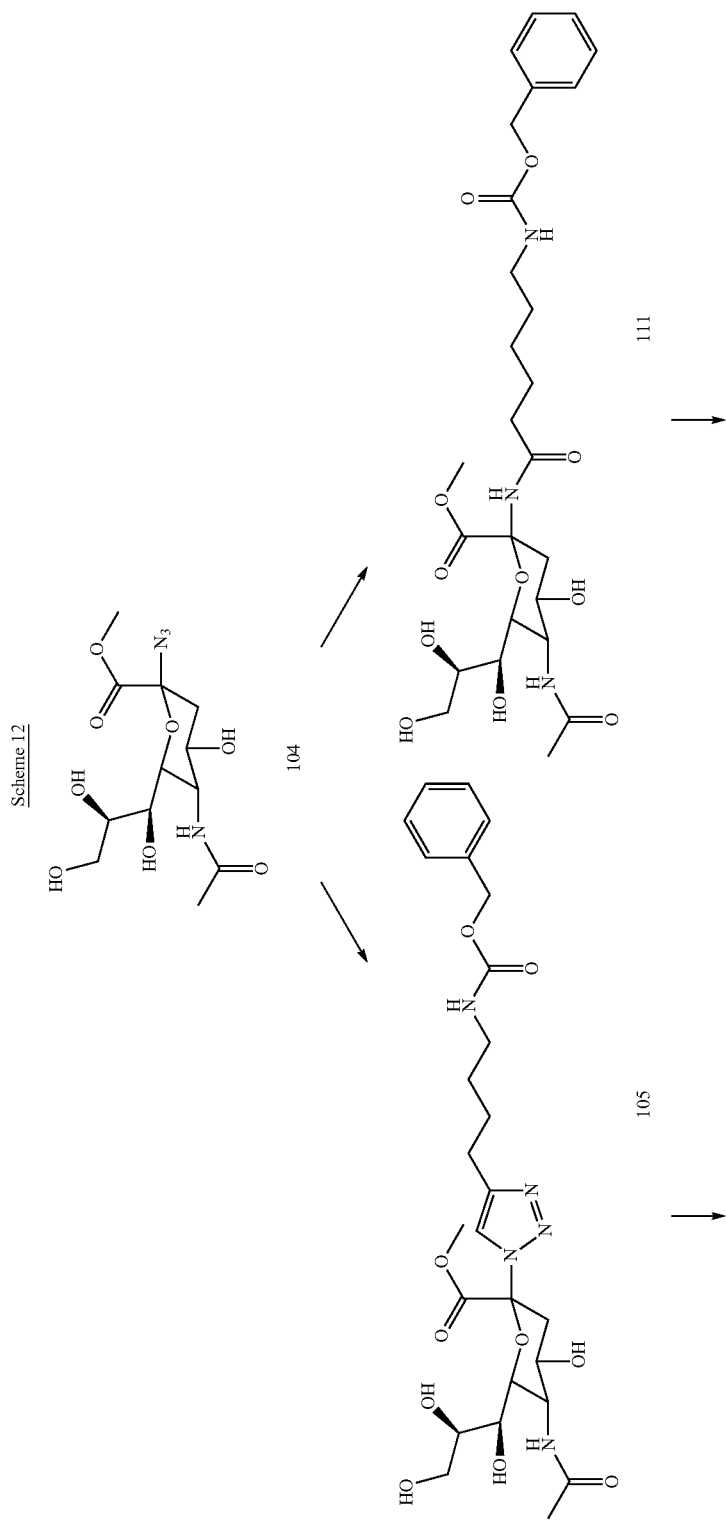
Scheme 12

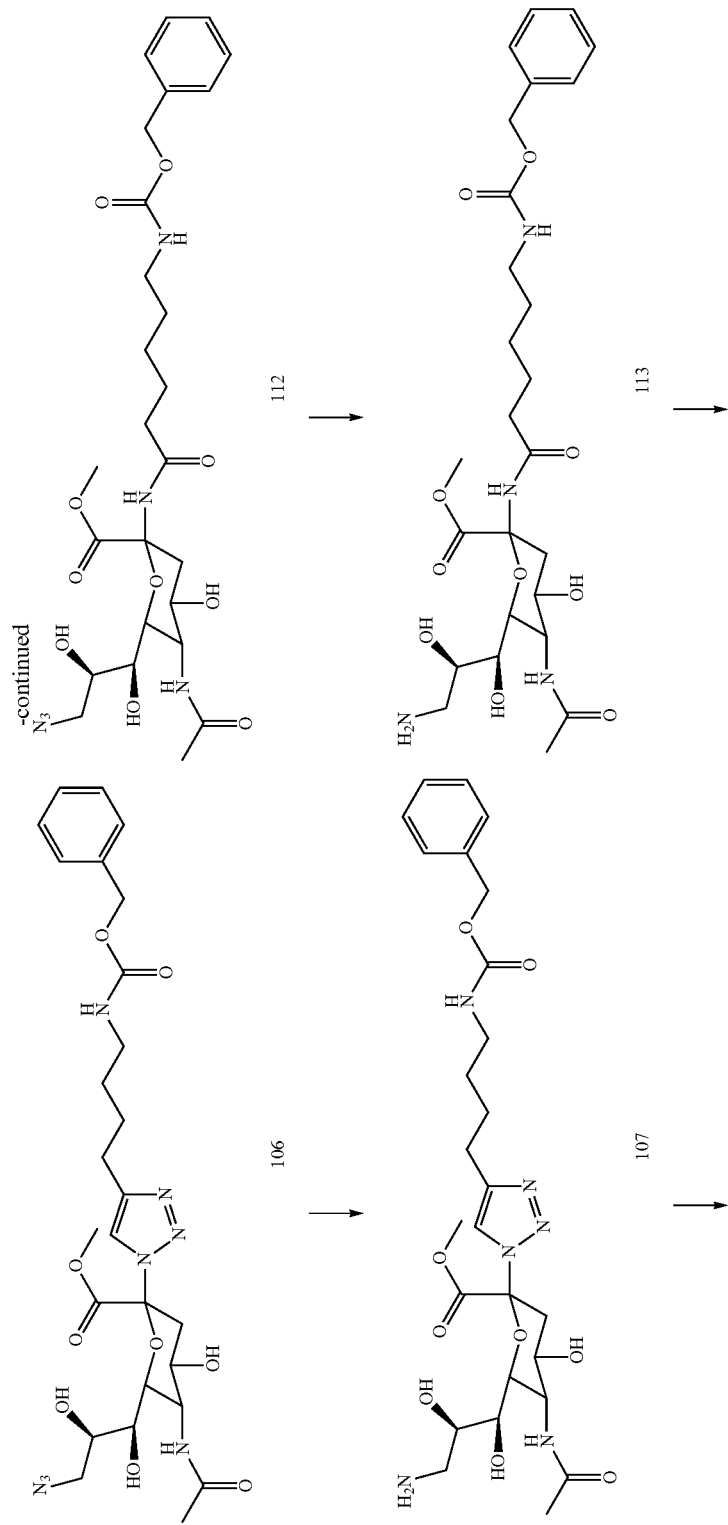

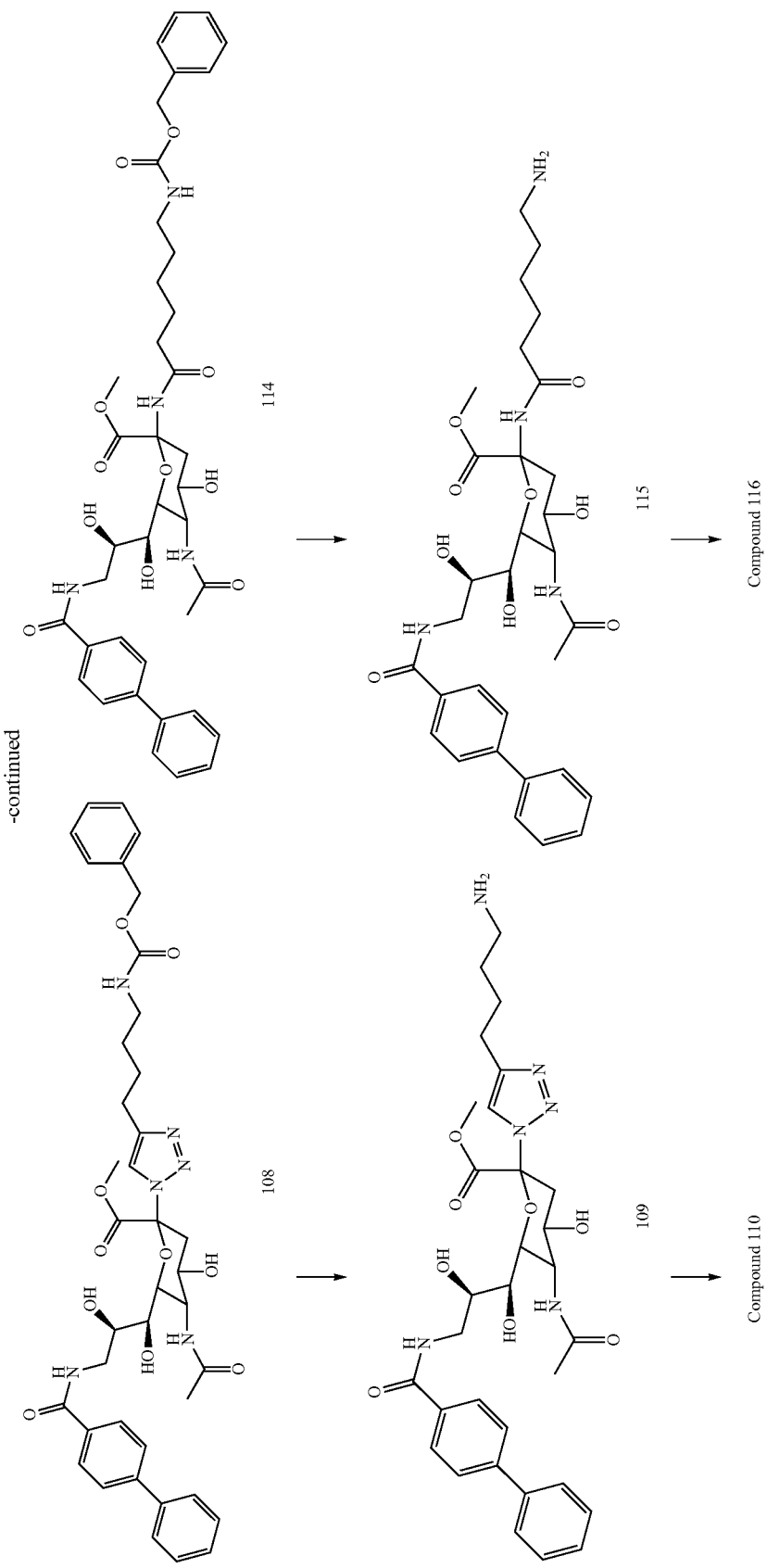

Scheme 13
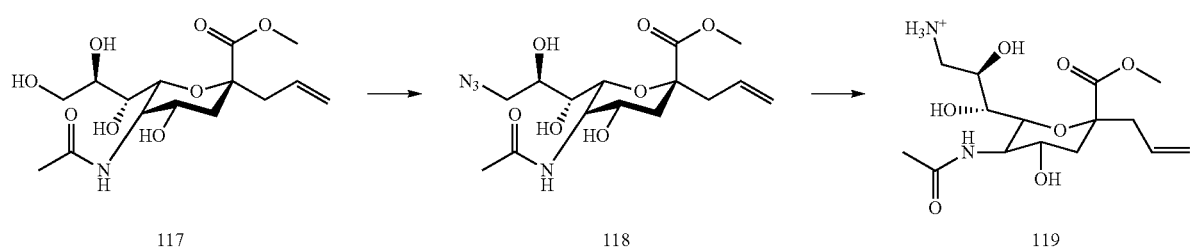
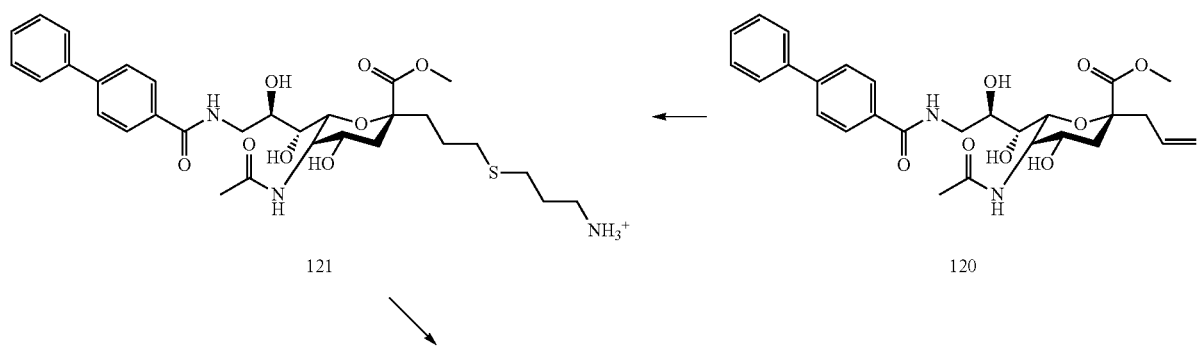
Compound 122
Scheme 14
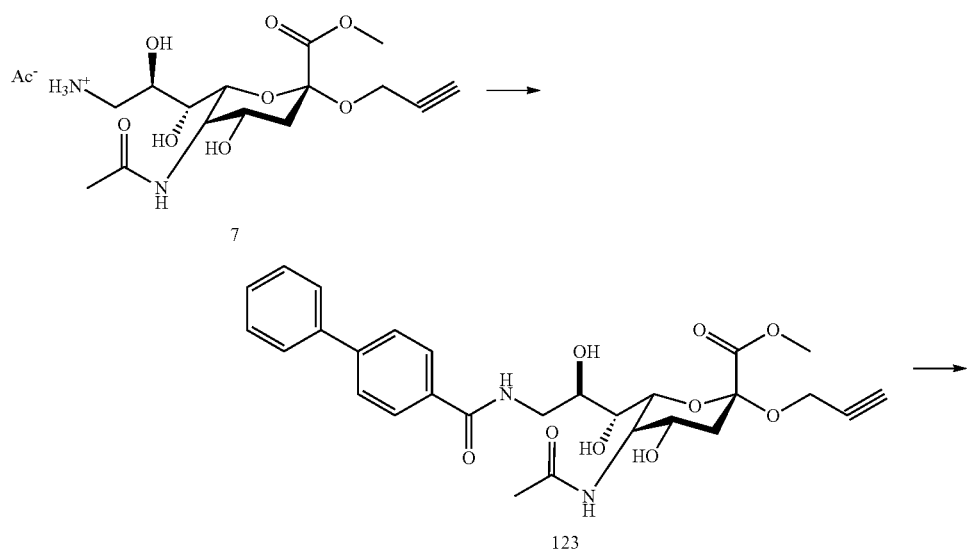

-continued
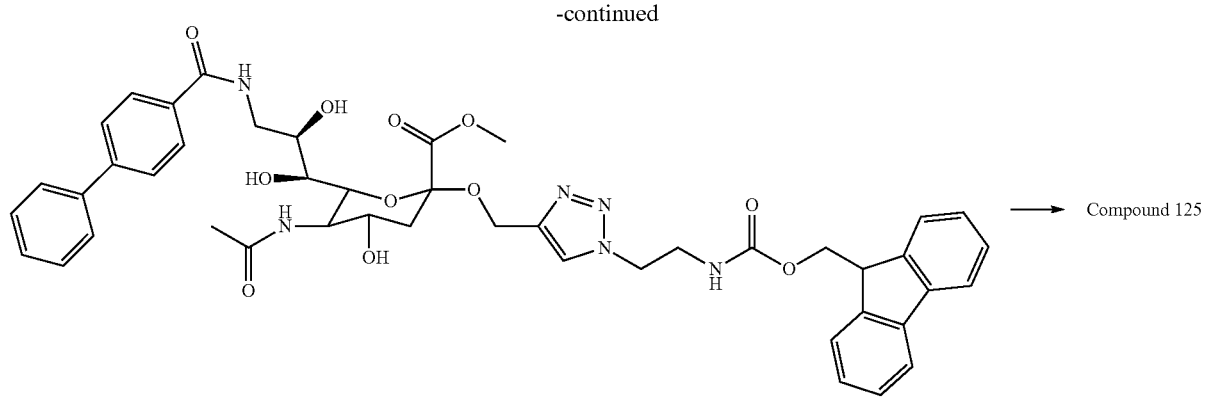
124

Scheme 15
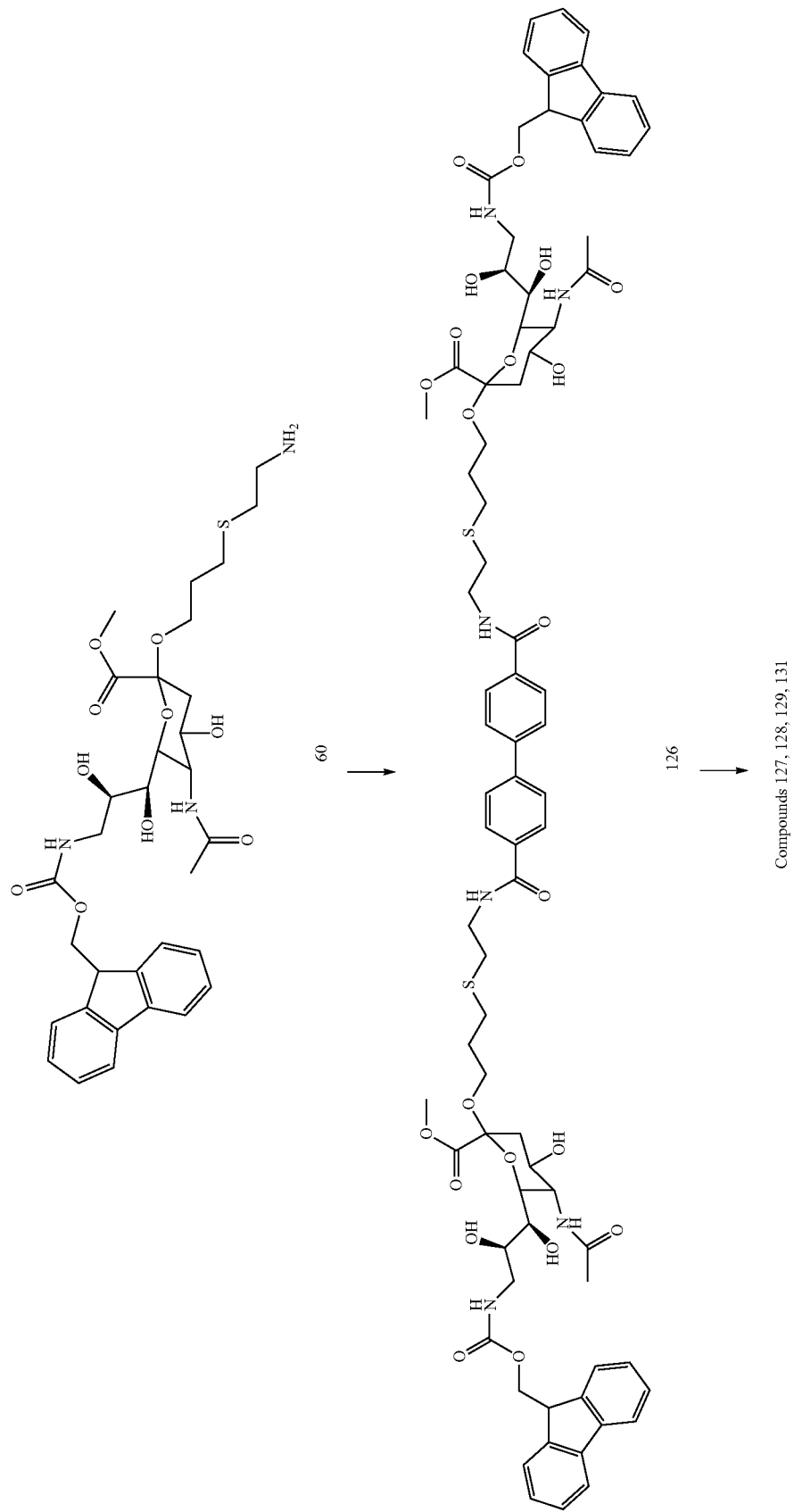

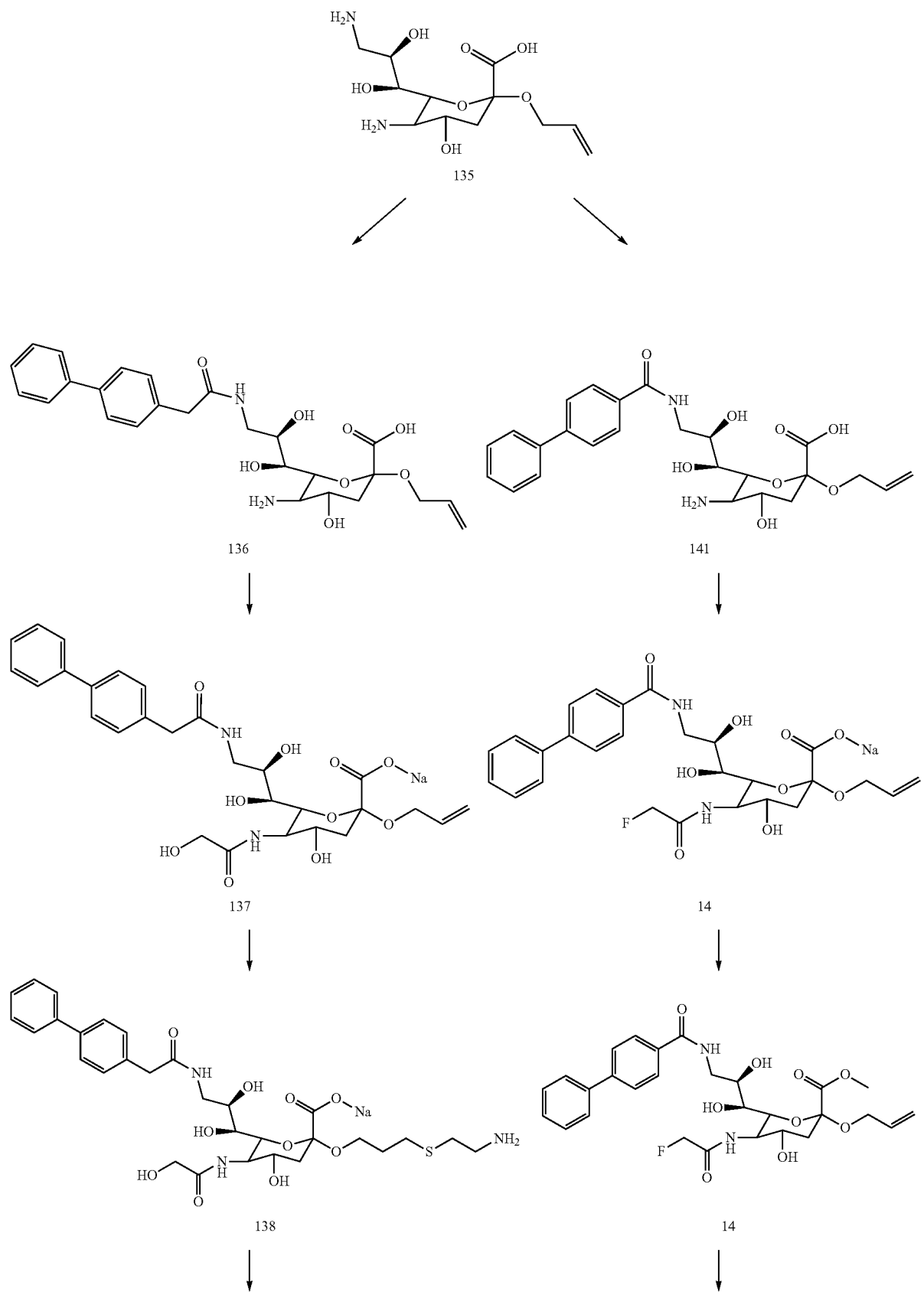

-continued
Compound 139
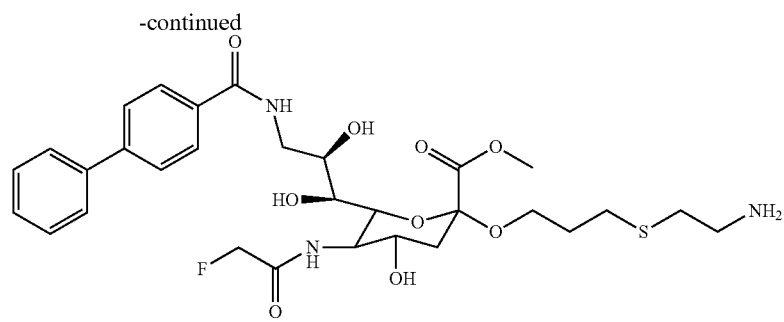
Compound 145

Scheme 17
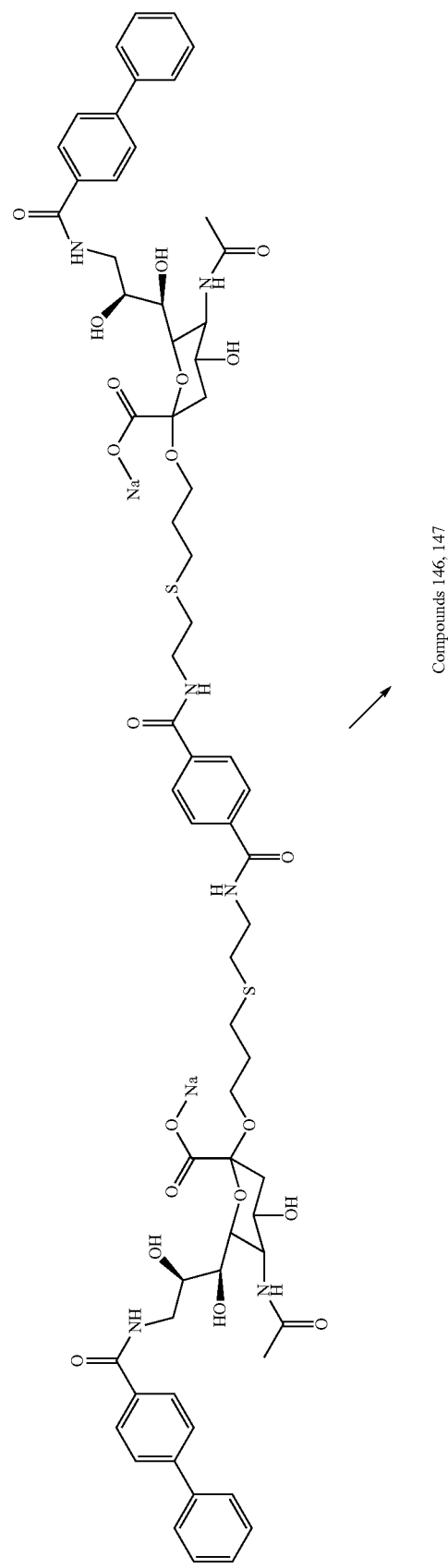

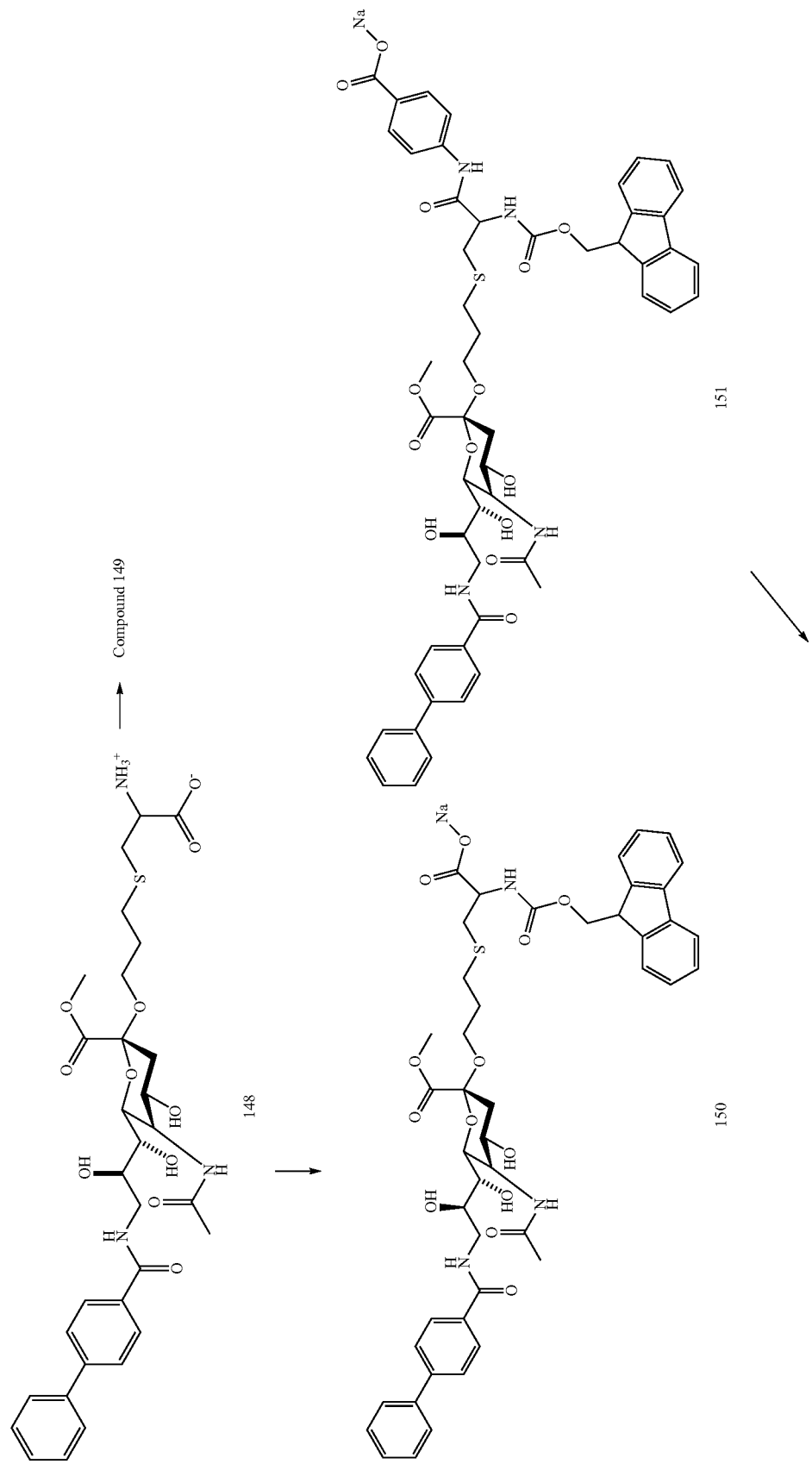

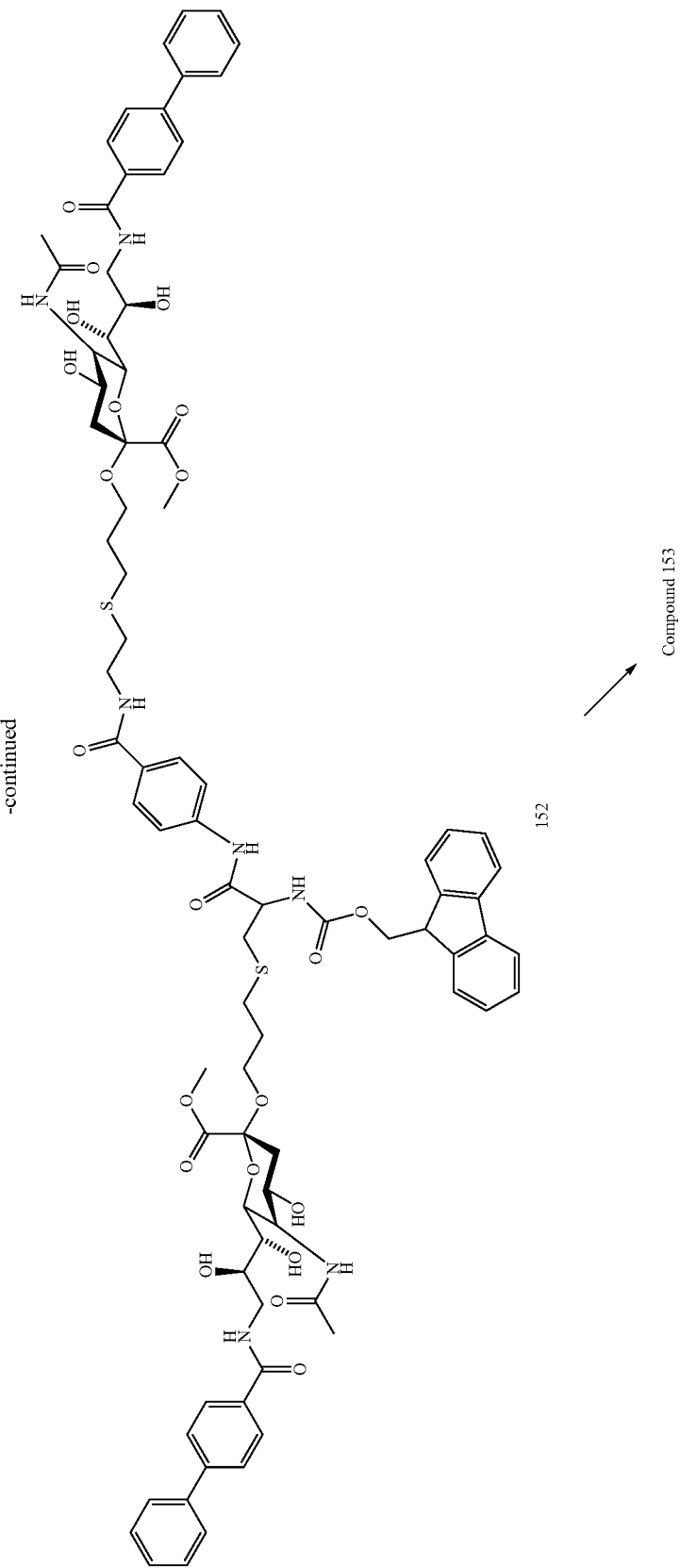
152
Compound 153

The compounds indicated were obtained as described below:

All compounds used but not described are available commercially or were prepared in accordance with known literature procedures.

For purifications with silica gel, silica gel Si60 43-60 μm was used. Approximately 100 g of silica gel was utilized per gram of substance.

For purifications on RP-18 silica gel (YMC CO LTD., YMC ODS-AQ), the gel was suspended in methanol, filled into a column and prewashed with water, and the substance was applied as a solution or suspension with water. The column volume was about 5 cm in height and 1 cm in diameter. The solvent was forced through the column at low pressure, generated by a manually operated pressure ball. Eluents are indicated in parentheses. Gradients are expressed with the symbol >>, e.g.: "(H2O>>MeOH)" means that a gradient from water to methanol was utilized.

Solvents were removed fully by means of a vacuum rotary evaporator under reduced pressure with a bath temperature of 40° C. In the syntheses below, this operation is identified as "removal of the solvent" or "concentration".

Lyophilization took place, unless otherwise stated, from water or from a water/dioxane mixture.

Photochemical reactions were carried out using the #RPR-100 photochemical reactor from the The Southern New England Ultraviolet Company.

The reactions and substances were monitored by thin-layer chromatography. This was done using silica gel-coated aluminium plates with fluorescence indicator (Merck TLC Silica gel 60 $F_{254}$). Substances were detected under UV light at 366 and 254 nm. The chromatograms were subsequently sprayed with dilute sulphuric acid and heated, in order to detect the carbohydrates Amines, for detection, were sprayed with ninhydrin solution and heated, thiols with nitroprusside solution. Details and further detection methods are elucidated in "Anfärbereagenzien für Dünnschicht- and Papierchromatographie" Merck, 1970.

All substances were tested by mass spectrometry.
Maldi-TOF: Matrix: 2,5-dihydroxybenzoic acid Method: dried droplet Instrument: Bruker BIFLEX III
ESI: Bruker ApexQe hybrid 9.4 T FT-ICR (ESI)
NMR: Varian 500 MHz or 300 MHz system
Abbreviations
abs. absolute (water-free)
AIBN Azaisobutyronitrile
CH3CN Acetonitrile
DMAP Dimethylaminopyridine
DMF N,N-Dimethylformamide
DIAD Diisopropyl azodicarboxylate
DIPEA N,N-Diisopropylethylamine
EE Ethyl acetate
EtOH Ethanol
Fmoc Fluorenylmethyloxycarbonyl
HAc Acetic acid
HATU O-(7-Azabenzotriazol-1-yl)-N,N,N',N'-tetramethyluronium
Fmoc (9H-Fluoren-9-ylmethoxy)carbonyl
MeOH Methanol
RT Room temperature
RF Reflux
TEA Triethylamine
Z Benzyloxycarbonyl
>> Gradient
eq Equivalents Compound 1

Prepared according to: Synthesis 2001, 7, 1049-1052

Compound 2

Prepared according to: J. Carbohydrate Chemistry, 1987, 6 (1), 161-165

Compound 3

Prepared analogously to compound 2

Compound 4

In a solution of 4 g of the compound 2 in 40 ml of abs. DMF, 2.16 g (4 eq) of dry lithium azide and 8.02 g (2.2 eq) of tetrabromomethane were dissolved with stirring. The yellow solution was admixed at 0° C. with 3.18 g (1.1 eq) of triphenylphosphine, warmed slowly to RT and stirred for 20 h. Addition of 20 ml of MeOH was followed by stirring at room temperature for 1 h, in the course of which there was slight evolution of gas. The solvent was removed, the residue was admixed with a little $H_2O$ and washed 3× with toluene, after which the product was extracted with EE, dried with $MgSO_4$, filtered and concentrated. Yield: 2.75 g of a slightly yellowish substance.

Alternatively, lithium azide was replaced by sodium azide, which does not dissolve fully. Addition of the methanol was followed by two days of stirring at RT.

Compound 5

Prepared analogously to compound 4

Compound 6

2.2 g of compound 4 were dissolved in 100 ml of MeOH, 4.45 g (3 eq) triphenylphosphine and 6 ml of $H_2O$ were added, and the suspension was stirred at room temperature for 18 h. With stirring, 20 ml of 20% strength acetic acid and 90 ml of $H_2O$ were added, the mixture was stirred for half an hour, and the suspension was concentrated to 100 ml and extracted by shaking with three times 100 ml of dichloromethane. The aqueous phase lyophilized Yield: 2.67 g of solid. Alternatively, 1 eq of HCl instead of 20 ml of 20% strength HAc was added.

Compound 7

Prepared analogously to compound 6
Compound 8
A solution of 620 mg of compound 2 and 388 mg (2 eq) of cysteamine hydrochloride in 2 ml of MeOH and 6 ml of $H_2O$ was flushed with nitrogen for 20 min. Following addition of a catalytic amount (2-3 mg) of AIBN, the mixture was irradiated with UV light for 24 h, the solvent was removed, and the residue was purified on a silica gel column (MeOH:EE:HAc (20%) 1:4:1). The product fractions were combined and lyophilized Yield: 700 mg of a white solid.

Compound 9

A solution of 1.0 g of compound 6 in 6 ml of abs. DMF was admixed with 607 L (1.5 eq) of diisopropylethylamine and 832 mg (1.1 eq) of nitrophenyl 4-biphenylcarboxylate at RT for 17 h. The solvent was removed, and purification took place on a silica gel column (EtOH:EE:HAc (20%) 1:8:1). Yield: 1.06 g of a white solid.

Compound 10

A solution of 460 mg of compound 9 in 3 ml of MeOH was admixed with 10 eq of sodium 3-mercaptopropynate in 3 ml of $H_2O$, and this mixture was flushed with nitrogen for 20 min. Following addition of a catalytic amount (2-3 mg) of AIBN, irradiation with UV light took place for 24 h. The solvent was removed and the residue was dissolved with $H_2O$ and purified on an RP-18 column ($H_2O$>>MeOH). The product fractions were combined, the MeOH was removed, and lyophilization was carried out. Yield: 564 mg of white solid.

Compound 11

A solution of 460 mg of compound 9 in 3 ml of MeOH was admixed with 193 mg (2 eq) of cysteamine hydrochloride in 3 ml of $H_2O$, and this mixture was flushed with nitrogen for 20 min. Following addition of a catalytic amount (2-3 mg) of AIBN, irradiation with UV light took place for 24 h, the solvent was removed, and the residue was dissolved with $H_2O$ and purified on an RP-18 column (HCl pH4 >>MeOH/HCl pH4). The product fractions were neutralized with dilute NaOH, the MeOH was removed, and lyophilization was carried out. Yield: 525 mg of white solid.

Compound 12

45 mg of compound 11 were dissolved in 2 ml of abs. DMF, 19.5 l (2 eq) of TEA and 31 mg (1.5 eq) of pentafluorophenyl-5-acetylthioglycolic acid were added, and the mixture was stirred overnight. The solvent was removed, the residue was dissolved with a little MeOH, $H_2O$ was added until colloidal clouding occurred, and the mixture was purified on an RP-18 column ($H_2O$>>EtOH) and lyophilized after removal of the ethanol. Yield: 50 mg of white solid.

Compound 13

A solution of 40 mg of compound 12 in 5 ml of $H_2O$ was admixed with 400 l of 2M NaOH. Following complete hydrolysis (TLC monitoring), a pH of 9 was set with dilute HCl, air was bubbled through the solution for 24 h, and purification took place on an RP18 column ($H_2O$>>$CH_3CN$). Yield: 12 mg of white solid.

$^1$H-NMR (300 MHz, $CD_3OD$): δ ppm 1.60 (t, J=11.27, 11.27 Hz, 2H, H3-a H3-a'), 1.73-1.83 (m, 4H, CH2CH2CH2 CH2CH2CH2'), 2.00 (s, 6H, NHAc NHAc'), 2.55-2.66 (m, 8H, CH2SCH2 CH2SCH2'), 2.79-2.87 (m, 2H, H3-e H3-e'), 3.36 (dt, J=7.06, 7.01, 2.33 Hz, 4H, CH2NH CH2NH'), 3.42-3.93 (m, 20H, H4 H4' H5 H5' H6 H6' H7 H7' H9a H9a' H9b H9b' OCH2a OCH2a' OCH2b OCH2b' COCH2S COCH2S), 4.09 (dt, J=8.28, 8.21, 2.62 Hz, 2H, H8), 7.36 (t, J=7.28, 7.28 Hz, 2H, Ar), 7.45 (t, J=7.37, 7.37 Hz, 4H, Ar), 7.64 (d, J=7.12 Hz, 4H, Ar), 7.69 (d, J=8.41 Hz, 4H, Ar), 7.91 (d, J=8.35 Hz, 4H, Ar) $^{13}$C NMR (75 MHz, CD3OD): δ ppm 22.7 29.4 31.4 32.1 40.7 42.8 43.0 44.6 54.2 63.8 69.6 71.6 72.5 74.3 101.9 128.0 128.2 129.0 129.1 130.1 134.5 141.3 145.5 170.0 171.3 174.47 175.48

HRMS (ESI-neg) [(M-2Na)/2] calculated: 677.2082 found: 677.2097

N-(19-Phenyl-3,6,9,12,15,18-hexaoxanonadecyl) trifluoroacetamide (compound 14)

A solution of 800 mg of 19-phenyl-3,6,9,12,15,18-hexaoxanonadecylammonium acetate in 5 ml of MeOH was admixed with 75 µl of TEA and 609 µl of ethyl trifluoroacetate, and stirred at RT for 17 h. Solvents and excess reagents were removed, and the residue was filtered on a silica gel column (EE). Yield: 672 mg of colourless oil.

N-(17-Hydroxy-3,6,9,12,15-pentaoxaheptadecyl) trifluoroacetamide (compound 15)

672 mg of compound 14 were dissolved in 5 ml of MeOH, and the solution was adjusted to a pH of 3 with HCl and, following addition of 76 mg of Pd on carbon (10%), was hydrogenated under atmospheric pressure for 17 h. The suspension was filtered over Celite, concentrated, and coevaporated twice with toluene. Solvent residues were removed overnight under an oil pump vacuum. Yield: 480 mg of colourless oil.

N-(17-Acetylthio-3,6,9,12,15-pentaoxaheptadecyl) trifluoroacetylamide (compound 16)

A solution of 1.632 g (2.1 eq) of triphenylphosphine in 10 ml of abs. DMF was admixed dropwise at 0° C. with 999 µl (1.6 eq) of DIAD and stirred for 20 min. Subsequently a mixture of 672 mg of compound 15 and 933 µl (4 eq) of thioacetic acid was added dropwise, followed by stirring at 0° C. for 4 h and then at RT overnight. The solvent was removed and the residue was purified on a silica gel column ($CHCl_3$>>$CHCl_3$:MeOH 50:1) and on a further silica gel column (diethyl ether). This gives a colourless oil.

17-Amino-3,6,9,12,15-pentaoxaheptadecanethiol hydrochloride (compound 17)

A solution of compound 16 in 1 ml of abs. MeOH was cooled to −40° C., and admixed with 1.3 ml of freshly prepared NaOMe solution (cooled to −40° C., 1.3 mM). The solution was warmed to RT over the course of 30 min, admixed with 1 ml of $H_2O$, and adjusted to a pH of 6 after 20 min with 1M HCl, and the solvent was removed. The residue was used without further purification.

Compound 18

40 mg of compound 17 and 80 mg of compound 9 were dissolved in 2 ml of a 1:1 $H_2O$-MeOH mixture, flushed with nitrogen for 20 min, admixed with a catalytic amount (2-3 mg) of AIBN, and irradiated with UV light for 24 h. The solvent was removed and the residue was dissolved with $H_2O$ and purified on an RP-18 column (HCl pH4 >>MeOH/HCl pH4). The product fractions were neutralized with dilute NaOH, the MeOH was removed, and lyophilization was carried out. Yield: 63 mg of white solid.

Compound 19

2.4 mg (1 eq) of adipic acid, 40 mg (2.8 eq) of compound 18 and 9 mg (1.44 eq) of HATU were dissolved in 1 ml of abs. DMF. Following addition of 10.3 µl (6.5 eq) of DIPEA, the mixture was stirred at RT for 30 min, the solvent was removed, the residue was dissolved in a little MeOH, $H_2O$ was added until colloidal clouding occurred, and purification was carried out on an RP-18 column ($H_2O$/HAc pH3 >>dioxane). The product fractions were concentrated, dissolved with a little MeOH, diluted with H₂O until clouding occurred, and brought to a pH of 12-13 with 2M NaOH. When the reaction was ended, neutralization was carried out with 20% HAc, purification was carried out on an RP18 column (H₂O>>dioxane), the MeOH was removed, and lyophilization was carried out. Yield: 21 mg of white solid.

¹H-NMR (300 MHz, CD₃OD): δ ppm 1.53-1.65 (m, 6H, CH2CH2CH2CH2, H3-a H3-a'), 1.74-1.84 (m, 4H, CH2 CH2CH2 CH2CH2CH2'), 2.00 (s, 6H, NHAc NHAc'), 2.16-2.25 (m, 4H, CH2CH2CH2CH2), 2.64-2.57 (m, 4H, CH2S CH2 CH2SCH2'), 2.66 (t, J=6.78, 6.78 Hz, 4H, CH2SCH2 CH2SCH2'), 2.83 (dd, J=12.14, 4.09 Hz, 2H, H3-e H3-e'), 3.35 (t, J=5.42, 5.42 Hz, 4H, CH2NHCO CH2NHCO'), 3.44 (dd, J=8.95, 1.69 Hz, 2H, H7 H7'), 3.47-3.91 (m, 66H, H4 H4' H5 H5' H6 H6' H9a H9a' H9b H9b' OCH2a OCH2a' OCH2b OCH2b' NHCH2 NHCH2' 3×CH2OCH2CH2OCH2 3× CH2OCH2CH2OCH2'), 4.07 (ddd, J=8.73, 7.63, 3.16 Hz, 2H, H8 H8'), 7.38 (d, J=7.30 Hz, 2H, Ar), 7.46 (t, J=7.35, 7.35 Hz, 4H, Ar), 7.69 (dd, J=15.46, 7.82 Hz, 8H, Ar), 7.93 (d, J=8.63 Hz, 4H, Ar) ¹³C NMR (75 MHz, CD3OD): δ ppm 22.7 26.5 29.9 31.6 32.2 36.8 40.3 42.8 44.6 54.3 64.0 64.5 69.6 71.0 71.1 71.2 71.30 71.35 71.4 71.6 71.8 72.6 74.3 102.0 128.1 128.2 129.0 129.1 130.1 134.5 141.3 145.6 169.9 174.4 175.5 176.0

Compound 20

Prepared analogously to compound 19

¹H-NMR (300 MHz, CD₃OD): δ1.58 (t, J=11.68, 11.68 Hz, 2H, H3-a H3-a'), 1.73-1.83 (m, 4H, CH2CH2CH2 CH2 CH2CH2'), 2.00 (s, 6H, NHAc NHAc'), 2.53-2.70 (m, 8H, CH2SCH2 CH2SCH2'), 2.83 (dd, J=12.21, 3.90 Hz, 2H, H3-e H3-e'), 3.41-3.92 (m, 68H, H4 H4' H5 H5' H6 H6' H7 H7' H9a H9a' H9b H9b' OCH2a OCH2a' OCH2b OCH2b' CH2NH CH2NH' 3×CH2OCH2CH₂OCH2 3×CH2O CH2CH2OCH2'), 4.07 (dt, J=8.20, 8.15, 3.19 Hz, 2H, H8 H8'), 7.33-7.49 (m, 6H, Ar), 7.67 (dd, J=14.28, 7.92 Hz, 8H, Ar), 7.89-7.94 (m, 8H, Ar) ¹³C NMR (75 MHz, CD3OD): δ ppm 22.7 29.9 31.6 32.2 41.0 42.8 44.6 54.3 64.0 69.7 70.9 71.1 71.3 71.3 71.5 71.8 72.7 74.3 102.0 128.0 128.2 128.6 129.0 130.1 134.5 138.4 141.3 145.5 169.4 169.9 174.4 175.5

HRMS (ESI-neg) [(M-2Na)/2] calculated: 889.3672 found: 889.3667

Compound 21

4.0 mg of terephthalic acid (1 eq), 38 mg (2.4 eq) of compound 11 and 22 mg (2.4 eq) of HATU were dissolved in 1 ml of abs. DMF. Following addition of 25 μl (6 eq) of DIPEA, the mixture was stirred at RT for 5 min, the solvent was removed, the residue was dissolved with a little MeOH, H₂O was added until clouding occurred, and purification took place on an RP-18 column (H₂O>>MeOH). The product fractions were concentrated, dissolved with a little MeOH, diluted with H₂O until clouding occurred, and brought to a pH of 12-13 with 2M NaOH. When the reaction was ended, neutralization took place with 20% HAc, purification was carried out on an RP18 column (H₂O>>CH₃CN), the CH₃CN was removed, and lyophilization was carried out.

Yield: 30 mg of white solid.

¹H-NMR (500 MHz, CD₃OD): δ ppm 1.57 (t, J=11.85, 11.85 Hz, 2H, H3-a, H3-a'), 1.79-1.86 (m, 4H, CH2CH2 CH2CH2'), 2.01 (s, 6H, NHCOCH3NHCOCH'), 2.66 (dt, J=7.12, 7.08, 3.77 Hz, 4H, SCH2CH2CH2 S CH2CH2CH2'), 2.74 (dt, J=6.78, 6.68, 4.69 Hz, 4H, CH2S CH2S'), 2.83 (dd, J=12.25, 4.25 Hz, 2H, H3-e H3-e'), 3.44 (dd, J=8.99, 1.81 Hz, 2H, H7 H7'), 3.47-3.58 (m, 6H, H9a H9a' CH2NHCO CH2NHCO'), 3.59 (td, J=9.55, 6.12, 6.12 Hz, 2H, OCH2a OCH2a'), 3.64 (dd, J=10.45, 1.96 Hz, 2H, H6 H6'), 3.68-3.73 (m, 4H, H4 H4' H5 H5'), 3.85 (dd, J=13.43, 3.25 Hz, 2H, H9b H9b'), 3.90 (td, J=9.50, 6.02, 6.02 Hz, 2H, OCH2bOCH2b'), 4.11 (dt, J=8.70, 8.39, 3.39 Hz, 2H, H8 H8'), 7.35 (t, J=7.36, 7.36 Hz, 2H, Ar), 7.43 (t, J=7.56, 7.56 Hz, 4H, Ar), 7.62 (dd, J=8.29, 1.19 Hz, 4H, Ar), 7.67 (d, J=8.53 Hz, 4H, Ar), 7.86 (s, 4H, Ar), 7.89 (d, J=8.34 Hz, 4H, Ar)¹³C NMR (125 MHz, CD₃OD): δ ppm 22.7 29.4 31.3 32.0 41.0 42.5 44.7 54.1 63.8 69.4 71.5 72.5 74.5 101.4 128.0 128.1 128.6 129.0 129.1 130.0 134.5 138.4 141.3 145.5 169.3 170.0 173.7 175.5

HRMS (ESI-neg) [(M-2Na)/2] calculated: 669.2362 found: 669.2353

Compounds 22, 23, 24, 25, 26, 27, 28, 29, 30, 31, 32, 33, 34, 35, 36, 37

Prepared analogously to compound 21

Compound 22

¹H-NMR (300 MHz, CD₃OD): δ ppm 1.53-1.65 (m, 6H, H3-a H3-a'CH2CH2CH2CH2), 1.72-1.84 (m, 4H, CH2 CH2CH2 CH2CH2CH2'), 2.00 (s, 6H, NHCOCH3 NHCO CH3'), 2.14-2.22 (m, 4H, CH2CH2CH2CH2), 2.55-2.64 (m, 8H, CH2SCH2 CH2SCH2'), 2.84 (dd, J=11.63, 3.31 Hz, 2H, H3-e H3-e'), 3.26-3.35 (m, 4H, CH2NH CH2NH'), 3.41-3.93 (m, 16H, H4 H4' H5 H5' H6 H6' H7 H7' H9a H9a'H9b H9b'OCH2a OCH2a' OCH2b OCH2b'), 4.09 (dt, J=8.18, 8.03, 3.24 Hz, 2H, H8 H8'), 7.36 (t, J=7.28, 7.28 Hz, 2H, Ar), 7.45 (t, J=7.51, 7.51 Hz, 4H, Ar), 7.65 (d, J=7.67 Hz, 4H, Ar), 7.70 (d, J=8.34 Hz, 4H, Ar), 7.91 (d, J=8.37 Hz, 4H, Ar) ¹³C NMR (75 MHz, CD₃OD): δ ppm 22.7 26.5 29.3 31.4 32.2 36.8 40.3 42.8 44.6 54.2 63.8 69.6 71.5 72.6 74.3 102.0 128.0 128.2 129.0 129.1 130.1 134.5 134.6 141.3 145.6 170.01 174.4 175.5 175.9

HRMS (ESI-neg) [(M-2Na)/2] calculated: 659.2518 found: 659.2519

Compound 23

¹H-NMR (300 MHz, CD₃OD): δ ppm 1.66-1.52 (m, 2H, H3-a H3-a'), 1.73-1.85 (m, 4H, CH2CH2CH2 CH2 CH2CH2'), 2.00 (s, 6H, NHAc NHAc'), 2.56-2.68 (m, 8H, CH2SCH2 CH2SCH2'), 2.79-2.88 (m, 2H, H3-e H3-e'), 3.33-3.94 (m, 20H, H4 H4' H5 H5' H6 H6' H7 H7' H9a H9a' H9b H9b' OCH2a OCH2a' OCH2b OCH2b' CH2NH CH2NH'), 4.09 (dt, J=8.32, 8.14, 2.80 Hz, 2H, H8 H8'), 6.30 (dd, J=11.43, 2.77 Hz, 2H, CHCHCHCH), 7.17 (dd, J=11.26, 2.90 Hz, 2H, CHCHCHCH), 7.32-7.40 (m, 2H, Ar), 7.44 (t, J=7.35, 7.35 Hz, 4H, Ar), 7.66 (dd, J=14.84, 7.78 Hz, 8H, Ar), 7.90 (d, J=8.34 Hz, 4H, Ar) ¹³C NMR (75 MHz, CD3OD): δ ppm 22.7 29.3 31.4 32.1 40.5 42.8 44.6 54.2 63.8 69.7 71.6 72.6 74.3 101.9 128.0 128.2 129.0 129.1 130.1 134.3 141.3 145.6 131.3 138.8 167.8 170.1 175.5 175.6

HRMS (ESI-neg) [(M-2Na)/2] calculated: 657.2362 found: 657.2396

Compound 24

¹H-NMR (300 MHz, CD₃OD): δ ppm 1.60 (dt, J=11.72, 11.60, 7.26 Hz, 2H, H3-a H3-a'), 1.78-1.89 (m, 4H, CH2 CH2CH2 CH2CH2CH2'), 2.00 (s, 6H, NHCOCH3NHCO CH3'), 2.68 (dt, J=7.03, 6.84, 4.36 Hz, 4H, CH2SCH2 CH2SCH2'), 2.76 (t, J=7.06, 7.06 Hz, 4H, CH2SCH2 CH2S CH2'), 2.85 (dd, J=12.16, 3.88 Hz, 2H, H3-e H3-e'), 3.42-3.97 (m, 20H, H4 H4' H5 H5' H6 H6' H7 H7' H9a H9a' H9b H9b' OCH2a OCH2a' OCH2b OCH2b' CH2NH CH2NH'), 4.12 (dt, J=7.96, 7.92, 3.27 Hz, 2H, H8 H8'), 7.30-7.37 (m, 2H, Ar), 7.41 (t, J=7.29, 7.29 Hz, 4H, Ar), 7.58-7.73 (m, 12H, Ar), 7.89 (d, J=8.25 Hz, 8H, Ar) $^{13}$C NMR (75 MHz, CD3OD): δ ppm 22.7 29.4 31.5 32.1 41.0 42.8 44.6 54.2 63.9 69.7 71.5 72.7 74.3 102.0 128.0 128.2 128.3 129.0 129.1 130.0 141.2 144.3 145.5 169.7 170.0 174.5 175.5

HRMS (ESI-neg) [(M-2Na)/2] calculated: 707.2518 found: 707.2504

Compound 25

$^1$H-NMR (300 MHz, CD$_3$OD): δ ppm 1.59 (t, J=11.72, 11.72 Hz, 2H, H3-e H3-e'), 1.73-1.84 (m, 4H, CH2CH2CH2, CH2CH2CH2'), 2.00 (s, 6H, NHCOCH3NHCOCH3'), 2.51-2.68 (m, 8H, CH2SCH2CH2SCH2'), 2.83 (dd, J=12.24, 3.93 Hz, 2H, H3-e H3-e'), 3.24 (t, J=6.81, 6.81 Hz, 4H, CH2NH CH2NH'), 3.35-3.94 (m, 16H, H4 H4' H5 H5' H6 H6' H7 H7' H9a H9a' H9b H9b' OCH2a OCH2a' OCH2b OCH2b'), 4.04-4.12 (m, 2H, H8 H8'), 7.36 (t, J=7.25, 7.25 Hz, 2H, Ar), 7.45 (t, J=7.42, 7.42 Hz, 4H, Ar), 7.64 (d, J=7.42 Hz, 4H, Ar), 7.69 (d, J=8.39 Hz, 4H, Ar), 7.91 (d, J=8.37 Hz, 4H, Ar) $^{13}$C NMR (75 MHz, CD3OD): δ ppm 22.7 29.3 31.4 32.1 40.7 42.8 44.5 54.2 63.8 69.7 71.5 72.6 74.3 102.0 128.0 128.2 129.0 129.1 130.1 134.5 141.3 145.6 153.6 170.0 174.5 175.5

HRMS (ESI-neg) [(M-2Na)/2] calculated: 643.2205 found: 643.2181

Compound 26

$^1$H-NMR (300 MHz, CD$_3$OD): δ ppm 1.59 (t, J=11.73, 11.73 Hz, 2H, H3-a H3-a'), 1.76-1.86 (m, 4H, CH2CH2CH2 CH2CH2CH2'), 2.00 (s, 6H, NHAc NHAc'), 2.64 (dt, J=6.87, 6.76, 1.44 Hz, 4H, CH2SCH2 CH2SCH2'), 2.72 (t, J=7.13, 7.13 Hz, 4H, CH2SCH2 CH2SCH2'), 2.84 (dd, J=12.07, 3.48 Hz, 2H, H3-e H3-e'), 3.41-3.94 (m, 20H, H4 H4' H5 H5' H6 H6' H7 H7' H9a H9a' H9b H9b' OCH2 a OCH2 a' OCH2b O CH2b' CH2NH CH2NH'), 4.10 (dt, J=8.40, 8.25, 3.15 Hz, 2H, H8 H8'), 7.31-7.54 (m, 7H, Ar), 7.59-7.69 (m, 8H, Ar), 7.86-7.95 (m, 6H, Ar), 8.28-8.30 (m, 1H, Ar) $^{13}$C NMR (75 MHz, CD3OD): δ ppm 22.7 29.3 31.4 32.0 41.0 42.8 44.6 54.2 63.8 69.7 71.5 72.6 74.3 102.0 127.3 128.0 128.1 129.0 129.1 129.9 130.0 131.4 134.5 136.1 141.3 145.5 169.3 170.0 174.5 175.5

HRMS (ESI-neg) [(M-2Na)/2] calculated: 669.2362 found: 669.2392

Compound 27

$^1$H-NMR (300 MHz, CD$_3$OD): δ ppm 1.54-1.72 (m, 2H, H3-a H3-a'), 1.76-1.88 (m, 4H, CH2CH2CH2 CH2 CH2CH2'), 1.98-2.03 (m, 6H, NHAc NHAc'), 2.57-2.89 (m, 10H, H3-e H3-e' CH2SCH2 CH2SCH2'), 3.40-3.97 (m, 20H, H4 H4' H5 H5' H6 H6' H7 H7' H9a H9a' H9b H9b' OCH2 OCH2' CH2NH CH2NH'), 4.06-4.20 (m, 2H, H8 H8'), 7.32-7.38 (m, 2H, Ar), 7.40-7.47 (m, 4H, Ar), 7.56-7.72 (m, 8H, Ar), 7.85-7.94 (m, 4H, Ar), 8.06 (d, J=8.04 Hz, 1H, Ar), 8.21-8.27 (m, 2H, Ar) $^{13}$C NMR (75 MHz, CD3OD): δ ppm 22.7 29.4 29.6 31.5 40.4 41.3 42.7 44.6 54.1 54.2 63.8 63.9 69.6 71.4 71.5 72.5 72.7 74.3 101.91 101.9 122.7 128.0 128.1 129.0 129.1 130.0 133.7 134.50 134.53 137.8 141.3 145.52 145.53 148.8 152.9 165.9 167.5 167.0 174.40 174.43 175.5 175.6

HRMS (ESI-neg) [(M-2Na)/2] calculated: 669.7338 found: 669.7335

Compound 28

$^1$H-NMR (300 MHz, CD$_3$OD): 1.68-1.82 (m, 6H, H3-a H3-a' CH2CH2CH2 CH2CH2CH2'), 1.99 (s, 6H, NHAc NHAc'), 2.50-2.62 (m, 8H, CH2SCH2CH2SCH2'), 2.71 (dd, J=12.73, 4.24 Hz, 2H, H3-e H3-e'), 3.24-3.32 (m, 4H, CH2NH CH2NH'), 3.40-3.93 (m, 20H, H4 H4' H5 H5' H6 H6' H7 H7' H9a H9a' H9b H9b' OCH2a OCH2a' OCH2b OCH2b' CH2ArCH2), 4.08 (dt, J=8.14, 7.97, 3.17 Hz, 2H, H8 H8'), 7.21 (s, 4H, Ar), 7.37 (t, J=7.24, 7.24 Hz, 2H, Ar), 7.45 (t, J=7.55, 7.55 Hz, 4H, Ar), 7.64 (d, J=7.84 Hz, 4H, Ar), 7.69 (d, J=8.19 Hz, 4H, Ar), 7.90 (d, J=8.19 Hz, 4H, Ar) $^{13}$C NMR (75 MHz, CD3OD): δ ppm 22.7 29.2 31.0 32.1 40.5 42.0 43.6 44.9 54.0 63.7 68.9 71.4 72.3 74.8 100.2 128.1 128.2 129.0 129.1 130.1 130.5 134.4 135.5 141.3 145.6 170.3 172.2 174.1 175.3

HRMS (ESI-neg) [(M-2Na)/2] calculated: 683.2518 found: 683.2503

Compound 29

$^1$H-NMR (300 MHz, CD$_3$OD): δ ppm 1.68-1.86 (m, 6H, H3-a H3-a' CH2CH2CH2 CH2CH2CH2'), 1.99 (s, 6H, NHAc NHAc'), 2.59-2.75 (m, 10H, H3-e H3-e' CH2SCH2 CH2SCH2'), 3.42-3.95 (m, 20H, H4 H4' H5 H5' H6 H6' H7 H7' H9a H9a' H9b H9b' OCH2a OCH2a' OCH2b OCH2b'CH2NH CH2NH'), 4.09 (dt, J=7.95, 7.94, 3.17 Hz, 2H, H8 H8'), 7.35 (t, J=7.22, 7.22 Hz, 2H, Ar), 7.57 (s, 2H, Ar), 7.61 (d, J=7.45 Hz, 4H, Ar), 7.67 (d, J=8.34 Hz, 4H, Ar), 7.89 (d, J=8.27 Hz, 4H, Ar)

$^{13}$C NMR (75 MHz, CD3OD): δ ppm 22.7 29.3 31.0 31.9 40.9 41.8 44.9 53.9 63.7 68.9 71.4 72.3 74.8 100.2 128.0 128.1 129.1 129.1 129.7 130.0 134.4 141.2 144.0 145.6 163.7 170.3 172.1 175.3

HRMS (ESI-neg) [(M-2Na)/2] calculated: 672.2144 found: 672.2146

Compound 30

$^1$H-NMR (300 MHz, CD$_3$OD): δ ppm 0.91 (t, J=6.29, 6.29 Hz, 3H, CH3), 1.30-1.44 (m, 4H, CH2CH2CH3), 1.68-1.87 (m, 8H, ArOCH2CH2 H3-a H3-a' CH2CH2CH2 CH2CH2CH2'), 1.99 (s, 6H, NHAc NHAc'), 2.58-2.76 (m, 10H, CH2SCH2 CH2SCH2' H3-e H3-e'), 3.44-4.15 (m, 24H, H4 H4' H5 H5'H6 H6' H7 H7' H8 H8' H9a H9a' H9b H9b' OCH2 OCH2' CH2NHCO CH2NHCO' ArOCH2), 7.29-7.49 (m, 8H, Ar), 7.55-7.68 (m, 8H, Ar), 7.82-7.96 (m, 5H, Ar) $^{13}$C NMR (75 MHz, CD3OD): δ ppm 14.6 22.7 22.8 23.5 29.0 29.2 29.5 29.9 31.0 31.9 32.2 40.3 41.0 41.8 44.9 53.9 63.7 68.8 70.6 71.4 72.4 74.8 100.1 112.9 120.3 125.6 128.0 128.1 129.0 129.1 130.0, 132.34, 134.32 139.64 141.14 145.49 158.3 167.3 169.0 170.1 170.2 172.1 175.2

HRMS (ESI-neg) [(M-2Na)/2] calculated: 712.2727 found: 6712.2708

Compound 31

$^1$H-NMR (300 MHz, CD$_3$OD): δ ppm 1.50-1.95 (m, 16H, H3-a H3-a' CH2CH2CH2 CH2CH2CH2', cyclohexyl), 2.00 (s, 6H, NHCOCH3 NHCOCH3'), 2.53-2.65 (m, 8H, CH2S CH2 CH2SCH2'), 2.83 (dd, J=12.10, 3.57 Hz, 2H, H3-e H3-e'), 3.26-3.31 (m, 4H, CH2NHCO CH2NHCO'), 3.41-3.93 (m, 16H, H4 H4' H5 H5' H6 H6' H9a H9a' H9b H9b' OCH2 OCH2'), 4.09 (dt, J=8.15, 8.06, 3.07 Hz, 2H, H8 H8'), 7.36 (t, J=7.25, 7.25 Hz, 2H, Ar), 7.45 (t, J=7.50, 7.50 Hz, 4H, Ar), 7.64 (d, J=7.75 Hz, 4H, Ar), 7.69 (d, J=8.21 Hz, 4H, Ar), 7.91 (d, J=8.28 Hz, 4H, Ar) $^{13}$C NMR (75 MHz, CD3OD): δ ppm 22.7 27.6 29.4 31.4 32.2 40.2 42.8 42.9 44.5 54.2 63.9 69.6 71.6 72.5 74.3 102.0 128.0 128.1 129.0 129.1 130.1 134.5 141.3 145.52 170.0 174.5 175.5 178.1

HRMS (ESI-neg) [(M-2Na)/2] calculated: 672.2596 found: 672.2631

Compound 32

$^1$H-NMR (300 MHz, CD$_3$OD): δ ppm 1.50-1.62 (m, 2H, H3-a H3-a'), 1.75-1.87 (m, 4H. CH2CH2CH2 CH2 CH2CH2'), 1.99 (s, 3H, NHCOCH3), 2.00 (s, 3H, NHCO CH3'), 2.58-2.80 (m, 8H, CH2SCH2 CH2SCH2'), 2.82 (dd, J=12.03, 2.46 Hz, 2H, H3-e H3-e'), 3.39-3.95 (m, 20H, H4 H4' H5 H5' H6 H6' H7 H7' H9a H9a' H9b H9b' OCH2a OCH2a' OCH2b OCH2b' CH2NHArNHCH2), 4.10 (dt, J=8.41, 8.26, 3.24 Hz, 2H, H8 H8'), 7.35 (t, J=7.32, 7.32 Hz, 2H, Ar), 7.39-7.48 (m, 5H, Ar), 7.62 (d, J=7.57 Hz, 4H, Ar), 7.67 (dd, J=8.35, 1.62 Hz, 4H, Ar), 7.81 (dd, J=7.94, 1.57 Hz, 1H, Ar), 7.89 (dd, J=8.36, 2.78 Hz, 4H, Ar), 8.02 (d, J=1.53 Hz, 1H, Ar) $^{13}$C NMR (75 MHz, CD3OD): δ ppm 22.7 29.4 29.5 31.5 31.7 31.9 32.0 40.9 41.1 42.8 44.6 54.2 63.8 69.6 71.5 72.6 74.3 102.0 120.7 128.0 128.2 129.0 129.1 130.0 133.1 134.5 138.3 141.3 142.4 145.6 167.8 170.0 170.2 174.5 175.5

HRMS (ESI-neg) [(M-2Na)/2] calculated: 708.1914 found: 708.1918

Compound 33

$^1$H-NMR (300 MHz, CD$_3$OD): δ ppm 1.51-1.64 (m, 2H, H3-a H3-a'), 1.76-1.88 (m, 4H, CH2CH2CH2 CH2 CH2CH2'), 2.00 (s, 6H, NHCOCH3 NHCOCH3'), 2.61-2.86 (m, 10H, H3-e H3-e' CH2SCH2 CH2SCH2'), 3.41-3.95 (m, 20H, H4 H4' H5 H5' H6 H6' H7 H7' H9a H9a' H9b H9b' OCH2a OCH2a' OCH2b OCH2b' CH2NH CH2NH'), 4.10 (ddd, J=8.97, 8.23, 3.14 Hz, 2H, H8 H8'), 7.35 (t, J=7.22, 7.22 Hz, 2H, Ar), 7.43 (t, J=7.49, 7.49 Hz, 4H, Ar), 7.60-7.69 (m, 9H, Ar), 7.89 (dd, J=8.28, 3.29 Hz, 4H, Ar), 8.16 (dd, J=7.89, 1.55 Hz, 1H, Ar), 8.46 (d, J=1.58 Hz, 1H, Ar) $^{13}$C NMR (75 MHz, CD3OD): δ ppm 22.7 29.3 29.4 31.4 31.8 31.9 40.9 41.2 42.8 44.5 54.2 63.8 69.6 71.5 72.6 74.3 101.9 124.6 128.0 128.1 129.0 129.1 130.0 130.7 133.5 134.5 136.2 138.1 141.3 145.5 148.0 167.0 168.7 170.0 174.5 175.5

HRMS (ESI-neg) [(M-2Na)/2] calculated: 691.7287 found: 691.7339

Compound 34

$^1$H-NMR (300 MHz, CD$_3$OD): δ ppm 1.43 (t, J=11.61, 11.61 Hz, 2H, H3-a H3-a'), 1.78-1.88 (m, 4H, CH2CH2CH2 CH2CH2CH2'), 2.00 (s, 6H, NHCOCH3 NHCOCH3'), 2.62-2.89 (m, 10H, H3-e H3-e' CH2SCH2CH2SCH2'), 3.39-3.74 (m, 16H, H4 H4' H5 H5' H6 H6' H7 H7' H9a H9a' OCH2a OCH2a' CH2NH CH2NH'), 3.84 (dd, J=13.57, 3.14 Hz, 2H, H9b H9b'), 3.86-3.94 (m, 2H, OCH2b OCH2b'), 4.13 (ddd, J=8.94, 7.94, 3.21 Hz, 2H, H8 H8'), 7.36 (t, J=7.24, 7.24 Hz, 2H, Ar), 7.44 (t, J=7.31, 7.31 Hz, 4H, Ar), 7.53 (dd, J=6.53, 3.32 Hz, 1H, Ar), 7.59-7.69 (m, 10H, Ar), 7.88 (d, J=8.61 Hz, 4H, Ar), 8.22 (dd, J=6.58, 3.28 Hz, 2H, Ar) $^{13}$C NMR (75 MHz, CD3OD): δ ppm 22.7 29.6 31.4 32.2 41.0 42.7 44.5 54.2 63.8 69.5 71.5 72.6 74.3 101.9 125.5 126.8 128.0 128.1 128.3 129.0 129.1 130.0 131.6 134.5 137.9 141.3 145.5 170.0 172.0 174.5 175.5

HRMS (ESI-neg) [(M-2Na)/2] calculated: 694.2440 found: 694.2447

Compound 35

$^1$H-NMR (300 MHz, CD$_3$OD): δ ppm 7.91 (d, J=8.55 Hz, 4H, Ar), 7.70 (d, J=8.44 Hz, 4H, Ar), 7.65 (d, J=7.15 Hz, 4H, Ar), 7.45 (t, J=7.41, 7.41 Hz, 4H, Ar), 7.36 (t, J=7.27, 7.27 Hz, 2H, Ar), 4.08 (ddd, J=8.65, 7.99, 3.20 Hz, 2H, H8 H8'), 3.88 (td, J=9.21, 6.36, 6.36 Hz, 2H, OCH2a OCH2a'), 3.83 (dd, J=13.27, 2.74 Hz, 2H, H9a H9a'), 3.74-3.52 (m, 8H, H4 H4' H5 H5' H6 H6' OCH2b OCH2b'), 3.52 (dd, J=13.55, 7.70 Hz, 2H, H9b H9b'), 3.44 (dd, J=8.92, 1.17 Hz, 2H, H7 H7'), 3.31-3.26 (m, 4H, CH2NH CH2NH'), 2.83 (dd, J=11.95, 3.62 Hz, 2H, H3-e H3-e'), 2.63-2.55 (m, 8H, CH2SCH2 CH2SCH2'), 2.45 (s, 4H, COCH2CH2CO), 2.00 (s, 6H, CH3 CH3'), 1.84-1.72 (m, 4H, CH2CH2CH2 CH2CH2CH2'), 1.59 (t, J=11.77, 11.77 Hz, 2H, H3-a H3-a') $^{13}$C NMR (125 MHz, CD3OD): δ ppm 175.5 174.6 174.5 170.0 145.5 141.3 134.5 130.0 129.1 129.0 128.2 128.0 102.0 74.3 72.6 71.5 69.7 63.8 54.2 44.6 42.8 40.4 32.6 32.1 31.4 29.3 22.7

HRMS (ESI-neg) [(M-2Na)/2] calculated: 645.2362 found: 645.2343

Compound 36

$^1$H-NMR (500 MHz, CD$_3$OD): δ ppm 7.89 (d, J=8.44 Hz, 4H, Ar), 7.67 (d, J=8.01 Hz, 4H, Ar), 7.63 (d, J=8.23 Hz, 4H, Ar), 7.49 (dd, J=7.45, 1.43 Hz, 2H, Ar), 7.44 (t, J=7.71, 7.71 Hz, 4H, Ar), 7.42-7.38 (m, 2H, Ar), 7.38-7.34 (m, 4H, Ar), 7.08 (d, J=7.37 Hz, 2H, Ar), 4.09 (ddd, J=8.59, 8.18, 3.30 Hz, 2H, H8 H8'), 3.84 (dd, J=13.64, 2.99 Hz, 2H, H9a H9a'), 3.84 (td, J=9.03, 6.05, 6.05 Hz, 2H, OCH2a OCH2a'), 3.73-3.68 (m, 4H, H4 H4' H5 H5'), 3.64 (dd, J=10.08, 1.61 Hz, 2H, H6 H6'), 3.53 (td, J=10.25, 6.38, 6.38 Hz, 2H, OCH2b OCH2b'), 3.51 (dd, J=14.02, 7.48 Hz, 2H, H9b H9b'), 3.44 (dd, J=8.97, 1.62 Hz, 2H, H7 H7'), 3.29-3.11 (m, 4H, CH2NH CH2NH'), 2.83 (dd, J=12.16, 4.00 Hz, 2H, H3-e H3-e'), 2.53-2.42 (m, 4H, SCH2 SCH2'), 2.30-2.14 (m, 4H, CH2S CH2S'), 2.00 (s, 6H, CH3 CH3'), 1.75-1.68 (m, 4H, CH2CH2CH2 CH2 CH2CH2'), 1.59 (t, J=11.73, 11.73 Hz, 2H, H3-a H3-a') $^{13}$C NMR (500 MHz, CD3OD): δ ppm 175.5 174.5 172.4 170.0 145.5 141.3 140.3 137.4 134.5 130.8 130.7 130.1 129.1 129.0 128.4 128.2 128.0 102.0 74.3 72.6 71.6 69.7 63.9 54.2 44.6 42.8 40.4 31.5 31.3 29.3 22.7

HRMS (ESI-neg) [(M-2Na)/2] calculated: 707.2518 found: 707.2496

Compound 37

$^1$H-NMR (500 MHz, CD$_3$OD): δ ppm 7.91 (d, J=8.25 Hz, 2H, Ar), 7.70 (d, J=8.24 Hz, 2H, Ar), 7.65 (dd, J=8.18, 1.38 Hz, 2H, Ar), 7.45 (t, J=7.80, 7.80 Hz, 2H, Ar), 7.36 (t, J=7.37, 7.37 Hz, 1H, Ar), 4.08 (ddd, J=8.68, 7.99, 3.27 Hz, 2H, H8 H8'), 3.87 (td, J=9.96, 6.27, 6.27 Hz, 2H, OCH2a OCH2a'), 3.84 (dd, J=13.58, 3.23 Hz, 2H, H9a H9a'), 3.73-3.68 (m, 4H, H4 H4' H5 H5'), 3.64 (dd, J=10.27, 1.73 Hz, 2H, H6 H6'), 3.57 (td, J=9.69, 6.22, 6.22 Hz, 2H, OCH2b OCH2b'), 3.51 (dd, J=13.70, 7.76 Hz, 2H, H9b H9b'), 3.44 (dd, J=8.90, 1.81 Hz, 2H, H7 H7'), 3.37-3.32 (m, 4H, CH2NH CH2NH'), 3.19 (dd, J=19.27, 7.94 Hz, 2H, COCH2CO), 2.83 (dd, J=12.21, 3.83 Hz, 2H, H3-e H3-e'), 2.65-2.55 (m, 8H, CH2SCH2 CH2SCH2'), 2.00 (s, 6H, CH3 CH3'), 1.81-1.75 (m, 4H, CH2 CH2CH2 CH2CH2CH2'), 1.59 (t, J=11.74, 11.74 Hz, 2H, H3-a H3-a) $^{13}$C NMR (125 MHz, CD3OD): δ ppm 175.5

174.5 170.0 169.6 145.6 141.3 134.6 130.1 129.1 129.0 128.2 128.1 102.0 74.3 72.7 71.5 69.7 63.8 54.2 44.6 43.8 42.8 40.4 32.0 31.4 29.3 22.7

HRMS (ESI-neg) [(M-2Na)/2] calculated: 639.2362 found: 639.2320

Compound 38

Prepared analogously to compound 21, with compound 8 instead of compound 11 HRMS (ESI-neg) [(M-2Na)/2] calculated: 490.1627 found: 490.1617

Compound 39

A solution of 36 mg (2.4 eq) of compound 10 and 20 mg (2.4 eq) of HATU in 1 ml of abs. DMF was admixed with 22.5 μl (6 eq) of DIPEA, stirred for 5 min, admixed with 4 mg (1 eq) of p-phenylenediamine dihydrochloride and then stirred for a further 5 min. The solvent was removed, the residue was dissolved with a little MeOH, $H_2O$ was added until clouding occurred, and purification took place in an RP-18 column ($H_2O$>>MeOH). The product fractions were concentrated, dissolved with a little MeOH, diluted with $H_2O$ until clouding occurred, and brought to a pH of 12-13 with 2M NaOH. When reaction was ended, neutralization took place with 20% HAc, purification was carried out on an RP18 column ($H_2O$>>$CH_3CN$), the $CH_3CN$ was removed, and lyophilization was carried out. Yield: 23 mg of white solid.

$^1$H NMR (300 MHz, CD3OD): δ ppm 1.68-1.77 (m, 2H, H3-a H3-a'), 1.75-1.86 (m, 4H, CH2CH2CH2 CH2CH2CH2'), 1.99 (s, 6H, NHAc NHAc'), 2.55-2.66 (m, 8H, CH2SCH2CH2SCH2'), 2.67-2.75 (m, 2H, H3-e H3-e'), 2.75-2.83 (m, 4H CH2CO CH2CO'), 3.45-3.94 (m, 16H, H4 H4' H5 H5' H6 H6' H7 H7' H9a H9a' H9b H9b' OCH2a OCH2a' OCH2b OCH2b'), 4.04-4.15 (m, 2H, H8 H8'), 7.14-7.22 (m, 2H, Ar), 7.26-7.48 (m, 8H, Ar), 7.58-7.69 (m, 8H, Ar), 7.86-7.92 (m, 4H, Ar) $^{13}$C NMR (75 MHz, CD3OD): δ ppm 22.8 28.6 29.4 31.0 38.5 41.9 44.6 53.9 63.8 68.9 71.4 72.4 74.8 100.3 113.2 117.1 128.1 128.2 129.0 129.1 130.0 134.4 140.2 141.3 145.6 170.3 172.2 172.6 175.3

HRMS (ESI-neg) [(M-2Na)/2] calculated: 669.2362 found: 669.2397

Compounds 40, 41, 42, 43, 44, 45, 46

Prepared analogously to compound 39

Compound 40

$^1$H-NMR (300 MHz, CD$_3$OD): δ ppm 1.53-1.64 (m, 2H, H3-a H3-a'), 1.73-1.83 (m, 4H, CH2CH2CH2 CH2CH2'), 2.00 (s, 6H, NHAc NHAc'), 2.45 (t, J=7.17, 7.17 Hz, 4H, CH2SCH2CH2SCH2'), 2.59 (dt, J=7.07, 7.00, 2.63 Hz, 4H, CH2SCH2 CH2SCH2'), 2.73 (t, J=7.11, 7.11 Hz, 4H, CH2CO CH2CO'), 2.83 (dd, J=12.14, 4.24 Hz, 2H, H3-e H3-e'), 3.30-3.35 (m, 4H, CH2CH2NHCO CH2CH2NHCO'), 3.45 (dd, J=8.87, 1.72 Hz, 2H, H7 H7'), 3.47-3.91 (m, 30H, H4 H4' H5 H5' H6 H6' H9a H9a' H9b H9b' OCH2a OCH2a' OCH2b OCH2b'CH2OCH2CH2OCH2 CH2OCH2CH2OCH2'), 4.09 (dt, J=8.20, 8.13, 3.37 Hz, 2H, H8 H8'), 7.36 (t, J=7.28, 7.28 Hz, 2H, Ar), 7.45 (t, J=7.45, 7.45 Hz, 4H, Ar), 7.68 (dd, J=15.02, 7.76 Hz, 8H, Ar), 7.92 (d, J=8.36 Hz, 4H, Ar) $^{13}$C NMR (75 MHz, CD3OD): δ ppm 22.7 28.8 29.4 31.4 37.5 40.5 42.8 44.6 45.0 54.3 64.0 69.7 71.4 70.7 71.4 71.5 71.7 72.7 74.3 102.0 128.0 128.2 129.0 129.1 130.1 134.6 141.3 145.6 170.0 174.5 174.6 175.5

HRMS (ESI-neg) [(M-2Na)/2] calculated: 802.3101 found: 802.3104

Compound 41

$^1$H-NMR (300 MHz, CD$_3$OD): δ ppm 1.67-1.78 (m, 2H, H3-a H3-a'), 1.75-1.86 (m, 4H, CH2CH2CH2 CH2CH2CH2'), 1.98 (s, 6H, NHAc NHAc'), 2.56-2.70 (m, 8H, CH2SCH2 CH2SCH2'), 2.73 (dd, J=12.66, 4.29 Hz, 2H, H3-e H3-e'), 2.78-2.87 (m, 4H, CH2CO CH2CO'), 3.42-3.62 (m, 6H, H7 H7' H9a H9a' OCH2a OCH2a'), 3.63-3.95 (m, 10H, H4 H4' H5 H5' H6 H6' H9b H9b' OCH2b OCH2b'), 4.09 (dt, J=8.33, 8.30, 3.24 Hz, 2H, H8 H8'), 7.16 (dd, J=6.01, 3.52 Hz, 2H, Ar), 7.31-7.52 (m, 8H, Ar), 7.59-7.70 (m, 8H, Ar), 7.89 (d, J=8.52 Hz, 4H, Ar) $^{13}$C NMR (75 MHz, CD3OD): δ ppm 22.7 28.7 29.5 31.0 38.0 41.9 44.8 54.0 63.8 69.0 71.4 72.3 74.7 100.4 126.5 127.1 128.0 128.2 129.0 129.1 130.1 132.0 134.3 141.3 145.6 170.3 172.6 173.2 175.3

HRMS (ESI-neg) [(M-2Na)/2] calculated: 669.2362 found: 669.2368

Compound 42

$^1$H-NMR (300 MHz, CD$_3$OD): δ ppm 1.70 (dd, J=12.14, 11.63 Hz, 2H, H3-a H3-a'), 1.77-1.86 (m, 4H, CH2CH2CH2 CH2CH2CH2'), 1.99 (s, 6H, NHCOCH3 NHCOCH3'), 2.57-2.66 (m, 8H, CH2SCH2 CH2SCH2'), 2.73 (dd, J=12.63, 4.27 Hz, 2H, H3-e H3-e'), 2.81 (t, J=7.14, 7.14 Hz, 4H, CH2CO CH2CO'), 3.47 (dd, J=8.72, 1.52 Hz, 2H, H7 H7'), 3.50-3.60 (m, 4H, OCH2a OCH2a' H9a H9a'), 3.64-3.94 (m, 10H, H4 H4' H5 H5' H6 H6' H9b H9b' OCH2b OCH2b'), 4.09 (ddd, J=8.42, 7.66, 3.29 Hz, 2H, H8 H8'), 7.31-7.50 (m, 10H, Ar), 7.65 (dd, J=16.48, 7.78 Hz, 8H, Ar), 7.90 (d, J=8.59 Hz, 4H, Ar) $^{13}$C NMR (75 MHz, CD3OD): δ ppm 22.7 28.7 29.5 31.0 38.4 41.1 44.8 54.0 63.8 69.0 71.4 72.4 74.7 100.5 121.8 128.1 128.3 127.0 129.1 130.1 to 134.4 136.0 141.3 145.7 170.3 172.5 172.7 175.3

HRMS (ESI-neg) [(M-2Na)/2] calculated: 669.2362 found: 669.2370

Compound 43

$^1$H-NMR (300 MHz, CD$_3$OD): δ ppm 1.52-1.22 (m, 8H, CH2CH2CH2CH2CH2CH2), 1.67-1.83 (m, 6H, CH2CH2CH2 CH2CH2CH2' H3-a H3-a'), 1.99 (s, 6H, NHCOCH3 NHCOCH3'), 2.41 (t, J=7.10, 7.10 Hz, 4H, CH2CO CH2CO'), 2.57 (t, J=7.14, 7.14 Hz, 4H, CH2SCH2 CH2SCH2'), 2.66-2.78 (m, 6H, CH2SCH2 CH2SCH2' H3-e H3-e'), 3.12 (t, J=6.85, 6.85 Hz, 4H, NHCH2 NHCH2'), 3.41-3.93 (m, 16H, H4 H4' H5 H5' H6 H6' H7 H7' H9a H9a' H9b H9b' OCH2a OCH2a' OCH2b OCH2b'), 4.08 (dt, J=8.47, 8.21, 2.79 Hz, 2H, H8 H8'), 7.32-7.48 (m, 6H, Ar), 7.66 (dd, J=16.40, 7.46 Hz, 8H, Ar), 7.91 (d, J=7.87 Hz, 4H, Ar) $^{13}$C NMR (75 MHz, CD3OD): δ ppm 22.8 27.5 28.8 29.3 30.3 30.9 37.5 40.4 41.9 44.8 54.0 63.8 68.9 71.4 72.3 74.8 100.3 128.0 128.1 129.0 129.1 130.0 134.3 141.2 145.6 170.2 172.4 174.2 175.3

HRMS (ESI-neg) [(M-2Na)/2] calculated: 687.2831 found: 687.2809

Compound 44

$^1$H-NMR (300 MHz, CD$_3$OD): 1.66-1.84 (m, 6H, H3-a H3-a' CH2CH2CH2 CH2CH2CH2'), 1.99 (s, 6H, NHAc NHAc'), 2.47 (t, J=7.11, 7.11 Hz, 4H, CH2SCH2 CH2SCH2'), 2.58 (t, J=7.11, 7.11 Hz, 4H, CH2SCH2 CH2SCH2'), 2.68-2.78 (m, 6H, H3-e H3-e' CH2CO CH2CO'), 3.44-3.91 (m, 16H, H4 H4' H5 H5' H6 H6' H7 H7' H9a H9a' H9b H9b' OCH2a OCH2a' OCH2b OCH2b'), 4.07 (dt, J=7.86, 7.85, 3.37 Hz, 2H, H8 H8'), 4.31 (s, 4H, ArCH2), 7.22 (s, 4H, Ar), 7.37 (t, J=7.23, 7.23 Hz, 2H, Ar), 7.45 (t, J=7.37, 7.37 Hz, 4H, Ar), 7.64 (d, J=7.17 Hz, 2H, Ar), 7.69 (d, J=8.49 Hz, 2H, Ar), 7.89 (d, J=8.39 Hz, 4H, Ar) $^{13}$C NMR (75 MHz, CD$_3$OD): δ ppm 22.7 28.8 29.4 31.0 37.5 41.9 43.9 44.8 54.0 63.8 68.9 71.4 72.4 74.8 100.3 128.1 128.2 128.8 129.0 129.1 130.1 134.4 138.8 141.3 145.6 170.3 172.3 174.3 175.3

HRMS (ESI-neg) [(M-2Na)/2] calculated: 683.2518 found: 683.2507

Compound 45

$^1$H NMR (300 MHz, CD3OD): δ ppm 1.71 (dd, J=12.14, 11.65 Hz, 2H, H3-a H3-a'), 1.79-1.90 (m, 4H, CH2CH2CH2 CH2CH2CH2'), 1.99 (s, 6H, NHCOCH3 NHCOCH3'), 2.10 (s, 12H, 4×ArCH3), 2.69 (dd, J=15.09, 7.37 Hz, 8H, CH2S CH2 CH2SCH2'), 2.75 (dd, J=12.69, 4.33 Hz, 2H, H3-e H3-e'), 2.86 (t, J=6.80, 6.80 Hz, 4H, CH2CO CH2CO'), 3.43-3.97 (m, 16H, H4 H4' H5 H5' H6 H6' H7 H7' H9a H9a' H9b H9b' OCH2a OCH2a' OCH2b OCH2b'), 4.08 (dt, J=8.00, 7.93, 3.30 Hz, 2H, H8 H8'), 7.36 (t, J=7.27, 7.27 Hz, 2H, Ar), 7.45 (t, J=7.32, 7.32 Hz, 4H, Ar), 7.64 (d, J=7.06 Hz, 4H, Ar), 7.68 (d, J=8.41 Hz, 4H, Ar), 7.89 (d, J=8.37 Hz, 4H, Ar) $^{13}$C NMR (75 MHz, CD3OD): δ ppm 15.7 22.7 28.8 29.5 31.2 37.2 42.1 44.8 54.0 63.9 69.1 71.3 72.5 74.7 100.6 128.1 128.2 129.0 129.1 130.1 134.4 134.6 141.3 145.6 170.2 172.7 175.3

HRMS (ESI-neg) [(M-2Na)/2] calculated: 713.2624 found: 713.2637

Compound 46

$^1$H-NMR (500 MHz, CD$_3$OD): δ ppm 7.91 (d, J=8.46 Hz, 4H, Ar), 7.70 (d, J=8.51 Hz, 4H, Ar), 7.65 (dd, J=8.25, 1.07 Hz, 4H, Ar), 7.45 (t, J=7.65, 7.65 Hz, 4H, Ar), 7.36 (t, J=7.38, 7.38 Hz, 2H, Ar), 4.08 (ddd, J=8.95, 7.87, 3.25 Hz, 2H, H8 H8'), 3.86 (td, J=9.65, 6.17, 6.17 Hz, 2H, H9a H9a'), 3.84 (dd, J=13.60, 3.28 Hz, 2H, OCH2a OCH2a'), 3.73-3.68 (m, 4H, H4 H4' H5 H5'), 3.64 (dd, J=10.42, 1.97 Hz, 2H, H6 H6'), 3.58 (td, J=9.72, 6.21, 6.21 Hz, 2H, OCH2b OCH2b'), 3.52 (dd, J=13.67, 7.70 Hz, 2H, H9b H9b'), 3.44 (dd, J=8.96, 1.85 Hz, 2H, H7 H7'), 2.84 (dd, J=12.21, 4.20 Hz, 2H, H3-e H3-e'), 2.71 (dt, J=7.26, 6.99, 3.72 Hz, 4H, CH2S CH2S'), 2.62-2.54 (m, 4H, SCH2 SCH2'), 2.44 (t, J=7.38, 7.38 Hz, 4H, NH CH2CH2NH), 2.00 (s, 6H, COCH3 COCH3'), 1.81-1.74 (m, 4H, CH2CH2CH2 CH2CH2CH2'), 1.59 (t, J=11.85, 11.85 Hz, 2H, H3-a H3-a') $^{13}$C NMR (125 MHz, CD3OD): δ ppm 175.5 174.7 174.5 170.0 145.6 141.3 134.5 130.0 129.1 129.0 128.2 128.0 102.0 74.3 72.6 71.5 69.7 63.9 54.2 44.5 42.8 40.0 37.6 31.3 29.4 28.7 22.7

HRMS (ESI-neg) [(M-2Na)/2] calculated: 645.2362 found: 645.2340

3,4-Di[2-[2-[2-(tert-butyloxycarbonylamino)ethyloxy]ethyloxy]ethylamine]-3-cyclobutene-1,2-dione (compound 47)

A solution of 50 mg (1 eq) of 3,4-diethoxy-3-cyclobutene-1,2-dione and 201 mg (2.75 eq) of compound 247 in 2 ml of MeOH was admixed with 0.40 ml (10 eq) of TEA and then stirred at RT for 2 h. Then 50 μl of 2M NaOH were added, stirring took place at RT for 10 min, the solvent was removed and the residue was purified on a silica gel column (EE>>EE: EtOH 5:1). Yield: 140 mg of colourless oil.

3,4-Di[2-[2-[2-(amino)ethyloxy]ethyloxy]ethylamine]-3-cyclobutene-1,2-dione dihydrochloride (compound 48)

A solution of 30 mg of compound 47 in 0.5 ml of EtOH and 1 ml of H$_2$O was admixed with 0.2 ml of 2M HCl, stirred overnight, and the solvent was removed, and the product was dissolved three times with H$_2$O and concentrated again. Yield: 23 mg of white solid.

Compound 49

A solution of 5 mg of 1,4-phenylene diisocyanate and 43 mg (2.1 eq) of compound 11 in 1 ml of DMF was admixed with 16 μl of DIPEA, and the mixture was stirred at RT for 30 min and at 50° C. for 15 min. The solvent was removed, the residue was dissolved with a little MeOH, H$_2$O was added until colloidal clouding occurred, and purification took place on an RP-18 column (H$_2$O>>MeOH). The product fractions were concentrated, dissolved with a little MeOH, diluted with H$_2$O until clouding occurred, and brought to a pH of 12-13 with 2M NaOH. When the reaction was ended, neutralization took place with 20% HAc and purification was carried out on an RP18 column (H$_2$O>>MeOH), the MeOH was removed, and lyophilization was carried out.

Yield: 38 mg of white solid.

$^1$H NMR (300 MHz, CD3OD): δ ppm 1.53-1.66 (m, 2H, H3-a H3-a'), 1.74-1.86 (m, 4H, CH2CH2CH2 CH2 CH2CH2'), 2.00 (s, 6H, NHAc NHAc'), 2.57-2.67 (m, 8H, CH2SCH2 CH2SCH2'), 2.85 (dd, J=12.09, 3.71 Hz, 2H, H3-e H3-e'), 3.31-3.37 (m, 4H, CH2NH CH2NH'), 3.42-3.93 (m, 16H, H4 H4' H5 H5' H6 H6' H7 H7' H9a H9a' H9b H9b'OCH2a OCH2a' OCH2b OCH2b'), 4.09 (dt, J=8.20, 8.09, 3.02 Hz, 2H, H8 H8'), 7.24 (s, 4H, Ar), 7.28-7.47 (m, 6H, Ar), 7.65 (dd, J=15.38, 7.85 Hz, 8H, Ar), 7.90 (d, J=8.20 Hz, 4H, Ar) $^{13}$C NMR (75 MHz, CD3OD): δ ppm 22.7 29.2 31.3 33.2 40.3 42.8 44.5 54.2 63.7 69.6 71.6 72.6 74.3 102.0 121.4 128.0 128.2 129.0 129.1 130.0 134.5 135.8 141.3 146.0 158.4 170.0 174.6 175.5

HRMS (ESI-neg) [(M-2Na)/2] calculated: 684.2471 found: 684.2517

Compound 50

A solution of 30 mg of compound 11 in 2 ml of H$_2$O was admixed with 100 μl of 2M NaOH, stirred at RT for 2 h, neutralized with 2M HCl, and purified on an RP-18 column (H$_2$O>>EtOH).

Compound 51

A solution of 15 mg of compound 11 and 7.0 mg (1.8 eq) of 3,4-diethoxy-3-cyclobutene-1,2-dione in 1 ml of MeOH was admixed with 65 μl (20 eq) of TEA, stirred for 30 min, concentrated, purified on an RP-18 column (H$_2$O>>EtOH) and concentrated. The residue was dissolved in 1 ml of H$_2$O, admixed with 15 mg of compound 13 and 100 μl of 2M NaOH, stirred for 2 h, neutralized with 20% strength HAc, purified on an RP-18 column (H$_2$O>>EtOH), and the EtOH was removed, and lyophilization was carried out. Yield: 19 mg of white solid $^1$H-NMR (300 MHz, CD$_3$OD): δ ppm 1.59 (t, J=11.73, 11.73 Hz, 2H, H3-a H3-a'), 1.81 (p, J=7.08, 7.08, 6.90, 6.90 Hz, 4H, CH2CH2CH2 CH2CH2CH2'), 1.99 (s, 6H, NHCO CH3 NHCOCH3'), 2.63 (dt, J=7.03, 6.78, 3.06 Hz, 4H, CH2S CH2S'), 2.71 (t, J=6.84, 6.84 Hz, 4H, SCH2 SCH2'), 2.83 (dd, J=12.23, 4.08 Hz, 2H, H3-e H3-e'), 3.45 (dd, J=8.94, 1.36 Hz, 2H, H7 H7'), 3.51-3.76 (m, 14H, H4 H4' H5 H5' H6 H6' H9a H9a' OCH2a OCH2a' CH2NH CH2NH'), 3.81 (dd, J=13.78, 3.31 Hz, 2H, H9b H9b'), 3.88 (td, J=8.50, 5.83, 5.83 Hz, 2H, OCH2b OCH2b'), 4.08 (ddd, J=8.94, 7.61, 3.19 Hz, 2H, H8 H8'), 7.36 (t, J=7.29, 7.29 Hz, 2H, Ar), 7.45 (t, J=7.34, 7.34 Hz, 4H, Ar), 7.65 (dd, J=7.19, 1.51 Hz, 4H, Ar), 7.70 (d, J=8.37 Hz, 4H, Ar), 7.92 (d, J=8.64 Hz, 4H, Ar) $^{13}$C NMR (75 MHz, CD3OD): δ ppm 22.7 29.3 31.4 34.1 42.7 44.3 44.5 54.1 63.9 69.7 71.7 72.5 74.2 102.0 128.0 128.1 129.0 130.0 134.5 141.3 145.7 170.0 174.5 175.4 182.3 189.9

Compound 52

A solution of 35.0 mg (2.3 eq) of compound 11 and 2.8 mg (1 eq) of terephthalaldehyde in abs. MeOH was admixed with 5.8 μl (2 eq) of TEA, after an hour with 4.6 mg (3 eq) of sodium cyanoborohydride, and after 24 h with 100 μl of acetic acid (20% strength). The solvent was removed, the residue was dissolved with H$_2$O and purified on an RP-18 column (H$_2$O>>MeOH), and the product fractions were concentrated and brought to a pH of 12-13 with 2M NaOH. When the reaction was ended, neutralization was carried out with 20% HAc, purification took place on an RP18 column (H$_2$O>>CH$_3$CN), the CH$_3$CN was removed, and lyophilization was carried out. Yield: 7 mg of white solid. $^1$H-NMR (300 MHz, CD$_3$OD): δ ppm 1.56 (t, J=11.57, 11.57 Hz, 2H, H3-a H-3a'), 1.70-1.80 (m, 4H, CH2CH2CH2 CH2CH2CH2'), 2.01 (s, 6H, NHCOCH3 NHCOCH3'), 2.59 (t, J=6.90, 6.90 Hz, 4H, CH2S CH2S'), 2.78-2.88 (m, 6H, H3-e H3-e' SCH2 SCH2'), 3.19 (t, J=7.27, 7.27 Hz, 4H, CH2NH CH2NH'), 3.33-3.93 (m, 18H, H4 H4' H5 H5' H6 H6' H7 H7' H9a H9a' H9b H9b' OCH2a OCH2a' OCH2b OCH2b' CH2ArCH2-a), 4.08 (dt, J=8.35, 8.34, 3.13 Hz, 2H, H8 H8'), 4.25 (s, 2H, CH2ArCH2-b), 7.36 (t, J=7.28, 7.28 Hz, 2H, Ar), 7.45 (t, J=7.32, 7.32 Hz, 4H, Ar), 7.58 (s, 4H, Ar), 7.64 (d, J=7.11 Hz, 4H, Ar), 7.69 (d, J=8.42 Hz, 4H, Ar), 7.90 (d, J=8.51 Hz, 4H, Ar)

HRMS (ESI-neg) [(M-2Na)/2] calculated: 655.2569 found: 655.2548

Compound 53

A solution of 25 mg of compound 10 and 16.1 mg (1.1 eq) of HATU is admixed with 19.9 μl (3 eq) of DIPEA, stirred at RT for 5 min, and admixed with 7.9 mg (1.5 eq) of 4-aminobenzoic acid. After a further 5 min it is concentrated and the product is purified on an RP-18 (H$_2$O>>EtOH), the EtOH is removed, and lyophilization is carried out. Yield: 15 mg of white solid.

Compound 54

A solution of 20 mg (1 eq) of compound 53 and 10 mg (1 eq) of HATU in 1 ml of abs. DMF was admixed with 13.4 μl (3 eq) of DIPEA, stirred at RT for 5 min, admixed with 19 mg (1.2 eq) of compound 11, and stirred for 5 min. The solvent was removed, the residue was dissolved with MeOH, H$_2$O was added until clouding occurred, and purification was carried out on an RP-18 column (H$_2$O>>MeOH). The product was dissolved with a little MeOH, diluted with H$_2$O until clouding occurred, and brought to a pH of 12-13 with 2M NaOH. When the reaction was ended, neutralization was carried out with 20% HAc, purification took place on an RP18 column (H$_2$O>>CH$_3$CN), the CH$_3$CN was removed, and lyophilization was carried out. Yield: 26 mg of white solid. $^1$H NMR (300 MHz, CD3OD): δ ppm, 1.68-1.87 (m, 6H, H3-a H3-a' CH2CH2CH2 CH2CH2CH2'), 1.99 (s, 6H, NHCOCH3 NHCOCH3'), 2.53-2.75 (m, 10H, CH2SCH2 CH2SCH2' H3-e H3-e'), 2.81 (t, J=7.02, 7.02 Hz, 2H, CH2CONH), 3.44-3.94 (m, 18H, H4 H4' H5 H5' H6 H6' H7 H7' H9a H9a' H9b H9b' OCH2 OCH2' CH2NHCO), 4.04-4.13 (m, 2H, H8 H8'), 7.32-7.47 (m, 6H, Ar), 7.58-7.77 (m, 12H, Ar), 7.86-7.94 (m, 4H, Ar) $^{13}$C NMR (75 MHz, CD3OD): δ ppm 22.7 22.8 28.5 29.0 29.4 30.9 31.0 32.0 38.5 40.1 41.9 44.9 53.9 63.8 68.9 71.4 72.4 74.8 100.2 120.4 128.0 128.1 129.0 129.129.2 130.0 130.6 134.4 141.3 143.0 145.6 170.3 169.6 172.2 172.9 175.3

HRMS (ESI-neg) [(M-2Na)/2] calculated: 669.2362 found: 669.2392

Compound 55

Prepared analogously to compound 9

Compound 56

Prepared analogously to compound 11

Compounds 57 and 58

Prepared analogously to compound 21

Compound 57

$^1$H-NMR (300 MHz, CD$_3$OD): δ ppm 1.21-1.50 (m, 10H, cyclohexyl cyclohexyl'), 1.57 (t, J=11.82, 11.82 Hz, 2H, H3-a H3a'), 1.70-1.87 (m, 14H, cyclohexyl cyclohexyl' CH2 CH2CH2CH2 CH2CH2CH2'), 1.99 (s, 6H, NHAc NHAc'), 2.47-2.59 (m, 2H, cyclohexyl cyclohexyl'), 2.65 (dt, J=6.88, 6.71, 1.42 Hz, 4H, CH2SCH2 CH2SCH2'), 2.74 (dt, J=7.11, 7.07, 0.92 Hz, 4H, CH2SCH2 CH2SCH2'), 2.82 (dd, J=12.24, 4.00 Hz, 2H, H3-e H3-e'), 3.40-3.93 (m, 20H, H4 H4' H5 H5' H6 H6' H7 H7' H9a H9a' H9b H9b' OCH2a OCH2a' OCH2b OCH2b' CH2NH CH2NH'), 4.07 (dt, J=7.84, 7.81, 3.23 Hz, 2H, H8 H8'), 7.26 (d, J=8.35 Hz, 4H, Ar), 7.73 (d, J=8.32 Hz, 4H, Ar), 7.90 (s, 4H, Ar) $^{13}$C NMR (75 MHz, CD3OD): δ ppm 22.7 27.2 27.9 35.4 29.4 31.4 31.9 41.0 42.7 44.4 45.9 54.2 63.8 69.6 71.6 72.5 74.3 102.0 128.0 128.4 128.6 133.3 138.4 153.2 169.3 170.3 174.5 175.5

HRMS (ESI-neg) [(M-2Na)/2] calculated: 677.2082 found: 677.2097

Compound 58

$^1$H-NMR (300 MHz, CD$_3$OD): δ ppm 1.28-1.51 1.81-1.89 (m, 24H, cyclohexyl cyclohexyl'), 1.56-1.66 (m, 6H, CH2 CH2CH2CH2 H3-a H3-a'), 1.72-1.82 (m, 4H, CH2CH2CH2 CH2CH2CH2'), 1.98 (s, 6H, NHAc NHAc'), 2.15-2.25 (m, 4H, CH2CH2CH2CH2), 2.50-2.67 (m, 10H, CH2SCH2 CH2SCH2' (CH) cyclohexyl (CH) cyclohexyl'), 2.83 (dd, J=12.29, 4.15 Hz, 2H, H3-e H3-e'), 3.27-3.36 (m, 4H, CH2NH CH2NH'), 3.38-3.93 (m, 16H, H4 H4' H5 H5' H6 H6' H7 H7' H9a H9a' H9b H9b' OCH2a OCH2a' OCH2b OCH2b'), 4.05 (dt, J=7.77, 7.68, 3.20 Hz, 2H, H8 H8'), 7.29 (d, J=8.28 Hz, 4H, Ar), 7.75 (d, J=8.29 Hz, 4H, Ar) $^{13}$C NMR (75 MHz, CD3OD): δ ppm 22.7 26.6 27.2 27.9 29.3 31.4 32.2 35.5 36.7 40.3 42.8 44.4 45.9 54.2 63.8 69.6 71.5 72.5 74.3 102.0 128.0 128.5 133.3 153.2 170.3 174.5 175.5 175.9

HRMS (ESI-neg) [(M-2Na)/2] calculated: 655.2988 found: 655.3010

Compound 59

A solution of 1.06 g (1 eq) of compound 6 and 660 ml of TEA (2 eq) in 10 ml of abs. DMF was admixed with 937 mg (1.2 eq) of Fmoc-NHS. After 2 h of stirring, the solvent was removed, the residue was purified on a silica gel column (EE:EtOH 10:1 >>5:1) and concentrated, and lyophilization took place from H$_2$O-dioxane. Yield: 1145 mg of white solid.

Compound 60

A solution of 1145 mg of compound 59 in 5 ml of MeOH was admixed with 2228 mg (10 eq) of cysteamine hydrochloride and flushed with nitrogen for 20 min. Following addition of a catalytic amount (2-3 mg) of AIBN, irradiation with UV light took place for 24 h, the solvent was removed, and the residue was dissolved with H$_2$O and purified on an RP-18 column (HCl pH4 >>MeOH/HCl pH4). The product fractions were neutralized with dilute NaOH, the MeOH was removed, and lyophilization was carried out. Yield: 1030 mg of white solid.

Compound 61

A solution of 40 mg of terephthalic acid, 370 mg (2.2 eq) of compound 60 and 220 mg (2.4 eq) of HATU in 5 ml of abs. DMF was admixed with 165 ml (4 eq) of DIPEA and stirred at RT for 5 min. The solvent was removed, the residue was dissolved with a little MeOH, H$_2$O was added until colloidal clouding occurred, and purification took place on an RP-18 column (H$_2$O>>MeOH). The product fractions were concentrated, dissolved with a dioxane-H2O mixture and lyophilized. Yield: 396 mg of white solid.

Compound 62

A solution of 35 mg (1 eq) of compound 61 in 800 μl of absolute DMF was admixed with 200 μl of piperidine and stirred at RT for 20 min. The solvent was removed, the residue was dissolved with 1 ml of abs. DMF, and concentration took place again. Following dissolution of the residue in 1 ml of abs. DMF, 12 mg (2.4 eq) of 2,2'-bithiothiophene-5-carboxylic acid and 22 mg (2.4 eq) of HATU were added, followed by addition of 25 μl (6 eq) of Dipea, with stirring, followed by stirring at RT for 5 min. The solvent was removed, the residue was dissolved with a little MeOH, H2O was added until colloidal clouding occurred, and purification took place on an RP-18 column (H$_2$O>>MeOH). The product fractions were concentrated, purified using thin-layer plates (EtOH:EE:HAc (20%) 1:5:1), dissolved with a little MeOH, diluted with H$_2$O until clouding occurred, and brought to a pH of 12-13 with 2M NaOH. When the reaction was ended, neutralization took place with 20% HAc, purification was carried out on an RP18 column (H$_2$O>>CH$_3$CN), the CH$_3$CN was removed, and lyophilization was carried out. Yield: 12 mg of white solid.

$^1$H-NMR (300 MHz, CD$_3$OD): δ ppm 1.57 (t, J=11.75, 11.75 Hz, 2H, H3-a H3-a'), 1.87-1.77 (m, 4H, CH2CH2CH2 CH2CH2CH2'), 2.00 (s, 6H, NHCOCH3 NHCOCH3'), 2.66 (t, J=7.10, 7.10 Hz, 4H, CH2SCH2 CH2SCH2'), 2.75 (dt, J=7.12, 7.10, 0.92 Hz, 4H, CH2SCH2 CH2SCH2'), 2.83 (dd, J=12.26, 3.62 Hz, 2H, H3-e H3-e'), 3.42 (dd, J=8.98, 1.57 Hz, 2H, H7 H7'), 3.40-3.74 (m, 10H, H4 H4' H5 H5'H6 H6' H9a H9a' OCH2a OCH2a'), 3.79 (dd, J=13.64, 3.07 Hz, 2H, H9b H9b'), 3.89 (td, J=9.47, 6.18, 6.18 Hz, 2H, OCH2b OCH2b'), 4.06 (ddd, J=8.94, 8.07, 3.05 Hz, 2H, H8 H8'), 7.04 (dd, J=5.12, 3.65 Hz, 2H, Ar), 7.16 (d, J=3.92 Hz, 2H, Ar), 7.28 (dd, J=3.63, 1.11 Hz, 2H, Ar), 7.39 (dd, J=5.12, 1.12 Hz, 2H, Ar), 7.59 (d, J=3.95 Hz, 2H, Ar), 7.88 (s, 4H, Ar) $^{13}$C NMR (75 MHz, CD3OD): δ ppm 22.7 29.4 31.5 32.0 41.0 42.8 44.4 54.2 63.8 69.6 71.5 72.5 74.3 102.0 125.1 126.1 127.0 128.6 129.2 130.5 134.5 137.6 138.4 138.5 143.3 164.2 169.4 175.5

HRMS (ESI-neg) [(M-2Na)/2] calculated: 681.1490 found: 681.1490

Compound 63, 64, 65, 66, 67, 68, 69, 70, 71, 72, 73, 74, 75, 76, 77, 78, 79, 80, 81, 82, 83

Prepared analogously to compound 62. Compound 130 was used.

Compound 63

$^1$H-NMR (300 MHz, CD$_3$OD): δ ppm 1.51-1.62 (m, 2H, H3-a H3-a'), 1.78-1.84 (m, 4H, CH2CH2CH2 CH2CH2CH2'), 1.99 (s, 6H, NHAc NHAc'), 2.65 (t, J=6.86, 6.86 Hz, 4H, CH2SCH2 CH2SCH2'), 2.74 (dt, J=7.20, 7.07, 1.46 Hz, 4H, CH2SCH2 CH2SCH2'), 2.82 (dd, J=12.13, 3.14 Hz, 2H, H3-e H3-e'), 3.37-3.94 (m, 20H, H4 H4' H5 H5' H6 H6' H7 H7' H9a H9a' H9b H9b' OCH2a OCH2a' OCH2b OCH2b' CH2NH CH2NH'), 4.07 (dt, J=8.02, 7.97, 3.05 Hz, 2H, H8 H8'), 6.96 (d, J=8.83 Hz, 4H, Ar), 7.02 (dd, J=8.63, 1.06 Hz, 4H, Ar), 7.17 (t, J=7.42, 7.42 Hz, 2H, Ar), 7.38 (dd, J=8.53, 7.42 Hz, 4H, Ar), 7.82 (d, J=8.79 Hz, 4H, Ar), 7.89 (s, 4H, Ar) $^{13}$C NMR (75 MHz, CD3OD): δ ppm 22.7 29.4 31.5 32.0 41.1 42.8 44.5 54.2 63.8 69.6 71.5 72.6 74.3 102.0 118.6 120.9 125.5 128.6 130.2 130.4 131.2 138.4 157.5 162.0 169.4 169.6 173.7 175.5

HRMS (ESI-neg) [(M-2Na)/2] calculated: 685.2311 found: 685.2362

Compound 64

$^1$H-NMR (300 MHz, CD$_3$OD): δ ppm 1.57 (t, J=11.77, 11.77 Hz, 2H, H3-a H3-a'), 1.74-1.87 (m, 4H, CH2CH2CH2 CH2CH2CH2'), 2.00 (s, 6H, NHCOCH3 NHCOCH3'), 2.62-2.70 (m, 4H, CH2SCH2 CH2SCH2'), 2.74 (dt, J=7.13, 7.02, 1.38 Hz, 4H, CH2SCH2CH2SCH2'), 2.83 (dd, J=12.23, 4.03 Hz, 2H, H3-e H3-e'), 3.41-3.74 (m, 16H, H4 H4' H5 H5' H6 H6' H7 H7' H9a H9a' OCH2a OCH2a' CH2NHCO CH2NHCO'), 3.84 (dd, J=13.60, 3.29 Hz, 2H, H9b H9b'), 3.85-3.94 (m, 2H, OCH2b OCH2b'), 4.10 (ddd, J=8.91, 8.00, 3.28 Hz, 2H, H8 H8'), 7.05 (t, J=8.74, 8.74 Hz, 4H, Ar), 7.50 (t, J=8.50, 8.50 Hz, 2H, Ar), 7.57 (dd, J=8.35, 1.49 Hz, 4H, Ar), 7.87 (s, 4H, Ar), 7.90 (d, J=8.45 Hz, 4H, Ar) $^{13}$C NMR (75 MHz, CD3OD): δ ppm 22.7 29.4 31.5 32.0 41.0 42.8 44.6 54.2 63.8 69.6 71.4 72.7 74.3 102.0 105.3 (dd, J=26.80, 25.89 Hz) 112.9 (dd, J=21.42, 3.91 Hz) 128.6 128.7 130.0 130.1 133.01 (dd, J=9.69, 4.65 Hz) 135.1 138.4 139.4 164.34 (dd, J=223.41, 12.15 Hz) 169.3 169.8 174.5 175.5

HRMS (ESI-neg) [(M-2Na)/2] calculated: 705.2173 found: 705.2179

Compound 65

$^1$H-NMR (300 MHz, CD$_3$OD): δ ppm 1.59 (t, J=11.67, 11.67 Hz, 2H, H3-a H3-a'), 1.76-1.87 (m, 4H, CH2CH2CH2 CH2CH2CH2'), 2.00 (s, 6H, NHCOCH3 NHCOCH3'), 2.65 (t, J=7.09, 7.09 Hz, 4H, SCH2CH2CH2 SCH2CH2CH2'), 2.74 (t, J=6.99, 6.99 Hz, 4H, CH2S CH2S'), 2.82 (dd, J=12.18, 3.64 Hz, 2H, H3-e H3-e'), 3.39-3.75 (m, 16H, H4 H4' H5 H5' H6 H6' H7 H7' H9a' H9b' CH2NH CH2NH' OCH2a OCH2a'), 3.81 (dd, J=13.49, 3.14 Hz, 2H, H9b H9b'), 3.89 (td, J=9.60, 6.16, 6.16 Hz, 2H, OCHb OCH2b'), 4.08 (ddd, J=8.80, 8.19, 3.05 Hz, 2H, H8 H8'), 7.26-7.45 (m, 8H, Ar), 7.59-7.70 (m, 6H, Ar), 7.87 (s, 4H, Ar) $^{13}$C NMR (75 MHz, CD3OD): δ ppm 22.7 29.4 31.4 32.0 41.0 42.7 44.4

54.2 63.8 69.6 71.6 72.5 74.3 101.8 124.8 124.9 127.0 127.1 128.6 129.6 129.7 130.2 130.7 134.9 138.4 139.0 150.2 164.4 169.3 174.3 175.5

Compound 66

$^1$H-NMR (300 MHz, CD$_3$OD): δ ppm 1.54 (t, J=11.66, 11.66 Hz, 2H, H3-a H3-a'), 1.70-1.81 (m, 4H, CH2CH2CH2 CH2CH2CH2'), 1.93 (s, 6H, NHCOCH3 NHCOCH3'), 2.61 (t, J=7.18, 7.18 Hz, 4H, SCH2CH2CH2 SCH2CH2CH2'), 2.71 (dt, J=6.85, 6.85, 3.64 Hz, 4H, SCH2 SCH2'), 2.81 (dd, J=12.22, 4.11 Hz, 2H, H3-e H3-e'), 3.21 (dd, J=13.65, 8.01 Hz, 2H, H9a H9a'), 3.30-3.36 (m, 2H, H7 H7'), 3.46-3.75 (m, 18H, H4 H4' H5 H5' H6 H6' H9b H9b' CH2NH CH2NH' CH2ArCH2Ar' OCH2a OCH2a'), 3.82 (td, J=9.52, 6.05, 6.05 Hz, 2H, OCH2b OCH2b'), 3.95 (dt, J=8.31, 8.23, 2.87 Hz, 2H, H8 H8'), 7.37-7.46 (m, 6H, Ar), 7.74-7.81 (m, 6H, Ar), 7.89 (s, 4H, Ar) $^{13}$C NMR (75 MHz, CD3OD): δ ppm 22.6 29.4 31.5 32.0 41.1 42.8 44.0 44.1 54.2 63.7 69.6 71.4 72.3 74.2 101.9 126.7 127.2 128.4 128.6 128.7 128.8 128.9 129.2 133.9 134.7 135.0 138.4 169.4 174.1 174.5 175.5

HRMS (ESI-neg) [(M-2Na)/2] calculated: 657.2362 found: 657.2367

Compound 67

$^1$H-NMR (300 MHz, CD$_3$OD): δ ppm 1.58 (t, J=11.73, 11.73 Hz, 2H, H3-a H3-a'), 1.77-1.87 (m, 4H, CH2CH2CH2 CH2CH2CH2'), 2.00 (s, 6H, NHCOCH3 NHCOCH3'), 2.65 (t, J=6.98, 6.98 Hz, 4H, CH2S CH2S'), 2.73 (t, J=7.12, 7.12 Hz, 4H, SCH2 SCH2'), 2.83 (dd, J=11.89, 3.30 Hz, 2H, H3-e H3-e'), 3.41-3.75 (m, 16H, H4 H4' H5 H5' H6 H6' H7 H7' H9a H9a' OCH2a OCH2a' CH2NH CH2NH'), 3.80-3.94 (m, 4H, H9b H9b' OCH2b OCH2b'), 4.10 (dt, J=8.20, 8.10, 3.17 Hz, 2H, H8 H8'), 6.85 (d, J=8.61 Hz, 4H, Ar), 7.47 (d, J=8.48 Hz, 4H, Ar), 7.59 (d, J=8.26 Hz, 4H, Ar), 7.84 (d, J=8.57 Hz, 4H, Ar), 7.85 (s, 4H, Ar) $^{13}$C NMR (75 MHz, CD3OD): δ ppm 22.7 29.3 31.5 31.9 41.0 42.8 44.5 54.2 63.8 69.6 71.5 72.6 74.3 102.0 116.8 127.3 128.6 128.9 129.3 132.5 133.5 138.4 145.5 158.9 169.3 170.1 174.5 175.5

HRMS (ESI-neg) [(M-2Na)/2] calculated: 685.2311 found: 685.2311

Compound 68

$^1$H-NMR (300 MHz, CD$_3$OD): δ ppm 1.62 (t, J=11.41, 11.41 Hz, 2H, H3-a H3-a'), 1.77-1.87 (m, 4H, CH2 CH2CH2), 2.00 (s, 6H, NHCOCH3 NHCOCH3'), 2.61-2.83 (m, 10H, CH2SCH2 CH2SCH2' H3-e H3-e'), 3.42-3.96 (m, 20H, H4 H4' H5 H5' H6 H6' H7 H7' H9a H9a' H9b H9b' OCH2a OCH2a' OCH2b OCH2b' CH2NH CH2NH'), 4.12 (dt, J=8.20, 8.08, 3.10 Hz, 8H, H8 H8'), 7.73 (d, J=8.51 Hz, 8H, Ar), 7.84 (s, 4H, Ar), 7.92 (d, J=8.25 Hz, 4H, Ar), 8.08 (d, J=8.28 Hz, 4H, Ar)

HRMS (ESI-neg) [(M-2Na)/2] calculated: 713.2260 found: 713.2239

Compound 69

$^1$H-NMR (300 MHz, CD$_3$OD): δ ppm 1.57 (t, J=11.69, 11.69 Hz, 2H, H3-a H3-a'), 1.77-1.87 (m, 4H, CH2CH2CH2 CH2CH2CH2'), 2.02 (s, 6H, NHCOCH3 NHCOCH3'), 2.66 (t, J=7.02, 7.02 Hz, 4H, CH2S CH2S'), 2.71-2.78 (m, 4H, SCH2 SCH2'), 2.83 (dd, J=12.51, 4.04 Hz, 2H, H3-e H3-e'), 3.41-3.97 (m, 20H, H4 H4' H5 H5' H6 H6' H7 H7' H9a H9a' H9b H9b' OCH2a OCH2a' OCH2b OCH2b' CH2NH CH2NH'), 4.13 (dt, J=8.28, 8.22, 2.88 Hz, 2H, H8 H8'), 7.53 (d, J=7.99 Hz, 2H, Ar), 7.71 (d, J=8.56 Hz, 2H, Ar), 7.86 (s, 4H, Ar), 8.26 (dd, J=7.95, 1.79 Hz, 2H, Ar), 8.61 (dd, J=8.47, 2.35 Hz, 2H, Ar), 8.75 (d, J=1.43 Hz, 2H, Ar), 9.03 (d, J=2.23 Hz, 2H, Ar) $^{13}$C NMR (75 MHz, CD3OD): δ ppm 22.7 29.4 31.5 32.0 41.0 42.8 44.9 54.2 63.8 69.6 71.4 72.7 74.3 102.0 121.1 125.0 128.6 129.0 132.4 133.6 133.9 136.4 138.0 138.4 141.0 148.1 148.5 149.4 167.3 169.3 174.5 175.6

HRMS (ESI-neg) [(M-2Na)/2] calculated: 804.1914 found: 804.1964

Compound 70

$^1$H-NMR (300 MHz, CD$_3$OD): δ ppm 1.69 (t, J=11.97, 11.97 Hz, 2H, H3a H3a'), 1.77-1.87 (m, 4H, CH2CH2CH2 CH2CH2CH2'), 1.99 (s, 6H, NHCOCH3 NHCOCH3'), 2.61-2.77 (m, 10H, H3-e H3-e' CH2SCH2 CH2SCH2'), 3.43-3.95 (m, 20H, H4 H4' H5 H5' H6 H6' H7 H7' H9a H9a' H9b H9b' OCH2a OCHa' OCH2b OCH2b' CH2NH CH2NH'), 4.09 (dt, J=7.93, 7.92, 3.21 Hz, 2H, H8 H8'), 7.36-7.42 (m, 4H, Ar), 7.82-7.89 (m, 8H, Ar), 7.93 (s, 2H, Ar)

HRMS (ESI-neg) [(M-2Na)/2] calculated: 649.1769 found: 649.1724

Compound 71

$^1$H-NMR (300 MHz, CD$_3$OD): δ ppm 1.57 (t, J=11.68, 11.68 Hz, 2H, H3-a H3-a'), 1.77-1.87 (m, 4H, CH2CH2CH2 CH2CH2CH2'), 2.00 (s, 6H, NHCOCH3 NHCOCH3'), 2.66 (t, J=7.08, 7.08 Hz, 4H, CH2S CH2S'), 2.75 (dt, J=7.10, 7.02, 2.21 Hz, 4H, SCH2 SCH2'), 2.83 (dd, J=12.07, 3.85 Hz, 2H, H3-e H3-e'), 3.39-3.74 (m, 16H, H4 H4' H5 H5' H6 H6' H7 H7' H9a H9a' OCH2a OCH2a' CH2NH CH2NH'), 3.79-3.92 (m, 4H, H9b H9b' OCH2b OCH2b'), 4.09 (dt, J=8.31, 8.20, 3.17 Hz, 2H, H8 H8'), 7.74 (d, J=8.36 Hz, 4H, Ar), 7.90 (s, 4H, Ar), 7.99 (d, J=8.15 Hz, 4H, Ar) $^{13}$C NMR (75 MHz, CD3OD): δ ppm 22.7 29.3 31.3 32.0 41.1 42.8 44.7 54.2 63.8 69.6 71.3 72.7 74.3 102.0 126.5 128.6 129.2 138.4 139.7 169.0 169.4 174.5 175.6

HRMS (ESI-neg) [(M-2Na)/2] calculated: 661.1922 found: 661.1973

Compound 72

$^1$H-NMR (500 MHz, CD$_3$OD): δ ppm 1.56 (t, J=11.71, 11.71 Hz, 2H, H3-a H3-a'), 1.78-1.85 (m, 4H, CH2CH2CH2 CH2CH2CH2'), 2.00 (s, 6H, NHCOCH3 NHCOCH3'), 2.66 (dt, J=7.02, 6.86, 2.63 Hz, 4H, CH2S CH2S'), 2.75 (dd, J=12.31, 6.75 Hz, 4H, SCH2 SCH2'), 2.82 (dd, J=12.25, 3.85 Hz, 2H, H3-e H3-e'), 3.42 (dd, J=8.97, 1.88 Hz, 2H, H7 H7'), 3.47 (dd, J=13.68, 7.86 Hz, 2H, H9a H9a'), 3.51-3.73 (m, 12H, H4 H4' H5 H5' H6 H6' OCH2a OCH2a' CH2NH CH2NH'), 3.80 (dd, J=13.57, 3.19 Hz, 2H, H9b H9b'), 3.88 (td, J=9.71, 6.19, 6.19 Hz, 2H, OCH2b OCH2b'), 4.07 (dt, J=8.71, 8.39, 3.24 Hz, 2H, H8 H8'), 7.43 (d, J=8.84 Hz, 4H, Ar), 7.80 (d, J=8.84 Hz, 4H, Ar), 7.90 (s, 4H, Ar) $^{13}$C NMR (125 MHz, CD3OD): δ ppm 22.7 29.4 31.5 32.0 41.1 42.8 44.6 54.2 63.8 69.6 71.4 72.6 74.3 102.0 128.6 129.7 130.1 134.6 138.4 138.6 169.2 169.4 174.5 175.5

HRMS (ESI-neg) [(M-2Na)/2] calculated: 627.1659 found: 627.1640

Compound 73

$^1$H-NMR (300 MHz, CD$_3$OD): δ ppm 1.57 (t, J=11.80, 11.80 Hz, 2H, H3-a H3-a'), 1.76-1.87 (m, 4H, CH2CH2CH2 CH2CH2CH2'), 1.99 (s, 6H, NHCOCH3 NHCOCH3'), 2.13 (s, 6H, NHCOCH3 NHCOCH3'), 2.61-2.69 (m, 4H, CH2S CH2S'), 2.70-2.77 (m, 4H, SCH2 SCH2'), 2.82 (dd, J=12.22, 4.05 Hz, 2H, H3-e H3-e'), 3.39-3.73 (m, 16H, H4 H4' H5 H5' H6 H6' H7 H7' H9a H9a' OCH2a OCH2a' CH2NH CH2NH'), 3.80 (dd, J=13.64, 3.10 Hz, 2H, H9b H9b'), 3.88 (td, J=9.66, 6.03, 6.03 Hz, 2H, OCH2b OCH2b'), 4.07 (dt, J=8.18, 7.96, 2.98 Hz, 2H, H8 H8'), 7.63 (d, J=8.74 Hz, 4H, Ar), 7.78 (d, J=8.74 Hz, 4H, Ar), 7.89 (s, 4H, Ar) $^{13}$C NMR (75 MHz, CD3OD): δ ppm 22.7 24.1 29.4 31.5 32.0 41.0 42.8 44.5 54.2 63.8 69.6 71.5 72.5 74.3 102.0 120.3 128.6 129.2 130.8 138.4 143.1 169.4 169.7 171.9 174.5 175.5

HRMS (ESI-neg) [(M-2Na)/2] calculated: 650.2263 found: 650.2258

Compound 74

$^1$H-NMR (300 MHz, CD$_3$OD): δ ppm 1.58 (t, J=11.80, 11.80 Hz, 2H, H3-a H3-a'), 1.77-1.87 (m, 4H, CH2$\underline{CH2}$CH2 CH2$\underline{CH2}$CH2'), 2.01 (s, 6H, NHCO$\underline{CH3}$ NHCO$\underline{CH3}$'), 2.66 (dt, J=7.34, 7.20, 0.97 Hz, 4H, $\underline{CH2}$S $\underline{CH2}$S'), 2.74 (dt, J=7.25, 7.14, 1.46 Hz, 4H, SCH2 SCH2'), 2.83 (dd, J=12.14, 4.08 Hz, 2H, H3-e H3-e'), 3.45 (dd, J=8.95, 1.70 Hz, 2H, H7 H7'), 3.47-3.79 (m, 14H, H4 H4' H5 H5' H6 H6' H9a H9a' OCH2a OCH2a' CH2NH CH2NH'), 3.77 (s, 6H, OCH3 OCH3'), 3.84 (dd, J=13.57, 3.24 Hz, 2H, H9b H9b'), 3.90 (td, J=9.68, 6.13, 6.13 Hz, 2H, OCH2b OCH2b'), 4.11 (ddd, J=8.74, 7.80, 3.30 Hz, 2H, H8 H8'), 7.00 (dt, J=7.45, 7.45, 1.08 Hz, 2H, Ar), 7.06 (dd, J=8.32, 0.89 Hz, 2H), 7.27 (dd, J=7.59, 1.66 Hz, 2H, Ar), 7.32 (dd, J=7.33, 1.74 Hz, 2H, Ar), 7.34 (dd, J=7.37, 1.75 Hz, 4H, Ar), 7.54 (d, J=8.63 Hz, 4H, Ar), 7.83 (d, J=8.62 Hz, 4H, Ar), 7.86 (s, 4H, Ar) $^{13}$C NMR (75 MHz, CD3OD): δ ppm 22.7 29.4 31.5 31.9 41.0 42.8 44.6 54.2 56.1 63.8 69.6 71.4 72.7 74.3 102.0 112.7 122.0 127.9 128.6 130.5 130.7 130.9 131.6 134.0 138.4 143.5 158.0 169.3 170.2 174.5 175.5

HRMS (ESI-neg) [(M-2Na)/2] calculated: 699.2467 found: 699.2469

Compound 75

$^1$H-NMR (500 MHz, CD$_3$OD): δ ppm 1.57 (t, J=11.87, 11.87 Hz, 2H, H3-a H3-a'), 1.79-1.85 (m, 4H, CH2$\underline{CH2}$CH2 CH2$\underline{CH2}$CH2'), 2.00 (s, 6H, NHCO$\underline{CH3}$ NHCO$\underline{CH3}$'), 2.66 (dt, J=7.09, 7.05, 3.84 Hz, 4H, $\underline{CH2}$S $\underline{CH2}$S'), 2.74 (dt, J=6.86, 6.75, 4.55 Hz, 4H, SCH2 SCH2'), 2.83 (dd, J=12.21, 4.22 Hz, 2H, H3-e H3-e'), 3.45 (dd, J=8.89, 1.93 Hz, 2H, H7 H7'), 3.49-3.74 (m, 14H, H4 H4' H5 H5' H6 H6' H9a H9a' OCH2a OCH2a' CH2NH CH2NH'), 3.84 (dd, J=13.62, 3.31 Hz, 2H, H9b H9b'), 3.90 (td, J=9.62, 6.22, 6.22 Hz, 2H, OCH2b OCH2b'), 4.11 (ddd, J=8.84, 7.76, 3.30 Hz, 2H, H8 H8'), 7.33-7.37 (m, 6H, Ar), 7.46-7.50 (m, 6H, Ar), 7.86-7.91 (m, 8H, Ar) $^{13}$C NMR (125 MHz, CD3OD): δ ppm 22.7 29.4 31.5 31.9 41.0 42.8 44.6 54.2 63.8 69.7 71.5 72.6 74.3 102.0 112.3 128.2 128.4 128.6 130.4 130.7 131.1 132.4 133.3 135.1 138.4 141.0 144.0 169.3 170.0 174.5 175.5

HRMS (ESI-neg) [(M-2Na)/2] calculated: 703.1972 found: 703.1992

Compound 76

$^1$H-NMR (300 MHz, CD$_3$OD): δ ppm 1.57 (t, J=11.76, 11.76 Hz, 2H, H3-a H3-a'), 1.75-1.88 (m, 4H, CH2$\underline{CH2}$CH2 CH2$\underline{CH2}$CH2'), 2.00 (s, 6H, NHCO$\underline{CH3}$ NHCO$\underline{CH3}$'), 2.36 (s, 6H, ArCH3 ArCH3'), 2.66 (dt, J=7.19, 7.11, 1.11 Hz, 4H, $\underline{CH2}$S $\underline{CH2}$S'), 2.73 (dt, J=7.04, 6.95, 1.14 Hz, 4H, SCH2 SCH2'), 2.83 (dd, J=12.19, 4.00 Hz, 2H, H3-e H3-e'), 3.45 (dd, J=8.96, 1.42 Hz, 2H, H7 H7'), 3.48-3.74 (m, 14H, H4 H4' H5 H5' H6 H6' H9a H9a' OCH2a OCH2a' CH2NH CH2NH'), 3.84 (dd, J=13.61, 3.18 Hz, 2H, H9b H9b'), 3.90 (td, J=10.39, 6.52, 6.52 Hz, 2H, OCH2b OCH2b'), 4.10 (ddd, J=8.80, 7.84, 3.23 Hz, 2H, H8 H8'), 7.24 (d, J=8.06 Hz, 2H, Ar), 7.51 (d, J=8.13 Hz, 4H, Ar), 7.62-7.69 (m, 6H, Ar), 7.84-7.92 (m, 8H, Ar) $^{13}$C NMR (125 MHz, CD3OD): δ ppm 22.2 22.7 29.4 31.5 31.9 41.0 42.8 44.6 54.2 63.8 69.6 71.5 72.7 74.3 102.0 127.7 128.0 128.6 128.9 130.0 130.7 134.2 138.4 139.1 141.3 145.5 169.3 170.0 174.5 175.5

HRMS (ESI-neg) [(M-2Na)/2] calculated: 683.2518 found: 683.2521

Compound 77

$^1$H-NMR (300 MHz, CD$_3$OD): δ ppm 1.58 (t, J=11.81, 11.81 Hz, 2H, H3-a H3-a'), 1.77-1.87 (m, 4H, CH2$\underline{CH2}$CH2 CH2$\underline{CH2}$CH2'), 2.01 (s, 6H, NHCO$\underline{CH3}$ NHCO$\underline{CH3}$'), 2.66 (dt, J=6.95, 6.93, 1.17 Hz, 4H, $\underline{CH2}$S $\underline{CH2}$S'), 2.74 (dt, J=7.33, 7.14, 1.23 Hz, 4H, SCH2 SCH2'), 2.83 (dd, J=12.19, 3.94 Hz, 2H, H3-e H3-e'), 3.45 (dd, J=9.02, 1.68 Hz, 2H, H7), 3.47-3.76 (m, 14H, H4 H4' H5 H5' H6 H6' H9a H9a' OCH2a OCH2a' CH2NH CH2NH'), 3.85 (dd, J=13.76, 3.42 Hz, 2H, H9b H9b'), 3.90 (td, J=9.37, 5.93, 5.93 Hz, 2H, OCH2b OCH2b'), 4.11 (ddd, J=8.84, 7.98, 3.15 Hz, 2H, H8 H8'), 7.38 (ddd, J=6.28, 4.92, 2.32 Hz, 2H, Ar), 7.86 (s, 4H, Ar), 7.86-7.90 (m, 4H, Ar), 7.94 (d, J=8.67 Hz, 4H, Ar), 8.01 (d, J=8.66 Hz, 4H, Ar), 8.60-8.63 (m, 2H, Ar) $^{13}$C NMR (75 MHz, CD3OD): δ ppm 22.7 29.3 31.5 31.9 41.0 42.8 44.6 54.2 63.8 69.6 71.5 72.6 74.3 102.0 122.8 124.3 128.2 128.6 128.9 129.1 136.3 138.4 139.0 143.2 150.6 157.7 169.3 169.8 174.5 175.5

HRMS (ESI-neg) [(M-2Na)/2] calculated: 670.2314 found: 670.2324

Compound 78

$^1$H-NMR (500 MHz, CD$_3$OD): δ ppm 1.59 (t, J=11.82, 11.82 Hz, 2H, H3-a H3-a'), 1.79-1.86 (m, 4H, CH2$\underline{CH2}$CH2 CH2$\underline{CH2}$CH2'), 2.02 (s, 6H, NHCO$\underline{CH3}$ NHCO$\underline{CH3}$'), 2.66 (dt, J=6.97, 6.90, 3.90 Hz, 4H, $\underline{CH2}$S $\underline{CH2}$S'), 2.73 (dt, J=6.97, 6.94, 2.36 Hz, 4H, SCH2 SCH2'), 2.84 (dd, J=12.14, 4.17 Hz, 2H, H3-e H3-e'), 3.43-3.75 (m, 16H, H4 H4' H5 H5' H6 H6' H7 H7' H9a H9a' OCH2a OCH2a' CH2NH CH2NH'), 3.85 (dd, J=13.68, 3.10 Hz, 2H, H9b H9b'), 3.92 (td, J=9.39, 6.14, 6.14 Hz, 2H, OCH2b OCH2b'), 4.12 (ddd, J=8.86, 8.30, 3.13 Hz, 2H, H8 H8'), 7.33 (dt, J=7.47, 7.45, 0.94 Hz, 2H, Ar), 7.51 (dd, J=7.47, 1.11 Hz, 2H, Ar), 7.54 (d, J=7.26 Hz, 2H, Ar), 7.58 (dd, J=7.53, 0.65 Hz, 4H, Ar), 7.80 (s, 4H, Ar), 7.93-7.97 (m, 4H, Ar) $^{13}$C NMR (75 MHz, CD3OD): δ ppm 22.7 29.3 31.4 32.0 41.0 42.8 44.6 54.2 63.9 69.6 71.6 72.6 74.3 102.0 121.7 122.5 123.8 125.2 128.5 131.1 135.2 135.4 135.6 136.5 136.7 138.2 144.8 148.3 168.8 169.2 174.5 175.6, 194.3

HRMS (ESI-neg) [(M-2Na)/2] calculated: 695.2154 found: 695.2165

Compound 79

$^1$H-NMR (500 MHz, CD$_3$OD): δ ppm 1.55 (t, J=11.79, 11.79 Hz, 2H, H3-a, H3-a'), 1.83-1.73 (m, 4H, CH2$\underline{CH2}$CH2 CH2$\underline{CH2}$CH2'), 1.97 (s, 6H, NHCO$\underline{CH3}$ NHCO$\underline{CH3}$'), 2.63 (t, J=7.17, 7.17 Hz, 4H, S$\underline{CH2}$CH2CH2 S$\underline{CH2}$CH2CH2'), 2.72 (dt, J=6.95, 6.94, 2.62 Hz, 4H, $\underline{CH2}$S $\underline{CH2}$S'), 2.81 (dd, J=12.26, 4.02 Hz, 2H, H3-e H3-e'), 3.21 (dd, J=13.66, 7.93 Hz, 2H, H9a H9a'), 3.35 (d, J=9.13, 1.71 Hz, 2H, H7 H7'), 3.49-3.75 (m, H, $\underline{CH2}$NHCO $\underline{CH2}$NHCO' OCH2a OCH2a' H4 H4' H5 H5' H6 H6' H9b H9b' CH2Ar CH2Ar'), 3.84 (td, J=9.57, 6.08, 6.08 Hz, 2H, OCH2b OCH2b'), 3.95 (dt, J=8.33, 8.16, 2.87 Hz, 2H, H8 H8'), 7.29 (t, J=7.31, 7.31 Hz, 2H, Ar), 7.36 (d, J=8.11 Hz, 4H, Ar), 7.41 (dd, J=8.38, 1.24 Hz, 4H, Ar), 7.53 (d, J=8.37 Hz, 4H, Ar), 7.57 (dd, J=8.33, 1.27 Hz, 4H, Ar), 7.90 (s, 4H, Ar) $^{13}$C NMR (125 MHz, CD3OD): δ ppm 22.7 29.4 31.5 32.0 41.1 42.8 43.5 44.1 54.2 63.7 69.6 71.3 72.3 74.2 101.9 127.9 128.2 128.3 128.6 129.9 130.7 136.2 138.4 141.0 142.1 169.4 174.1 174.5 175.5

HRMS (ESI-neg) [(M-2Na)/2] calculated: 683.2518 found: 683.2566

Compound 80

$^1$H-NMR (500 MHz, CD$_3$OD): δ 7.86 (s, 4H, Ar), 7.83 (d, J=8.71 Hz, 4H, Ar), 7.68 (d, J=8.70 Hz, 4H, Ar), 7.45 (dd, J=3.64, 1.14 Hz, 2H, Ar), 7.42 (dd, J=5.09, 1.12 Hz, 2H, Ar), 7.10 (dd, J=5.10, 3.64 Hz, 2H, Ar), 4.10 (ddd, J=8.93, 7.87, 3.33 Hz, 2H, H8 H8'), 3.90 (td, J=9.70, 6.19, 6.19 Hz, 2H, OCH2a OCH2a'), 3.83 (dd, J=13.60, 3.28 Hz, 2H, H9a H9a'), 3.72-3.69 (m, 4H, H4 H4' H5 H5'), 3.64 (dd, J=10.48, 1.97 Hz, 2H, H6 H6'), 3.59 (td, J=9.61, 6.11, 6.11 Hz, 2H, OCH2b OCH2b'), 3.54 (ddd, J=14.63, 6.83, 0.51 Hz, 4H, CH2NH CH2NH'), 3.49 (dd, J=13.68, 7.82 Hz, 2H, H9b H9b'), 3.44 (dd, J=8.98, 1.84 Hz, 2H, H7 H7'), 2.83 (dd, J=12.26, 4.24 Hz, 2H, H3-e H3-e'), 2.74 (ddd, J=7.45, 6.79, 4.16 Hz, 4H, CH2S CH2S'), 2.66 (dt, J=7.08, 7.06, 4.19 Hz, 4H, SCH2 SCH2'), 2.00 (s, 6H, CH3 CH3'), 1.85-1.79 (m, 4H, CH2CH2CH2 CH2CH2CH2'), 1.57 (t, J=12.16, 11.64 Hz, 2H, H3-a H3-a') $^{13}$C NMR (125 MHz, CD3OD): δ ppm 175.5 174.5 169.7 169.3 144.2 138.8 138.4 134.4 129.4 129.2 128.6 127.1 126.5 125.5 102.0 74.3 72.7 71.5 69.6 63.8 54.2 44.5 42.8 41.0 31.9 31.5 29.3 22.7

HRMS (ESI-neg) [(M-2Na)/2] calculated: 675.1926 found: 675.1924

Compound 81

$^1$H-NMR (500 MHz, CD$_3$OD): δ ppm 7.86 (s, 4H, Ar), 7.85 (d, J=8.39 Hz, 4H, Ar), 7.73-7.69 (m, 6H, Ar), 7.50-7.46 (m, 4H, Ar), 4.10 (ddd, J=9.37, 8.29, 3.22 Hz, 2H, H8 H8'), 3.90 (td, J=9.71, 6.23, 6.23 Hz, 2H, OCH2a OCH2a'), 3.84 (dd, J=13.63, 3.20 Hz, 2H, H9a H9a'), 3.73-3.62 (m, 6H, H4 H4' H5 H5' H6 H6'), 3.59 (td, J=9.85, 6.09, 6.09 Hz, 2H, OCH2b OCH2b'), 3.54 (dd, J=14.82, 7.28 Hz, 4H, CH2NH CH2NH'), 3.49 (dd, J=13.30, 7.02 Hz, 2H, H9b H9b'), 3.44 (d, J=8.93 Hz, 2H, H7 H7'), 2.83 (dd, J=12.22, 4.14 Hz, 2H, H3-e H3-e'), 2.74 (dt, J=6.89, 6.82, 4.18 Hz, 4H, CH2S CH2S'), 2.66 (dt, J=6.98, 6.91, 4.66 Hz, 4H, SCH2 SCH2'), 2.00 (s, 6H, COCH3 COCH3'), 1.82 (p, J=6.70, 6.70, 6.68, 6.68 Hz, 4H, CH2CH2CH2 CH2CH2CH2'), 1.57 (t, J=11.85, 11.85 Hz, 2H, H3-a H3-a') $^{13}$C NMR (125 MHz, CD3OD): δ ppm 175.5 174.5 169.9 169.3 142.4 140.2 138.4 134.1 129.0 128.6 127.7 127.2 127.1 122.7 102.0 74.3 72.7 71.5 69.6 54.2 44.6 42.8 41.0 32.0 31.5 29.4 22.7

HRMS (ESI-neg) [(M-2Na)/2] calculated: 675.1926 found: 675.1929

Compound 82

$^1$H-NMR (500 MHz, CD$_3$OD): δ ppm 7.87 (s, 4H, Ar), 7.84 (d, J=8.65 Hz, 4H, Ar), 7.73 (d, J=8.53 Hz, 4H, Ar), 7.58 (dd, J=1.73, 0.57 Hz, 2H, Ar), 6.86 (dd, J=3.39, 0.53 Hz, 2H, Ar), 6.53 (dd, J=3.41, 1.81 Hz, 2H, Ar), 4.09 (ddd, J=8.68, 7.90, 3.28 Hz, 2H, H8 H8'), 3.89 (td, J=9.58, 6.15, 6.15 Hz, 2H, OCH2a OCH2a'), 3.82 (dd, J=13.65, 3.27 Hz, 2H, H9a H9a'), 3.74-3.62 (m, 6H, H4 H4' H5 H5' H6 H6'), 3.59 (td, J=9.63, 5.99, 5.99 Hz, 2H, OCH2b OCH2b'), 3.54 (dd, J=14.87, 7.73 Hz, 4H, CH2NH CH2NH'), 3.49 (dd, J=13.90, 8.00 Hz, 2H, H9b H9b'), 3.44 (dd, J=8.93, 1.84 Hz, 2H, H7 H7'), 2.83 (dd, J=12.24, 4.16 Hz, 2H, H3-e H3-e'), 2.74 (dt, J=6.88, 6.83, 4.20 Hz, 4H, CH2S CH2S'), 2.66 (dt, J=7.06, 7.00, 4.10 Hz, 4H, SCH2 SCH2'), 2.00 (s, 6H, COCH3 COCH3'), 1.85-1.79 (m, 4H, CH2CH2CH2 CH2CH2CH2'), 1.57 (t, J=11.85, 11.85 Hz, 2H, H3-a H3-a') $^{13}$C NMR (125 MHz, CD3OD): δ ppm 175.5 174.5 169.8 169.3 154.3 144.4 138.4 135.0 134.0 129.0 128.6 124.5 113.1 107.9 102.0 74.3 72.6 71.5 69.6 63.8 54.2 44.5 42.8 41.0 32.0 31.5 29.4 22.7

HRMS (ESI-neg) [(M-2Na)/2] calculated: 660.2233 found: 660.2210

Compound 83

$^1$H-NMR (500 MHz, CD$_3$OD): δ ppm 7.89 (s, 4H, Ar), 7.55-7.48 (m, 6H, Ar ArCH=), 7.38-7.31 (m, 6H, Ar), 6.70 (d, J=15.79 Hz, 2H, COCH=), 4.01 (ddd, J=9.30, 8.40, 2.75 Hz, 2H, H8 H8'), 3.88 (td, J=9.50, 6.18, 6.18 Hz, 2H, OCH2a OCH2a'), 3.79 (dd, J=13.72, 2.20 Hz, 2H, H9a H9a'), 3.73-3.66 (m, 4H, H4 H4' H5 H5'), 3.65-3.51 (m, 8H, H6 H6' OCH2b OCH2b' CH2NH'), 3.40 (dd, J=8.91, 1.85 Hz, 2H, H7 H7'), 3.34 (dd, J=13.75, 7.93 Hz, 2H, H9b H9b'), 2.83 (dd, J=12.21, 3.78 Hz, 2H, H3-e H3-e'), 2.76 (dt, J=6.86, 6.80, 4.04 Hz, 4H, CH2S CH2S'), 2.66 (t, J=7.04, 7.04 Hz, 4H, SCH2 SCH2'), 2.01 (s, 6H, COCH3 COCH3'), 1.85-1.79 (m, 4H, CH2CH2CH2 CH2CH2CH2), 1.57 (t, J=11.86, 11.86 Hz, 2H, H3-a H3-a') $^{13}$C NMR (500 MHz, CD3OD): δ ppm 175.5 174.5 169.4 168.8 141.6 138.8 136.5 130.7 129.9 128.9 128.6 122.2 102.0 74.3 72.4 71.4 69.7 63.8 54.3 44.1 42.8 41.1 32.0 31.5 29.4 22.7

HRMS (ESI-neg) [(M-2Na)/2] calculated: 620.2283 found: 620.2241

Compound 84

A solution of 35 mg (1 eq) of compound 61 in 800 μl of absolute DMF was admixed to 200 μl of piperidine and stirred at RT for 20 min. The solvent was removed, the residue was dissolved with 1 ml abs. DMF, and concentration took place again. Following dissolution of the residue in 0.5 ml of abs. DMF and 0.5 ml of H$_2$O, 12 mg (6 eq) of NaHCO$_3$ and 18.3 mg (3 eq) of biphenyl-4-sulphonyl chloride were added. The mixture was stirred at RT for 15 min, the solvent was removed, the residue was dissolved with MeOH, H$_2$O was added until colloidal clouding occurred, and purification took place on an RP-18 column (H$_2$O>>MeOH). The product fractions were concentrated, dissolved with a little MeOH, diluted with H$_2$O until clouding occurred, and brought to a pH of 12-13 with 2M NaOH. When the reaction has ended, neutralization was carried out with 20% HAc, purification took place on an RP18 column (H$_2$O>>CH$_3$CN), the CH$_3$CN was removed, and lyophilization was carried out. Yield: 16 mg of white solid.

$^1$H-NMR (300 MHz, CD$_3$OD): δ ppm 1.53 (t, J=11.66, 11.66 Hz, 2H, H3-a H3-a'), 1.66-1.77 (m, 4H, CH2CH2CH2 CH2CH2CH2'), 2.00 (s, 6H, NHCOCH3 NHCOCH3'), 2.59 (dt, J=7.24, 7.19, 1.27 Hz, 4H, SCH2CH2CH2 S CH2CH2CH2'), 2.73 (dt, J=7.32, 7.10, 2.10 Hz, 4H, SCH2S CH2'), 2.79 (dd, J=12.62, 4.66 Hz, 2H, H3-e H3-e'), 2.91 (dd, J=12.81, 7.79 Hz, 2H, H9a H9a'), 3.32-3.38 (m, 4H, H7 H7' H9 H9b'), 3.46-3.49 (m, 14H, H4 H4' H5 H5' H6 H6' OCH2a OCH2a' CH2NH CH2NH'), 3.74 (td, J=9.92, 6.05, 6.05 Hz, 2H, OCH2b OCH2b'), 3.87 (ddd, J=9.08, 8.22, 2.59 Hz, 2H, H8 H8'), 7.39 (t, J=7.27, 7.27 Hz, 2H, Ar), 7.46 (t, J=7.46, 7.46 Hz, 4H, Ar), 7.67 (d, J=7.69 Hz, 4H, Ar), 7.78 (d, J=8.39 Hz, 4H, Ar), 7.89-7.94 (m, 8H, Ar) $^{13}$C NMR (75 MHz, CD3OD): δ ppm 22.7 29.2 31.6 31.9 41.0 42.8 47.5 54.3 63.6

69.4 71.1 72.0 74.2 101.9 128.4 128.6 128.7 129.5 130.2 138.4 140.6 140.7 146.5 169.3 174.4 175.7

Compound 85

A solution of 50 mg of compound 61 in 1 ml of MeOH and 1 ml of H$_2$O was admixed with 60 µl of 2M NaOH. After 2 h of stirring, the mixture was neutralized with acetic acid, the solvent was removed, dissolved in H$_2$O and extracted by shaking with EE. The aqueous phase was concentrated, dissolved in 2 ml of MeOH, admixed with 9.2 µl (0.07 eq) of TEA and 11.3 mg (1.8 eq) of biphenyl-4-aldehyde, and stirred for an hour. Then 4.8 mg (2.2 eq) of sodium cyanoborohydride were added, stirring was continued for 30 min, and 0.1 ml of 20% strength acetic acid was added. The solvent was removed, the residue was dissolved with a little MeOH, H$_2$O was added until colloidal clouding occurred, and purification took place on an RP-18 column (H$_2$O>>MeOH). The product fractions were concentrated and lyophilized with dioxane-H$_2$O. Yield: 12 mg of white solid.

$^1$H-NMR (300 MHz, CD$_3$OD): δ ppm 1.58 (t, J=11.84, 11.84 Hz, 2H, H3-a H3-a'), 1.76-1.86 (m, 4H, CH2CH2CH2 CH2CH2CH2'), 2.02 (s, 6H, NHCOCH3 NHCOCH3'), 2.65 (t, J=7.18, 7.18 Hz, 2H, CH2SCH2 CH2SCH2'), 2.74 (t, J=7.00, 7.00 Hz, 2H, CH2SCH2 CH2SCH2'), 2.83 (dd, J=12.06, 4.84 Hz, 2H, H3-e H3-e'), 3.01 (dd, J=12.61, 9.63 Hz, 2H, H9a H9a'), 3.35-3.78 (m, 16H, H4 H4' H5 H5' H6 H6' H7 H7' H9b H9b' OCH2a OCH2a' CH2NHCO CH2NHCO'), 3.85 (td, J=9.27, 6.22, 6.22 Hz, 2H, OCH2b OCH2b'), 4.19 (dt, J=9.33, 9.33, 3.05 Hz, 2H, H8 H8'), 4.27 (s, 4H, NH CH2Ar NHCH2Ar'), 7.35 (t, J=7.25, 7.25 Hz, 2H, Ar), 7.43 (t, J=7.35, 7.35 Hz, 4H, Ar), 7.54 (d, J=8.34 Hz, 4H, Ar), 7.60 (dd, J=7.13, 1.41 Hz, 4H, Ar), 7.66 (d, J=8.29 Hz, 4H, Ar), 7.85 (s, 4H, Ar) $^{13}$C NMR (75 MHz, CD3OD): δ ppm 22.7 29.4 31.3 32.1 40.9 42.6 51.4 52.0 54.2 63.8 68.4 69.3 72.8 74.1 102.1 128.1 128.6 128.7 129.0 130.1 131.4 131.7 138.4 141.3 143.7 169.4 174.4 175.9

HRMS (ESI-neg) [(M-2Na)/2] calculated: 655.2569 found: 655.2568

Compound 86

A solution of 150 mg of compound 9 in 3 ml of pyridine was cooled to 0° C., and 1 ml of acetic anhydride was slowly added dropwise. Following addition of a spatula tip of DMAP, the mixture was stirred for 3 h, concentrated and coevaporated with toluene. The residue was dissolved in CH$_2$Cl$_2$ and extracted by shaking with HCl-acidic H$_2$O. The aqueous phase was washed with a little CH$_2$Cl$_2$, and the organic phases were combined, dried (MgSO$_4$), filtered and concentrated. Yield: 180 mg of white solid.

Compound 87

A solution of 225 mg of sodium acetate (12.25 eq) in 25 ml of H$_2$O was admixed with 302 mg (5.85 eq) of KIO$_4$. Following addition of 150 mg of compound 86 in 25 ml of dioxane, 90 mg (2.55 eq) of potassium permanganate were added, and the mixture was stirred for 17 h, filtered over Celite, concentrated to about 3-5 ml, diluted with H$_2$O, acidified with dilute HCl, and extracted by shaking 3× with dichloromethane. The organic phase was dried with MgSO$_4$, filtered and concentrated. Yield: 149 mg of white solid.

1,4-Bis[benzyloxycarbonylamino-3-propylcarbonylamino]benzene (compound 88)

A solution of 30 mg of 1,4-phenylenediamine dihydrochloride in 1 ml of abs. DMF was admixed with 130 mg (2.4 eq) of Z-aminobutyric acid-NPE and 56 µl (2.4 eq) of TEA, and stirred for 17 h, and the solvent was removed, and purification took place on an RP-18 column (H$_2$O>>EtOH). The product remained undissolved, and was washed from the column with DMF. Yield: 90 mg of white solid.

1,4-Bis[3-aminopropylcarbonylamino]benzene dihydrochloride (compound 89)

A suspension of 70 mg of compound 88 in 15 ml of MeOH and 3 ml of H$_2$O was admixed with 25 mg of palladium on carbon and 0.5 ml of 2N HCl and hydrogenated with stirring at atmospheric pressure over 17 h, then filtered over Celite, and the solvent was removed. Yield: 48 mg of solid. TLC-RF: 0.37 in 1:1:1 EtOH:EE:HAc(20%)

Compound 90

A solution of 6 mg of compound 89 and 25.8 mg (2.2 eq) of compound 87 in 1 ml of abs. DMF was admixed with 14.3 mg (2.2 eq) of HATU and 9 µl (3 eq) of DIPEA, concentrated after 5 min, and purified on RP-18 (H$_2$O>>EtOH). The material was dissolved in a little EtOH, admixed with H2O until clouding occurred, brought to a pH of 12-13 with 2M NaOH, neutralized after the reaction with acetic acid; the EtOH was removed, and purification took place on RP-18 (H$_2$O>>EtOH). Lyophilization was carried out following removal of the ethanol. Yield: 14 mg of white substance.

$^1$H-NMR (300 MHz, CD$_3$OD): δ ppm 1.71 (t, J=11.70, 11.70 Hz, 2H, H3-a H3-a'), 1.84-1.96 (m, 4H, CH2CH2CH2 CH2CH2CH2'), 2.00 (s, 6H, NHCOCH3 NHCOCH3'), 2.32-2.46 (m, 4H, CH2CO CH2CO'), 2.90 (dd, J=12.13, 3.89 Hz, 2H, H3-e H3-e'), 4.39-3.30 (m, 22H, H4 H4' H5 H5' H6 H6' H7 H7' H8 H8' H9a H9a' H9b H9b' OCH2a OCH2a' OCH2b OCH2b' CH2NH CH2NH'), 7.36 (t, J=7.27, 7.27 Hz, 2H, Ar), 7.40-7.51 (m, 8H, Ar), 7.57-7.74 (m, 8H, Ar), 7.87-7.95 (m, 4H, Ar) $^{13}$C NMR (75 MHz, CD3OD): δ ppm 22.7 26.8 35.2 39.5 42.1 44.5 54.0 64.7 69.5 71.5 72.4 74.6 101.9 121.7 128.0 128.1 129.0 129.1 130.0 134.5 136.1 141.3 145.6 170.0 173.1 173.8 175.0 175.5

HRMS (ESI-neg) [(M-2Na)/2] calculated: 666.2543 found: 666.2532

Compound 91

A solution of 155 mg (17 eq) of terephthalic acid, 40 mg (1 eq) of compound 9 and 25 mg (1.2 eq) of HATU in 1 ml of abs. DMF was admixed with 235 µl (25 eq) of DIPEA, stirred for 5 min, concentrated, dissolved with NaHCO$_3$ solution pH8, and purified on an RP18 column (H$_2$O>>MeOH). The product fractions were combined, the MeOH was removed, and lyophilization was carried out. Yield: 38 mg of white substance.

Compound 92

A solution of 10.0 mg (1 eq) of compound 91, 8.88 mg (1.1 eq) of compound 173 and 5.78 mg (1.2 eq) of HATU was admixed with 6.5 µl (3 eq) of DIPEA and stirred for 5 min. Following removal of the solvent, the residue was dissolved with a little MeOH, H$_2$O was added until clouding occurred, and purification was carried out on an RP-18 column (H₂O>>MeOH). The product fractions were concentrated, dissolved with a little MeOH, diluted with H₂O until clouding occurred, and brought to a pH of 12-13 with 2M NaOH. When the reaction was ended, neutralization took place with 20% HAc, purification took place on an RP18 column (H₂O>>CH₃CN), the CH₃CN was removed, and lyophilization was carried out. Yield: 20 mg of white solid.

$^1$H-NMR (500 MHz, CD₃OD): δ ppm 1.35-1.46 (m, 4H, CH2CH2 CH2CH2'), 1.51-1.64 (m, 6H, H3-a H3-a' CH2CH2CH2CH2 CH2CH2CH2CH2'), 1.76-1.87 (m, 2H, SCH2CH2CH2), 2.00 (s, 6H, NHCOCH3 NHCOCH3'), 2.66 (dt, J=6.87, 6.57, 2.19 Hz, 2H, SCH2), 2.74 (t, J=6.93, 6.93 Hz, 2H, CH2S), 2.80-2.87 (m, 2H, H3-e H3-e'), 3.32-3.95 (m, 20H, H4 H4' H5 H5' H6 H6' H7 H7' H9a H9a' H9b H9b' OCH2a OCH2a' OCH2b OCH2b' CH2NH CH2NH'), 4.02-4.15 (m, 2H, H8 H8'), 7.35 (t, J=7.23, 7.23 Hz, 2H, Ar), 7.43 (t, J=7.48, 7.48 Hz, 4H, Ar), 7.61 (d, J=7.56 Hz, 4H, Ar), 7.67 (d, J=7.80 Hz, 4H, Ar), 7.85 (s, 4H, Ar), 7.89 (dd, J=8.26, 1.49 Hz, 4H, Ar) $^{13}$C NMR (125 MHz, CD3OD): δ ppm 22.7 26.9 27.9 29.4 30.4 30.9 31.5 32.0 41.0 41.2 42.8 44.6 54.2 63.8 65.2 69.6 71.5 72.6 74.3 102.0 102.1 128.0 128.1 128.5 128.9 129.1 130.0 134.5 138.2 138.6 141.3 145.5 169.3 170.0 174.5 174.5 175.5

HRMS (ESI-neg) [(M-2Na)/2] calculated: 660.2580 found: 660.2597

Compound 93

A solution of 50 mg of compound 4 in 1 ml of H₂O and 2 ml of tert-butanol was admixed 3 times at intervals of 17 h with in each case 42 mg (2 eq) of phenylacetylene, 5.4 mg (0.15 eq) of ascorbic acid and 4.8 mg (0.15 eq) of CuSO₄. This was followed by concentration, purification on an RP-18 column (H₂O>>EtOH), removal of the EtOH, and lyophilization. Yield: 27 mg of white solid.

Compound 94

Prepared analogously to compound 11

Compound 95

Prepared analogously to compound 21

$^1$H-NMR (300 MHz, CD₃OD): δ ppm 1.56 (t, J=11.89, 11.89 Hz, 2H, H3-a H3-a'), 1.75-1.84 (m, 4H, CH2CH2CH2 CH2CH2CH2'), 1.99 (s, 6H, NHCOCH3 NHCOCH3'), 2.64 (dt, J=6.95, 6.86, 4.05 Hz, 4H, CH2SCH2 CH2SCH2'), 2.72 (dt, J=7.15, 7.12, 1.96 Hz, 4H, CH2SCH2 CH2SCH2'), 2.81 (dd, J=12.26, 4.15 Hz, 2H, H3-e H3-e'), 3.38 (dd, J=9.07, 1.91 Hz, 2H, H7 H7'), 3.48-3.74 (m, 12H, H4 H4' H5 H5' H6 H6' OCH2a OCH2a' CH2NH CH2NH'), 3.84 (td, J=9.81, 6.15, 6.15 Hz, 2H, OCH2b OCH2b'), 4.27 (ddd, J=8.96, 7.78, 2.34 Hz, 2H, H8 H8'), 4.50 (dd, J=14.00, 7.72 Hz, 2H, H9a H9a'), 4.82 (dd, J=14.13, 2.39 Hz, 2H, H9b H9b'), 7.31 (t, J=7.35, 7.35 Hz, 2H, Ar), 7.40 (t, J=7.40, 7.40 Hz, 4H, Ar), 7.79 (dd, J=8.35, 1.27 Hz, 4H, Ar), 7.90 (s, 4H, Ar), 8.31 (s, 2H, Ar) $^{13}$C NMR (75 MHz, CD3OD): δ ppm 22.6 29.3 31.4 31.9 41.0 42.8 54.2 54.6 63.8 69.5 71.6 74.1 102.0 126.7 128.6 129.3 130.0 131.9 138.4 148.5 169.4 174.5 175.6

HRMS (ESI-neg) [(M-2Na)/2] calculated: 617.2161 found: 617.2165

Compound 96

Prepared analogously to compound 4

Compound 97

Prepared analogously to compound 6

Compound 98

Prepared analogously to compound 9

Compound 99

Prepared analogously to compound 86

Compound 100

276 mg of compound 99 and 481 mg (5 eq) of 6-benzyloxycarbonylaminohexanol were dissolved in a mixture of 2 ml of CH₃CN and 1 ml of CH₂Cl₂, and stirred under argon for 1 h following addition of 150 mg of freshly calcined, ground molecular sieve A4. At −78° C., 172 mg (2 eq) of NIS and 10 µl (0.3 eq) of trifluoromethanesulphonic acid were added, and the mixture was stirred at −40° C. for 3 h. Addition of 30 ml of CH₂Cl₂ was followed by extraction by shaking with saturated Na₂CO₃ solution (20 ml) and then with 1M Na₂SO₃, drying (MgSO₄), filtration, concentration, and purification on a silica gel column (EE). This gives 130 mg of an isomer mixture (α:β~3:2). The mixture was dissolved in 1 ml of abs. MeOH, admixed with 0.1 ml of 0.1M NaOMe solution, neutralized after 1 h RT with 2 ml of 20% strength HAc, concentrated, and purified on a silica gel column (EtOH:EE:HAc (20%) 1:12:1) and lyophilized Yield: 40 mg of white substance.

Compound 101

40 mg of compound 100 were dissolved in a mixture of 2 ml of MeOH and 1 ml of H₂O, adjusted to a pH of 3 with HCl, admixed with 10 mg of Pd on carbon (10%) and then hydrogenated under atmospheric pressure for 4 h. Following filtration, the product was neutralized with dilute NaOH, the MeOH was removed, and lyophilization was carried out. Yield: 39 mg of white solid.

Compound 102

Prepared analogously to compound 21, starting from compound 101

$^1$H-NMR (300 MHz, CD₃OD): δ ppm 1.34-1.67 (m, 7H, CH2CH2CH2CH2CH2CH2 CH2CH2CH2CH2CH2CH2' H3-a H3-a'), 2.00 (s, 6H, NHCOCH3 NHCOCH3'), 2.84 (dd, J=12.36, 4.01 Hz, 2H, H3-e H3-e'), 3.29-3.92 (m, 20H, H4 H4' H5 H5' H6 H6' H7 H7' H9a H9a' H9b H9b' OCH2a OCH2a' OCH2b OCH2b' CH2NHCO CH2NHCO'), 4.06 (dt, J=7.93, 7.89, 3.30 Hz, 2H, H8 H8'), 7.35 (t, J=7.22, 7.22 Hz, 2H, Ar), 7.43 (t, J=7.35, 7.35 Hz, 4H, Ar), 7.62 (d, J=7.89 Hz, 4H, Ar), 7.67 (d, J=8.05 Hz, 4H, Ar), 7.84 (s, 4H, Ar), 7.90 (d, J=8.29 Hz, 4H, Ar) $^{13}$C NMR (75 MHz, CD3OD): δ ppm 22.7 26.9 27.9 30.4 30.9 29.4 41.2 42.9 44.6 54.2 65.1 69.7 71.5 72.7 74.3 102.1 128.0 128.1 128.5 129.0 129.1 130.0 134.5 138.5 141.3 145.5 169.3 170.0 174.6 175.5

HRMS (ESI-neg) [(M-2Na)/2] calculated: 651.2797 found: 651.2797

Compound 103

Prepared analogously to compound 92

Instead of compound 101, compound 56 was used $^1$H-NMR (500 MHz, CD$_3$OD): δ ppm 1.21-1.46 (m, 6H, cyclohexyl), 1.57 (t, J=11.92, 11.92 Hz, 1H, H3-a), 1.58 (t, J=11.68, 11.68 Hz, 1H, H3-a'), 1.71-1.86 (m, 8H, cyclohexyl CH2CH2CH2 CH2CH2CH2'), 1.99 (s, 3H, NHCOCH3), 2.01 (s, 3H, NHCOCH3'), 2.49-2.57 (m, 1H, cyclohexyl), 2.62-2.69 (m, 4H, CH2S CH2S'), 2.71-2.77 (m, 4H, SCH2 SCH2'), 2.80-2.85 (m, 2H, H3-e H3-e'), 3.41-3.74 (m, 16H, H4 H4' H5 H5' H6 H6' H7 H7' H9a H9a' OCH2a OCH2a' CH2NH CH2NH'), 3.80 (dd, J=13.66, 3.32 Hz, 1H, H9b), 3.84 (dd, J=13.54, 3.19 Hz, 1H, H9b'), 3.86-3.92 (m, 2H, OCH2b OCH2b'), 4.05-4.13 (m, 2H, H8 H8'), 7.25 (d, J=8.13 Hz, 2H, Ar), 7.36 (t, J=7.37, 7.37 Hz, 1H, Ar), 7.44 (t, J=7.90, 7.90 Hz, 2H, Ar), 7.63 (d, J=7.20 Hz, 2H, Ar), 7.68 (d, J=8.13 Hz, 2H, Ar), 7.72 (d, J=8.42 Hz, 2H, Ar), 7.92-7.87 (m, 6H, Ar) $^{13}$C NMR (75 MHz, CD3OD): δ ppm 22.7 27.2 27.9 35.4 29.4 31.5 31.9 41.0 42.8 44.5 44.6 45.9 54.2 63.8 69.6 71.5 72.6 74.3 102.0 128.0 128.1 128.4 128.6 129.0 129.1 130.0 133.3 134.5 138.4 141.3 145.5 153.2 169.3 170.0 170.3 174.5 175.5

HRMS (ESI-neg) [(M-2Na)/2] calculated: 672.2596 found: 672.2591

Compound 104

Prepared according to: Eur. J. Org. Chem. 2009, 16, 2611-2620

Compound 105

200 mg (0.575 mmol) of compound 104 and 159 mg (0.690 mmol) of 4-(benzyloxycarbonylamino)hex-1-yne were dissolved in 2 ml of tert-butanol. 50 mg (0.29 mmol) of ascorbic acid and 46 mg (0.29 mmol) of CuSO$_4$ were dissolved in 2 ml of H$_2$O and added to the solution; after 2 days, the tert-butanol was removed, 1 ml of 20% HAc was added, purification took place on RP18 (H$_2$O>>EtOH), and lyophilization was carried out. Yield: 110 mg of solid.

Compound 106

Prepared analogously to compound 4

Compound 107

Prepared analogously to compound 6

Compound 108

Prepared analogously to compound 9

Compound 109

Prepared analogously to compound 101

Instead of HCl, HAc was used, and the material was subsequently applied with H$_2$O to an RP-18 column, rinsed with dilute HCl, rinsed with H$_2$O, and then rinsed from the column with H$_2$O>>EtOH. The resulting hydrochloride salt of the compound was lyophilized

Compound 110

Prepared analogously to compound 21.

$^1$H-NMR (500 MHz, CD$_3$OD): δ ppm 7.94 (s, 2H, triazole), 7.90 (d, J=8.12 Hz, 4H, Ar), 7.84 (s, 4H, Ar), 7.68 (dd, J=7.84, 0.78 Hz, 4H, Ar), 7.63 (d, J=7.79 Hz, 4H, Ar), 7.44 (t, J=7.64 Hz, 4H, Ar), 7.36 (t, J=7.37 Hz, 2H, Ar), 4.08 (ddd, J=8.94, 8.37, 3.18 Hz, 2H, H8 H8'), 3.98 (ddd, J=11.14, 9.77, 6.13 Hz, 2H, H4 H4'), 3.89-3.86 (m, 4H, H5 H5' H6 H6'), 3.83 (dd, J=13.57, 3.04 Hz, 2H, H9a H9a'), 3.56-3.49 (m, 4H, H7 H7' H9b H9b'), 3.43 (dd, J=12.55, 4.69 Hz, 2H, H3-e H3-e'), 3.39 (t, J=6.93 Hz, 4H, CH2NH CH2NH'), 2.73 (t, J=7.28 Hz, 4H, CH2triazole CH2triazole'), 2.30 (t, J=11.84 Hz, 2H, H3-a H3-a'), 2.02 (s, 6H, COCH3 COCH3'), 1.77-1.69 (m, 4H, CH2CH2CH2CH2 CH2CH2CH2CH2'), 1.69-1.61 (m, 4H, CH2CH2CH2CH2 CH2CH2CH2CH2') $^{13}$C NMR (125 MHz, CD3OD): δ ppm 175.4 171.5 170.1 169.3 148.3 145.6 141.3 138.5 134.5 130.0 129.1 129.0 128.5 128.1 121.6 92.2 76.0 72.2 71.3 69.5 53.8 44.6 41.2 40.8 29.8 27.9 25.9 22.7

HRMS (ESI-neg) [(M-2Na)/2] calculated: 674.2706 found: 674.2723

Compound 111

190 mg of compound 104 were dissolved in 1 ml of abs. MeOH, admixed with 10 mg of Pd on carbon (10%), hydrogenated under atmospheric pressure for 1 h, filtered over Celite, and evaporated. The residue (177 mg; 0.55 mmol) was dissolved with 728 mg (2.75 mmol) of 6-(benzyloxycarbonylamino)hexanoic acid in 6 ml of abs. DMF, concentrated 10 min after addition of 835 mg (2.2 mmol) of HATU and 0.939 ml (5.5 mmol) of DIPEA, and purified on RP-18. The products were freeze-dried, dissolved in 5 ml of abs. MeOH and admixed with 0.5 ml of fresh, approximately 0.5 M NaOMe solution; after the end of the reaction, neutralization was carried out with 20% strength HAc, followed by concentration and purification again on RP-18. Yield: 125 mg.

Compound 112

Prepared analogously to compound 4

Compound 113

Prepared analogously to compound 6

Compound 114

Prepared analogously to compound 9

Compound 115

Prepared analogously to compound 109

Compound 116

Prepared analogously to compound 21

$^1$H-NMR (500 MHz, CD$_3$OD): δ 7.90 (d, J=8.36 Hz, 4H, Ar), 7.82 (s, 4H, Ar), 7.68 (d, J=8.34 Hz, 4H, Ar), 7.61 (d, J=7.46 Hz, 4H, Ar), 7.45 (t, J=7.56 Hz, 4H, Ar), 7.37 (t, J=7.14 Hz, 2H, Ar), 4.11 (dd, J=10.05, 1.36 Hz, 2H, H6 H6'), 3.99 (dt, J=8.41, 3.04 Hz, 2H, H8 H8'), 3.88-3.77 (m, 4H, H4 H4' H9a H9a'), 3.80 (t, J=10.43 Hz, 2H, H5 H5'), 3.48 (dd, J=13.49, 8.22 Hz, 1H, H9b H9b'), 3.44 (dd, J=8.82, 1.41 Hz, 2H, H7 H7'), 3.36 (t, J=7.04 Hz, 4H, CH2NH CH2NH'), 2.77 (dd, J=12.47, 3.98 Hz, 2H, H3-e H3-e'), 2.22 (t, J=7.22 Hz, 4H, CH2CO CH2CO), 2.02 (s, 6H, CH3 CH3'), 1.91 (t,

J=11.49 Hz, 2H, H3-a H3-a'), 1.69-1.56 (m, 8H, CH2CH2 CH2 CH2CH2CH2'), 1.44-1.37 (m, 4H, CH2CH2CH2 CH2 CH2CH2') $^{13}$C NMR (125 MHz, CD3OD): δ ppm 175.8 175.6 175.3 170.4 169.5 145.5 141.0 138.3 134.1 130.1 130.0 129.2 129.2 19.0 128.5 128.1 128.0 86.6 74.6 72.2 71.4 69.0 53.9 44.6 41.6 41.0 37.1 30.0 27.4 26.1 22.8

HRMS (ESI-neg) [(M-2Na)/2] calculated: 664.2750 found: 664.2748

Compound 117

Prepared according to "Liebigs Ann Chem. 1991, 487-495"

Compound 118

Prepared analogously to compound 4

Compound 119

Prepared analogously to compound 6

Compound 120

Prepared analogously to compound 9

Compound 121

Prepared analogously to compound 11

Compound 122

Prepared analogously to compound 21
$^1$H-NMR (500 MHz, CD$_3$OD): δ ppm 1.60-1.74 (m, 6H, H3-a H3-a' CH2CH2NH CH2CH2NH'), 1.80-1.88 (m, 8H, CH2CH2CH2S CH2CH2CH2S'), 2.00 (s, 6H, NHCOCH3 NHCOCH3'), 2.48-2.59 (m, 8H, CH2SCH2CH2SCH2'), 2.70 (dd, J=12.58, 4.58 Hz, 2H, H3-e H3-e'), 3.38-3.46 (m, 6H, H7 H7' CH2NH CH2NH'), 3.48 (ddd, J=13.43, 7.85, 1.42 Hz, 2H, H9a H9a'), 3.62-3.72 (m, 4H, H5 H5' H6 H6'), 3.84 (dd, J=13.52, 3.22 Hz, 2H, H9b H9b'), 4.04 (ddd, J=8.52, 8.05, 3.40 Hz, 2H, H8 H8'), 7.35 (t, J=7.41, 7.41 Hz, 2H, Ar), 7.43 (t, J=7.61, 7.61 Hz, 4H, Ar), 7.62 (dd, J=8.20, 1.02 Hz, 4H, Ar), 7.67 (d, J=8.55 Hz, 4H, Ar), 7.83 (s, 4H, Ar), 7.89 (d, J=8.19 Hz, 4H, Ar)

HRMS (ESI-neg) [(M-2Na)/2] calculated: 667.2569 found: 667.2593

Compound 123

A solution of 300 mg of compound 7 and 198 µL (2 eq) of diisopropylethylamine in 10 ml of abs. DMF was admixed with 250 mg (1.1 eq) of nitrophenyl 4-biphenylcarboxylate and stirred for 3 h. The solvent was removed, the residue was purified on a silica gel column (CHCl$_3$:MeOH 10:1) and concentrated, and this product was lyophilized from dioxane. Yield: 300 mg of white solid.

Compound 124

A solution of 50 mg of compound 123 and 40 mg (1.4 eq) of 1-azido-2-Fmoc-aminoethane in 2 ml of tert-butanol and 1 ml of DMF was admixed with 8.1 mg (0.5 eq) of ascorbic acid and 7.4 mg (0.5 eq) of CuSO$_4$ in 0.3 ml of H$_2$O, stirred at RT for 2 h, concentrated, purified on RP-18 (H$_2$O>>EtOH); the EtOH was removed, and lyophilization was carried out. Yield: 65 mg of white solid.

Compound 125

A solution of 40.5 mg (2.4 eq) of compound 124 in 1.6 ml of DMF and 0.4 ml of piperidine was stirred for 20 min, concentrated, coevaporated with DMF, and admixed with a solution of 3.3 mg (1 eq) of terephthalic acid in 1 ml of DMF. 5 min after addition of 18.1 mg (2.4 eq) of HATU and 22 µl (6 eq) of DIPEA, the mixture was concentrated and purified on an RP-18 column (H$_2$O>>EtOH). The product fractions were concentrated, dissolved with a little EtOH, diluted with H$_2$O until clouding occurred, and brought to a pH of 12-13 with 2M NaOH. When the reaction was ended, neutralization was carried out with 20% HAc and purification took place on an RP18 column (H$_2$O>>EtOH), the EtOH was removed, and lyophilization was carried out.

Yield: 10 mg of white solid.
$^1$H-NMR (500 MHz, CD$_3$OD): δ ppm 1.59 (t, J=11.68, 11.68 Hz, 2H, H3-a H3-a'), 2.00 (s, 6H, NHCOCH3 NHCOCH3'), 2.87 (dd, J=11.87, 3.69 Hz, 2H, H3-e H3-e'), 3.44 (dd, J=8.90, 1.50 Hz, 2H, H7 H7'), 3.49 (dd, J=13.71, 7.91 Hz, 2H, H9a H9a'), 3.65-3.85 (m, 12H, H4 H4' H5 H5' H6 H6' H9b H9b' CH2NH CH2NH'), 4.02 (dt, J=8.31, 8.26, 3.16 Hz, 2H, H8 H8'), 4.60 (t, J=5.86, 5.86 Hz, 4H, CH2N CH2N2), 4.70 (d, J=12.31 Hz, 2H, OCH2a OCH2a'), 4.96 (d, J=12.54 Hz, 2H, OCH2b OCH2b'), 7.36 (t, J=7.39, 7.39 Hz, 2H, Ar), 7.44 (t, J=7.75, 7.75 Hz, 4H, Ar), 7.63 (dd, J=8.27, 1.28 Hz, 4H, Ar), 7.67 (d, J=8.36 Hz, 4H, Ar), 7.79 (s, 4H, Ar), 7.89 (d, J=8.39 Hz, 4H, Ar), 7.99 (s, 2H, triazole)

HRMS (ESI-neg) [(M-2Na)/2] calculated: 676.2498 found: 676.2499

Compound 126

Prepared analogously to compound 61

Compounds 127, 128, 129

Prepared analogously to compound 62

Compound 127

$^1$H-NMR (500 MHz, CD$_3$OD): δ 7.93 (d, J=8.43 Hz, 4H, Ar), 7.81-7.74 (m, 12H, Ar), 7.45-7.39 (m, 6H, Ar), 3.98 (ddd, J=9.00, 8.25, 3.10 Hz, 2H, H8 H8'), 3.85 (td, J=9.59, 6.17 Hz, 2H, OCH2a OCH2a'), 3.75-3.64 (m, 10H, OCH2b OCH2b' ArCH2 ArCH2' H5 H5' H6 H6'), 3.62-3.50 (m, 8H, H4 H4' H7 H7' CH2NH CH2NH'), 3.35-3.31 (m, 2H, H9a H9a'), 3.22 (dd, J=13.61, 8.06 Hz, 2H, H9b H9b'), 2.83 (dd, J=12.26, 3.97 Hz, 2H, H3-e H3-e'), 2.77-2.71 (m, 4H, CH2SCH2 CH2S CH2'), 2.63 (t, J=7.30 Hz, 4H, CH2SCH2 CH2SCH2'), 1.94 (s, 6H, CH3 CH3'), 1.82-1.75 (m, 4H, CH2CH2CH2, CH2 CH2CH2'), 1.57 (t, J=11.94 Hz, 2H, H3-a H3-a')

HRMS (ESI-neg) [(M-2Na)/2] calculated: 695.2518 found: 695.2551

Compound 128

$^1$H-NMR (500 MHz, CD$_3$OD): δ ppm 7.93 (d, J=8.45 Hz, 4H, Ar), 7.76 (d, J=8.43 Hz, 4H, Ar), 7.57 (dd, J=8.23, 1.30 Hz, 4H, Ar), 7.54 (d, J=8.23 Hz, 4H, Ar), 7.42-7.35 (m, 8H, Ar), 7.30 (t, J=7.38 Hz, 2H, Ar), 3.98 (ddd, J=9.07, 8.18, 3.08 Hz, 2H, H8 H8'), 3.87 (td, J=9.78, 6.23 Hz, 2H, OCH2a OCH2a'), 3.73-3.65 (m, 6H, OCH2b OCH2b' H5 H5' H6 H6'), 3.63-3.51 (m, 12H, CH2Ar CH2Ar' H4 H4' H9a H9a' CH2NH CH2NH'), 3.35 (dd, J=9.04, 1.94 Hz, 2H, H7 H7'), 3.22 (dd, J=13.66, 7.95 Hz, 2H, H9b H9b'), 2.83 (dd, J=12.10, 3.96 Hz, 2H, H3-e H3-e'), 2.75 (dt, J=6.84, 2.89 Hz, 4H, OCH2S OCH2S'), 2.66 (dt, J=6.96, 2.85 Hz, 4H, SCH2 SCH2'), 1.98 (s, 6H, CH3 CH3'), 1.81 (t, J=6.43 Hz, 4H, CH2 CH2CH2 CH2CH2CH2'), 1.58 (t, J=11.84 Hz, 2H, H3-a H3-a')

HRMS (ESI-neg) [(M-2Na)/2] calculated: 721.2675 found: 721.2703

Compound 129

$^1$H-NMR (500 MHz, CD$_3$OD): δ ppm 7.96-7.88 (m, 4H, Ar), 7.81-7.70 (m, 4H, Ar), 7.57-7.50 (m, 4H, Ar), 7.46-7.42 (m, 2H, Ar), 7.40-7.36 (m, 4H, Ar), 4.03 (ddd, J=8.96, 8.09, 2.93 Hz, 2H, H8 H8'), 3.90 (td, J=9.90, 6.16 Hz, 2H, OCH2a OCH2a'), 3.75 (dd, J=13.84, 2.91 Hz, 2H, H9a H9a'), 3.73-3.49 (m, 14H, H4 H4' H5 H5' H6 H6' H9b H9b' OCH2b OCH2b' CH2NH CH2NH'), 3.39 (dd, J=8.96, 1.94 Hz, 2H, H7 H7'), 2.84 (dd, J=12.23, 4.08 Hz, 2H, H3-e H3-e'), 2.82-2.63 (m, 8H, CH2SCH2 CH2SCH2'), 2.03 (s, 6H, Ch3 CH3'), 1.88-1.80 (m, 4H CH2CH2CH2 CH2CH2CH2'), 1.60 (t, J=11.79 Hz, 2H, H3-a H3-a') $^{13}$C-NMR (125 MHz, CD$_3$OD): δ ppm 175.7 174.5 169.9 156.0 144.4 134.9 133.5 131.1 129.8 129.0 128.3 121.6 86.2 83.8 74.2 72.3 71.1 69.6 64.0 54.1 44.2 42.7 41.0 32.1 31.4 29.4 22.7

HRMS (ESI-neg) [(M-2Na)/2] calculated: 665.2205 found: 665.2208

Compound 130

A solution of 35 mg (1 eq) of compound 61 in 800 µl of absolute DMF was admixed with 200 µl of piperidine and stirred at RT for 20 min. The solvent was removed, and the residue was dissolved with 1 ml of abs. DMF and concentrated again. The residue was purified on RP-18 (H$_2$O pH4 (HCl)>>EtOH) and lyophilized

Compound 131

Prepared analogously to compound 21. No HATU was added, and fluoresceincarboxylic-NHS was used.

HRMS (ESI-neg) [(M-2Na)/2] calculated: 885.2420 found: 885.2459

Compound 132

4.0 mg of terephthalic acid (1 eq), 38 mg (2.4 eq) of compound 11 and 22 mg (2.4 eq) of HATU were dissolved in 1 ml of abs. DMF. Following addition of 25 µl (6 eq) of DIPEA, the mixture was stirred at RT for 5 min, the solvent was removed, the residue was dissolved with a little MeOH, H$_2$O was added until clouding occurred, and purification took place on an RP-18 column (H$_2$O>>MeOH). The product was dissolved in a mixture of 2 ml of tert-butanol and 0.5 ml of H$_2$O, 1 ml of 30% strength H$_2$O$_2$ was added, and the mixture was left to stand at RT for 9 days. Careful addition of manganese dioxide was followed by filtration, concentration, dissolution with a little MeOH, dilution with H$_2$O until clouding occurred, and the bringing of the reaction mixture to a pH of 12-13 with 2M NaOH. When the reaction was ended, neutralization was carried out with 20% HAc, purification took place on an RP18 column (H20>>CH$_3$CN), the CH$_3$CN was removed, and lyophilization was carried out. Yield: 30 mg of white solid.

$^1$H-NMR (500 MHz, CD$_3$OD): δ ppm 1.49-1.66 (m, 2H, H3-a H3-a'), 1.95-2.06 (m, 10H, NHCOCH3NHCOCH3' CH2CH2CH2 CH2CH2CH2'), 2.76-3.28 (m, 10H, H3-e H3-e' CH2SOCH2CH2SOCH2'), 3.39-4.01 (m, 20H, H4 H4' H5 H5' H6 H6' H7 H7' H9a H9a' H9b H9b' OCH2a OCH2a' OCH2b OCH2b' CH2NH CH2NH'), 4.02-4.11 (m, 2H, H8 H8'), 7.36 (t, J=7.07, 7.07 Hz, 2H, Ar), 7.44 (t, J=7.47, 7.47 Hz, 4H, Ar), 7.59-7.79 (m, 8H, Ar), 7.87-7.93 (m, 8H, Ar) $^{13}$C NMR (125 MHz, CD3OD): δ ppm 22.7 24.5 35.3 35.5 42.8 44.6 50.5 50.6 52.5 52.7 54.2 63.5 69.6 71.5 72.6 74.3 102.0 128.0 128.1 128.7 129.0 130.0 134.5 138.2 141.3 145.5 169.5 170.0 174.4 174.5 175.5

HRMS (ESI-neg) [(M-2Na)/2] calculated: 685.2311 found: 685.2295

2,2',4'-Trinitrobiphenyl-4-carboxylic acid (compound 133)

A solution of 10 ml of concentrated nitric acid and 14 ml of concentrated sulphuric acid was admixed at 0° C. with 1 g of biphenyl-4-carboxylic acid in small portions. When the reaction was ended, stirring took place at 95° C. for 30 min, followed by cooling to RT, and the product was placed onto ice, isolated by filtration with suction, and recrystallized from nitromethane. Yield: 500 mg of yellowish needles.

Compound 134

A solution of 35 mg (1 eq) of compound 61 in 800 µl of absolute DMF was admixed with 200 µl of piperidine, stirred at RT for 20 min, and neutralized with HAc. The solvent was removed and purification took place in an RP-18 column (H$_2$O>>EtOH). Following dissolution of the intermediate in 0.5 ml of EtOH, 30 mg (3 eq) of 3-benzylamino-4-ethoxycyclobutene-1,2-dione, 1 ml of H$_2$O and 0.1 ml of 2M NaOH were added, and the mixture was stirred for 17 h, a further 2 eq of 3-benzylamino-4-ethoxycyclobutene-1,2-dione were added, and stiffing was continued for 17 h more. The solvent was removed, the residue was dissolved with a little MeOH, H$_2$O was added until colloidal clouding occurred, purification was carried out on an RP-18 column (H$_2$O>>EtOH), the EtOH was removed, and lyophilization was carried out.

Yield: 24 mg of white solid.

$^1$H-NMR (300 MHz, CD$_3$OD): δ ppm 1.55 (t, J=11.78, 11.78 Hz, 2H, H3-a H3-a'), 1.72-1.83 (m, 4H, CH2CH2CH2 CH2CH2CH2'), 1.99 (s, 6H, NHCOCH3 NHCOCH3'), 2.61 (dt, J=6.81, 6.79, 4.62 Hz, 4H, CH2S CH2S'), 2.73 (dt, J=6.90, 6.81, 1.00 Hz, 4H, SCH2 SCH2'), 2.80 (dd, J=12.14, 3.47 Hz, 2H, H3-e H3-e), 3.44 (dd, J=8.57, 1.46 Hz, 2H, H7 H7'), 3.47-3.77 (m, 16H, H4 H4' H5 H5' H6 H6' H9a H9a' H9b H9b' OCH2a OCH2a' CH2NH CH2NH'), 3.82 (td, J=9.49, 6.15, 6.15 Hz, 2H, OCH2b OCH2b'), 3.98 (ddd, J=8.42, 7.20, 2.58 Hz, 2H, H8 H8'), 4.78 (s, 4H, ArCH2 ArCH2'), 7.25-7.35 (m, 10H, Ar), 7.90 (s, 4H, Ar) $^{13}$C NMR (75 MHz, CD3OD): δ ppm 22.8 29.4 31.3 32.0 41.0 42.6 47.9 48.8 54.3 63.7 69.4 71.6 72.2 74.3 101.9 128.7 128.8 129.9 138.4 139.8 169.4 174.5 175.6 183.7

HRMS (ESI-neg) [(M-2Na)/2] calculated: 674.2263 found: 674.2267

Compound 135

Prepared in analogy to: Bioorganic & Med. Chem. Letters 1995, 5 (23), 2809-2814

Compound 136

380 mg (1.24 mmol) of compound 135 were dissolved in 30 ml of DMF and 5 ml of H$_2$O, and 355 mg (1.67 mmol) of 4-biphenylacetic acid-NHS and 0.5 ml of saturated NaHCO$_3$ solution was added. After 72 hours, the reaction mixture was concentrated and was purified on a silica gel column (EtOH:EE:HAc 20% 1:8:1), and the product is purified on RP-18 and lyophilized Yield: 310 mg Compound 137

270 mg (054 mmol) of compound 136 and 174 mg (0.73 mmol) of acetoxyacetic acid-NPE were dissolved in 5 ml of abs. DMF, 0.154 ml (1.08 mmol) of TEA was added, and the mixture was stirred for 17 h. Addition of 2 ml of 2M NaOH was followed by 17 h of stirring, neutralization with 20% HAc, concentration, and purification on a silica gel column (EtOH:EE:HAc20% 1:8:1). Yield: 270 mg Compound 138

Prepared analogously to compound 11

Compound 139

6.0 mg of terephthalic acid (1 eq) and 22 mg (2.4 eq) of HATU were dissolved in 1 ml of abs. DMF. 2 min after addition of 25 µl (6 eq) of DIPEA, 55 mg (2.4 eq) of compound 138 were added and the mixture was stirred at RT for 5 min, the solvent was removed, the residue was dissolved with a little MeOH, $H_2O$ was added until clouding occurred, and purification took place on an RP-18 column ($H_2O$>>MeOH). Yield: 30 mg of white solid.

$^1$H-NMR (500 MHz, $CD_3OD$): δ ppm 7.90 (s, 4H, Ar), 7.57 (dd, J=8.26, 1.23 Hz, 4H, Ar), 7.53 (dd, J=8.20, 1.39 Hz, 4H, Ar), 7.39 (t, J=7.35, 7.35 Hz, 4H, Ar), 7.35 (d, J=8.15 Hz, 4H, Ar), 7.29 (t, J=7.38, 7.38 Hz, 2H, Ar), 4.04 (d, J=1.94 Hz, 4H, $CH_2OH$ $CH_2OH'$), 3.96 (ddd, J=9.06, 8.54, 2.91 Hz, 2H, H8 H8'), 3.85 (td, J=9.61, 6.11, 6.11 Hz, 2H, OCH2a OCH2a'), 3.82-3.77 (m, 2H, H5 H5'), 3.75 (dd, J=10.04, 1.72 Hz, 2H, H6 H6'), 3.71 (dd, J=13.90, 2.83 Hz, 2H, H9a H9a'), 3.69-3.66 (m, 2H, H4 H4'), 3.61-3.47 (m, 10H, ArCH2 ArCH2' OCH2b OCH2b' CH2NH CH2NH'), 3.36 (dd, J=8.84, 1.97 Hz, 2H, H7 H7'), 3.18 (dd, J=13.18, 7.64 Hz, 2H, H9b H9b'), 2.83 (dd, J=12.29, 4.66 Hz, 2H, H3-e H3-e'), 2.72 (dd, J=12.84, 6.52 Hz, 4H, SCH2 SCH2'), 2.63 (dt, J=6.58, 6.51, 1.19 Hz, 4H, CH2S CH2S), 1.81-1.75 (m, 4H, CH2 CH2SCH2CH2'), 1.56 (t, J=11.88, 11.88 Hz, 2H, H3-a H3-a')
$^{13}$C NMR (125 Hz, CD3OD): δ ppm 29.5 31.5 32.0 41.1 42.8 43.5 44.1 53.8 62.7 63.8 69.4 71.5 72.3 74.0 102.0 127.9 128.2 128.3 128.6 129.9 130.7 136.2 138.4 141.0 142.1 169.4 174.1 174.6 177.3

HRMS (ESI-neg) [(M-2Na)/2] calculated: 699.2467 found: 699.2520

Compound 140

Prepared analogously to compound 139. Instead of compound 138, compound 86 was used. The material was not admixed with NaOH.

HRMS (ESI-neg) [(M-2Na)/2] calculated: 723.2194 found: 723.2176

Compound 141

Prepared analogously to compound 136

Compound 142

Prepared analogously to compound 137

Compound 143

54 mg (0.095 mmol) of compound 142 were dissolved in a little abs. MeOH, ran over Dowex W 650C H+ in abs. MeOH, and admixed directly with diazomethane in ether until the solution remained yellowish. Addition of a little dilute HAc was followed by concentration. Yield: 48 mg.

Compound 144

Prepared analogously to compound 11

Compound 145

Prepared analogously to compound 21

$^1$H-NMR (500 MHz, $CD_3OD$): δ ppm 7.90 (d, J=8.50 Hz, 4H, Ar), 7.87 (s, 4H, Ar), 7.68 (d, J=8.44 Hz, 4H, Ar), 7.63 (dd, J=7.62, 1.74 Hz, 4H, Ar), 7.44 (t, J=7.61 Hz, 4H, Ar), 7.36 (t, J=7.38 Hz, 2H, Ar), 4.85 (d, J=46.96 Hz, 4H, FCH2 FCH2'), 4.11 (ddd, J=8.85, 7.95, 3.20 Hz, 2H, H8 H8'), 3.91 (td, J=9.79, 6.52 Hz, 2H, OCH2a OCH2a'), 3.88 (dd, J=10.02, 9.44 Hz, 2H, H5 H5'), 3.86 (dd, J=13.67, 3.23 Hz, 2H, H9a H9a'), 3.81 (dd, J=10.58, 1.61 Hz, 2H, H6 H6'), 3.83-3.77 (m, 2H, H4 H4'), 3.60 (td, J=9.31, 6.05 Hz, 2H, OCH2b OCH2b'), 3.54 (dd, J=13.64, 6.56 Hz, 4H, CH2NH CH2NH'), 3.51 (dd, J=13.60, 7.74 Hz, 2H, H9b H9b'), 3.48 (dd, J=8.96, 1.77 Hz, 2H, H7 H7'), 2.85 (dd, J=12.22, 4.67 Hz, 2H, H3-e H3-e'), 2.74 (dt, J=6.94, 2.42 Hz, 4H, SCH2 SCH2'), 2.70-2.63 (m, 4H, CH2S CH2S), 1.86-1.79 (m, 4H, CH2CH2CH2 CH2CH2CH2'), 1.60 (t, J=11.99 Hz, 2H, H3-a H3-a') $^{13}$C NMR (125 MHz, $CD_3O$): δ ppm 174.6 170.1 169.3 172.19 (d, J=18.61 Hz) 145.6 141.3 138.4 134.5 130.0 129.1 129.0 128.6 128.2 128.0 102.0 81.00 (d, J=182.75 Hz) 73.7 72.4 71.8 69.6 63.9 53.7 44.5 42.8 41.8 32.0 31.5 29.4

HRMS (ESI-neg) [(M-2Na)/2] calculated: 687.2267 found: 687.2244

Compound 146 and 147

25 mg (1 eq) of compound 21 were stirred with 20 l (20 eq) of TEA and 41 mg (10 eq) of benzoic anhydride at 38° C. for three days, the TEA was removed, dilution took place with water, and purification was carried out on RP18 ($H_2O$>>EtOH). The two products were each applied with EE to a silica gel column, washed with EE, rinsed from the column with MeOH, and lyophilized from $H_2O$/dioxane. Yield: 10 mg of compound 146 and 10 mg of compound 147

Compound 146

$^1$H-NMR (500 MHz, $CD_3OD$): δ ppm 8.00 (dd, J=8.14, 1.08 Hz, 4H, Ar), 7.91 (d, J=8.28 Hz, 4H, Ar), 7.85 (s, 4H, Ar), 7.77-7.71 (m, 4H, Ar), 7.68 (d, J=8.40 Hz, 4H, Ar), 7.64-7.57 (m, 6H, Ar), 7.49-7.42 (m, 4H, Ar), 7.36 (t, J=7.34 Hz, 2H, Ar), 5.24 (ddd, J=11.41, 10.61, 4.78 Hz, 2H, H4 H4'), 4.36 (t, J=10.35 Hz, 2H, H5 H5'), 4.12 (ddd, J=8.50, 7.72, 3.24 Hz, 2H, H8 H8'), 4.02 (dd, J=10.68, 1.47 Hz, 2H, H6 H6'), 3.95 (td, J=9.19, 6.08 Hz, 2H, OCH2a OCH2a'), 3.88 (dd, J=13.76, 3.10 Hz, 2H, H9a H9a'), 3.63-3.49 (m, 10H, H7 H7' H9b H9b' OCH2b OCH2b' CH2NH CH2NH'), 2.90 (dd, J=12.74, 5.06 Hz, 2H, H3-e H3-e'), 2.73 (t, J=7.06 Hz, 4H, CH2S CH2S'), 2.66 (q, J=6.87 Hz, 4H, SCH2 SCH2'), 1.96 (t, J=12.14 Hz, 2H, H3-a H3-a'), 1.84 (s, 6H, CH3 CH3'), 1.89-1.80 (m, 4H, CH2CH2CH2 CH2CH2CH2')

HRMS (ESI-neg) [(M-2Na)/2] calculated: 773.2624 found: 773.2621

Compound 147

$^1$H-NMR (500 MHz, $CD_3OD$): δ ppm 8.00 (d, J=7.27 Hz, 2H, Bz), 7.90 (t, J=8.31 Hz, 4H, BIP), 7.85 (s, 4H, Ar), 7.75

(t, J=7.48 Hz, 2H, Bz), 7.70-7.65 (m, 4H, BIP), 7.64-7.58 (m, 5H, 1xBz 4xBIP), 7.45-7.41 (m, 4H, BIP), 7.38-7.33 (m, 2H, BIP), 5.24 (ddd, J=11.60, 10.46, 4.99 Hz, 1H, H4), 4.36 (t, J=10.52 Hz, 1H, H5), 4.15-4.07 (m, 2H, H8 H8'), 4.02 (dd, J=10.61, 1.28 Hz, 1H, H6), 3.96 (td, J=9.54, 6.29 Hz, 1H, OCH2a), 3.92-3.82 (m, 2H, H4' OCH2a'), 3.86 (dd, J=13.82, 3.11 Hz, 1H, H9a), 3.80 (t, J=10.04 Hz, 1H, H5'), 3.75-3.69 (m, 1H, OCH2b'), 3.68 (dd, J=10.46, 1.41 Hz, 1H, H6'), 3.62-3.43 (m, 10H, H7 H7' H9a' H9b H9b' OCH2b CH2NH CH2NH'), 2.90 (dd, J=12.32, 4.84 Hz, 1H, H3-e), 2.76-2.61 (m, 9H, H3-e' CH2SCH2 CH2SCH2'), 2.00 (s, 3H, CH3'), 1.96 (t, J=12.22 Hz, 1H, H3-a), 1.88-1.79 (m, 5H, CH3 CH2 CH2CH2), 1.76-1.67 (m, 2H, CH2CH2CH2'), 1.63-1.57 (m, 1H, H3-a')

HRMS (ESI-neg) [(M-2Na)/2] calculated: 721.2493 found: 721.2482

Compound 148

Prepared analogously to compound 11. Instead of cysteamine, cystein was used.

Compound 149

A solution of 3 mg (1 eq) of terephthalic acid and 21.5 mg (2.3 eq) of HATU in 1 ml of abs. DMF was admixed with 14 µl of DIPEA (6 eq). Following addition of 27.6 mg (2.3 eq) of compound 148, the mixture was stirred for 5 min, concentrated and purified on RP18. The product was hydrolysed analogously to compound 25. Yield 13 mg.

$^1$H-NMR (500 MHz, CD$_3$OD): δ ppm 1.58 (t, J=11.68, 11.68 Hz, 2H, H3-a H3-a'), 1.77-1.84 (m, 4H, CH2CH2CH2 CH2CH2CH2'), 1.99 (s, 6H, NHCOCH3 NHCOCH3'), 2.67 (dd, J=14.57, 7.13 Hz, 4H, SCH2CH2CH2 SCH2CH2CH2'), 2.81 (dd, J=12.15, 4.01 Hz, 2H, H3-e H3-e'), 3.02 (dd, J=13.84, 8.18 Hz, 2H, CH2CHa), 3.17 (dd, J=13.79, 4.65 Hz, 2H, CH2CHb), 3.44 (dd, J=8.92, 1.73 Hz, 2H, H7 H7'), 3.52-3.75 (m, 10H, H4 H4' H5 H5' H6 H6' H9a H9a' OCH2a OCH2a'), 3.80 (dd, J=13.62, 3.07 Hz, 2H, H9b H9b'), 3.88 (td, J=9.40, 6.20, 6.20 Hz, 2H, OCH2b OCH2b'), 4.10 (ddd, J=8.78, 7.95, 3.16 Hz, 2H, H8 H8'), 4.70 (dd, J=8.11, 4.65 Hz, 2H, CH2CH CH2CH'), 7.35 (t, J=7.36, 7.36 Hz, 2H, Ar), 7.44 (t, J=7.63, 7.63 Hz, 4H, Ar), 7.62 (d, J=7.21 Hz, 4H, Ar), 7.67 (d, J=8.44 Hz, 4H, Ar), 7.87-7.94 (m, 8H, Ar) $^{13}$C NMR (125 MHz, CD3OD): δ ppm 22.7 30.1 31.3 34.9 42.6 44.5 54.1 55.4 63.8 69.6 71.5 72.5 74.3 101.8 128.0 128.2 128.7 129.0 129.1 130.0 134.5 138.3 141.3 145.5 169.1 170.1 174.3 175.3 175.4

HRMS (ESI-neg) [(M-2Na)/2] calculated: 713.2260 found: 713.2331

Compound 150

A solution of 190 mg of compound 148 in abs. DMF was admixed with 115 mg (1.2 eq) of Fmoc-NHS and 85 µl (2.2 eq) of TEA. After 30 minutes the mixture was concentrated, and the product was purified on an RP-18 column (H$_2$O>>EtOH) and freeze-dried. Yield: 218 mg of white solid.

Compound 151

A solution of 87 mg of compound 150 in 1 ml of abs. DMF was admixed with 51 µl (3 eq) of DIPEA and 45 mg (1.2 eq) of HATU. Then 403 mg (30 eq) of 4-aminobenzoic acid and 530 µl (30 eq) of DIPEA in 2 ml of abs. DMF were added, the solvent was removed after 5 minutes, and purification was carried out on a silica gel column (EtOH:EE:HAc20% 1:12:1). The product was purified further on an RP-18 column (H$_2$O>>EtOH) and lyophilized after removal of the ethanol. Yield: 41 mg of white solid.

Compound 152

A solution of 33 mg of compound 151, 26 mg (1.2 eq) of compound 11 and 12.7 mg (1.2 eq) of HATU in 3 ml of abs. DMF was admixed with 17.4 µl of DIPEA, stirred at RT for 5 min, concentrated, and purified on an RP-18 column (H$_2$O>>EtOH); the ethanol was removed, and lyophilization was carried out. Yield: 43 mg of white solid.

Compound 153

A solution of 11 mg of compound 152 in a little ethanol was admixed with water until clouding occurred, adjusted to a pH of 12-13 with 2M NaOH, diluted with water after 17 h, neutralized to a pH of 7-8 with 20% HAc, and purified on an RP-18 column (H$_2$O>>EtOH); the ethanol was removed, and lyophilization was carried out. Yield: 8 mg of white solid.

$^1$H-NMR (300 MHz, CD$_3$OD): δ ppm 1.50-1.68 (m, 2H, H3-a H3-a'), 1.75-1.87 (m, 4H, CH2CH2CH2 CH2CH2CH2'), 2.00 (s, 6H, NHCOCH3 NHCOCH3'), 2.60-2.76 (m, 8H, H3-e H3-e' CH2SCH2 CH2SCH2), 2.79-2.89 (m, 1H, SCH2a), 2.91-3.03 (m, 1H, SCH2b), 3.33-3.95 (m, 19H, H4 H4' H5 H5' H6 H6' H7 H7' H9a H9a' H9b H9b' OCH2a OCH2a' OCH2b OCH2b'CH2NH2 CHNH), 4.05-4.15 (m, 2H, H8 H8'), 7.35 (t, J=7.28, 7.28 Hz, 2H, Ar), 7.44 (t, J=7.64, 7.64 Hz, 4H, Ar), 7.62 (dd, J=8.29, 1.28 Hz, 4H, Ar), 7.65-7.72 (m, 6H, Ar), 7.77 (d, J=8.47 Hz, 2H, Ar), 7.90 (d, J=8.30 Hz, 4H, Ar)

2-(18-Biotinoylamino-1,4,7,10,13,16-hexaoxoocta-decyl)terephthalic acid (compound 154)

A solution of 240 mg (1 eq) of dimethyl terephthalate and 386 mg (1.1 eq) of 17-azido-1-hydroxy-3,6,9,12,15-heptaoxo-heptadecane in 5 ml of abs. DMF was admixed at 0° C. with 449 mg (1.5 eq) of triphenylphosphine and 330 µl (1.5 eq) of DIAD, and stirred overnight. 2 h after addition of 2 ml of MeOH, it was concentrated, taken up in CH$_2$Cl$_2$, washed with H$_2$O, dried with MgSO$_4$, filtered, purified on silica gel (hexane>>EE) and concentrated. The oil obtained was dissolved in 5 ml of MeOH and 1 ml of H$_2$O, admixed with Pd on carbon (10%) and 80 µl of HAc (20%), hydrogenated for 2 h, concentrated, and dissolved in H$_2$O. The solution was adjusted to a pH of 3-4 with HCl, and purified on RP18 (H$_2$O>>EtOH). The product was dissolved in DMF, admixed with biotin-NHS (1 eq) and DIPEA (3 eq), concentrated and purified on RP-18. The material obtained was dissolved with an EtOH—H$_2$O mixture, the pH was adjusted to 12-13 with 2M NaOH, the pH was adjusted to 3 with HCl after 3 h, and purification on RP18 was repeated.

Substance 155

Prepared analogously to compound 21 with compound 154.

$^1$H NMR (500 MHz, CD$_3$OD): δ ppm 7.92-7.87 (m, 4H), 7.94 (d, J=8.08 Hz, 1H), 7.69-7.65 (m, 4H), 7.63-7.60 (m, 4H), 7.52 (d, J=1.37 Hz, 1H), 7.46 (dd, J=8.19, 1.55 Hz, 1H), 7.46-7.40 (m, 4H), 7.38-7.33 (m, 2H), 4.46 (ddd, J=7.86, 5.05, 0.66 Hz, 1H), 4.30-4.25 (m, 3H), 4.13-4.06 (m, 2H), 3.94-3.83 (m, 6H), 3.75-3.42 (m, 34H), 3.33-3.31 (m, 2H), 3.15 (ddd, J=8.76, 5.64, 4.59 Hz, 1H), 2.89 (dd, J=12.75, 5.00

Hz, 1H), 2.86-2.81 (m, 2H), 2.77-2.72 (m, 4H), 2.71-2.61 (m, 5H), 2.19 (t, J=7.37 Hz, 2H), 2.01 (s, 6H), 1.87-1.79 (m, 4H), 1.75-1.51 (m, 6H), 1.44-1.32 (2H, m) $^{13}$C-NMR (125 MHz, CD$_3$OD): δ ppm 175.5 173.7 170.0 169.3 145.5 141.3 138.4 134.5 130.0 129.1 129.0 128.6 128.1 128.0 101.4 74.5 72.5 71.5 69.4 63.8 54.1 44.7 42.5 41.0 32.0 31.3 29.4 22.7

HRMS (Esi-neg) [(M-2Na)/2]calculated: 1844.7254 found 1844.7362

Biological Tests

The affinity of a number of dimers was measured using a known assay (Bock et al., Methods Mol. Biol. 2006, 347, 359-375). A greatly increased affinity was found. Exact values were undeterminable, however, owing to fluctuating values. In order to be able to determine the affinity of the new derivatives reliably, a new assay was drawn up. For this assay, compound 155 was prepared.

(inhibitor). The reaction volume was 50 μl. Then 50 microliters of compound 155 (4-micromolar) were added, and incubation took place for 20 min Washing with FACS buffer (PBS, 0.1 BSA, 0.01% sodium azide) was followed by incubation with streptavidin-PE in the dark for 15 min, followed by washing and measurement of the bound amount of substance 390 via the streptavidin-PE in the FACS. For the determination of 0% displacement of the compound 155, cells without inhibitor were measured. For the determination of 100% displacement, cells were measured without compound 155 and without inhibitor. For each assay, four substances and one reference were measured. The IC50 values determined in each assay were subsequently converted into values of rIP (relative Inhibitory Potency). The rIP values were determined using substance 21 as a reference in the assays.

Greatly increased rIP values were found for the dimers. Exact comparison of the monomer "BPCNeu5Ac" (J. Exp. Med. 2002, 195, 1207-1213) with the dimers (compounds of

155

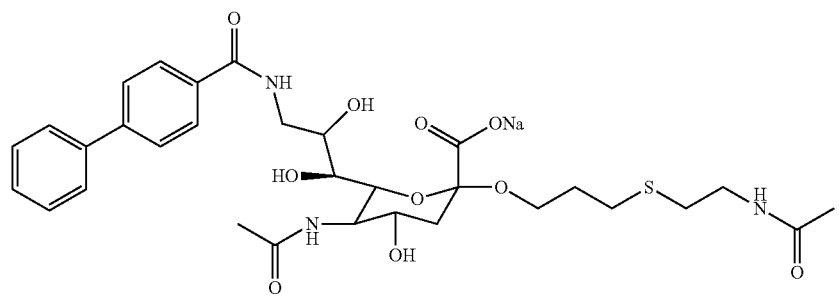

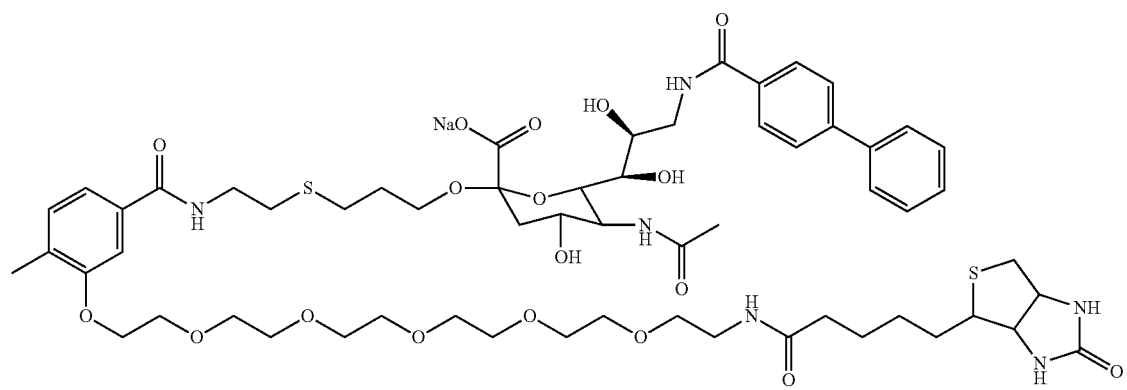

This substance was used to carry out the assay below.

To determine the affinity of the compound of the formula (I), approximately 5×10$^6$ to 2×10$^8$ cells of the human B-cell lymphoma line "Daudi" were incubated with sialidase (*A. ureafaciens*) at 37° C. for 1 h (final concentration 0.1 unit/ml). The enzyme was subsequently blocked with 1.5 mM 2,3-DehydrNeu5Ac, and the cells were washed twice with FACS buffer (PBS, 0.1% BSA, 0.01% NaN$_3$). Batches of 1-2×10$^6$ cells were transferred to sample vessels, and incubated on ice for 15 min with serial concentrations (10-fold dilutions, 1 mM to 1×10$^{-7}$ mM) of the substance under measurement the formula (I)) is not possible even with the new assay, since the IC50 values of the two classes of substance behave differently from one another, and fluctuated from assay to assay.

The IC50 values also fluctuated within the group of the dimers. Surprisingly, however, they fluctuated synchronously. As a result it was possible to form stable rIP values relative to a dimeric reference compound. Table I shows the known monomeric compound BPCNeu5Ac, and also the dimeric compounds 38 and 21, with rIP values from different assays.

TABLE I

| No. | Structure | rIP (Literature assay) | rIP (New assay) |
|---|---|---|---|
| BPC Neu5Ac | 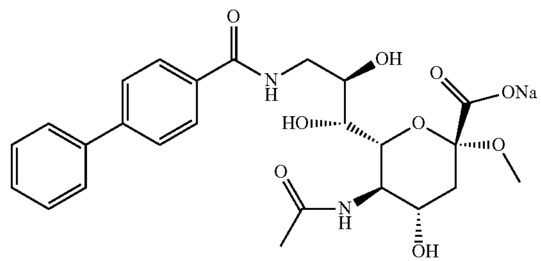 | | 1 |
| 38 | 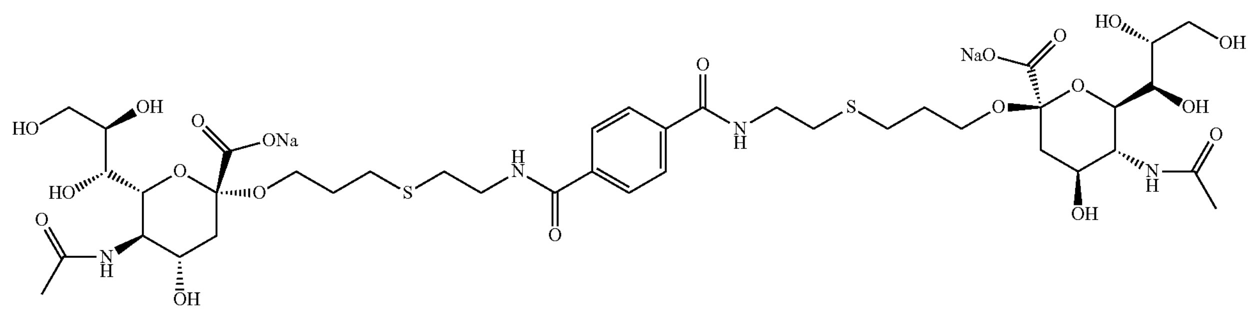 | ~1-3 | 1 |
| 21 | 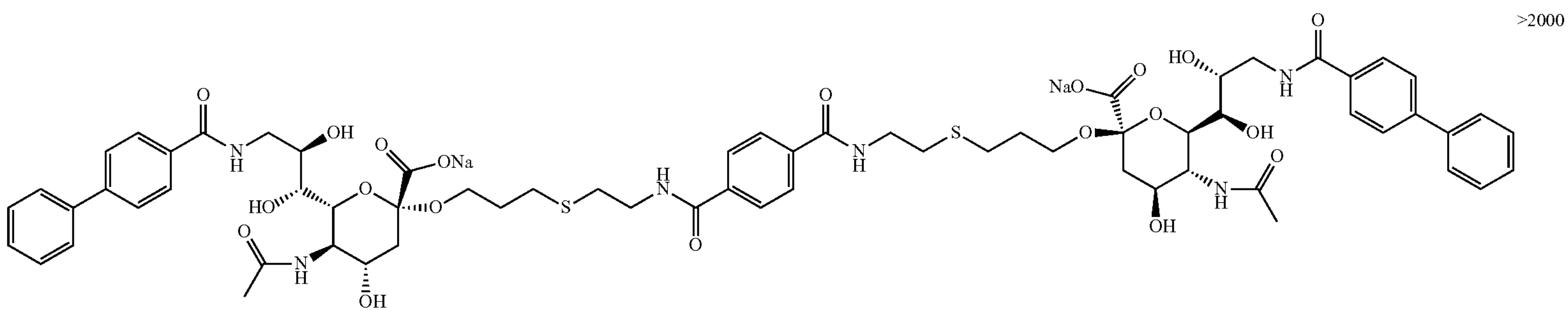 | >2000 | 2979 |

A greatly increased affinity was achieved simply by dimerizing the sialic acid. By introducing a substituted nitrogen into the 9-position of the dimer, surprisingly, the affinity was further increased to a particularly great extent.

All of the compounds of the formula (I) (labelled exclusively with a number in the synthesis schemes) are listed in Table II. The rIP values in Table II are set relative to compound 38.

TABLE II

| No. | Structure | nP |
|---|---|---|
| 38 | (chemical structure) | 1 |
| 13 | (chemical structure) | 251 |
| 19 | (chemical structure) | 368 |

TABLE II-continued

| No. | Structure | nP |
|-----|-----------|-----|
| 20 | 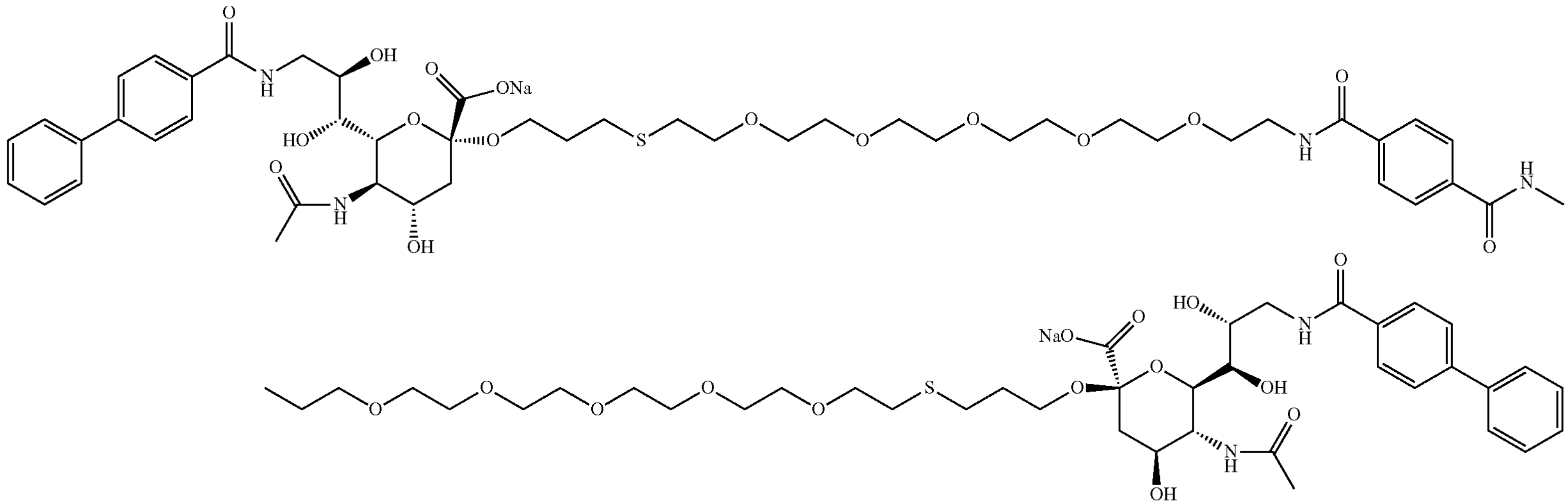 | 292 |
| 21 | 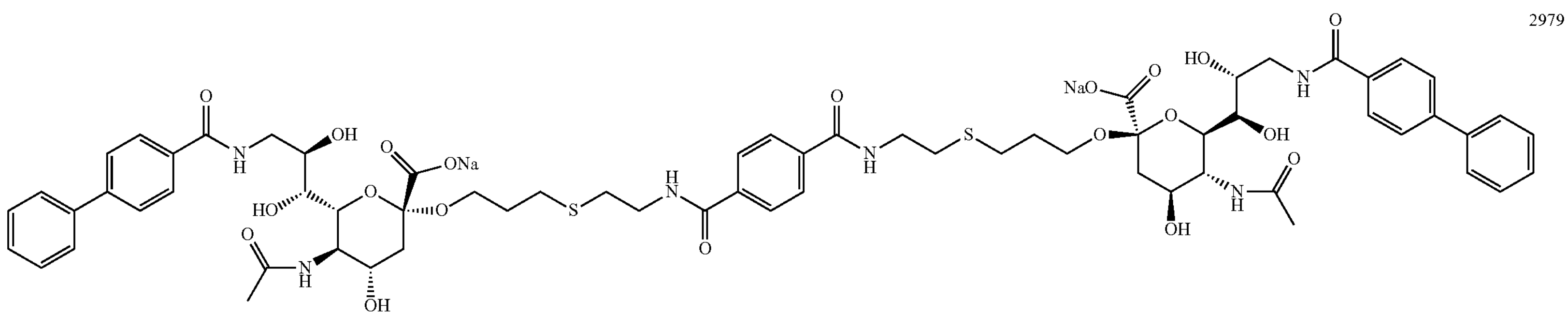 | 2979 |

TABLE II-continued

| No. | Structure | nP |
|---|---|---|
| 22 | 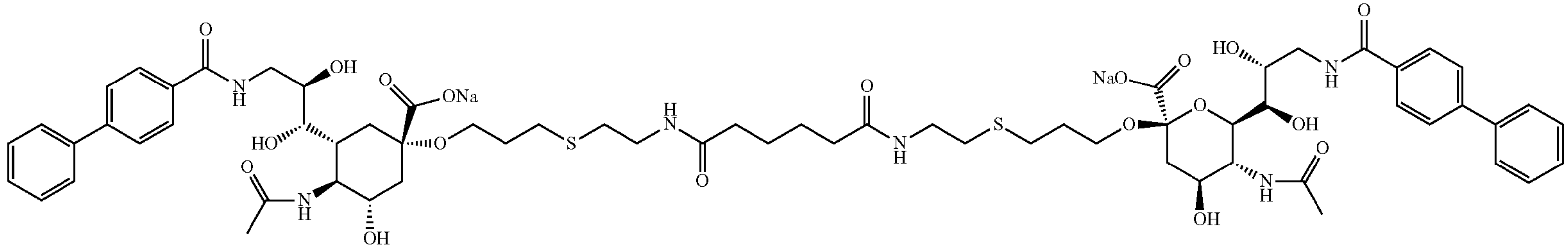 | 192 |
| 23 | 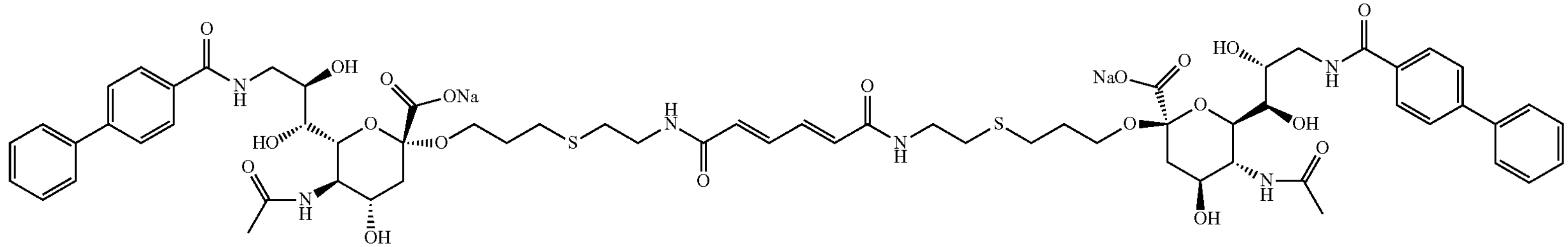 | 309 |
| 24 | 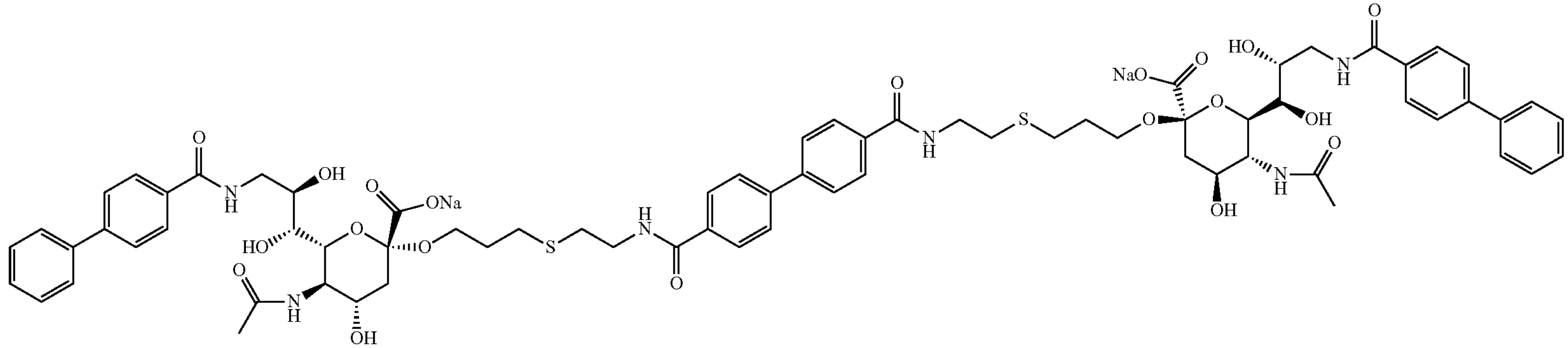 | 75 |

TABLE II-continued

| No. | Structure | nP |
|---|---|---|
| 25 | 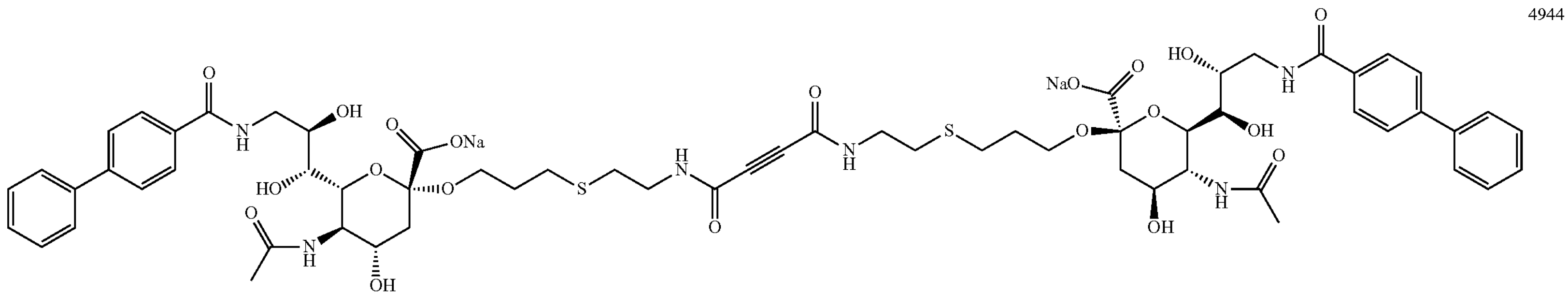 | 4944 |
| 26 | 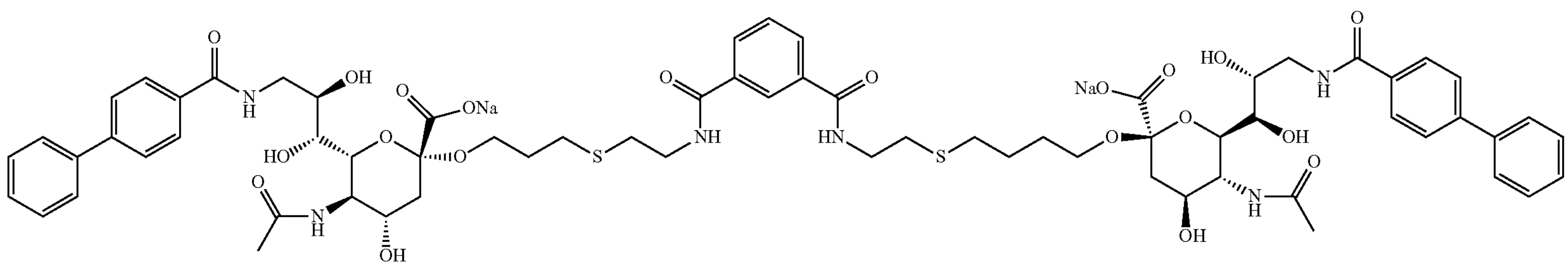 | 308 |
| 27 | 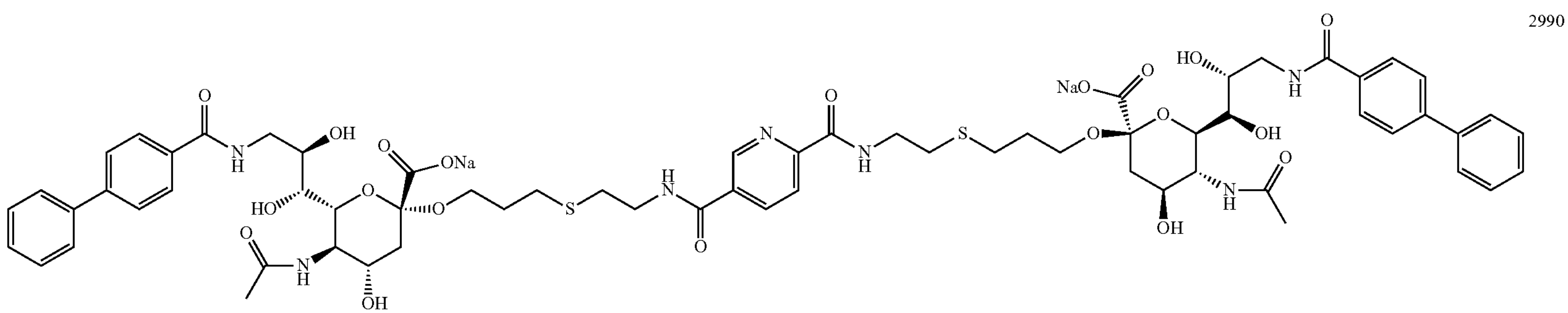 | 2990 |

TABLE II-continued

| No. | Structure | rIP |
|---|---|---|
| 28 | 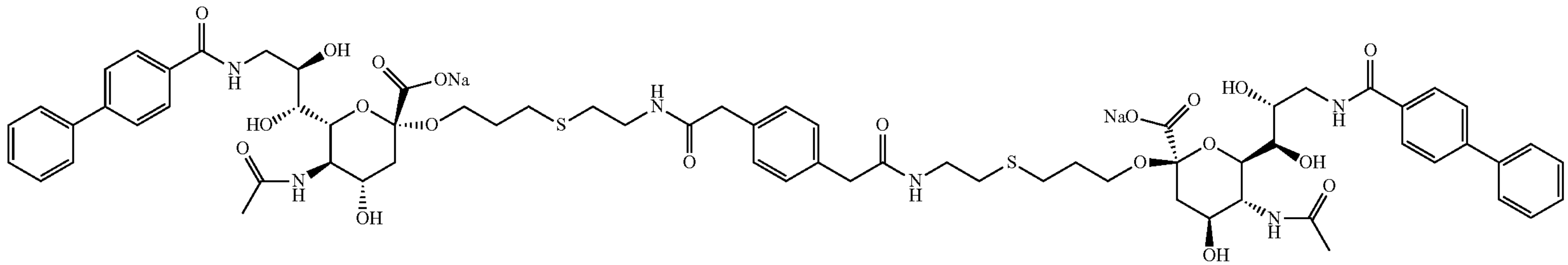 | 129 |
| 29 | 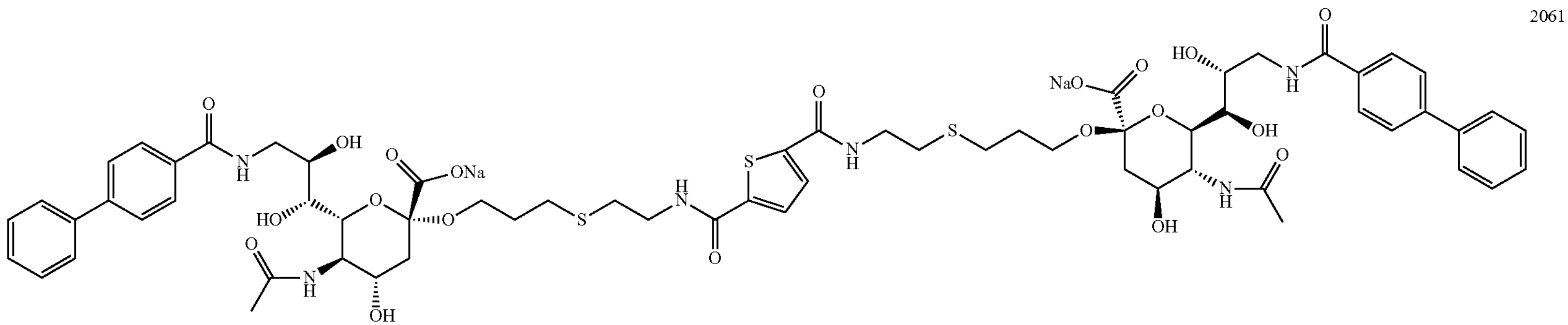 | 2061 |
| 30 | 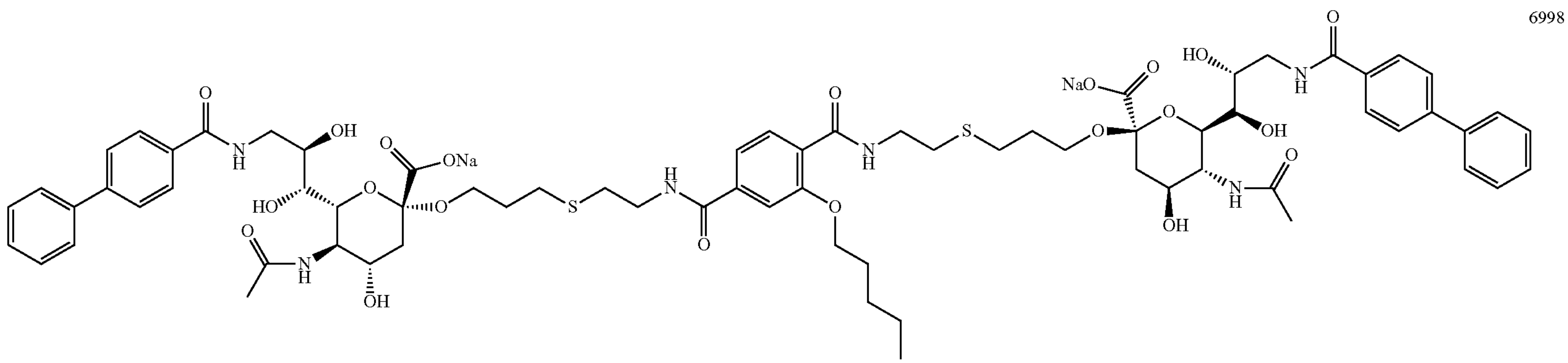 | 6998 |

TABLE II-continued

| No. | Structure | rIP |
|---|---|---|
| 31 | 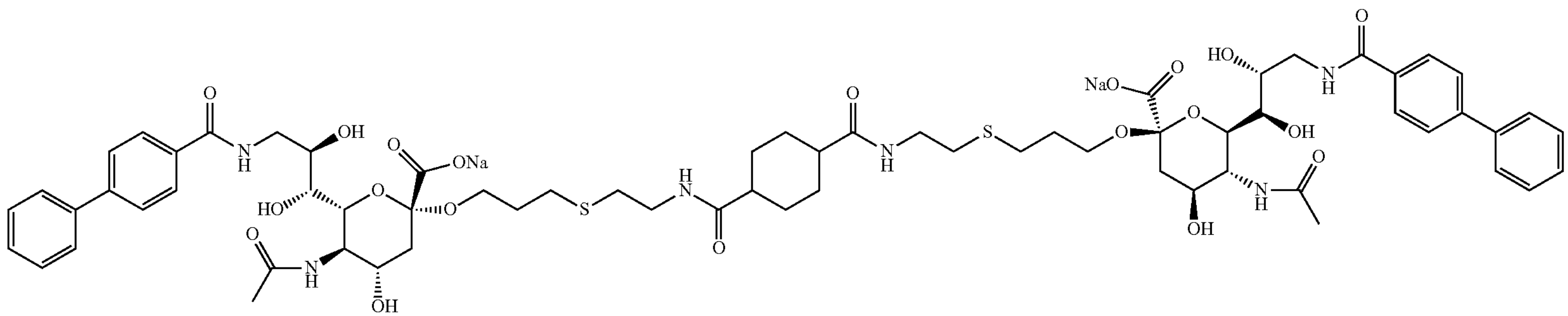 | 643 |
| 32 | 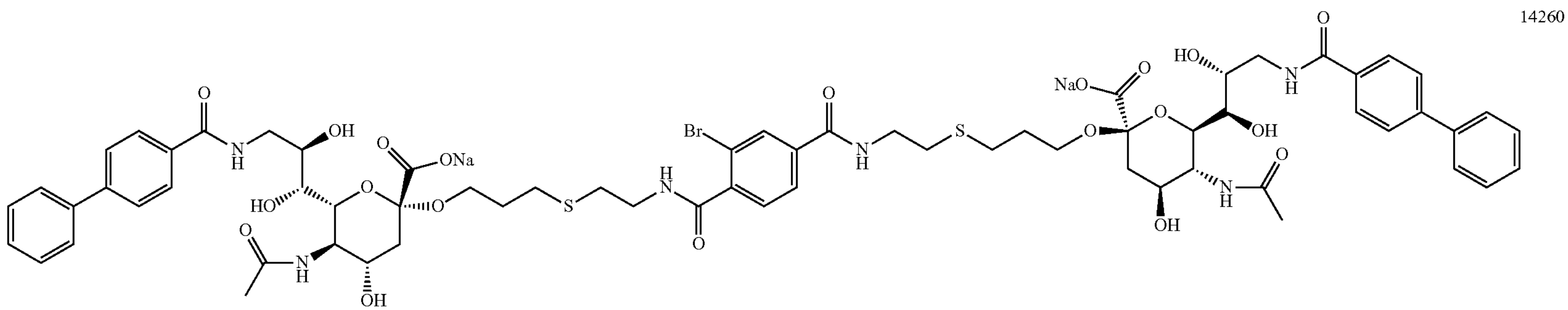 | 14260 |
| 33 | 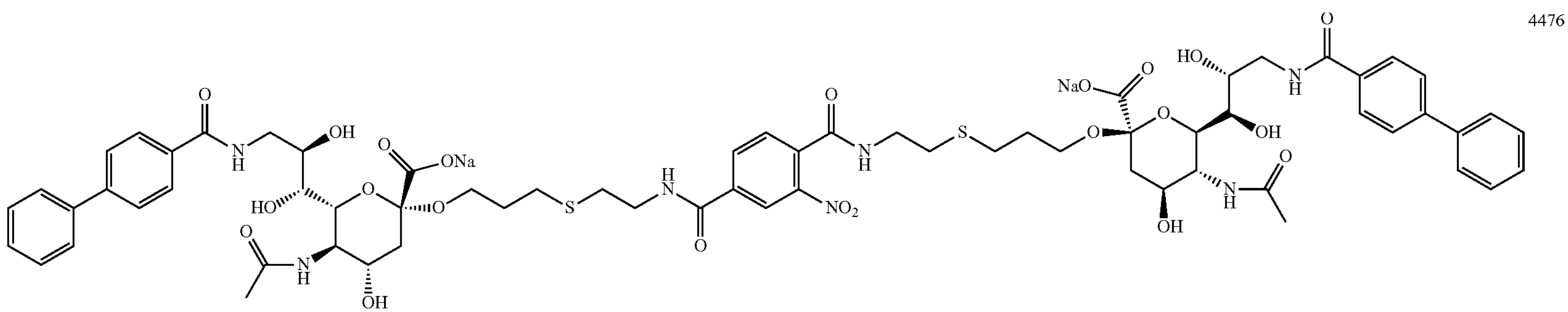 | 4476 |

TABLE II-continued

| No. | Structure | nP |
|---|---|---|
| 34 | 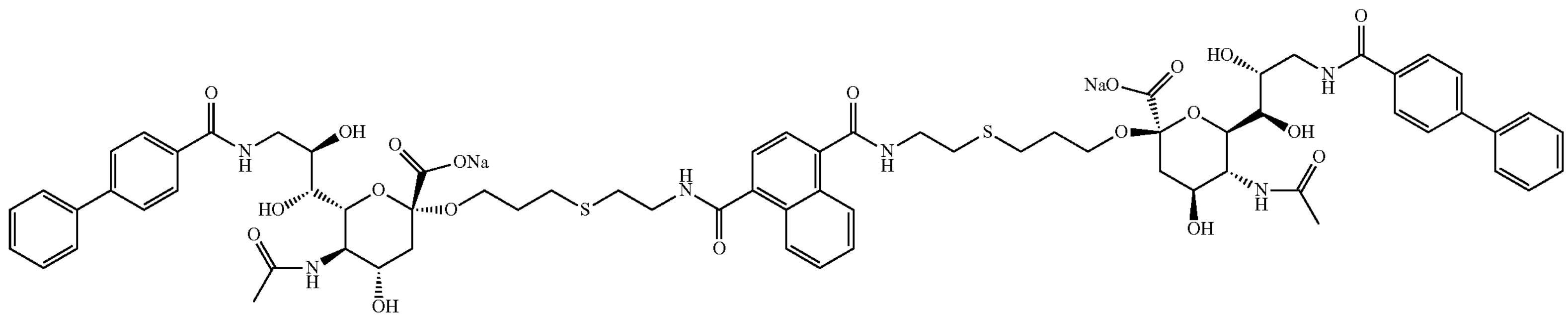 | 899 |
| 35 | 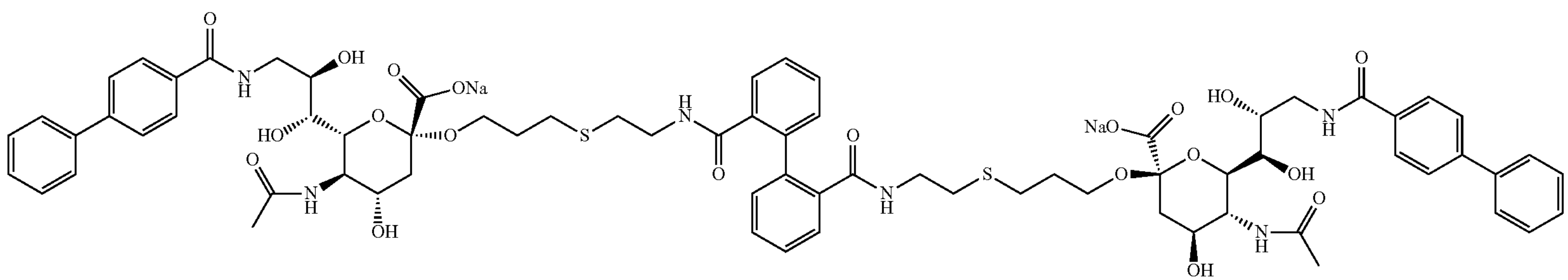 | 717 |
| 36 | 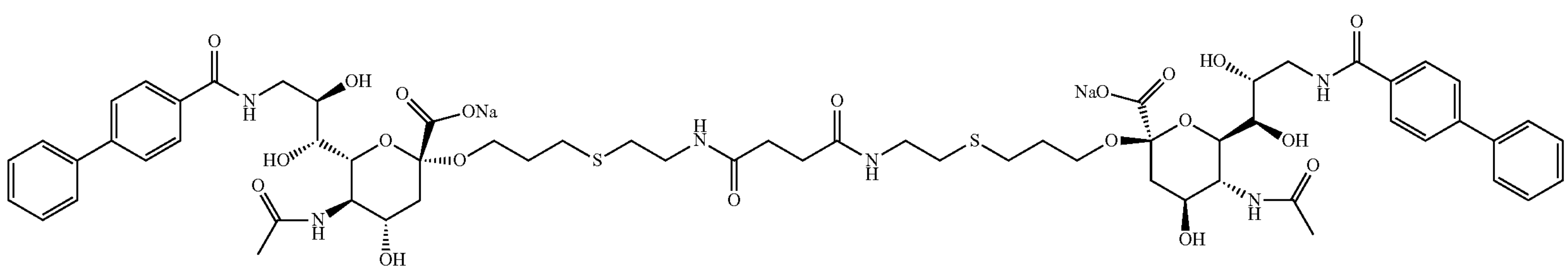 | 23 |

TABLE II-continued

| No. | Structure | nP |
|---|---|---|
| 37 | 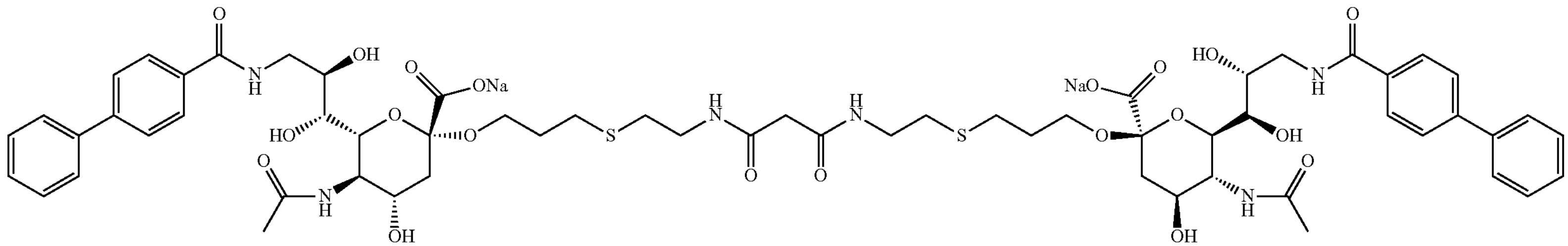 | 177 |
| 39 | 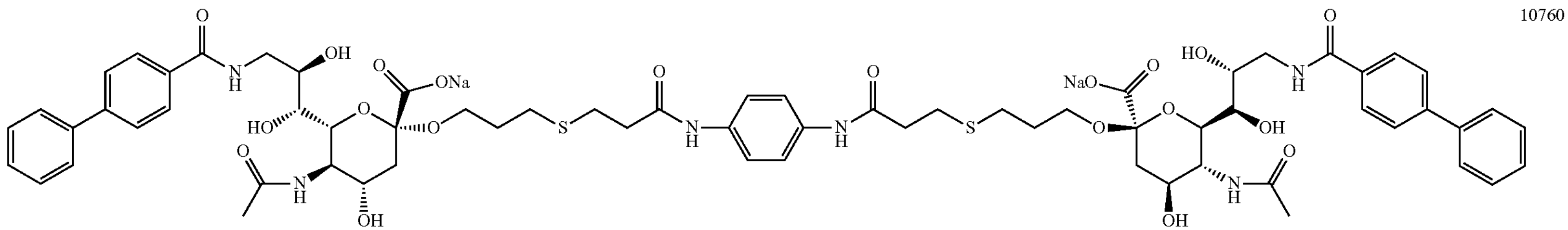 | 10760 |
| 40 | 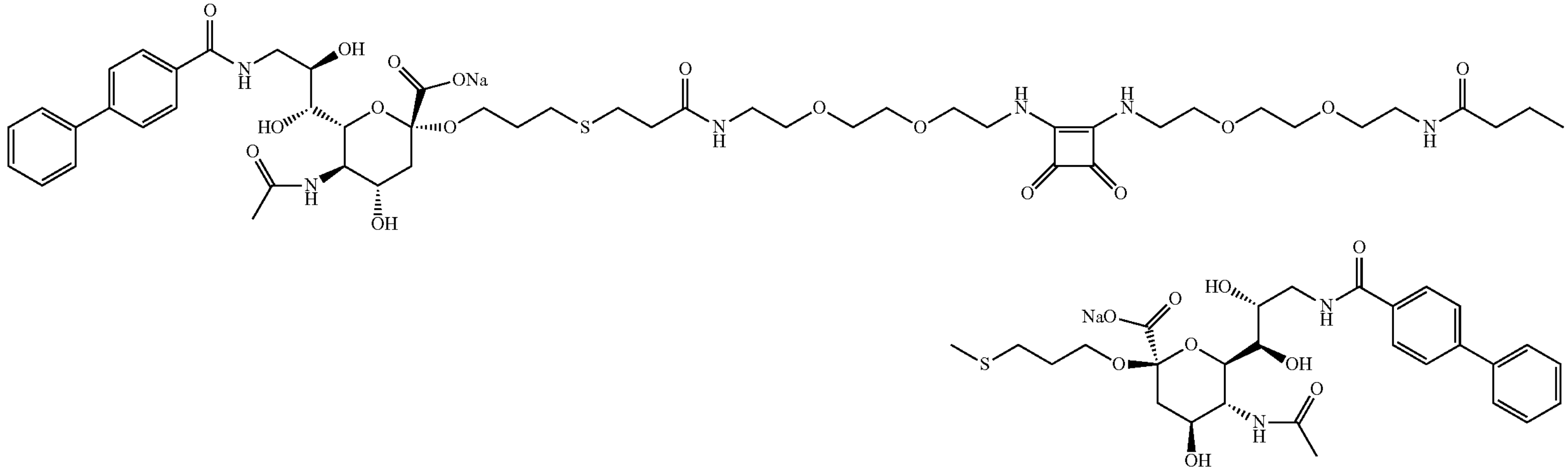 | 433 |

TABLE II-continued

| No. | Structure | nP |
|---|---|---|
| 41 | 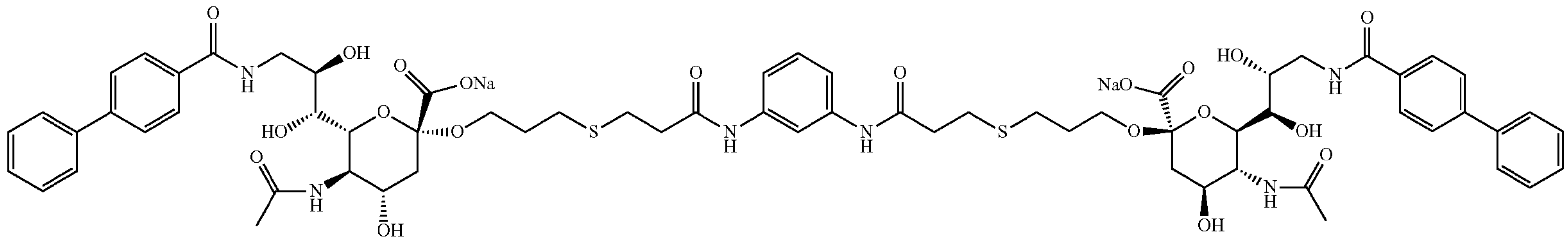 | 423 |
| 42 | 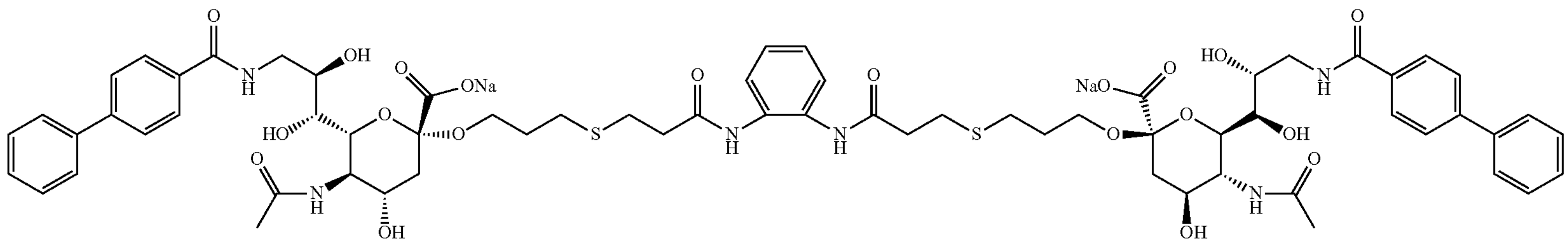 | 359 |
| 43 | 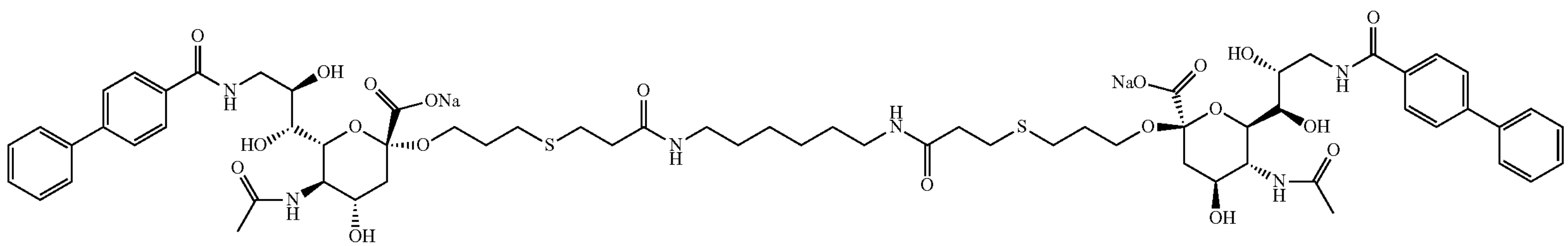 | 15 |
| 44 | 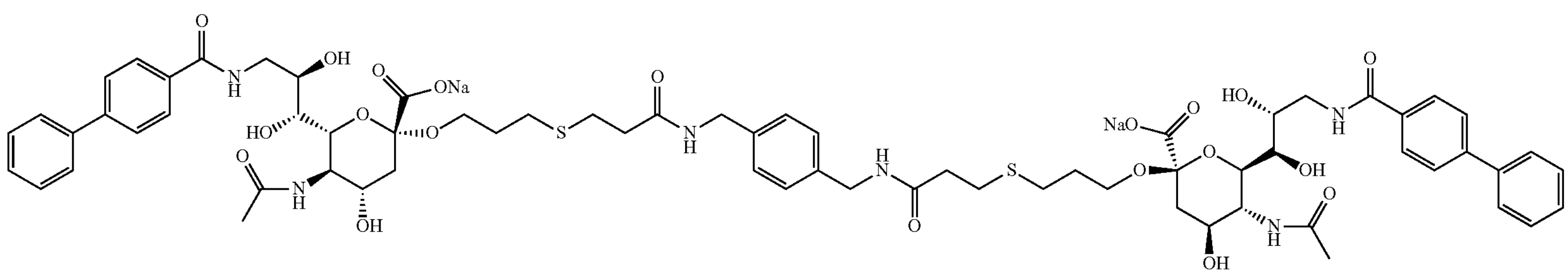 | 177 |

TABLE II-continued

| No. | Structure | nP |
|---|---|---|
| 45 | 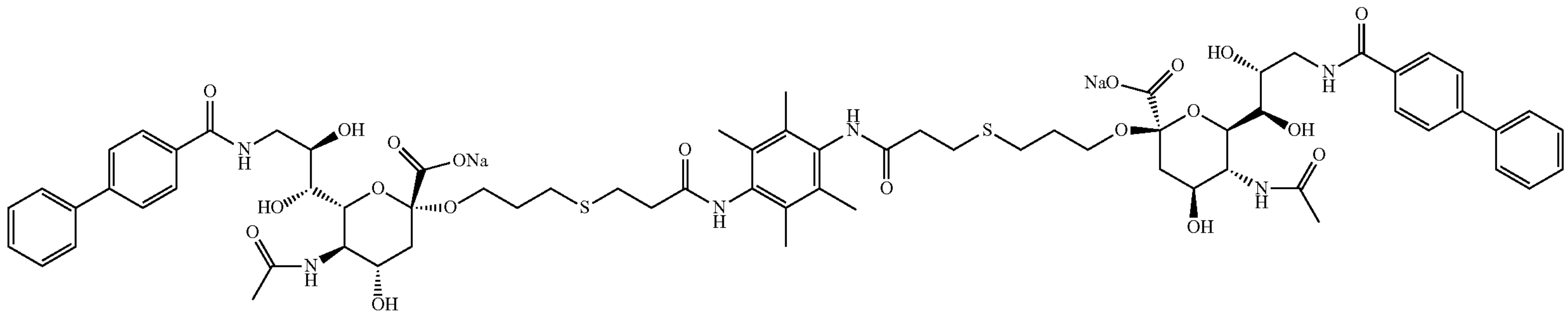 | 523 |
| 46 | 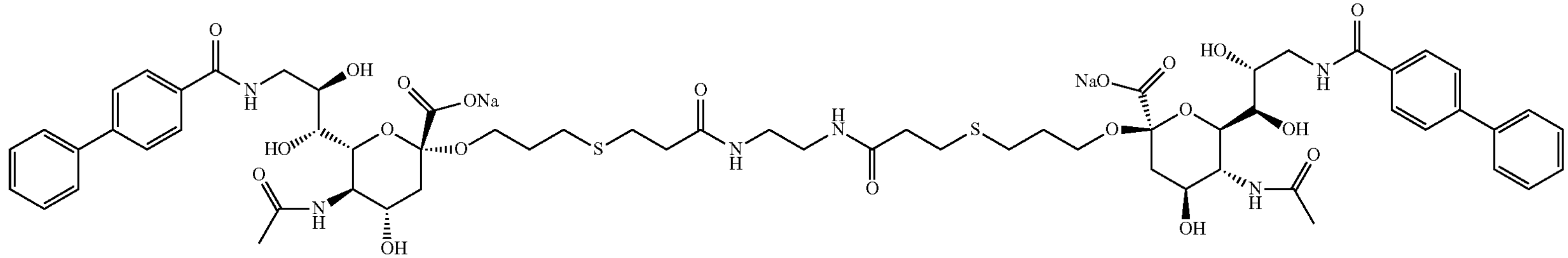 | 290 |
| 49 | 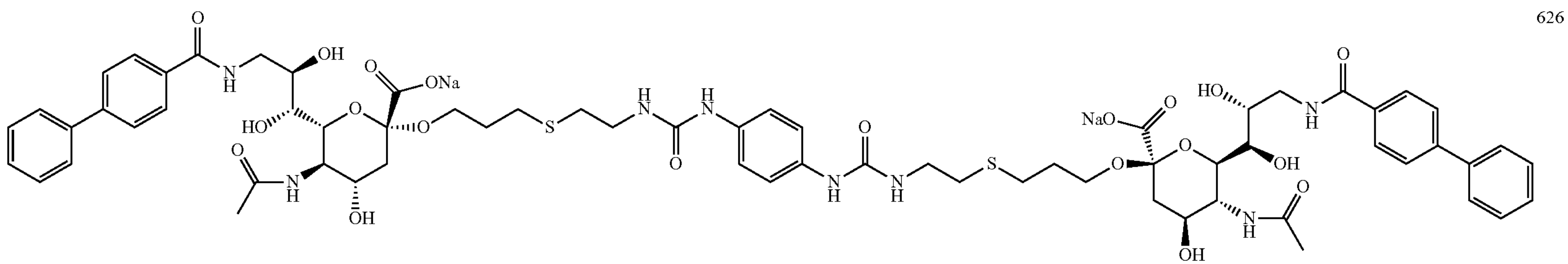 | 626 |

TABLE II-continued

| No. | Structure | nP |
|---|---|---|
| 51 | 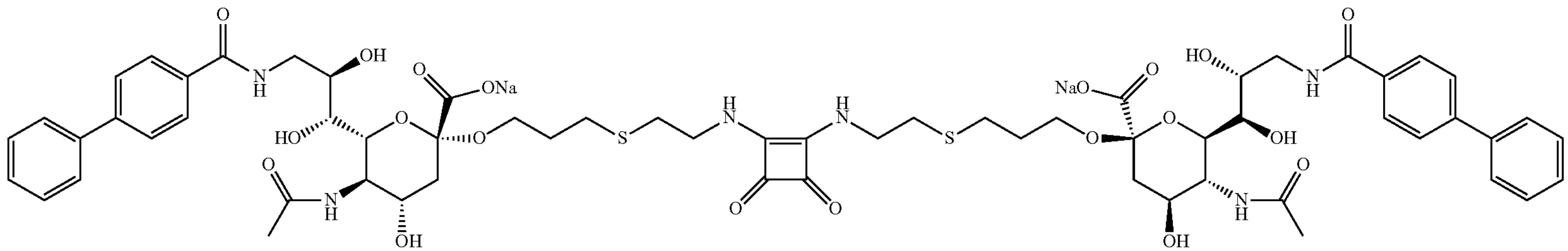 | 299 |
| 52 | 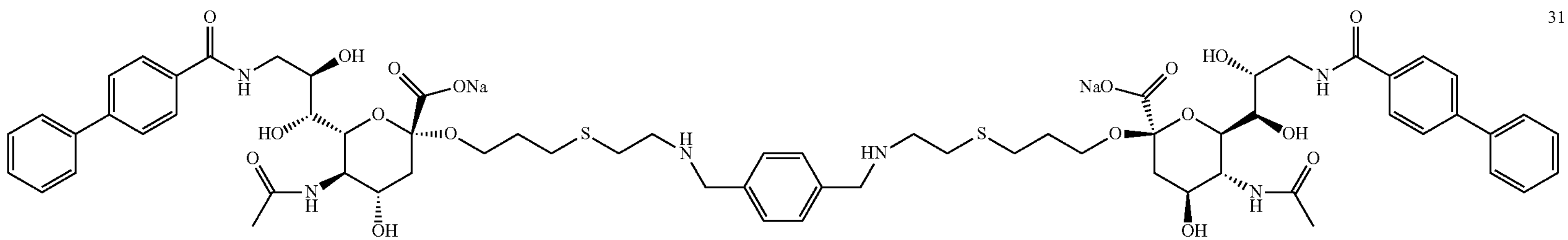 | 31 |
| 54 | 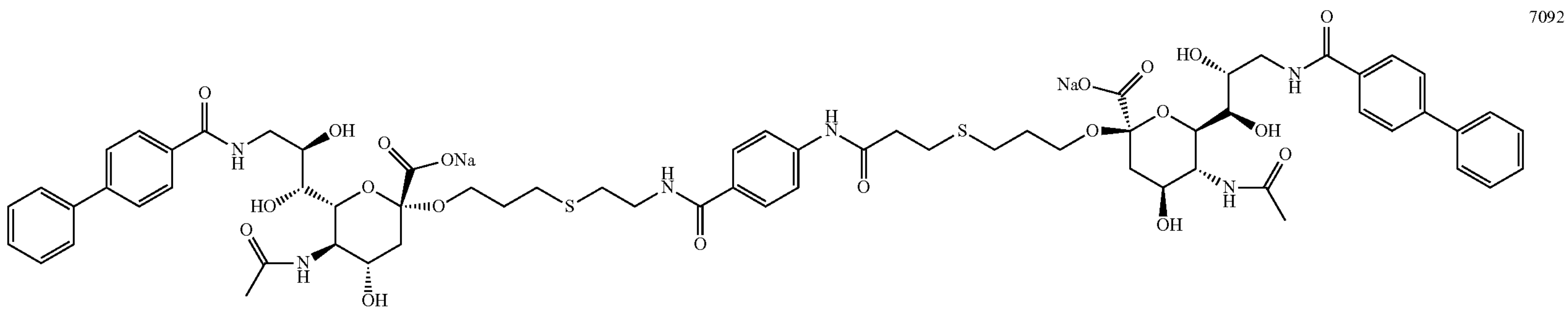 | 7092 |

TABLE II-continued

| No. | Structure | nP |
|---|---|---|
| 57 | 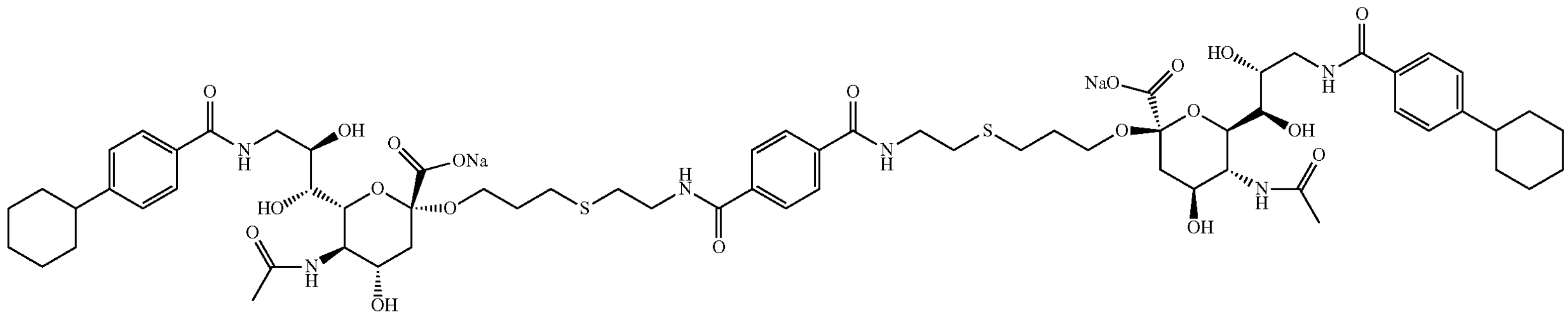 | 22 |
| 58 | 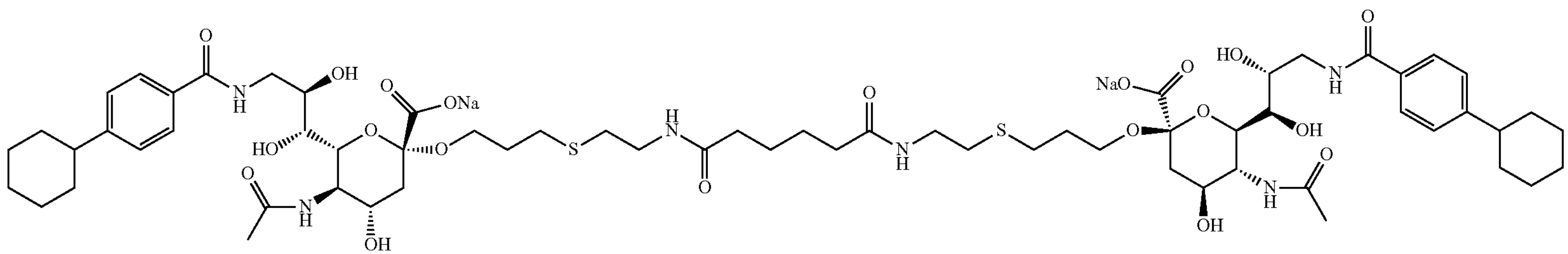 | 24 |
| 62 | 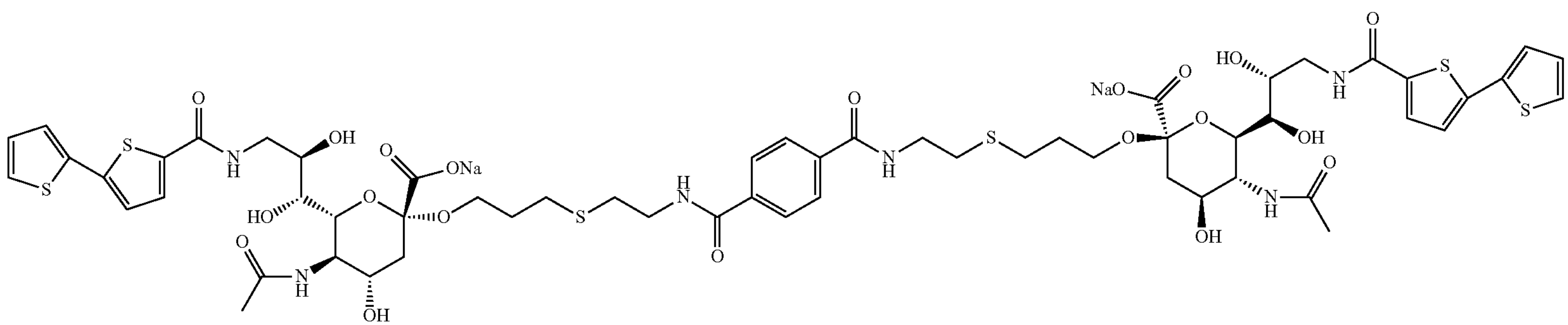 | 203 |

| No. | Structure | nP |
|---|---|---|
| 63 | 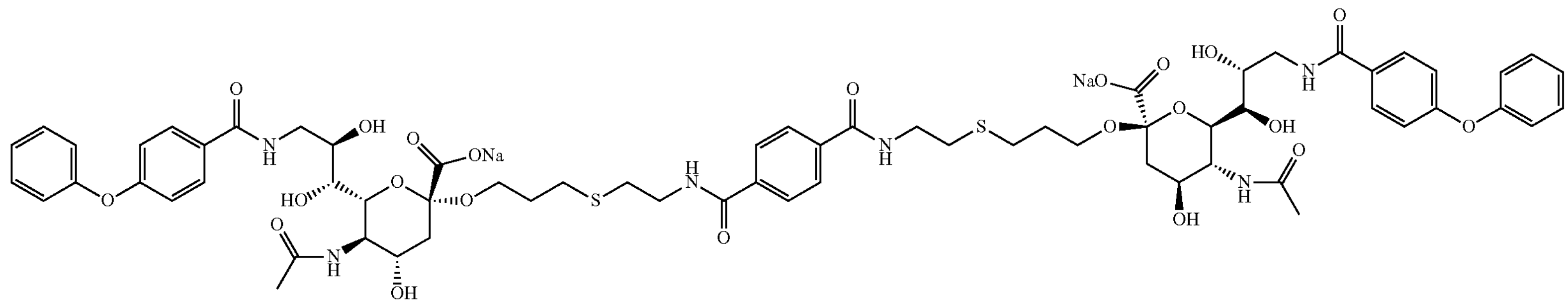 | 20 |
| 64 | 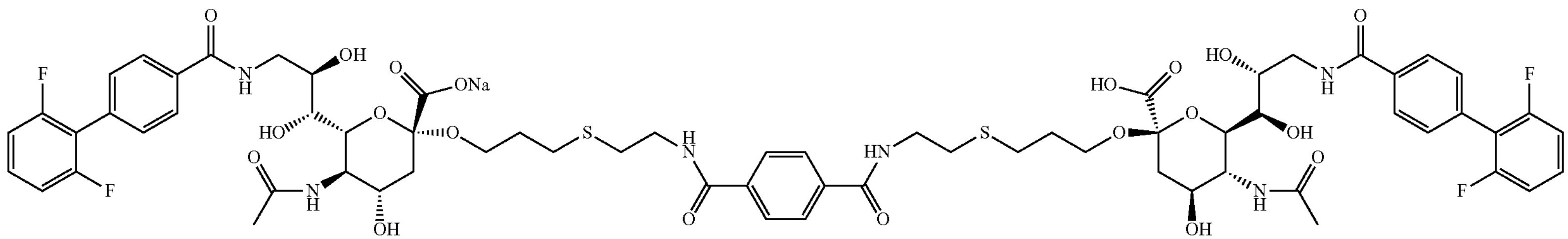 | 158 |
| 65 | 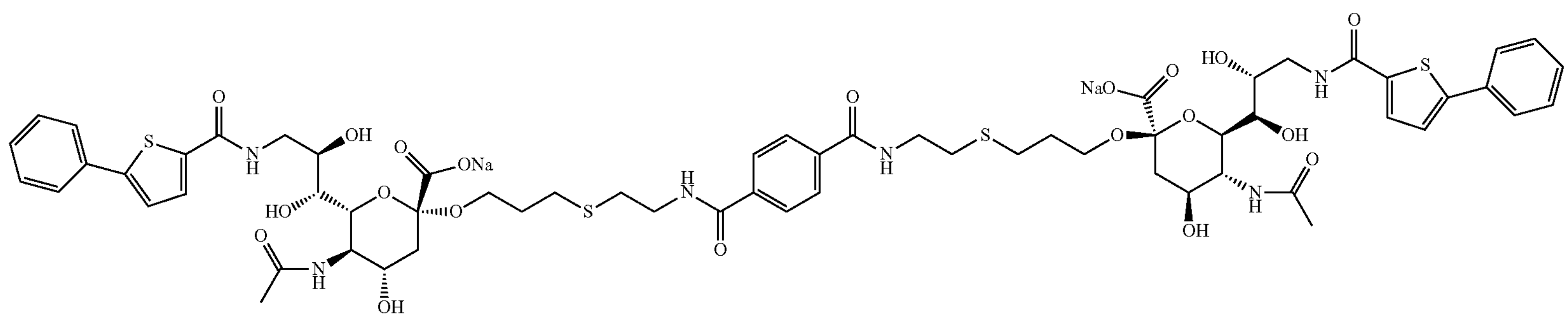 | 106 |

TABLE II-continued

| No. | Structure | nP |
|---|---|---|
| 66 | 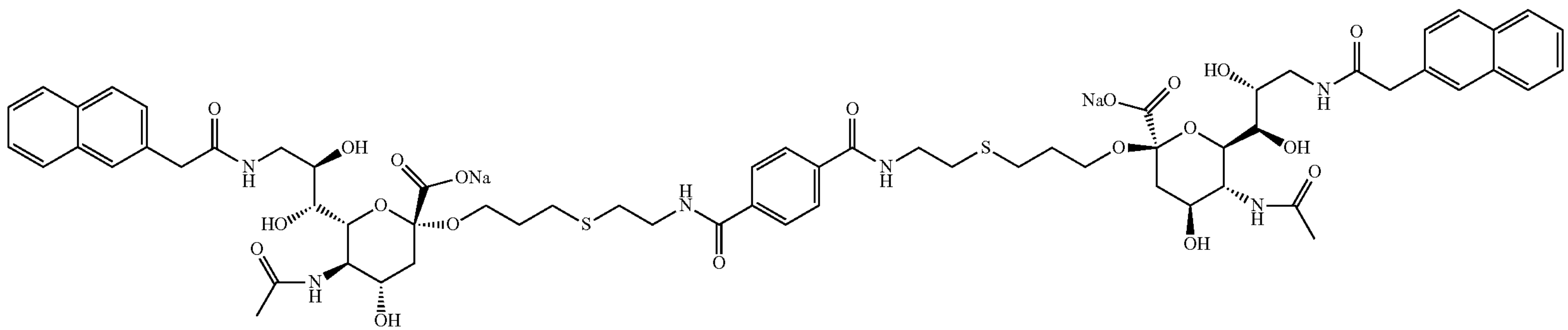 | 197 |
| 67 | 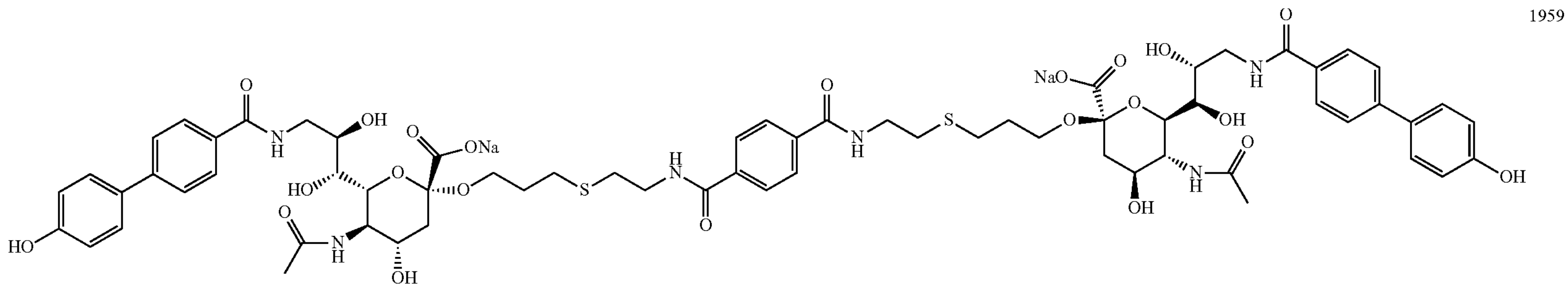 | 1959 |
| 68 | 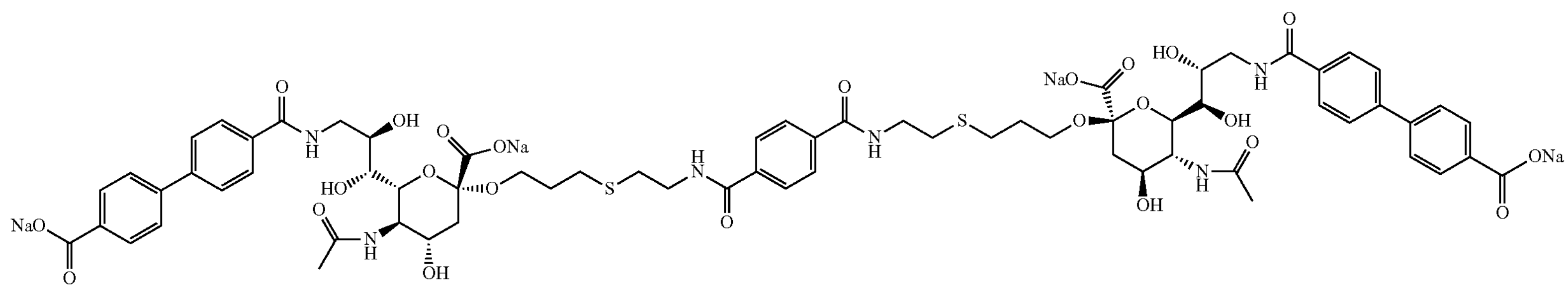 | 5 |

TABLE II-continued

| No. | Structure | nP |
|-----|-----------|-----|
| 69  | 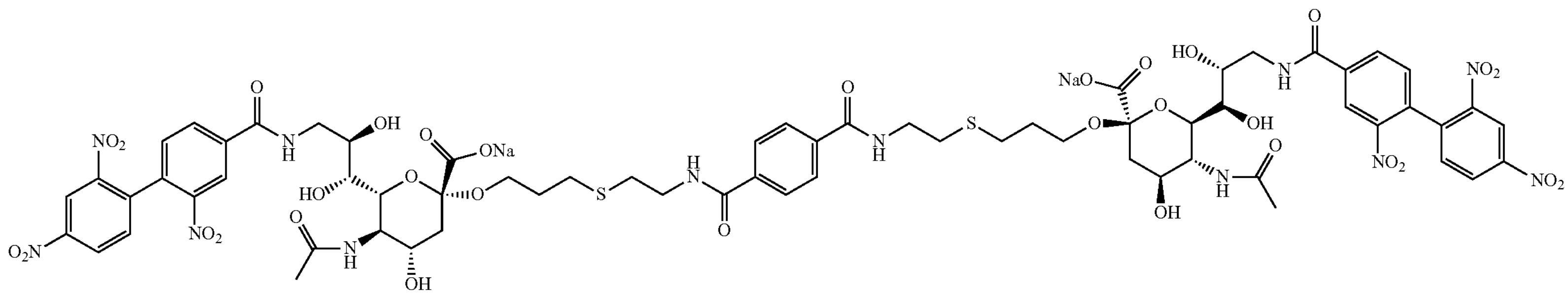          | 14  |
| 70  | 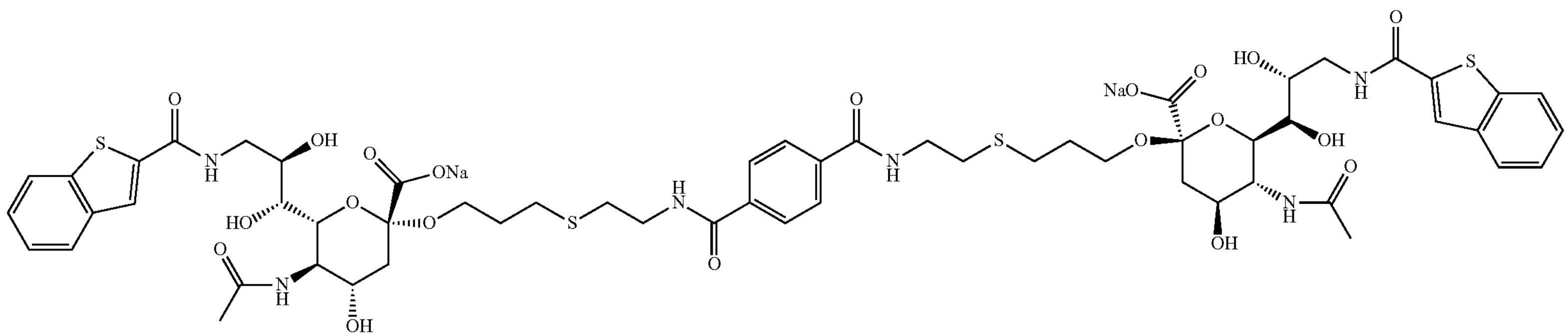          | 137 |
| 71  | 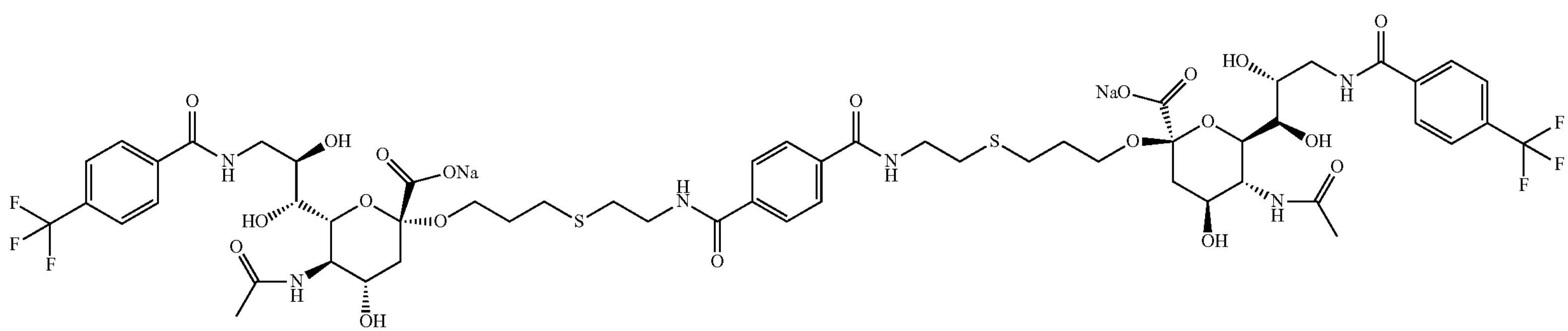          | 32  |

TABLE II-continued

| No. | Structure | nP |
|---|---|---|
| 72 | 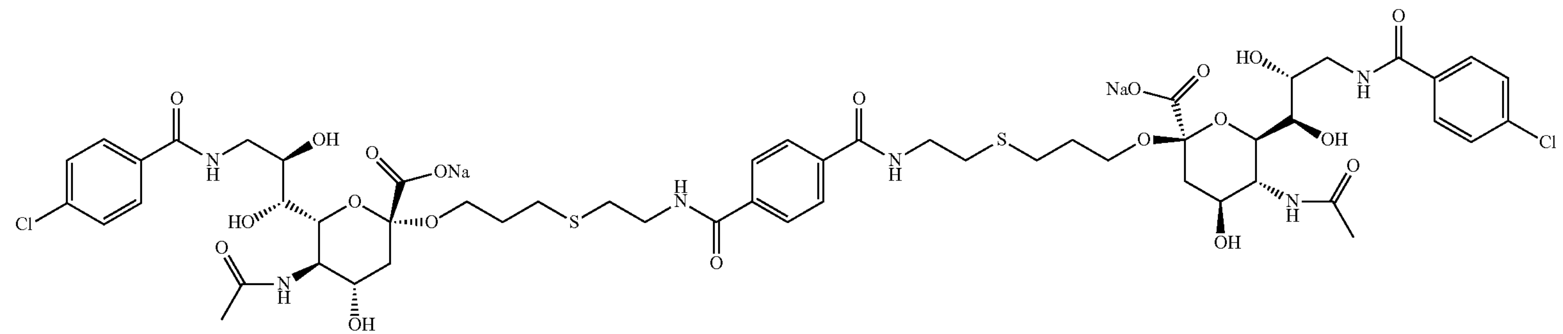 | 38 |
| 73 | 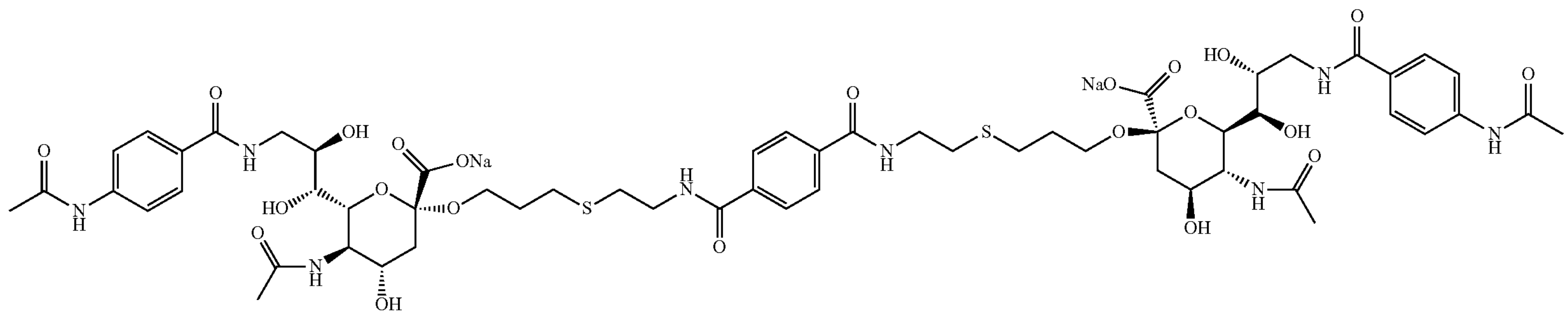 | 13 |
| 74 | 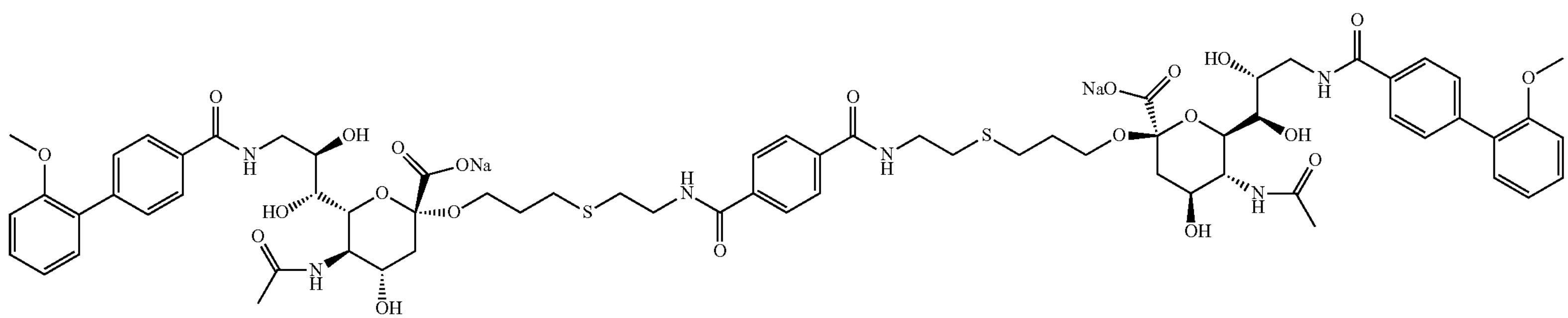 | 27 |

TABLE II-continued

| No. | Structure | nP |
|---|---|---|
| 75 | 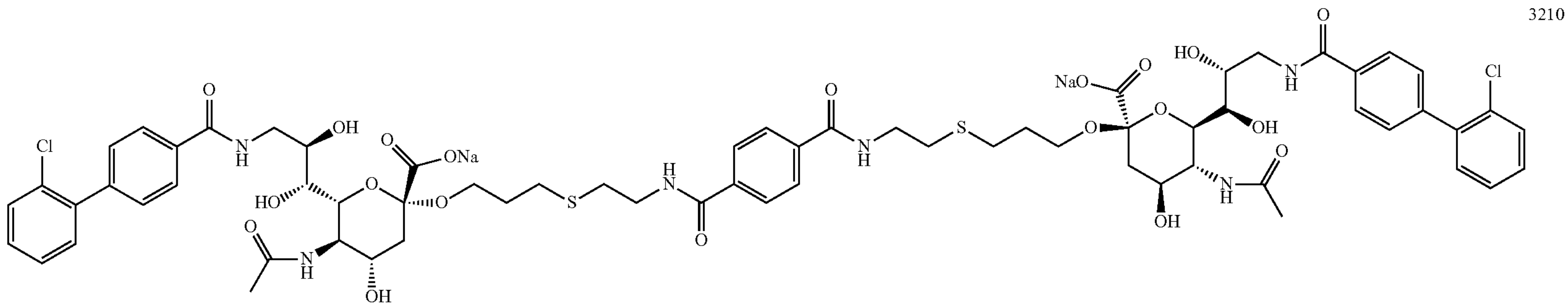 | 3210 |
| 76 | 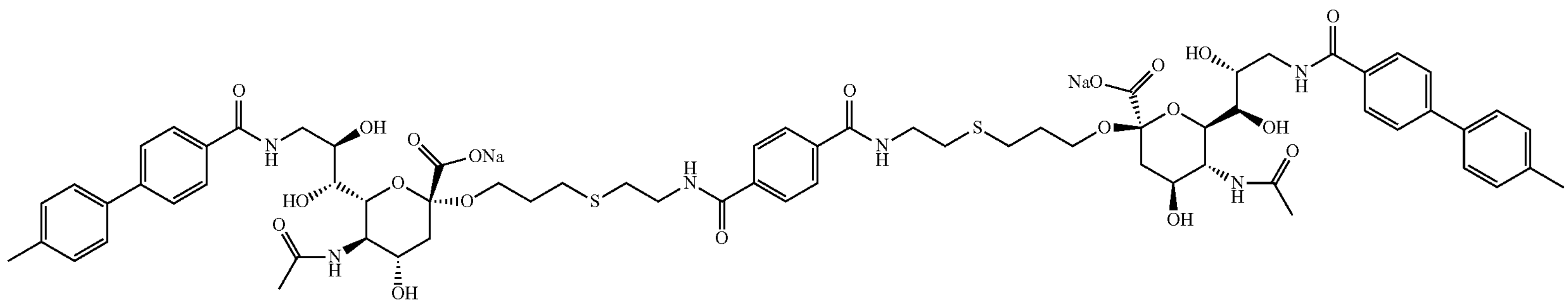 | 188 |
| 77 | 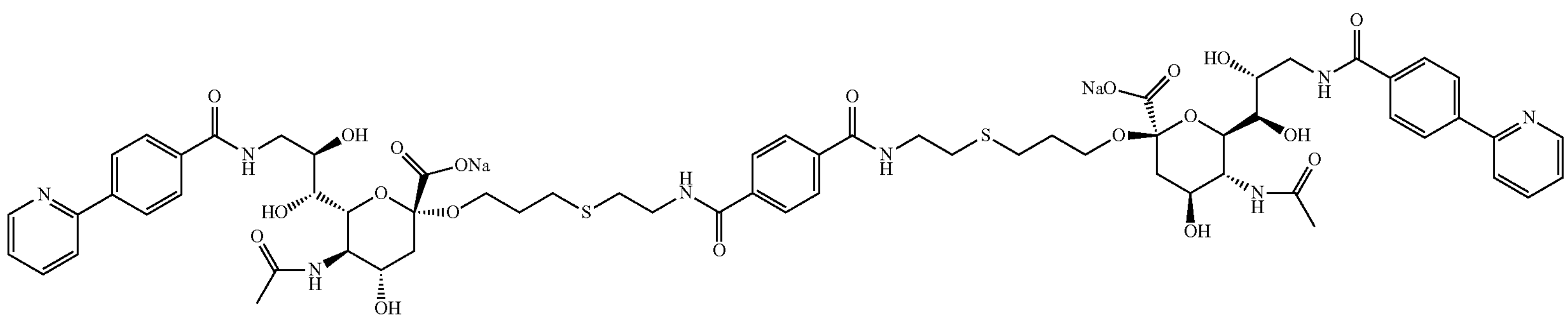 | 95 |

TABLE II-continued

| No. | Structure | nP |
|---|---|---|
| 78 | 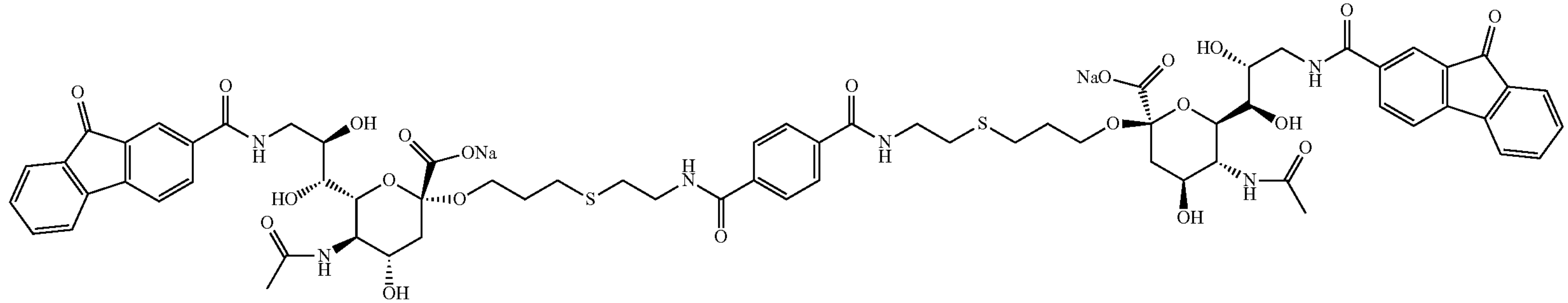 | 27 |
| 79 | 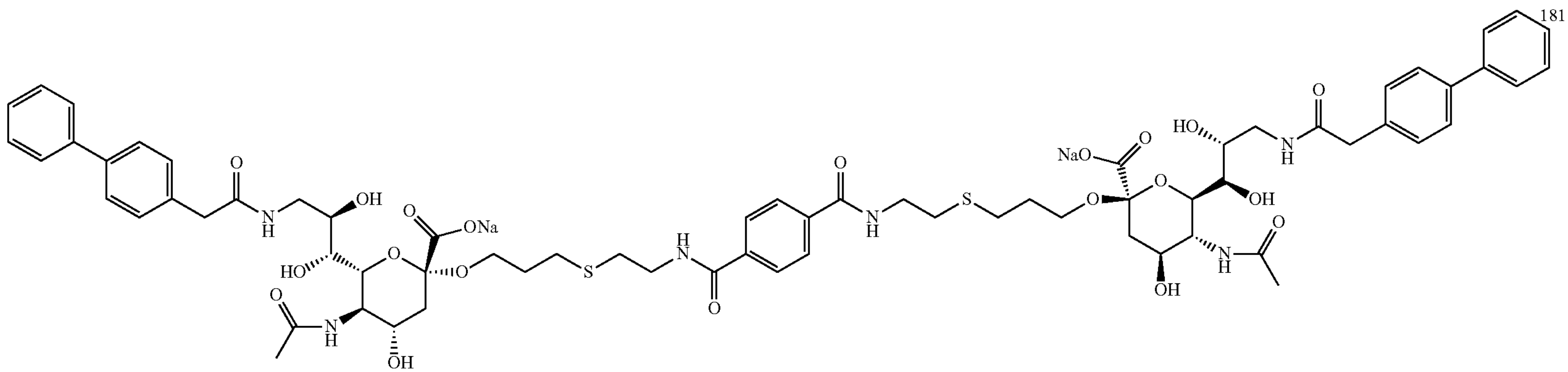 | 181 |
| 80 | 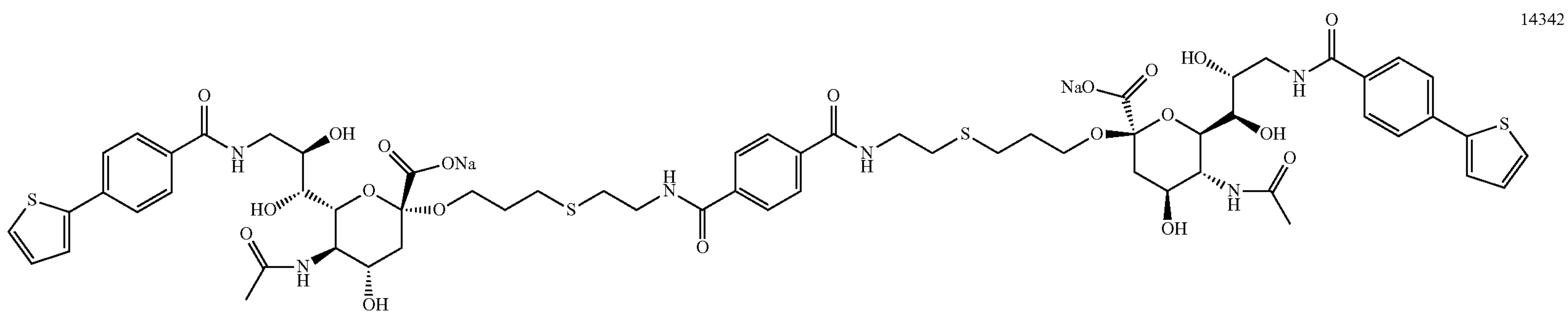 | 14342 |

TABLE II-continued

| No. | Structure | nP |
|---|---|---|
| 81 | 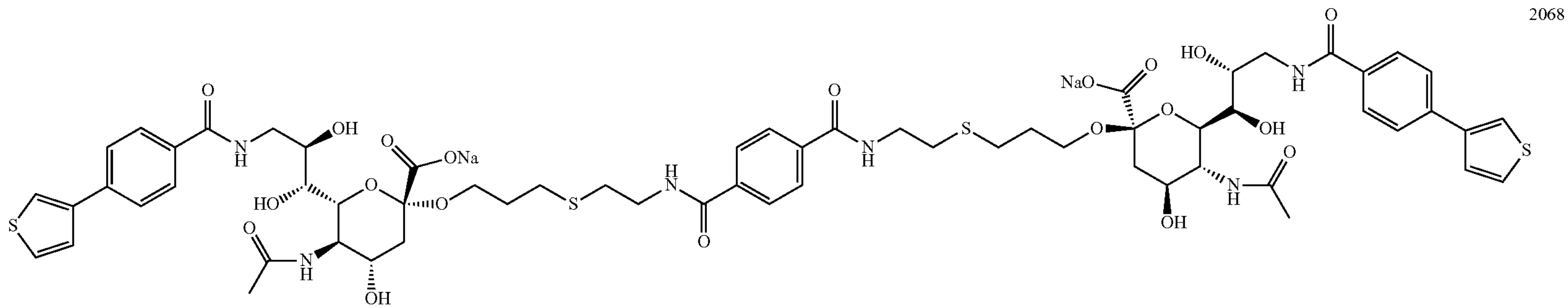 | 2068 |
| 82 | 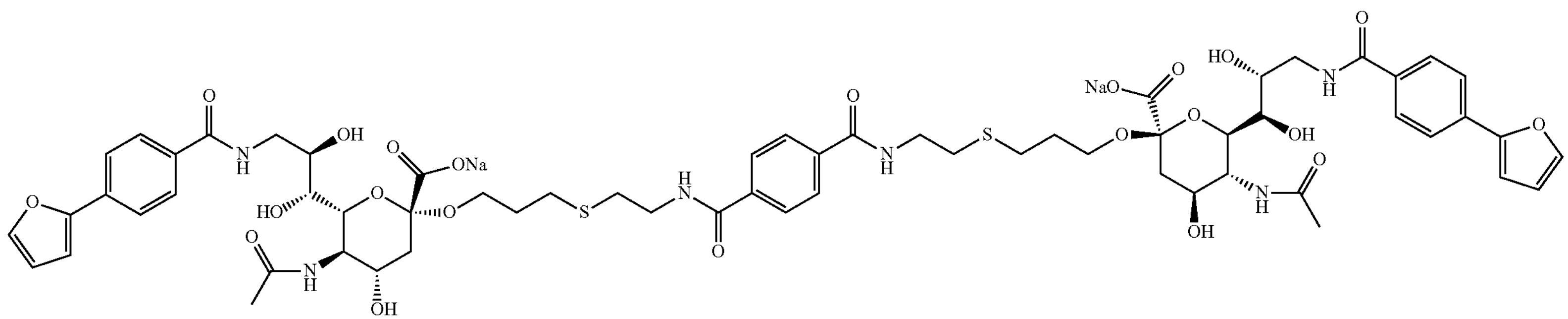 | 752 |
| 83 | 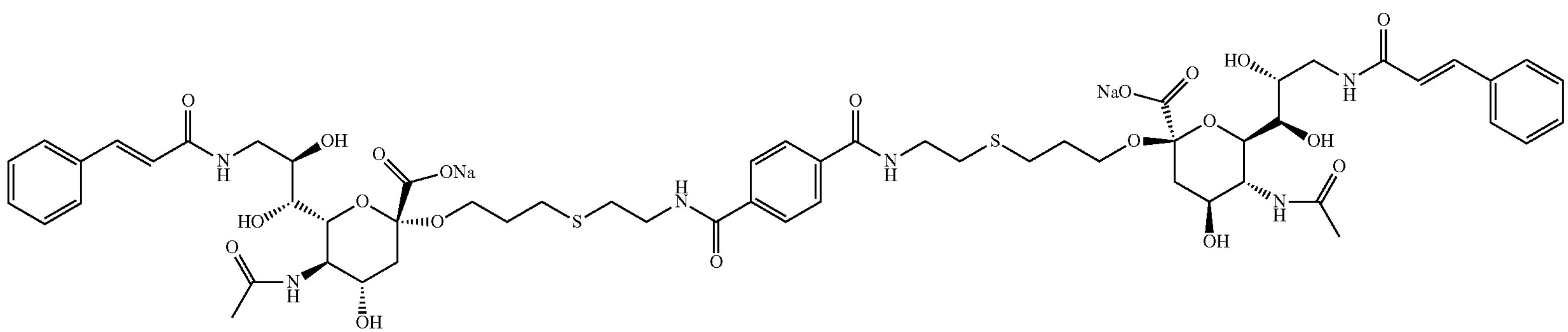 | 73 |

TABLE II-continued

| No. | Structure | nP |
|---|---|---|
| 84 | 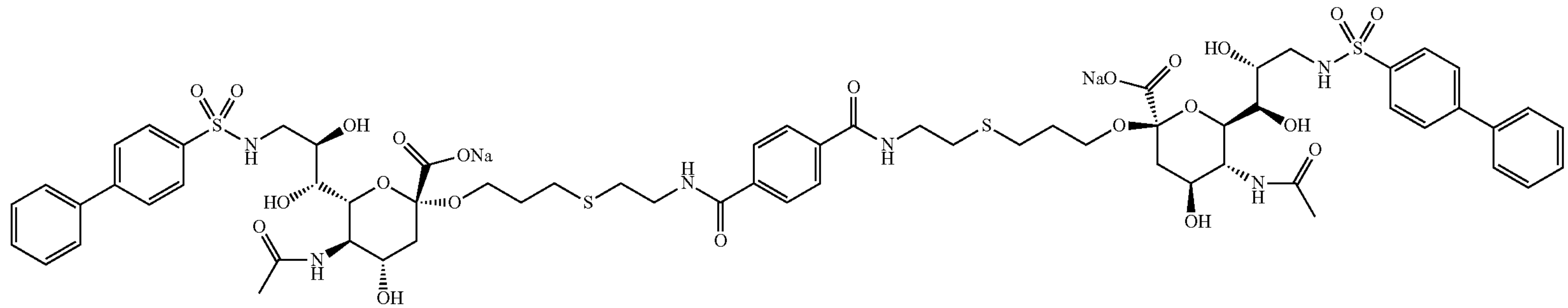 | 9 |
| 85 | 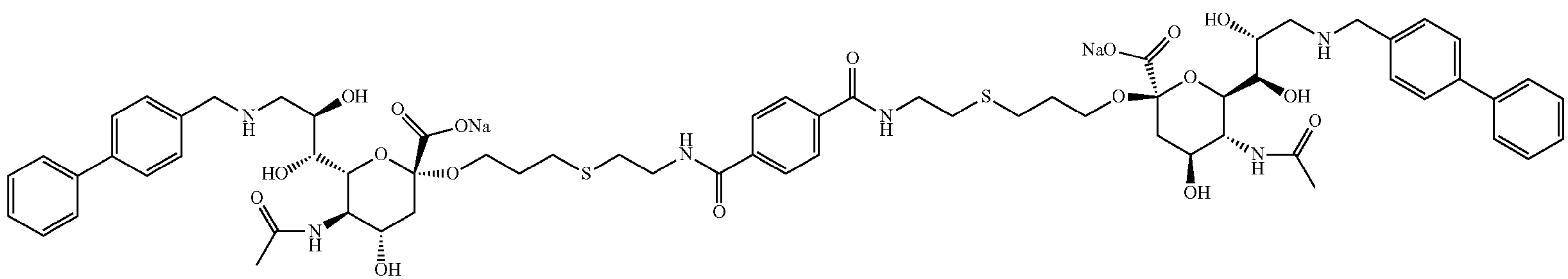 | 1 |
| 90 | 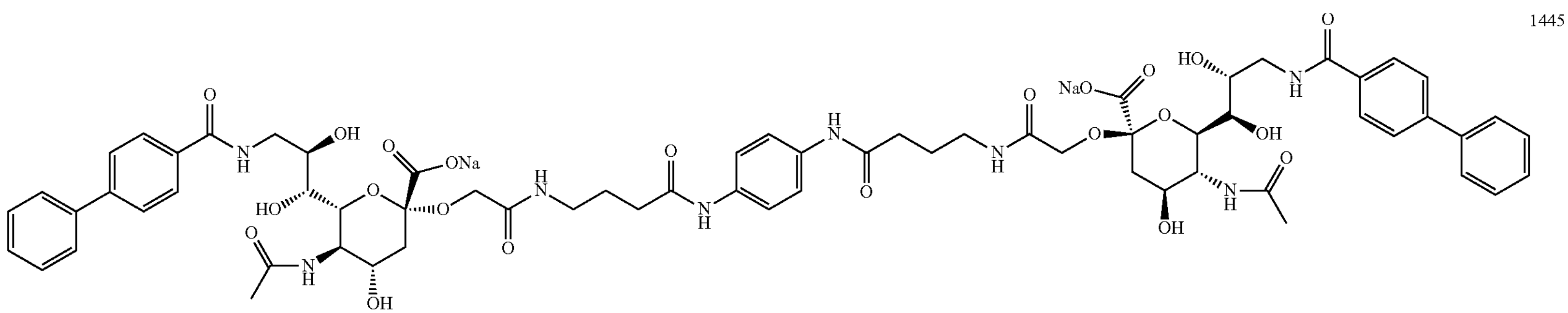 | 1445 |

TABLE II-continued

| No. | Structure | nP |
|---|---|---|
| 92 | 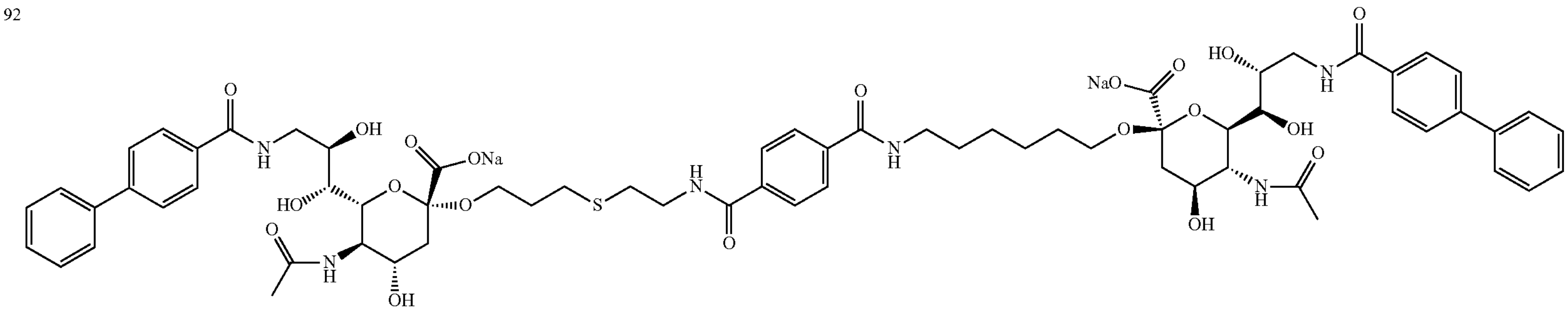 | 3788 |
| 95 | 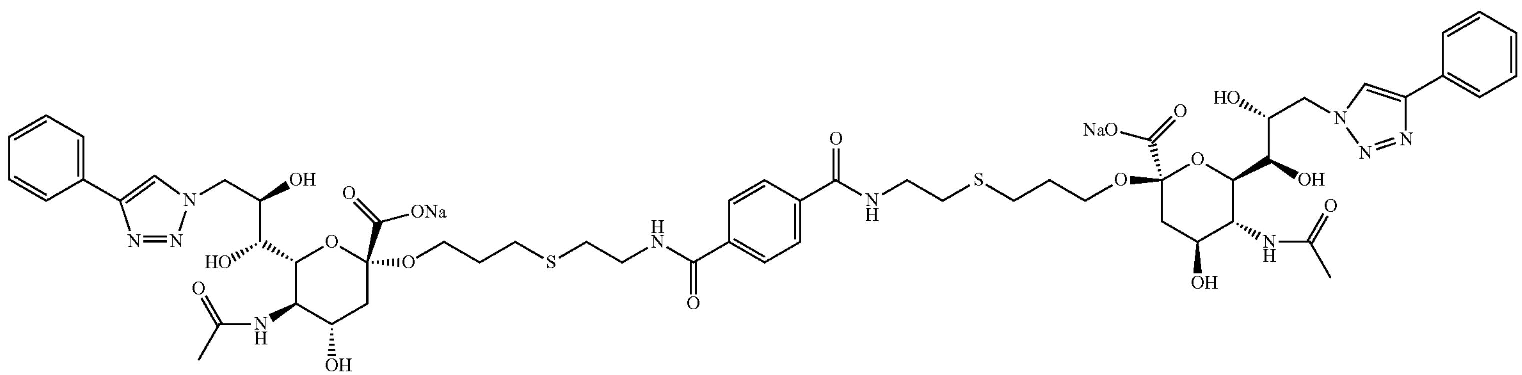 | 6 |
| 102 | 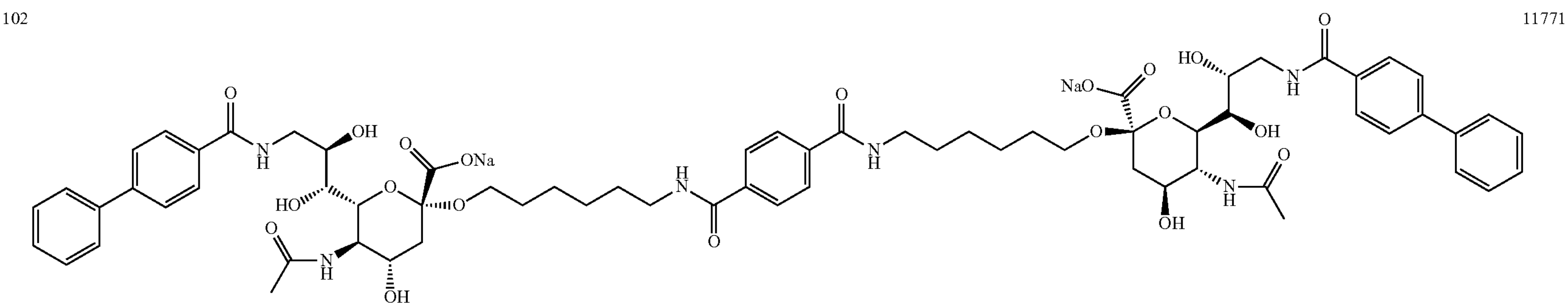 | 11771 |

TABLE II-continued

| No. | Structure | nP |
|---|---|---|
| 103 | 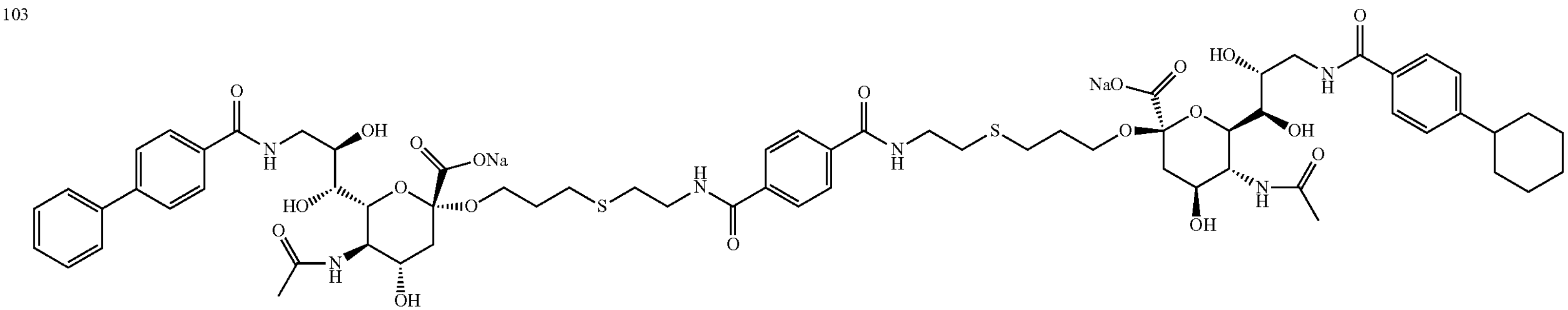 | 185 |
| 110 | 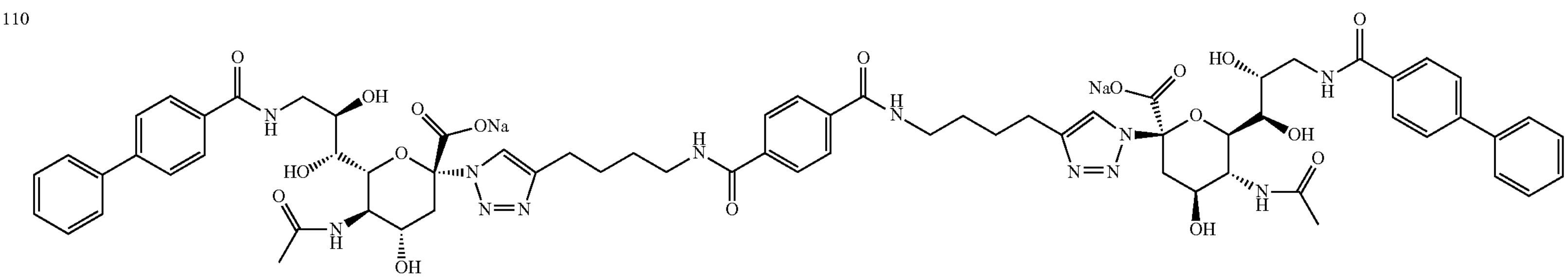 | 12 |
| 113 | 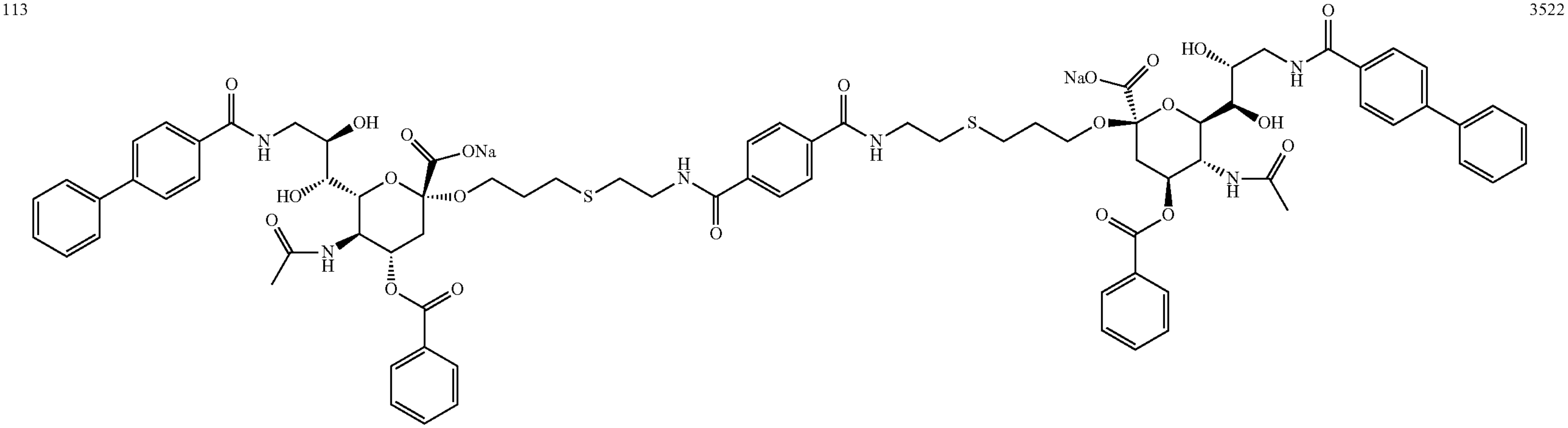 | 3522 |

TABLE II-continued

| No. | Structure | nP |
|---|---|---|
| 116 | 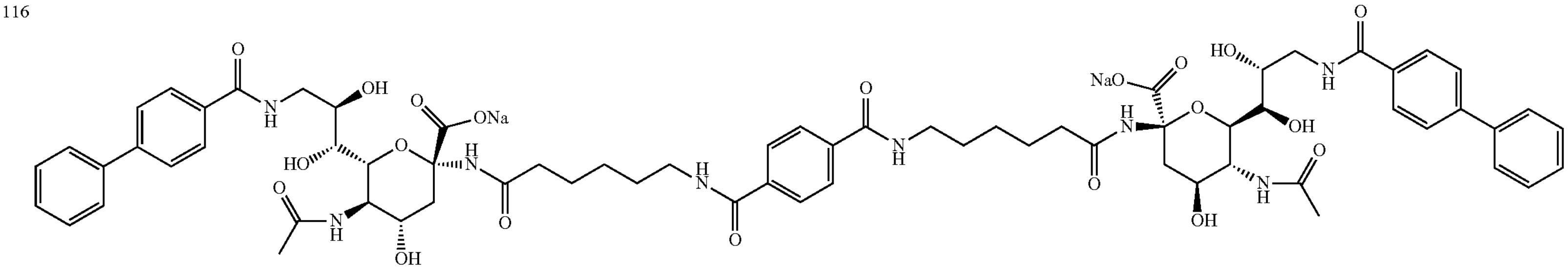 | <1 |
| 122 | 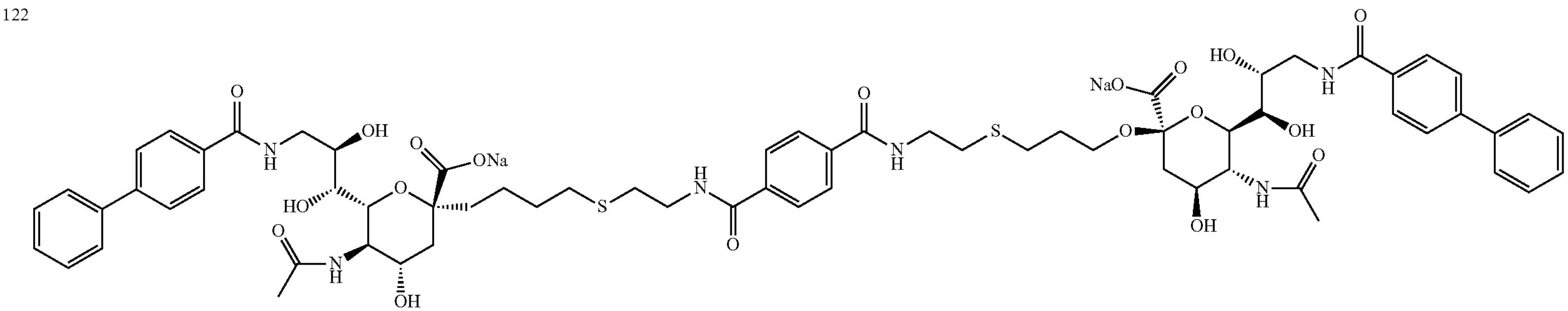 | 884 |
| 125 | 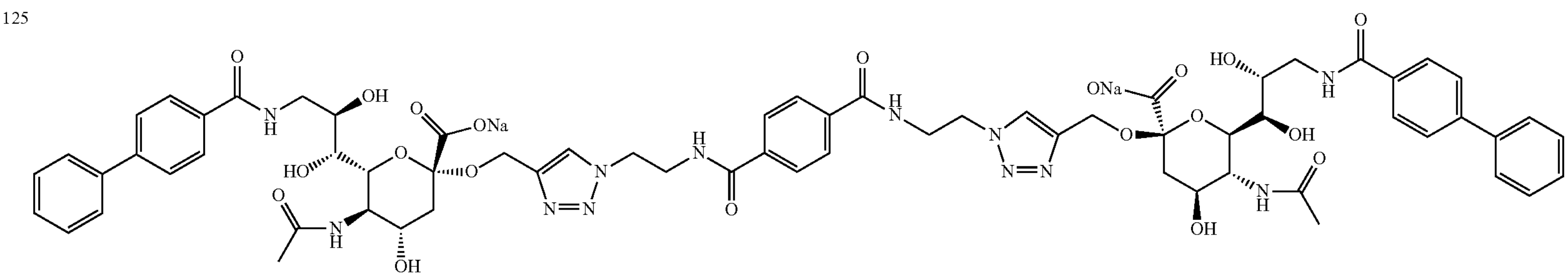 | 8 |

TABLE II-continued

| No. | Structure | nP |
|---|---|---|
| 127 | 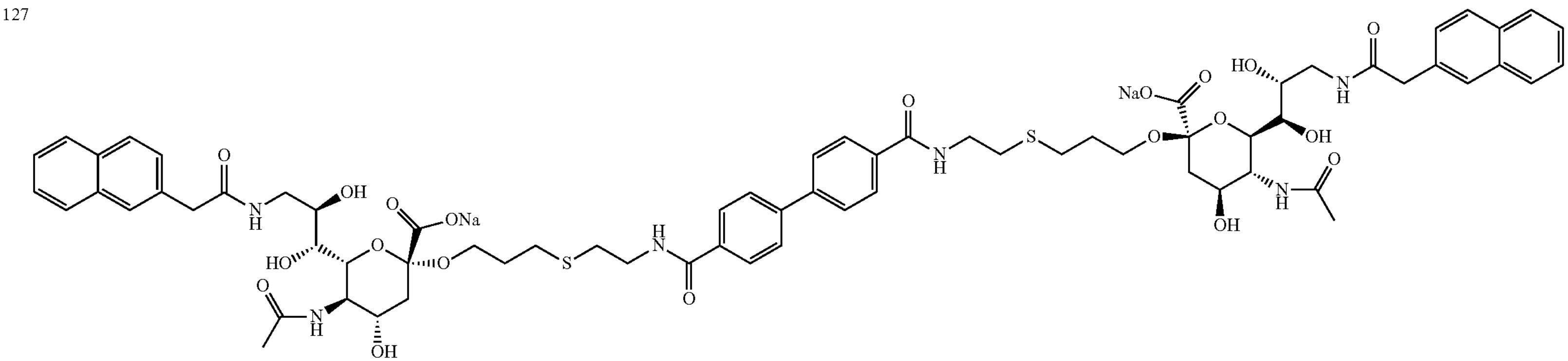 | 74 |
| 128 | 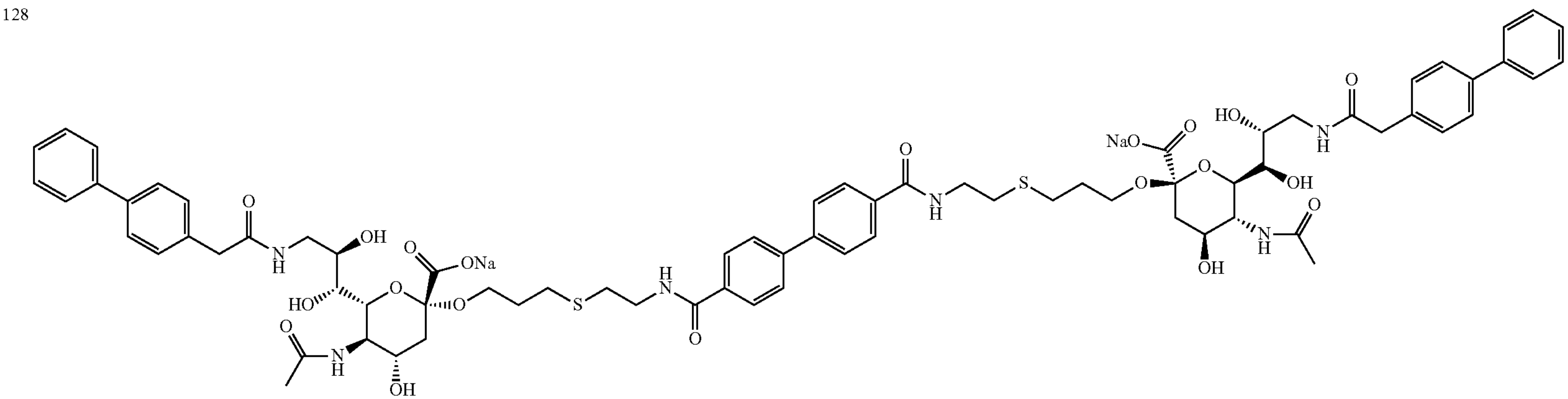 | 19 |

TABLE II-continued

| No. | Structure | nP |
|---|---|---|
| 129 | 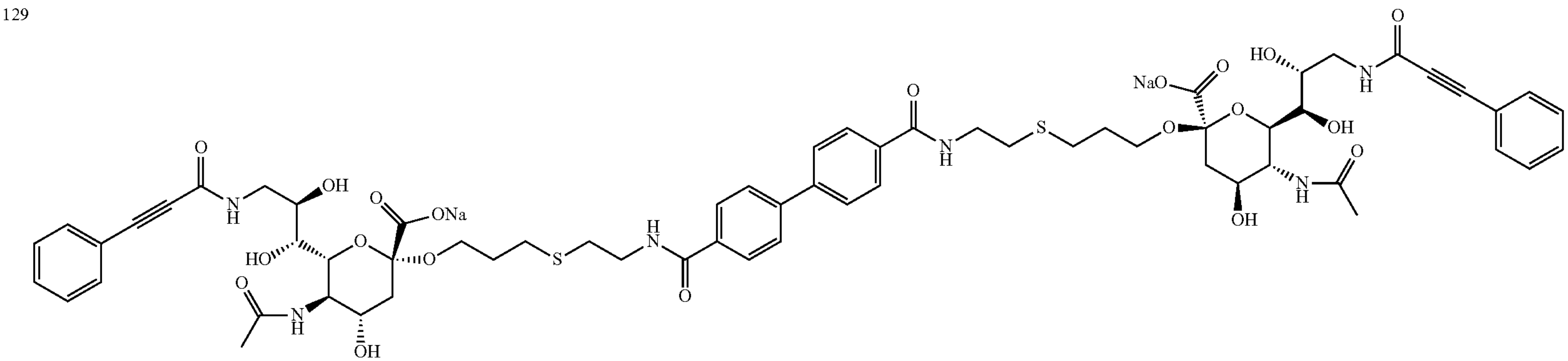 | 21 |
| 131 | 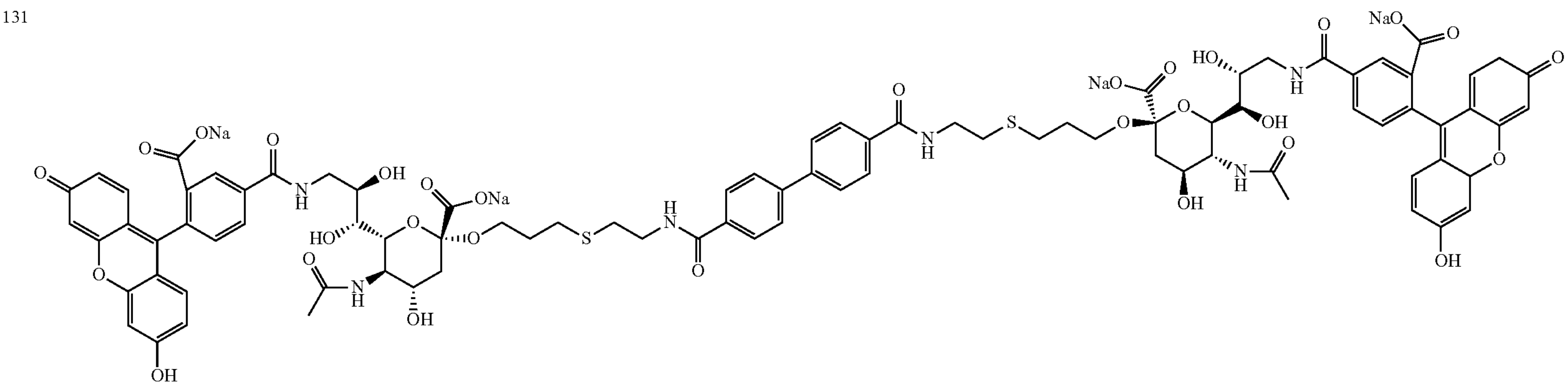 | 4 |

TABLE II-continued

| No. | Structure | nP |
|---|---|---|
| 132 | 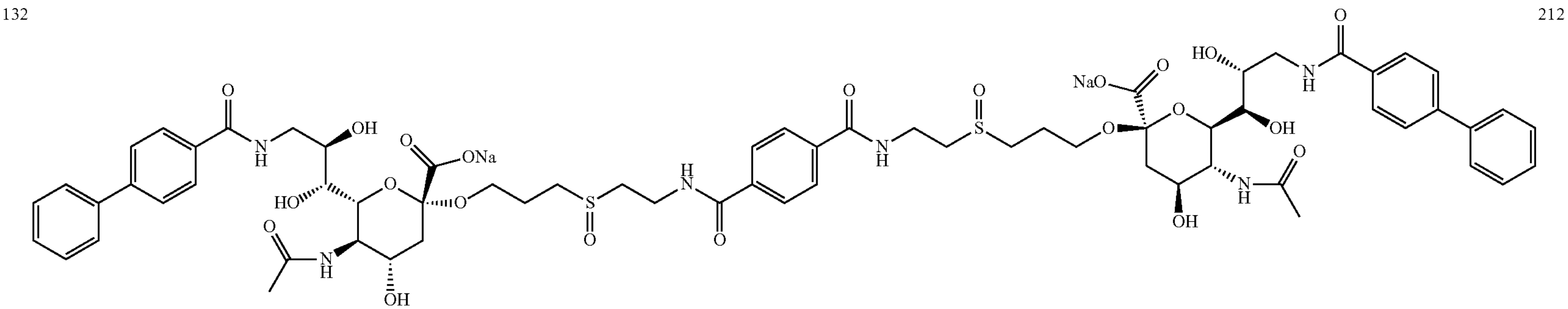 | 212 |
| 134 | 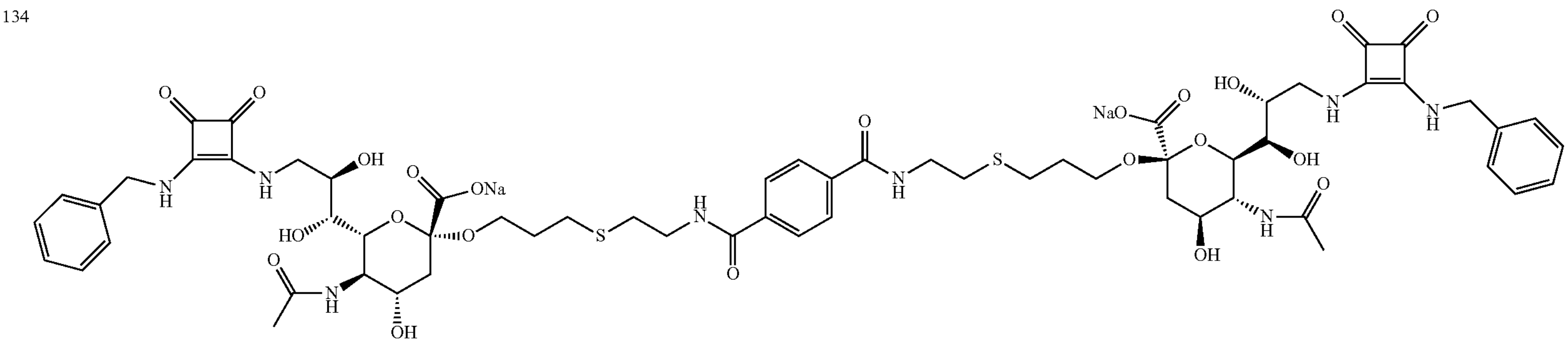 | 70 |
| 139 | 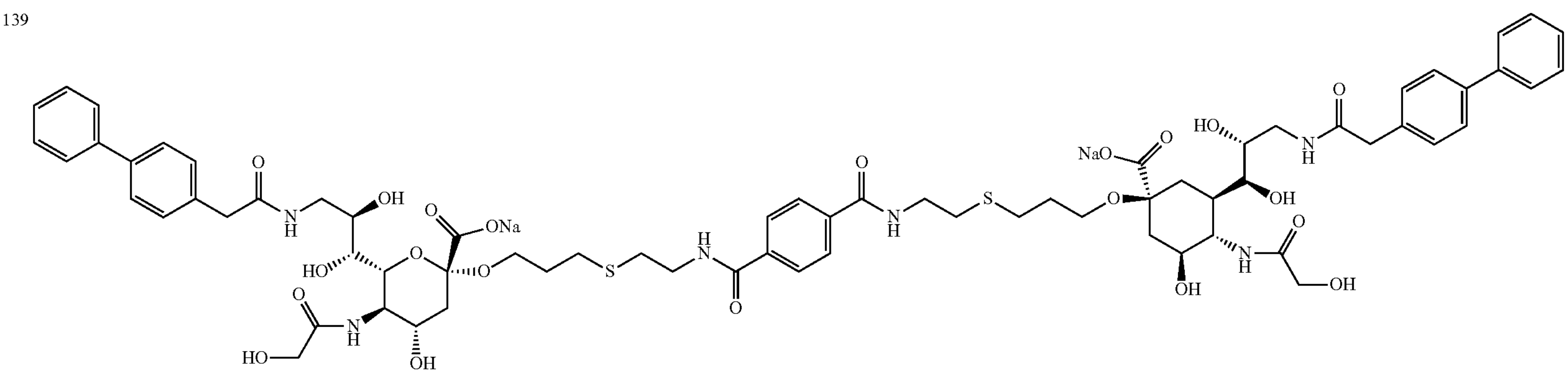 | 63 |

TABLE II-continued

| No. | Structure | nP |
|---|---|---|
| 140 | 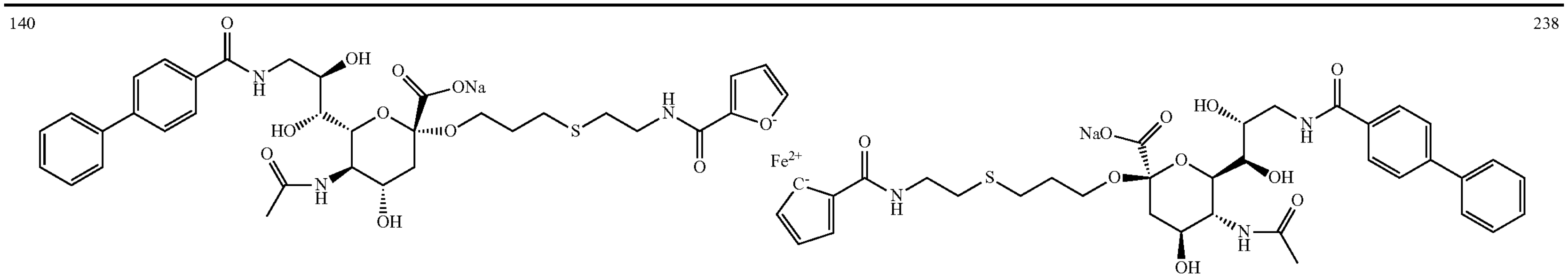 | 238 |
| 145 | 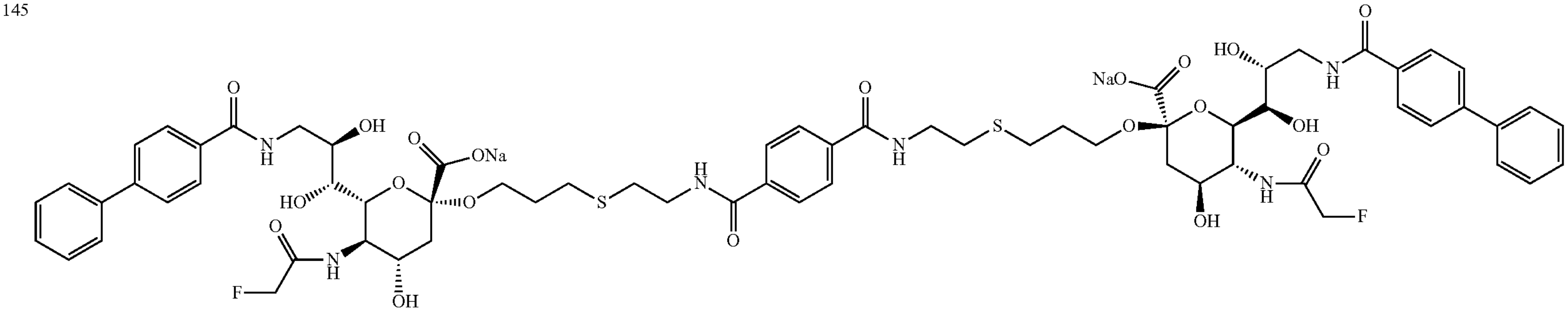 | 7003 |
| 147 | 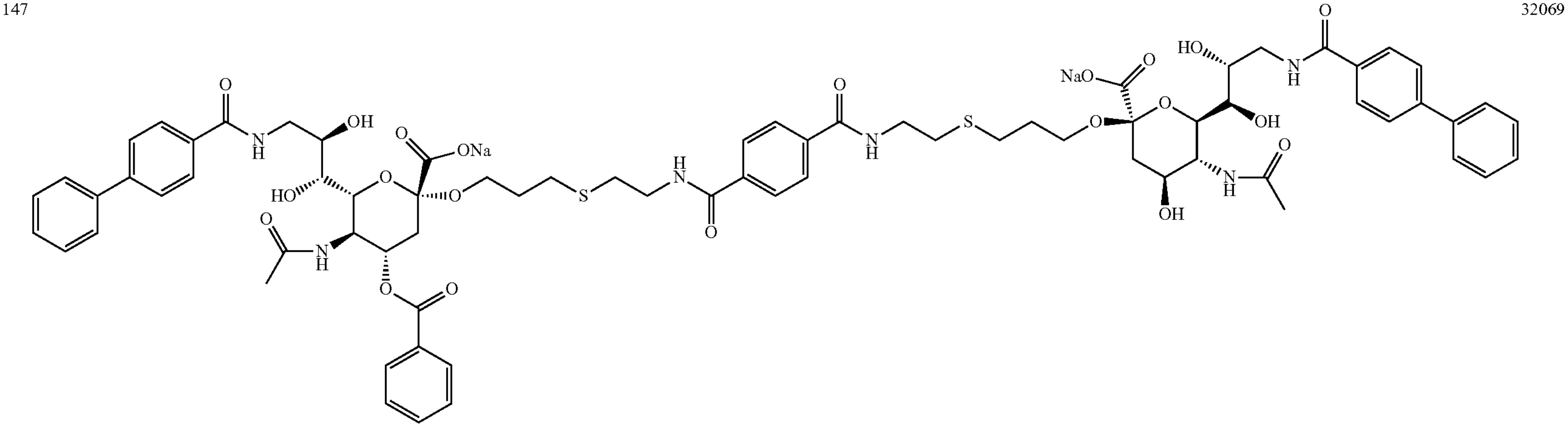 | 32069 |

TABLE II-continued

| No. | Structure | nP |
|---|---|---|
| 149 | 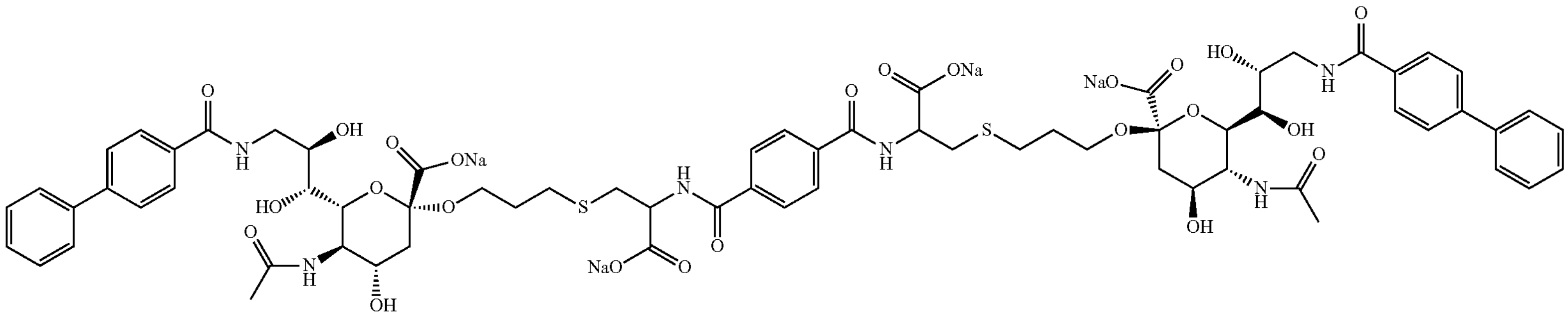 | 378 |
| 153 | 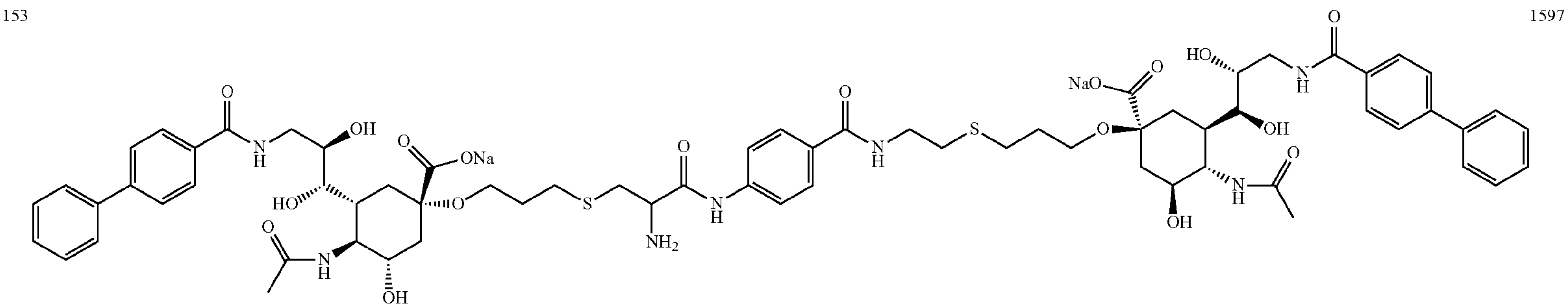 | 1597 |

Figure 2:
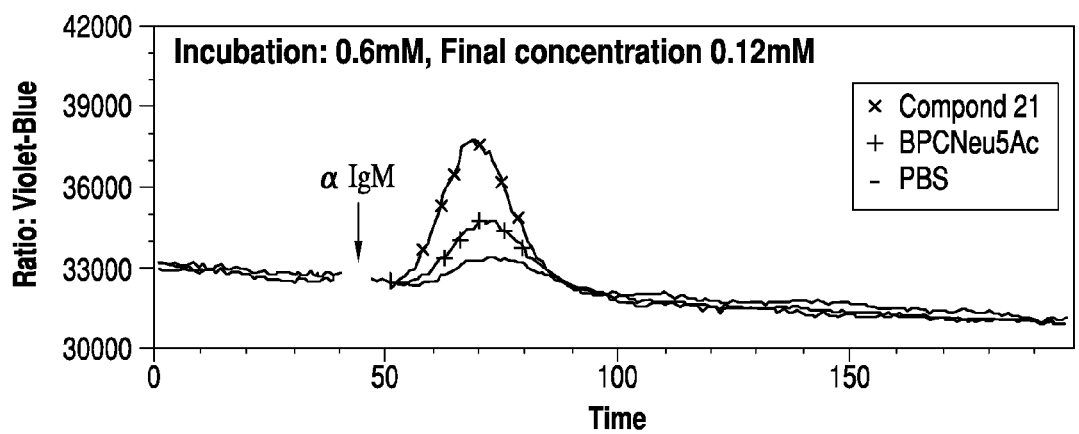
FIG. 2 is a graph showing the calcium flux of exemplary compound 21 in comparison to BPC Neu5Ac at a final concentration of 0.12 mM.
Figure 3:
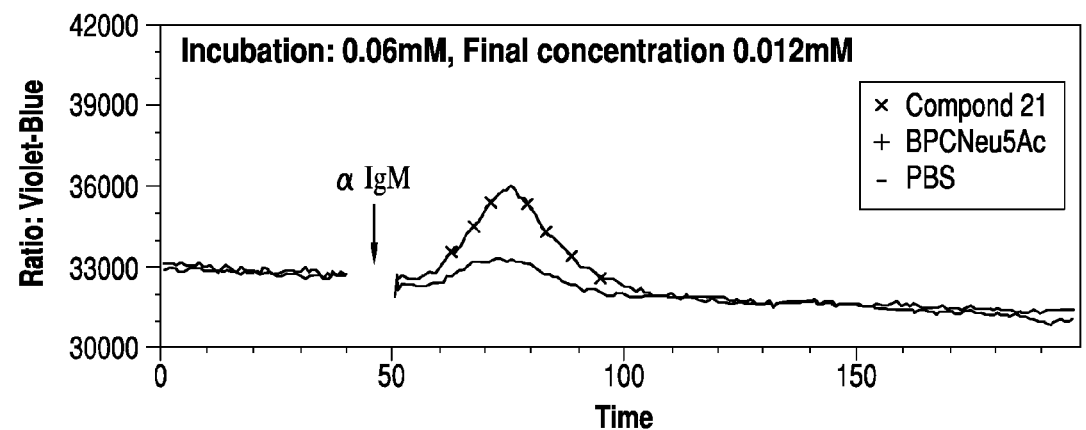
FIG. 3 is a graph showing the calcium flux of exemplary compound 21 in comparison to BPC Neu5Ac at a final concentration of 0.012 mM.

In a further assay, a number of the substances were investigated for the capacity to influence the calcium flux in B cells. The assay was carried out as described in J. Exp. Med. 2002, 195, 1207-1213. The substances exhibit strong boosting of calcium mobilization, even at low concentrations. For example, the calcium flux of substance 21 in comparison to BPC Neu5Ac is shown in FIGS. 1-3.

The invention claimed is:

1. Sialic acid derivative of the formula (I),

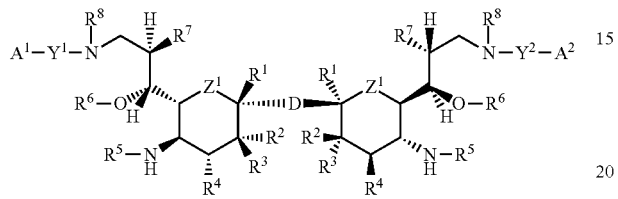

(I)

where the symbols have the following definitions:

$A^1$, $A^2$ are identically or differently a group $D^1$-[$Y^3$-$D^2$-]$_m$-;

$D^1$, $D^2$ are identically or differently a mono- or polycyclic aromatic, partially unsaturated or saturated $C_3$-$C_{14}$ hydrocarbon radical or an aromatic, partially unsaturated or saturated three- to eight-membered heterocyclic radical, the stated radicals being unsubstituted or substituted one or more times by a group $X^1$;

$X^1$ is identically or differently halogen, cyano, nitro, hydroxyl, mercapto, amino, carboxyl, hydroxylamino, azido, $B(OH)_2$, SO, $SO_3M$, $OSO_3M$, $SO_2NH_2$, $SO_2CF_3$, $PO_3M$, $OPO_3M$, cyanomethyl, alkyl, haloalkyl, alkenyl, alkynyl, alkyloxy, haloalkyloxy, alkenyloxy, alkynyloxy, alkylthio, alkylamino, dialkylamino, trialkylamino, formyl, alkylcarbonyl, alkylsulphonyl, alkylsulphoxyl, alkylaminosulphoxyl, dialkylaminosulphoxyl, alkyloxycarbonyl, alkylcarbonyloxy, aminocarbonyl, aminothiocarbonyl, alkylaminocarbonyl, alkylcarbonylamino, dialkylaminocarbonyl, alkylaminothiocarbonyl, oxo (=O), thioxo (=S), $C_1$-$C_8$ alkylimino (=N—$C_1$-$C_8$ alkyl), $C_1$-$C_8$ alkyloximino (=N—O—$C_1$-$C_8$ alkyl), the alkyl groups in these radicals containing 1 to 8 carbon atoms, and the stated alkenyl or alkynyl groups in these radicals containing 2 to 8 carbon atoms;

$Y^1$, $Y^2$ are identically or differently ~($C_1$-$C_4$ alkyl)-, ~($C_1$-$C_4$ haloalkyl)-, ~($C_1$-$C_4$ alkyl)-(CO)—, ~C(O)—, ~$CH_2$—C(O)—, ~CH=CH—C(O)—, ~C≡C—C(O)—, ~$S(O)_2$—, ~$CH_2$—$S(O)_2$—, ~$NR^x$—C(O)—, ~$CH(CF_3)$—, ~$NR^x$-3-cyclobutene-1,2-dione-4-, ~$CH_2$—$NR^x$-3-cyclobutene-1,2-dione-4-, ~$NR^x$-3-2,5-thiadiazole 1-oxide-4-, ~$NR^x$-3-2,5-thiadiazole 1,1-dioxide-4-, where ~ denotes the bond to the group A, or $Y^1$, $Y^2$ form, independently of one another, together with the nitrogen to which they are bonded, and with the group $R^8$, a group ~4-1H-(1,2,3)triazol-1-yl-, ~5-1H-(1,2,3)triazol-1-yl-, ~$CH_2$-4-1H-(1,2,3)triazol-1-yl- or —$CH_2$-5-1H-(1,2,3)triazol-1-yl-, where ~ denotes the bond to the group A;

$Y^3$ is a bond, O, S, S(O), $S(O)_2$, $CH_2$, C(O), $CR_2^x$; or $NR^x$;

m is 0, 1 or 2;

$Z^1$ is O, S, $CH_2$ or $NR^x$;

D is a group $Z^2$-$T^1$-$Y^4$-$A^3$-$Y^5$-$T^2$-$Z^2$;

$Z^2$ is identically or differently —O~, —S~, —$NR^x$~, —NH—C(O)~, —$CH_2$~, —$CF_2$~, —CH(OH)~, —$N(R^x)$—O~, —O—$NR^x$~, —O—N=CH—, ~4-1H-(1,2,3)triazol-1-yl-, or ~5-1H-(1,2,3)triazol-1-yl-, where ~ denotes the bond to the group T;

$T^1$, $T^2$ are identically or differently a straight-chain or branched alkanediyl group having 1 to 30 C atoms, where
(i) optionally one or more non-terminal $CH_2$ groups are replaced by —O—, —S—, —S(O)—, —$S(O)_2$—, —$S^+(CH_3)$—, —$P(O_2)$— and/or —$NR^x$—, and/or
(ii) optionally one or more H atoms are replaced by F, Cl, $OR^x$, $OSO_3M$, (=O), (=S), carboxyl, $NH_2$, $NHR^y$ and/or $NHR^z$, and/or
(iii) optionally one or more non-terminal —$CH_2$—$CH_2$— groups are replaced by -5-1H-(1,2,3)triazol-1-yl-, —$CR^x$=$CR^x$— and/or —C≡C—, and/or
(iv) optionally a —$CH_2CH_2CH_2$— group is replaced by -4-1H-(1,2,3)triazol-1-yl- and/or —O—N=CH—, and/or
(v) optionally a —$CH_2CH_2CH_2CH_2$— group is replaced by phenyl-1,4-diyl;

$Y^4$, $Y^5$ are identically or differently a bond, O, S, $NR^x$, S(O), $S(O)_2$, C(O), ~C(O)—$NR^x$—, ~$NR^x$—C(O)—, ~C(O)—O—, ~O—C(O)—, ~$NR^x$—CO—$NR^x$—, ~$NR^x$—$S(O)_2$—, ~$S(O)_2$—$NR^x$—, ~$CH_2$—$NR^x$—C(O)—, ~$CH_2$—C(O)—$NR^x$—, ~$CH(CF_3)$—$NR^x$—, ~CH=N—O— or ~O—N=CH—, where ~ a denotes the bond to group A;

$A^3$ is
a) $C_1$-$C_8$ alkanediyl, $C_2$-$C_8$ alkenediyl, $C_2$-$C_8$ alkynediyl, $C_4$-$C_8$ alkadienediyl, two or more $CH_2$ groups in the stated groups being replaced by O, S, S(O), $S(O)_2$, $NR^x$ and/or C(O), and optionally one or more H atoms in the stated groups being replaced by a group $X^2$,
b) a group $A^4$-[$Z^3$-$A^5$]$_n$,
c) 1,1'-ferrocenediyl, 1,1'-cobaltocenediyl, 1,1'-ruthenocene or dichloroplatinumdiaminodiyl;

$A^4$, $A^5$ are identically or differently a saturated, partially unsaturated or aromatic, mono- or polycyclic hydrocarbon radical having 3 to 14 C atoms, or a three- to eight-membered aromatic, partially unsaturated or saturated mono- or polycyclic heterocyclic radical, the stated groups being each optionally substituted by one or more groups $X^2$;

$Z^3$ is a bond, O, S, S(O), $S(O)_2$, $NR^x$, C(O) or $CR_2^x$;

$X^2$ is identically or differently fluoro, chloro, bromo, nitro, hydroxylamino, $B(OH_2)$, $SO_3M$, $OSO_3M$, $SO_2NH_2$, $PO_3M$, $OPO_3M$, alkyl, haloalkyl, alkyloxy, haloalkyloxy, alkylthio, alkylamino, dialkylamino, trialkylamino, alkylcarbonyl, alkylsulphonyl, alkylsulphoxyl, alkylaminosulphoxyl, dialkylaminosulphoxyl, alkyloxycarbonyl, alkylcarbonyloxy, aminocarbonyl, alkylaminocarbonyl, alkylcarbonylamino, dialkylaminocarbonyl, alkylaminothiocarbonyl, $C_1$-$C_4$ alkylimino (=N—$C_1$-$C_4$ alkyl), $C_1$-$C_4$ alkyloximino (=N—O—$C_1$-$C_4$ alkyl), the alkyl groups in these radicals containing 1 to 4 carbon atoms, and the groups haloalkyl and haloalkyloxy containing the halogens F and/or Cl;

n is 0, 1;

$R^1$ is identically C(O)OM, O—$PO_3M_2$, O—$SO_3M$, $SO_3M$, C(O)—NH—$S(O)_2R^x$, $PO_3M_2$ or C(O)NOM;

$R^2$, $R^3$ are identically or differently H or F;

$R^4$, $R^7$ are identically or differently H, OH, $OR^z$, OC(O) $NHR^y$ or $NR^x$;

$R^6$ is identically or differently H or $R^z$;

$R^5$ is identically or differently H, $R^x$, $R_2^x$, C(O)H, C(O)CH$_2$OH or C(O)-haloalkyl;

$R^8$ is identically or differently $R^x$;

M is H, $C_1$-$C_6$ alkyl or a cation;

$R^x$ is identically or differently H, $R^y$ or $R^z$;

$R^y$ is identically or differently $C_1$-$C_6$ alkyl, phenyl or benzyl, and $R^z$ is identically or differently —C(O)—$C_1$-$C_6$ alkyl, —C(O) phenyl or —C(O)—$C_1$-$C_4$ alkyl-phenyl, and also its pharmacologically tolerated salts, metabolites and prodrugs.

2. The sialic acid derivative according to claim 1, where the symbols in the formula (I) have the following definitions:

$A^1$, $A^2$ are identically or differently a group $D^1$-[$Y^3$-$D^2$-]$_m$-;

$D^1$ is identically or differently
a) $C_6$-$C_{14}$-aryl,
b) $C_3$-$C_{14}$ cycloalkenyl or $C_5$-$C_{14}$ cycloalkadienyl,
c) $C_3$-$C_8$ cycloalkyl,
d) non-aromatic, saturated or partially unsaturated 5- or 6-membered heterocyclyl, containing one to three nitrogen atoms and/or one oxygen or sulphur atom or one or two oxygen and/or sulphur atoms,
e) 5-membered heteroaryl, containing one to four nitrogen atoms or one to three nitrogen atoms and/or one sulphur or oxygen atom,
f) 6-membered heteroaryl, containing one to three or one to four nitrogen atoms,
g) polycyclic heterocyclic radicals,
the stated groups being unsubstituted or substituted by one or more groups $X^1$;

$D^2$ is identically or differently
a) $C_6$-$C_{14}$ aryldiyl,
b) $C_3$-$C_8$ cycloalkyldiyl,
c) non-aromatic, saturated or partially unsaturated 5- or 6-membered heterocyclodiyl, containing one to three nitrogen atoms and/or one oxygen or sulphur atom or one or two oxygen and/or sulphur atoms,
d) 5-membered heteroaryldiyl, containing one to four nitrogen atoms or one to three nitrogen atoms and one sulphur or oxygen atom,
e) 6-membered heteroaryldiyl, containing one to three or one to four nitrogen atoms,
the stated groups being unsubstituted or substituted by one or more groups $X^1$;

$X^1$ is identically or differently F, Cl, Br, I, cyano, nitro, hydroxy, mercapto, amino, carboxyl, hydroxylamino, azido, SO$_3$M, OSO$_3$M, SO$_2$NH$_2$, OPO$_3$M, alkyl, haloalkyl, alkenyl, alkynyl, alkyloxy, haloalkyloxy, alkenyloxy, alkynyloxy, alkylthio, alkylamino, dialkylamino, trialkylamino, formyl, alkylcarbonyl, alkylsulphonyl, alkylsulphoxyl, aminocarbonyl, alkylaminocarbonyl, alkylcarbonylamino, oxo (=O), thioxo (=S), the alkyl groups in these radicals containing 1 to 8 carbon atoms, and the stated alkenyl or alkynyl groups in these radicals containing 2 to 8 carbon atoms;

$Y^1$, $Y^2$ are identically or differently ~CH$_2$—, ~CH$_2$CH$_2$—, ~CH$_2$CH$_2$CH$_2$—, ~C(O)—, ~CH$_2$C(O)—, ~CH$_2$CH$_2$C(O)—, ~CH$_2$CH$_2$CH$_2$C(O)—, ~CH=CH—C(O)—, ~C≡C—C(O)—, ~S(O)$_2$—, ~CH$_2$S(O)$_2$—, ~NH—C(O)—, ~NR$^x$-3-cyclobutene-1,2-dione-4-, ~CH$_2$—NR$^x$-3-cyclobutene-1,2-dione-4-, ~NR$^x$-3-2,5-thiadiazole 1,1-dioxide-4-, where ~ denotes the bond to the group A, or $Y^1$,$Y^2$ form, independently of one another, together with the nitrogen to which they are bonded, and with the group $R^8$, a ~4-1H-(1,2,3)triazol-1-yl-, ~5-1H-(1,2,3)triazol-1-yl-, ~CH$_2$-4-1H-(1,2,3)triazol-1-yl- or ~CH$_2$-5-1H-(1,2,3)triazol-1-yl-ring, where ~ denotes the bond to the group A;

$Y^3$ is a bond, O, S(O), S(O$_2$), CH$_2$, NR$^x$ or C(O);

m is 0, 1 or 2;

$Z^1$ is O, S or CH$_2$;

D is a group $Z^2$-$T^1$-$Y^4$-$A^3$-$Y^5$-$T^2$-$Z^2$;

$Z^2$ is identically or differently —O~, —S~, —NR$^x$~, —NHC(O)~, —CH$_2$~, —O—NR$^x$~ or ~4-1H-(1,2,3) triazol-1-yl-, where ~ a denotes the bond to the group T;

$T^1$, $T^2$ are identically or differently a straight-chain or branched alkanediyl group having 4 to 30 C atoms, where
(i) optionally one or more non-terminal CH$_2$ groups are replaced by ~O—, —S—, —S(O)—, —S(O)$_2$—, —P(O$_2$)— and/or —NR$^x$—, and/or
(ii) optionally one or more H atoms are replaced by F, Cl, OR$^x$, —OSO$_3$M, (=O), carboxyl, NH$_2$, NHR$^y$ or NHR$^z$, and/or
(iii) optionally a non-terminal —CH$_2$—CH$_2$ group is replaced by -5-1H-(1,2,3)triazol-1-yl- and/or
(iv) optionally a non-terminal —CH$_2$CH$_2$CH$_2$— group is replaced by -4-1H-(1,2,3)triazol-1-yl- or —O—N=CH—;

$Y^4$, $Y^5$ are identically or differently O, NR$^x$, S(O), S(O)$_2$, C(O), ~C(O)—NR$^x$—, ~NR$^x$—C(O)—, ~NR$^x$—CO—NR$^x$—, ~NR$^x$—S(O)$_2$—, ~S(O)$_2$—NR$^x$—, ~CH$_2$—NR$^x$—C(O)—, ~CH$_2$—C(O)—NR$^x$— or ~CH$_2$—NR$^x$—, where ~ a denotes the bond to group A;

$A^3$ is
a) $C_1$-$C_8$ alkanediyl, $C_2$-$C_8$ alkenediyl, $C_2$-$C_8$ alkynediyl, $C_4$-$C_8$ alkadiendiyl, optionally 1, 2, 3 or 4 CH$_2$ groups in the stated groups being replaced by O, S(O), S(O)$_2$, NR$^x$ and/or S, and optionally one or more H atoms in the stated groups being replaced by F or Cl,
b) a group $A^4$-[$Z^3$-$A^5$]$_n$,
c) 1,1'-ferrocenediyl, 1,1'-cobaltocenediyl, 1,1'-ruthenocene or dichloroplatinumdiamonodiyl;

$A^4$, $A^5$ are identically or differently
a) aryldiyl, $C_6$-$C_{14}$
b) $C_3$-$C_8$ cycloalkyldiyl,
c) non-aromatic, saturated or partially unsaturated 5- or 6-membered heterocyclodiyl, containing one to three nitrogen atoms and/or one oxygen or sulphur atom or one or two oxygen and/or sulphur atoms,
d) 5-membered heteroaryldiyl, containing one to four nitrogen atoms or one to three nitrogen atoms and/or one sulphur or oxygen atom,
e) 6-membered heteroaryldiyl, containing one to three or one to four nitrogen atoms,
f) polycyclic heterocyclyl from the group,
the stated radicals being unsubstituted or substituted by one or more groups $X^2$;

$Z^3$ is a bond, O, S(O), S(O)$_2$ or C(O);

$X^2$ is identically or differently fluoro, chloro, nitro, bromo, hydroxylamino, SO$_3$M, OSO$_3$M, SO$_2$NH$_2$, PO$_3$M, OPO$_3$M, alkyl, haloalkyl, alkyloxy, haloalkyloxy, alkylamino, dialkylamino, trialkylamino, alkylcarbonyl, alkylsulphonyl, alkylsulphoxyl, alkylaminosulphoxyl, dialkylaminosulphoxyl, alkyloxycarbonyl, alkylcarbonyloxy, aminocarbonyl, alkylaminocarbonyl, alkylcarbonylamino, dialkylaminocarbonyl, $C_1$-$C_4$ alkylimino (=N—$C_1$-$C_4$ alkyl), $C_1$-$C_4$ alkyloximino (=N—O—$C_1$-$C_4$ alkyl), the alkyl groups in these radicals containing 1 to 4 carbon atoms, and the groups haloalkyl and haloalkyloxy containing the halogens F and/or Cl;

n is 0 or 1;

$R^1$ is identical and is C(O)OM, $SO_3$M, C(O)—NH—S$(O)_2$—$R^x$, $PO_3M_2$ or C(O)NOM;

$R^2$, $R^3$ are identically or differently H or F;

$R^4$, $R^7$ are identically or differently H, OH, $OR^z$, OC(O)$NHR^y$ or $NR^x$;

$R^6$ is identically or differently H or $R^z$;

$R^5$ is identically or differently H, $R^x$, C(O)$CH_2$OH, C(O)-haloalkyl or C(O)H;

$R^8$ is identically or differently $R^x$;

M is H, $C_1$-$C_4$ alkyl or a cation from the group of the alkali metals, alkaline earth metals, manganese, copper, zinc, iron and optionally substituted ammonium;

$R^x$ is identically or differently H, $R^y$ or $R^z$;

$R^y$ is identically or differently $C_1$-$C_4$ alkyl, phenyl or benzyl and $R^z$ is identically or differently —C(O)—$C_1$-$C_6$ alkyl, C(O) phenyl or C(O)$CH_2$ phenyl, and also its pharmacologically tolerated salts, metabolites and prodrugs.

3. The sialic acid derivative according to claim 1, where symbols and indices in the formula (I) have the following definitions:

$A^1$, $A^2$ are identically or differently a group $D^1$-[$Y^3$-$D^2$-]$_m$-;

$D^1$ is identically or differently
  phenyl, 1-naphthyl, 2-naphthyl, 2-biphenylene, 2-fluorenyl, 3-fluorenyl, 2-phenanthrenyl, cyclopropyl, cyclobutyl, cyclopentyl, cyclohexyl, 2-piperidinyl, 3-piperidinyl, 4-piperidinyl, 1,3-dioxan-5-yl, 4-tetrahydropyranyl, 3-hexahydropyridazinyl, 4-hexahydropyridazinyl, 2-hexahydropyrimidinyl, 4-hexahydro-pyrimidinyl, 5-hexahydro-pyrimidinyl, 1-piperazinyl, 2-piperazinyl, 4-morpholinyl, 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,3-triazol-1-yl, 1,2,3-triazol-4-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1-benzofuran-2-yl, 1-benzofuran-5-yl, 1-benzofuran-6-yl, 2-benzofuran-5-yl, 2-benzofuran-6-yl, 2H-chromen-3-yl, 2H-chromen-6-yl, 2H-chromen-7-yl, indol-2-yl, 1-benzothiophen-2-yl or benzimidazol-2-yl, the stated groups being unsubstituted or substituted by one or more groups $X^1$;

$D^2$ is identically or differently
  phenylene-1,4-diyl, phenylene-1,3-diyl, biphenyl-4,4'-diyl, naphthalene-1,4-diyl, trans-cyclohexane-1,4-diyl, furan-2,5-diyl, thiophene-2,4-diyl, thiophene-2,5-diyl, 1H(1,2,3)-triazole-1,4-diyl or pyrrole-2,5-diyl, pyridine-2,5-diyl, pyridine-2,4-diyl, pyridazine-3,6-diyl, pyrimidine-2,5-diyl, pyrimidine-2,6-diyl, pyrazine-2,5-diyl or tetrazine-3,5-diyl, the stated groups being unsubstituted or substituted by one or more groups $X^1$;

$X^1$ is identically or differently F, Cl, Br, I, cyano, nitro, hydroxyl, amino, carboxyl, azido, $SO_3$M, $SO_2NH_2$, alkyl, haloalkyl, alkyloxy, haloalkyloxy, alkylamino, dialkylamino, trialkylamino, alkylcarbonyl, alkylsulphoxyl, aminocarbonyl, alkylaminocarbonyl, alkylcarbonylamino, oxo (=O), the alkyl groups in these radicals containing 1 to 6 carbon atoms;

$Y^1$, $Y^2$ are identically or differently ~$CH_2$—, ~C(O)—, ~$CH_2$—C(O)—, ~$CH_2CH_2$C(O)—, ~CH=CH—C(O)—, ~$CH_2$—C(O)—, ~C≡C—C(O)—, ~NH—C(O)—, ~$CH_2$-$MR^x$-3-cyclobutene-1,2-dione-4-, ~S$(O)_2$— or ~$CH_2$S$(O)_2$— where ~ denotes the bond to the group A, or $Y^1$, $Y^2$ form, independently of one another, together with the nitrogen to which they are bonded, and with the group $R^8$, a group ~4-1H-(1,2,3)triazol-1-yl-, where ~ denotes the bond to the group A;

$Y^3$ is a bond, O, S$(O_2)$, $CH_2$ or C(O);

m is 0, 1 or 2;

$Z^1$ is O;

D is a group $Z^2$-$T^1$-$Y^4$-$A^3$-$Y^5$-$T^2$-$Z^2$;

$Z^2$ is identically O, S, ~4-1H-(1,2,3)triazol-1-yl-, —NH—C(O)~ or $CH_2$, where ~ denotes the bond to the group T;

$T^1$, $T^2$ are identically or differently a straight-chain or branched alkanediyl group having 4 to 20 C atoms, where
  (i) optionally one or more non-terminal $CH_2$ groups are replaced by —S—, —S(O)—, —S$(O)_2$—, and/or —$NR^z$—, and/or
  (ii) optionally one or more H atoms are replaced by fluoro, chloro, (=O), carboxyl, $NH_2$, $NHR^y$ or $NHR^z$, and/or
  (iv) optionally a non-terminal —$CH_2CH_2CH_2$— group is replaced by -4-1H-(1,2,3)triazol-1-yl-;

$Y^4$, $Y^5$ are identically or differently ~$NR^x$—C(O)—, ~C(O)—$NR^x$—, ~$NR^x$—S$(O)_2$, ~$NR^x$—, ~$CH_2NR^x$—, ~$NR^x$C(O)$NR^x$—, ~$CH_2NR^x$C(O)—, ~$CH_2$C(O)$NR^x$— or ~S$(O)_2$—$NR^x$—, where ~ denotes the bond to group A;

$A^3$ is
  a) $C_1$-$C_6$ alkanediyl, $C_2$-$C_4$ alkyndiyl, one or more H atoms in the stated groups being optionally replaced by F or Cl, or
  b) a group $A^4$;

$A^4$ is identically
  phenylene-1,4-diyl, biphenyl-4,4'-diyl, naphthalene-1,4-diyl, trans-cyclohexane-1,4-diyl, thiophene-2,5-diyl, 1H-(1,2,3)triazole-1,4-diyl, pyridine-2,5-diyl, pyridine-2,4-diyl, pyridazine-2,5-diyl, pyrimidine-2,5-diyl, pyrimidine-2,4-diyl, pyrazine-2,5-diyl or tetrazine-2,5-diyl, the stated radicals being unsubstituted or substituted by a group $X^2$;

$X^2$ is identically or differently fluoro, chloro, bromo, nitro, $SO_3$M, alkyl, haloalkyl, alkyloxy, haloalkyloxy, alkylamino, dialkylamino, trialkylamino, alkylcarbonyl, alkylsulphoxyl, alkylcarbonyloxy, aminocarbonyl, alkylaminocarbonyl, alkylcarbonylamino, the alkyl groups in these radicals containing 1 to 4 carbon atoms, and the groups haloalkyl and haloalkyloxy containing the halogens F and/or Cl;

$R^1$ is identical and is C(O)OM or C(O)NOM;

$R^2$, $R^3$ are identically H;

$R^4$, $R^7$ are identically OH or $OR^z$;

$R^6$ is identically H or $R^z$;

$R^5$ is identically $R^x$, C(O)$CH_2$OH or C(O)-haloalkyl;

$R^8$ is identically or differently $R^x$;

M is H, methyl, ethyl or a cation from the group Li, Na, K, Ca, Mg and optionally substituted ammonium;

$R^x$ is identically or differently H, $R^y$ or $R^z$;

$R^y$ is identically or differently methyl, ethyl, 1-methylethyl, propyl, 1-methylpropyl, 1,1-dimethylpropyl or benzyl;

$R^z$ is identically or differently methylcarbonyl, ethylcarbonyl, propylcarbonyl, 1-methylethylcarbonyl, 1,1-dimethylethylcarbonyl or phenylcarbonyl.

4. The sialic acid derivative according claim 1, where the symbols and indices in the formula (I) have the following definitions:

$A^1$, $A^2$ are identically or differently a group $D^1$-[$Y^3$-$D^2$-]$_m$-;

$D^1$ is identically or differently
phenyl, 1-naphthyl, 2-naphthyl, 2-biphenylene, 2-fluorenyl, 3-fluorenyl, 2-phenanthrenyl, cyclopropyl, cyclobutyl, cyclopentyl, cyclohexyl, 2-piperidinyl, 3-piperidinyl, 4-piperidinyl, 1,3-dioxan-5-yl, 4-tetrahydropyranyl, 3-hexahydropyridazinyl, 4-hexahydropyridazinyl, 2-hexahydropyrimidinyl, 4-hexahydro-pyrimidinyl, 5-hexahydropyrimidinyl, 1-piperazinyl, 2-piperazinyl, 4-morpholinyl, 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,3-triazol-1-yl, 1,2,3-triazol-4-yl, 1,2,3-triazol-5-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1-benzofuran-2-yl, 1-benzofuran-5-yl, 1-benzofuran-6-yl, 2-benzofuran-5-yl, 2-benzofuran-6-yl, 2H-chromen-3-yl, 2H-chromen-6-yl, 2H-chromen-7-yl, indol-2-yl, 1-benzothiophen-2-yl or benzimidazol-2-yl, the stated groups being unsubstituted or substituted by one or more groups $X^1$;

$D^2$ is identically or differently
phenylene-1,4-diyl, phenylene-1,3-diyl, biphenyl-4,4'-diyl, naphthalene-1,4-diyl, trans-cyclohexane-1,4-diyl, furan-2,5-diyl, thiophene-2,4-diyl, thiophene-2,5-diyl, 1H(1,2,3)-triazole-1,4-diyl or pyrrole-2,5-diyl, pyridine-2,5-diyl, pyridine-2,4-diyl, pyridazine-3,6-diyl, pyrimidine-2,5-diyl, pyrimidine-2,6-diyl, pyrazine-2,5-diyl or tetrazine-3,5-diyl,
the stated groups being unsubstituted or substituted by one or more groups $X^1$;

$X^1$ is identically or differently F, Cl, Br, I, cyano, nitro, hydroxyl, amino, carboxyl, azido, $SO_3M$, $SO_2NH_2$, alkyl, haloalkyl, alkyloxy, haloalkyloxy, alkylamino, dialkylamino, trialkylamino, alkylcarbonyl, alkylsulphoxyl, aminocarbonyl, alkylaminocarbonyl, alkylcarbonyl-amino, oxo (═O), the alkyl groups in these radicals containing 1 to 6 carbon atoms;

$Y^1$, $Y^2$ are identically or differently ~$CH_2$—, ~C(O)—, ~$CH_2$—C(O)—, ~$CH_2CH_2$C(O)—, ~CH═CH—C(O)—, ~C≡C—C(O)—, ~NH—C(O)—, ~$CH_2$—NR$^x$-3-cyclobutene-1,2-dione-4-, ~S(O)$_2$— or ~$CH_2$S(O)$_2$— where ~ denotes the bond to the group A, or $Y^1$, $Y^2$ form, independently of one another, together with the nitrogen to which they are bonded, and with the group $R^8$, a group ~4-1H-(1,2,3)triazol-1-yl- where, ~ denotes the bond to the group A;

$Y^3$ is a bond, O, S(O$_2$), $CH_2$ or C(O);

m is 0, 1 or 2;

$Z^1$ is O;

D is a group $Z^2$-$T^1$-$Y^4$-$A^3$-$Y^5$-$T^2$-$Z^2$;

$Z^2$ is identically O, S, ~4-1H-(1,2,3)triazol-1-yl-, —NH—C(O)~ or $CH_2$, where ~ denotes the bond to the group T;

$T^1$, $T^2$ are identically or differently a straight-chain or branched alkanediyl group having 4 to 20 C atoms, where
(i) optionally one or more non-terminal $CH_2$ groups are replaced by —NH—, —S—, —S(O)— and/or —S(O)$_2$—, and/or
(ii) optionally one or more H atoms are replaced by fluoro, chloro, (═O), carboxyl, $NH_2$, NHR$^y$ or NHR$^z$, and/or
(iv) optionally a non-terminal —$CH_2CH_2CH_2$— group is replaced by -4-1H-(1,2,3)triazol-1-yl-;

$Y^4$, $Y^5$ are identically or differently ~NR$^x$—C(O)—, ~C(O)—NR$^x$—, ~NR$^x$—S(O)$_2$, ~NR$^x$—, ~$CH_2$NR$^x$, ~NR$_x$C(O)NR$^x$—, ~$CH_2$NR$^x$C(O)—, ~$CH_2$C(O)NR$^x$— or ~S(O)$_2$—NR$^x$—, where ~ denotes the bond to group A;

$A^3$ is
a) $C_1$-$C_6$ alkanediyl, $C_2$-$C_4$ alkynediyl, one or more H atoms in the stated groups being optionally replaced by F or Cl, or
b) a group $A^4$;

$A^4$ is identically
phenylene-1,4-diyl, biphenyl-4,4'-diyl, naphthalene-1,4-diyl, trans-cyclohexane-1,4-diyl, thiophene-2,5-diyl or 1H-(1,2,3)triazole-1,4-diyl, pyridine-2,5-diyl, pyridine-2,4-diyl, pyridazine-2,5-diyl, pyrimidine-2,5-diyl, pyrimidine-2,4-diyl, pyrazine-2,5-diyl or tetrazine-2,5-diyl,
the stated radicals being unsubstituted or substituted by a group $X^2$;

$X^2$ is identically or differently fluoro, chloro, bromo, nitro, $SO_3M$, alkyl, haloalkyl, alkyloxy, haloalkyloxy, alkylamino, dialkylamino, trialkylamino, alkylcarbonyl, alkylsulphoxyl, alkylcarbonyloxy, aminocarbonyl, alkylaminocarbonyl, alkylcarbonylamino, the alkyl groups in these radicals containing 1 to 4 carbon atoms, and the groups haloalkyl and haloalkyloxy containing the halogens F and/or Cl;

$R^1$ is identical and is C(O)OM or C(O)NOM;

$R^2$, $R^3$ are identically H;

$R^4$, $R^7$ are identically OH or OR$^z$;

$R^6$ is identically H or R$^z$;

$R^5$ is identically R$^x$, C(O)$CH_2$OH or C(O)-haloalkyl;

$R^8$ is identically or differently R$^x$;

M is H, methyl, ethyl or a cation from the group Li, Na, K, Ca, Mg and optionally substituted ammonium;

$R^x$ is identically or differently H, R$^y$ or R$^z$;

$R^y$ is identically or differently methyl, ethyl, 1-methylethyl, propyl, 1-methylpropyl, 1,1-dimethylpropyl or benzyl;

$R^z$ is identically or differently methylcarbonyl, ethylcarbonyl, propylcarbonyl, 1-methylethylcarbonyl, 1,1-dimethylethylcarbonyl or phenylcarbonyl.

5. The sialic acid derivatives according to claim 1, where the symbols and indices in the formula (I) have the following definitions:

$A^1$, $A^2$ are identically a group $D^1$-[$Y^3$-$D^2$-]$_m$-;

$D^1$ is identically phenyl, 2-naphthyl, cyclohexyl, 2-fluorenyl, 2-furanyl, 2-benzothiophenyl, 2-thienyl, 3-thienyl, 2-pyridinyl, 3-pyridinyl, 4-pyridinyl, 3-pyridazinyl, 4-pyridazinyl, 2-pyrimidinyl, 4-pyrimidinyl, 5-pyrimidinyl or 2-pyrazinyl,
the stated groups being unsubstituted or substituted by a group $X^1$;

$D^2$ is identically phenylene-1,4-diyl, naphthalene-1,4-diyl, thiophene-2,5-diyl, pyridine-2,5-diyl, pyridazine-3,6-diyl, pyrimidine-2,5-diyl or pyrazine-2,5-diyl, the stated groups being unsubstituted or substituted by a group $X^1$;

$X^1$ is F, Cl, Br, nitro, hydroxyl, carboxyl, alkyl, haloalkyl, alkyloxy, haloalkyloxy, alkylamino, dialkylamino, trialkylamino, alkylcarbonyl, alkylsulphoxyl, aminocarbonyl, alkylaminocarbonyl, alkylcarbonylamino, the alkyl groups in these radicals containing 1 to 4 carbon atoms;

$Y^1$, $Y^2$ are identically ~$CH_2$—, ~C(O)—, ~$CH_2$—C(O)—, ~C≡C—C(O)—, ~CH=CH—C(O)—, ~$CH_2$—$NR^x$-3-cyclobutene-1,2-dione-4- or ~$S(O)_2$—, where ~ denotes the bond to the group A, or $Y^1$, $Y^2$ form, independently of one another, together with the nitrogen to which they are bonded, and with the group $R^8$, a group ~4-1H-(1,2,3)triazole-1-yl-, where ~ denotes the bond to the group A;

$Y^3$ is a bond or O;

m is 0 or 1;

$Z^1$ is O;

D is a group $Z^2$-$T^1$-$Y^4$-$A^3$-$Y^5$-$T^2$-$Z^2$;

$Z^2$ is identically O, ~4-1H-(1,2,3)triazol-1-yl-, —NH—C(O)~ or $CH_2$, where ~ denotes the bond to the group T;

$T^1$, $T^2$ are identically a straight-chain alkanediyl group having 4 to 10 C atoms, where
 (i) optionally one or more non-terminal $CH_2$ groups are replaced by —S— and/or —NH—, and/or
 (ii) optionally one or more H atoms are replaced by F, Cl or (=O), carboxyl or $NH_2$;

$Y^4$, $Y^5$ are identically ~$NR^x$—C(O)—, ~$NR^x$—, ~$CH_2NR^x$—, ~$NR^x$(O)$NR^x$—, ~$CH_2NR^xC(O)$—, ~$CH_2C(O)NR^x$— or ~C(O)—$NR^x$—, where ~ denotes the bond to group A;

$A^3$ is
 a) $C_1$-$C_6$ alkanediyl, one or more H atoms in the stated groups being optionally replaced by F or Cl, or
 b) a group $A^4$;

$A^4$ is identically phenylene-1,4-diyl, biphenyl-4,4'-diyl, naphthalene-1,4-diyl, pyridine-2,5-diyl, pyridazine-2,5-diyl, pyrimidine-2,5-diyl, pyrazine-2,5-diyl, tetrazine-2,5-diyl, ethyne-1,2-diyl, thiophene-2,5-diyl, cyclohexane-1,4-diyl or -3-cyclobutene-1,2-dione-4-;
 the stated radicals being unsubstituted or substituted by a group $X^2$;

$X^2$ is identically a fluoro, chloro, bromo, nitro, $SO_3M$, alkyl, haloalkyl, alkyloxy, haloalkyloxy, alkylamino, dialkylamino, trialkylamino, alkylsulphoxyl, alkylcarbonyloxy, the alkyl groups in these radicals containing 1 to 4 carbon atoms, and the groups haloalkyl and haloalkyloxy containing the halogens F and/or Cl;

$R^1$ is identical and is C(O)OM;

$R^2$, $R^3$ are identically H;

$R^4$, $R^7$ are identically OH or $OR^z$;

$R^6$ is identically H or $R^z$;

$R^5$ is identically $R^x$, $C(O)CH_2OH$ or C(O)-haloalkyl;

$R^8$ is identically $R^x$;

M is H, methyl, ethyl or a cation from the group Li, Na and K;

$R^x$ is identically or differently H, $R^y$ or $R^z$;

$R^y$ is identically or differently methyl or ethyl;

$R^z$ is identically methylcarbonyl, ethylcarbonyl or 1-methylethylcarbonyl.

6. The sialic acid derivative of formula (I) according to claim 1, where the symbols and indices in the formula (I) have the following definitions:

$A^1$, $A^2$ are identically a group $D^1$-$[Y^3$-$D^2$-$]_m$-;

$D^1$ is identically
phenyl, cyclohexyl, naphth-2-yl, fluoren-2-yl, furan-2-yl, benzothiophen-2-yl, thien-2-yl, thien-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl or pyrazin-2-yl,
the stated groups being unsubstituted or substituted by a group $X^1$;

$D^2$ is identically
phenylene-1,4-diyl, naphthalene-1,4-diyl, thiophene-2,5-diyl, pyridine-2,5-diyl, pyridazine-3,6-diyl, pyrimidine-2,5-diyl or pyrazine-2,5-diyl,
the stated groups being unsubstituted or substituted by a group $X^1$;

$X^1$ is identically F, Cl, nitro, hydroxy, carboxyl, alkyl, haloalkyl, alkyloxy, haloalkyloxy, alkylamino, dialkylamino, trialkylamino, alkylsulphoxyl, aminocarbonyl, alkylaminocarbonyl, alkylcarbonylamino, the alkyl groups in these radicals containing 1 to 3 carbon atoms;

$Y^1$, $Y^2$ are identically ~$CH_2$—, ~C(O)—, ~$CH_2$—C(O)—, ~C≡C—C(O)—, ~CH=CH—C(O)—, ~$CH_2$—$NR^x$-3-cyclobutene-1,2-dione-4- or ~$S(O)_2$—, where ~ denotes the bond to the group A, or $Y^1$, $Y^2$ form, independently of one another, together with the nitrogen to which they are bonded, and with the group $R^8$, a group ~4-1H-(1,2,3)triazol-1-yl-, where ~ denotes the bond to the group A;

$Y^3$ is a bond;

m is 0 or 1;

$Z^1$ is O;

D is a group $Z^2$-$T^1$-$Y^4$-$A^3$-$Y^5$-$T^2$-$Z^2$;

$Z^2$ is identically O, $CH_2$ or ~4-1H-(1,2,3)triazol-1-yl-, where ~ denotes the bond to the group T;

$T^1$, $T^2$ are identically or differently a straight-chain alkanediyl group having 4 to 6 C atoms, where
 (i) optionally one or more non-terminal $CH_2$ groups are replaced by —S—, and/or NH, and/or
 (ii) optionally one or more H atoms are replaced by F, Cl, (=O), carboxyl or $NH_2$;

$Y^4$, $Y^5$ are identically or differently ~C(O)—$NR^x$—, ~$NR^x$—, ~$CH_2NR^x$—, ~NHC(O)NH—, ~$CH_2NHC(O)$—, ~$CH_2C(O)NH$— or ~$NR^x$—(O)—, where ~ denotes the bond to group A;

$A^3$ is
 a) $C_1$-$C_6$ alkanediyl, one or more H atoms in the stated groups being optionally replaced by F or Cl, or
 b) a group $A^4$;

$A^4$ is identically phenylene-1,4-diyl, biphenyl-4,4'-diyl, naphthalene-1,4-diyl, pyridine-2,5-diyl, pyridazine-2,5-diyl, pyrimidine-2,5-diyl, pyrazine-2,5-diyl, tetrazine-2,5-diyl, ethyne-1,2-diyl, thiophene-2,5-diyl, cyclohexane-1,4-diyl or -3-cyclobutene-1,2-dione-4-;
 the stated radicals being unsubstituted or substituted by a group $X^2$;

$X^2$ is identically fluoro, chloro, bromo, nitro, $SO_3M$, alkyl, haloalkyl, alkyloxy, haloalkyloxy, alkylamino, dialkylamino, trialkylamino, alkylsulphoxyl, alkylcarbonyloxy, the alkyl groups in these radicals containing 1 to 3 carbon atoms, and the groups haloalkyl and haloalkyloxy containing the halogens F and/or Cl;

$R^1$ is C(O)OM;

$R^2$, $R^3$ are identically H;

$R^4$, $R^7$ are identically OH or $OR^z$;

$R^6$ is identically H or $R^z$;

$R^5$ is identically $R^x$, $C(O)CH_2OH$ or C(O)-haloalkyl;

$R^8$ is identically H;

M is H, methyl or a cation from the group Li, Na and K;

$R^x$ is identically or differently H, $R^y$ or $R^z$;

$R^y$ is identically or differently methyl or ethyl;

$R^z$ is identically methylcarbonyl, ethylcarbonyl or 1-methylethylcarbonyl.

7. The sialic acid derivative according to claim 1, where the symbols and indices in the formula (I) have the following definitions:

$A^1$, $A^2$ are identically a group $D^1$-[$Y^3$-$D^2$-]$_m$;

$D^1$ is identically
  phenyl, pyridin-2-yl, fluoren-2-yl, cyclohexyl, naphth-2-yl, benzothiophen-2-yl, furan-2-yl, thien-2-yl or thien-3-yl,
  the stated groups being unsubstituted or substituted by a group $X^1$;

$D^2$ is identically
  phenylene-1,4-diyl or thiophene-2,5-diyl,
  the stated groups being unsubstituted or substituted by a group $X^1$;

$X^1$ is identically F, chloro, nitro, hydroxy, carboxyl, methyl, trifluoromethyl, methyloxy;

$Y^1$, $Y^2$ are identically ~C(O)—, ~CH$_2$—, ~C≡C—C(O)—, ~CH=CH—C(O)—, ~S(O)$_2$—, ~CH2-NH-3-cyclobutene-1,2-dione-4- or ~CH$_2$—C(O)—, where ~ denotes the bond to the group A, or $Y^1$, $Y^2$ form, independently of one another, together with the nitrogen to which they are bonded, and with the group $R^8$, a group ~4-1H-(1,2,3)triazol-1-yl-, where ~ denotes the bond to the group A;

$Y^3$ is a bond;

m is 0 or 1;

$Z^1$ is O;

D is a group $Z^2$-$T^1$-$Y^4$-$A^3$-$Y^5$-$T^2$-$Z^2$;

$Z^2$ is identically O, CH$_2$, ~CONH— or ~4-1H-(1,2,3)triazol-1-yl-, where ~ denotes the bond to the group T;

$T^1$, $T^2$ are identically or differently ~CH$_2$CH$_2$CH$_2$SCH$_2$CH$_2$—, ~CH$_2$CH$_2$CH$_2$S(O)CH$_2$CH$_2$—, ~CH$_2$C(O)NHCH$_2$CH$_2$CH$_2$—, ~CH$_2$-4-1H-(1,2,3)triazole-1-CH$_2$CH$_2$—, butane-1,4-diyl, pentane-1,5-diyl or hexane-1,6-diyl, where ~ denotes the bond to the group $Z^2$;

$Y^4$, $Y^5$ are identically ~C(O)—NH—, ~NH—, ~CH$_2$NH—, ~NHC(O)NH—, ~CH$_2$NHC(O)—, ~CH$_2$C(O)NH— or ~NH—C(O)—, where ~ denotes the bond to group A;

$A^3$ is methanediyl, ethane-1,2-diyl, butane-1,4-diyl, hexane-1,6-diyl, -3-cyclobutene-1,2-dione-4-, thiophene-2,5-diyl, cyclohexane-1,4-diyl, phenylene-1,4-diyl, naphthalene-1,4-diyl, ethyne-1,2-diyl, biphenyl-4,4'-diyl or pyridine-2,5-diyl,
  the stated radicals being unsubstituted or substituted by one or more groups $X^2$;

$X^2$ is identically bromo, nitro, methyl or pentyloxy;

$R^1$ is C(O)ONa;

$R^2$, $R^3$ are identically H;

$R^4$, $R^7$ are identically OH;

$R^6$ is identically H;

$R^5$ is identically C(O)CH$_3$, C(O)CH$_2$F or C(O)CH$_2$OH;

$R^8$ is identically H.

8. The sialic acid derivatives according to claim 1, having the following structural formulae 207
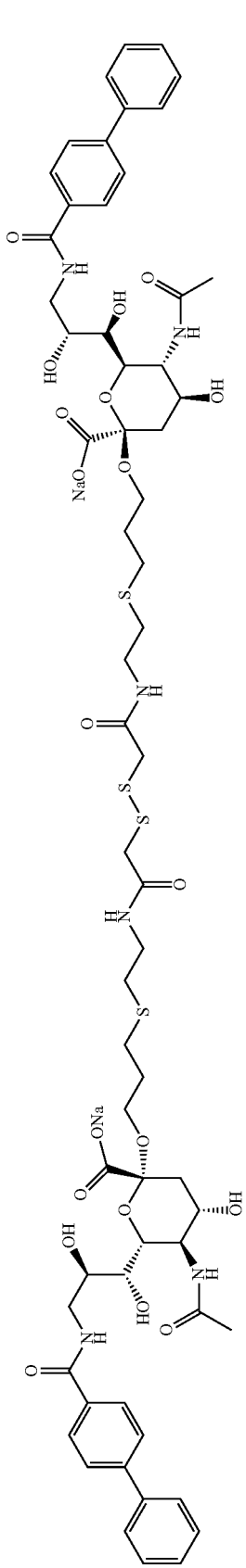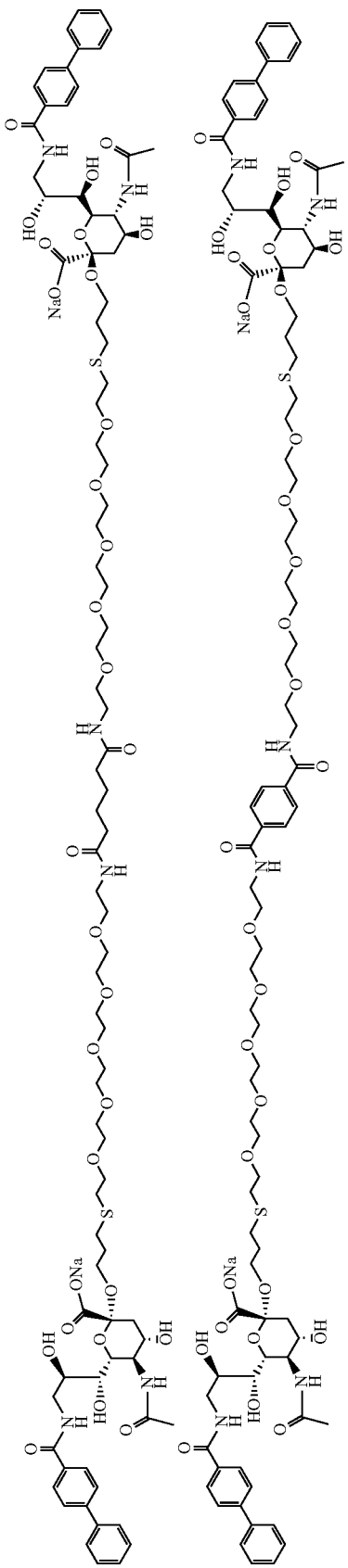
208
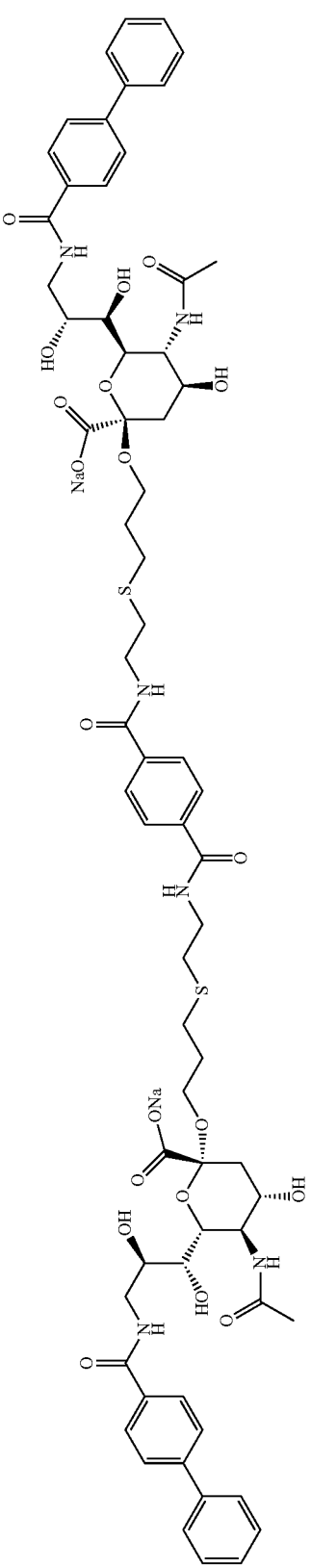

-continued
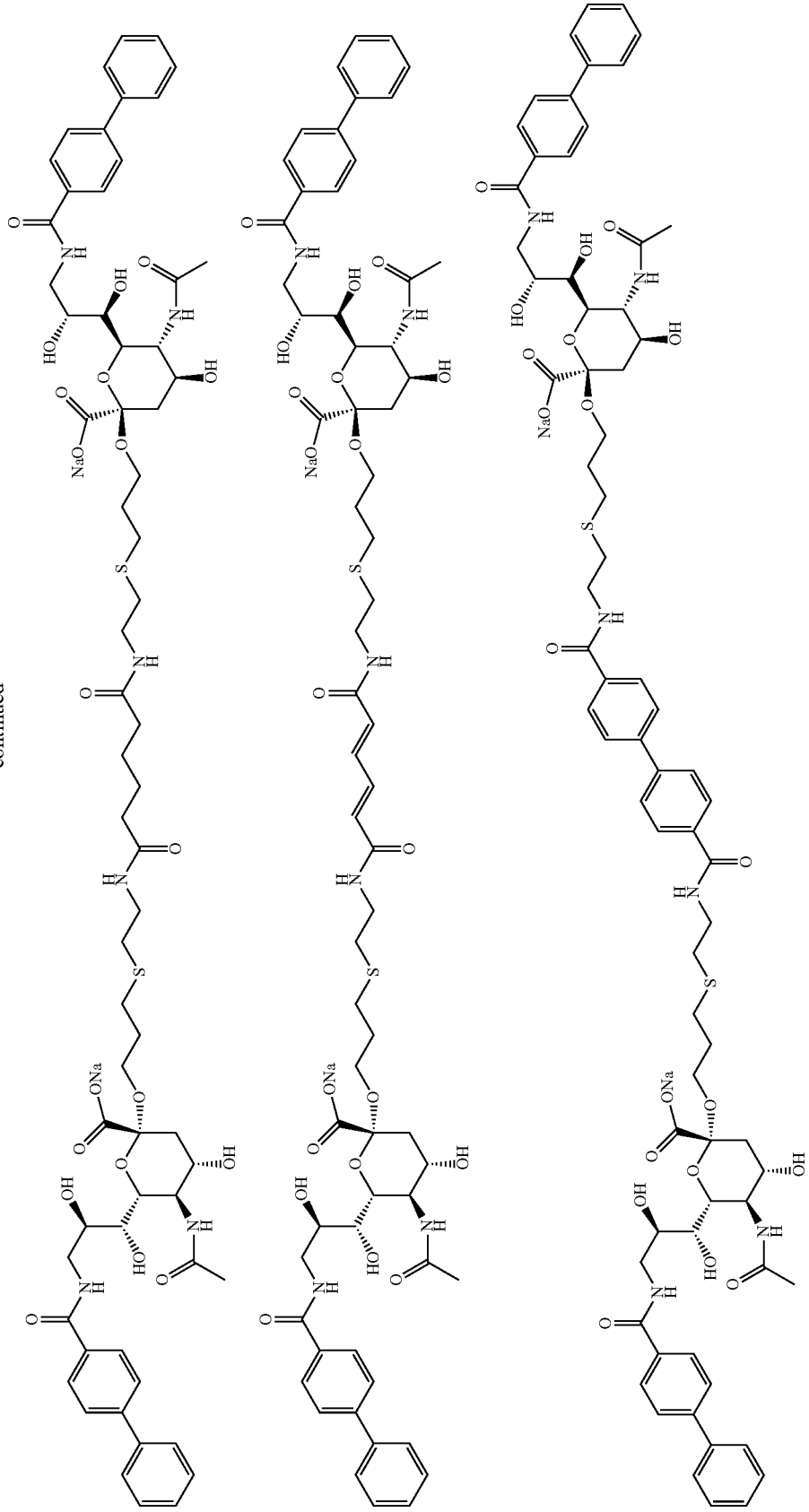

211 212
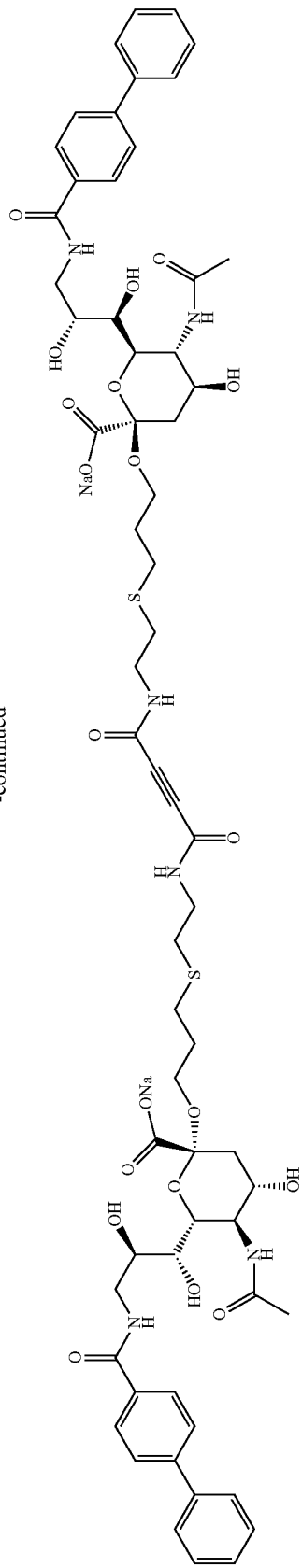
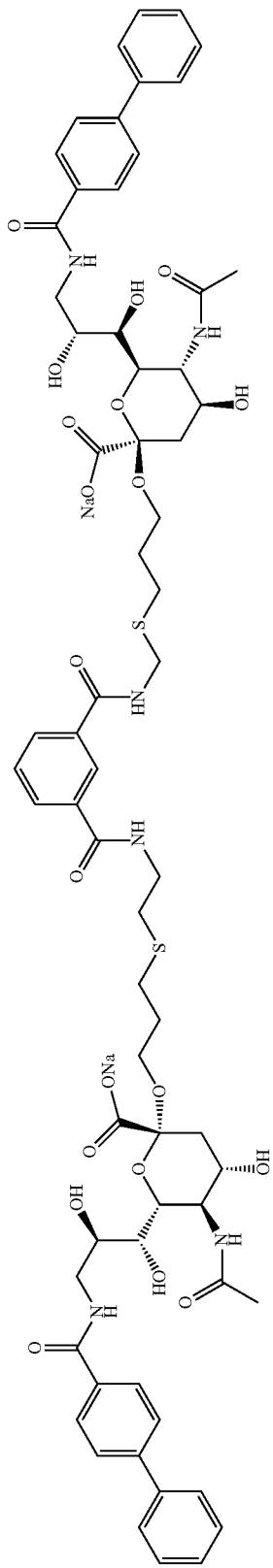
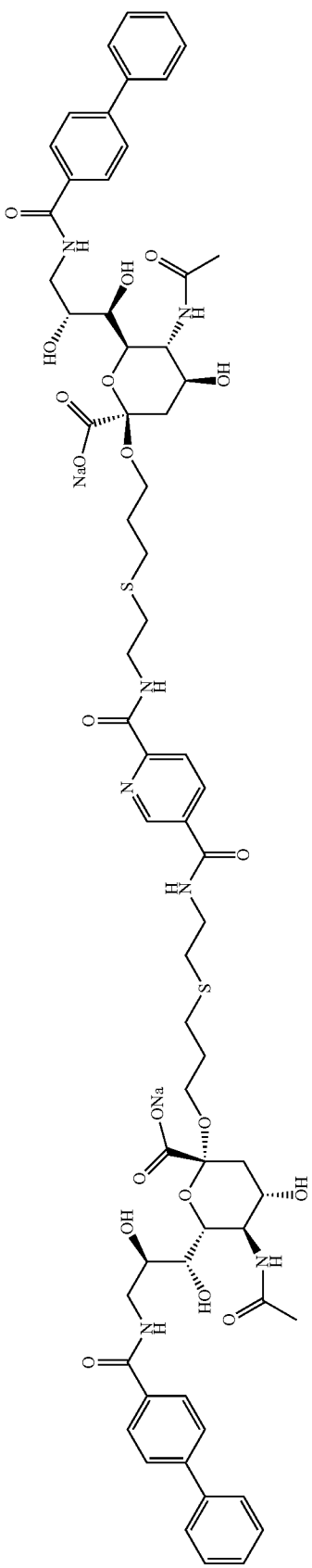

213 214
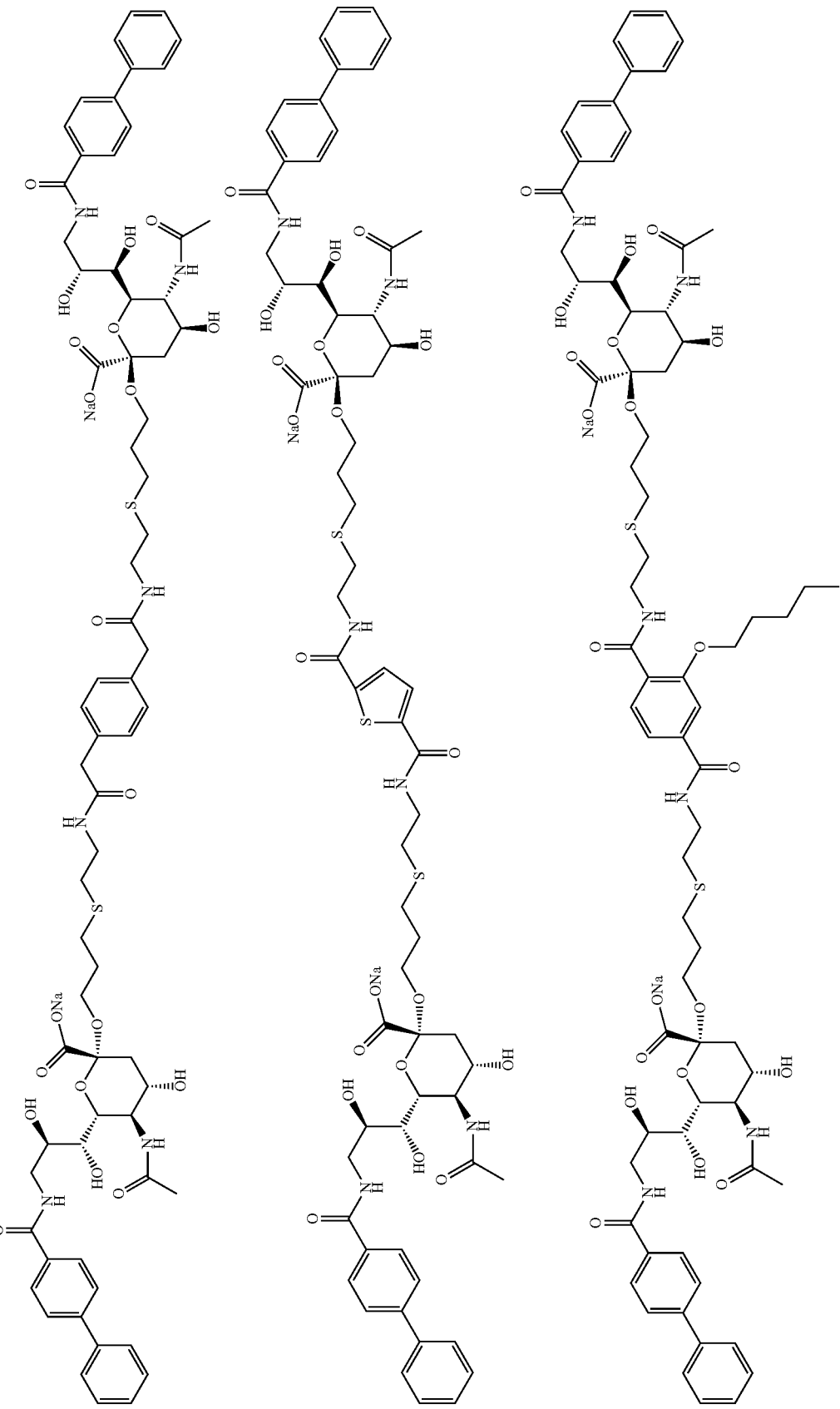

215 216
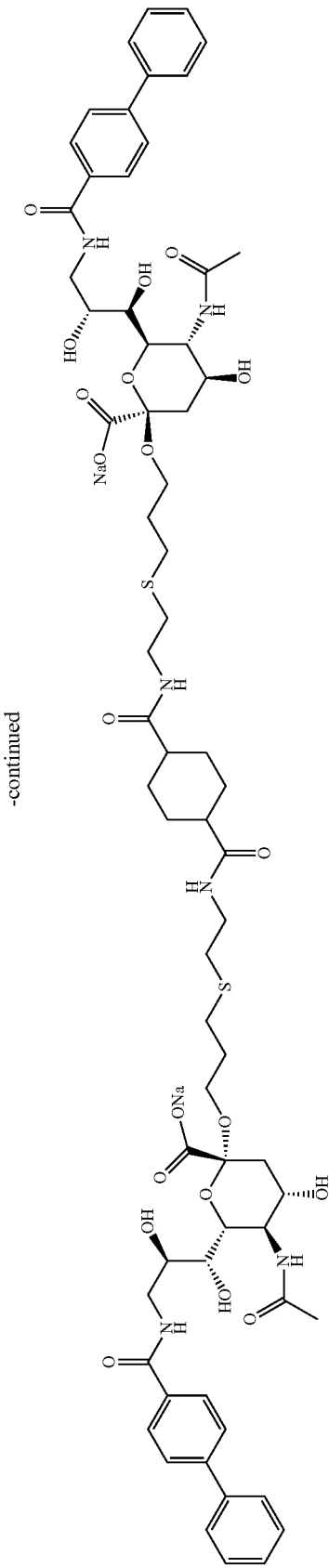
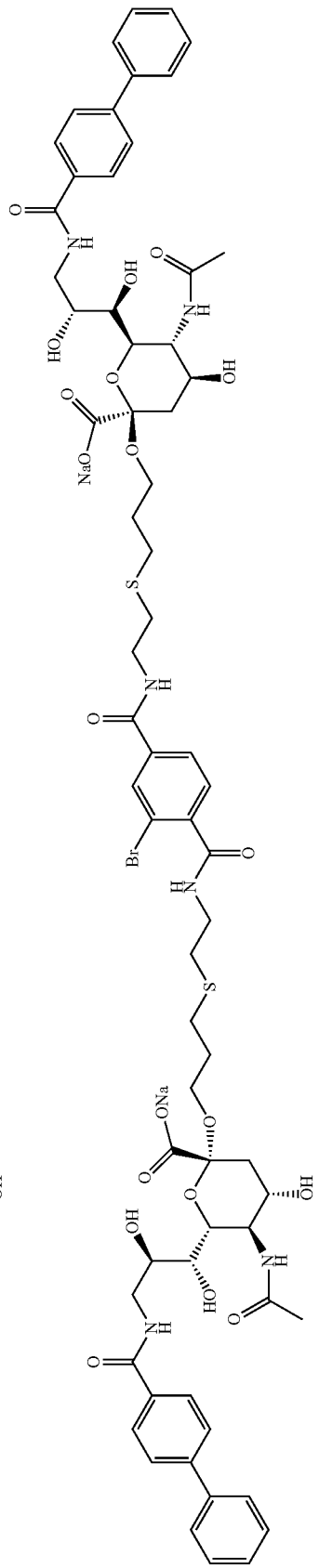
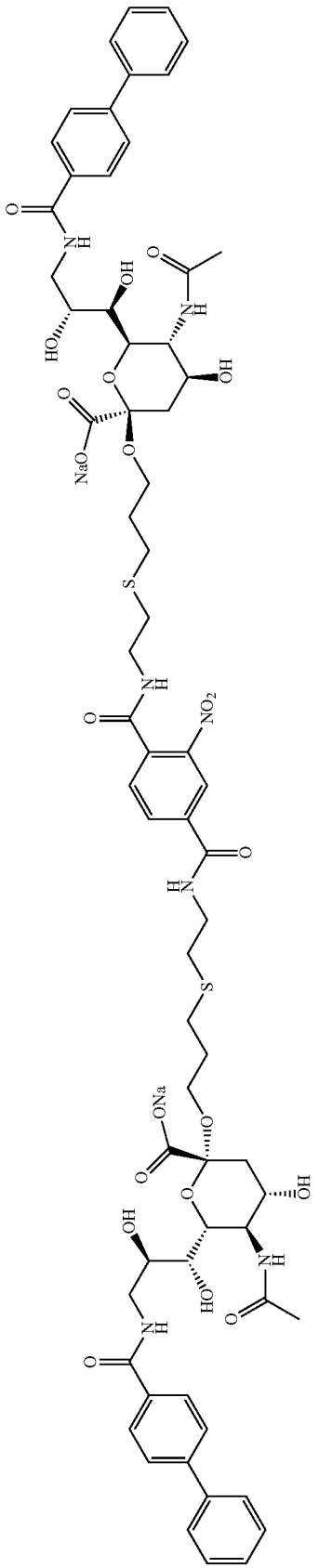

-continued
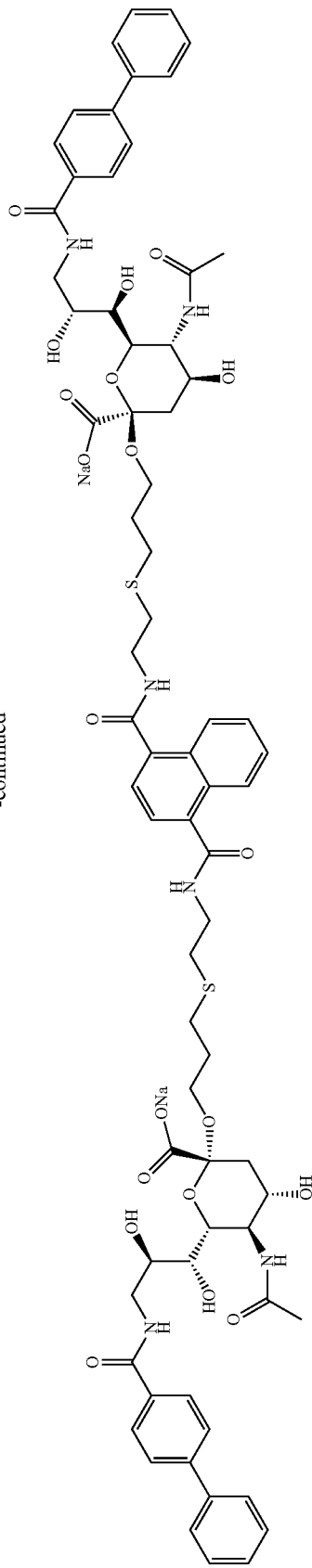 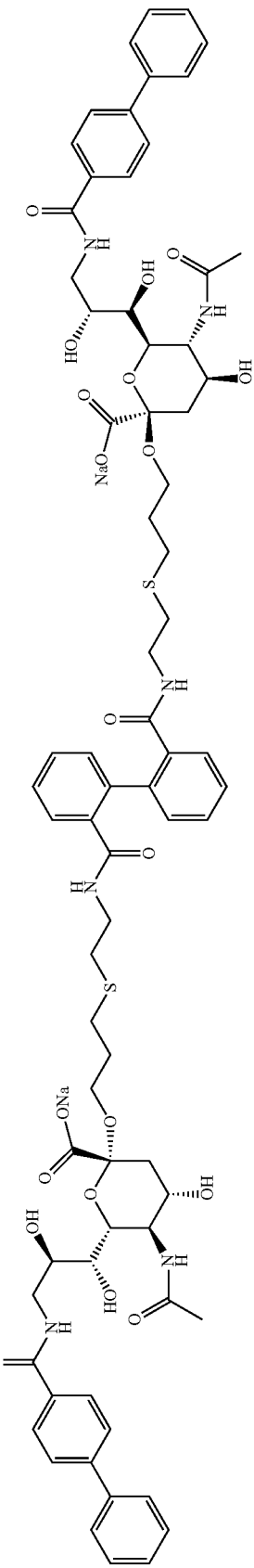 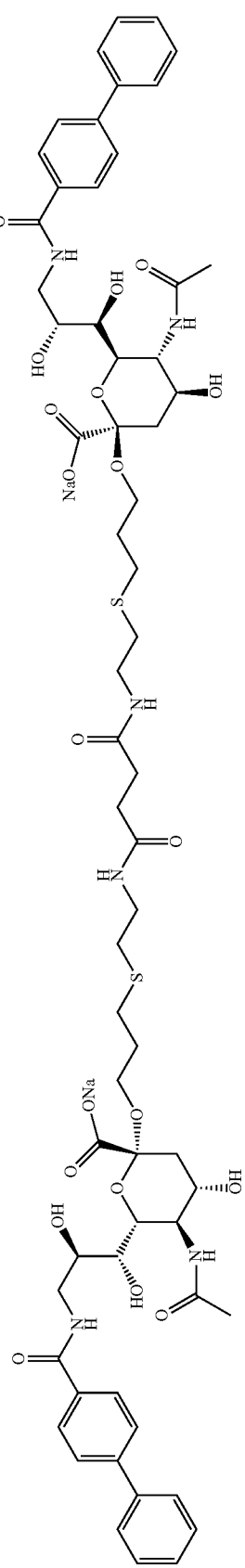 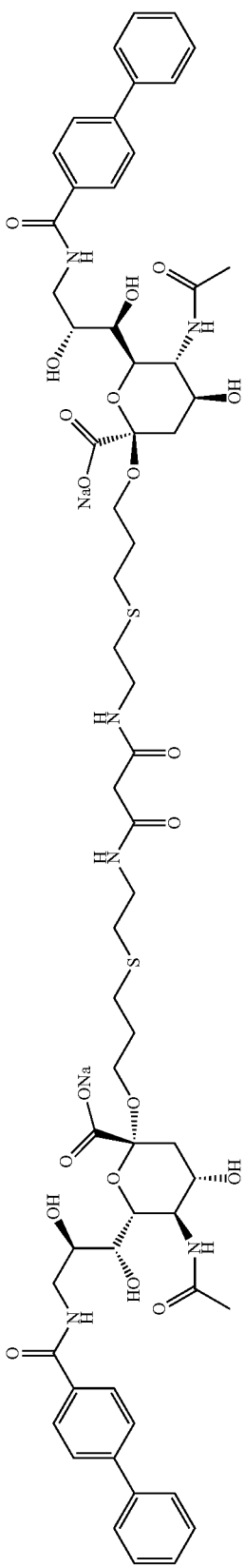

219 220
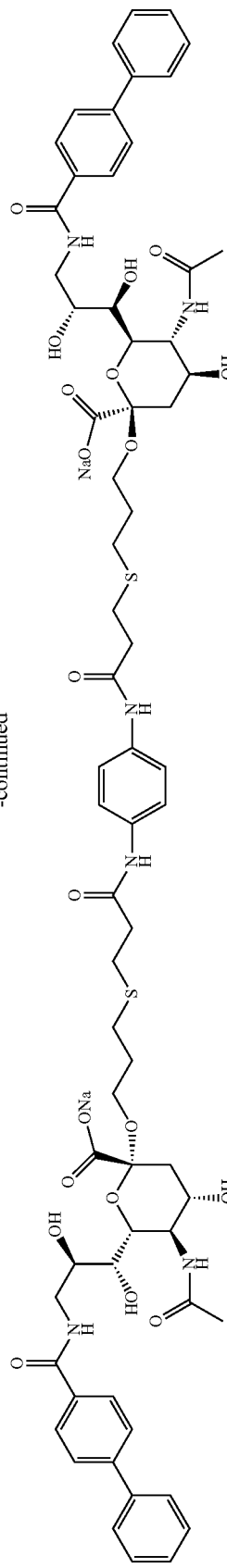
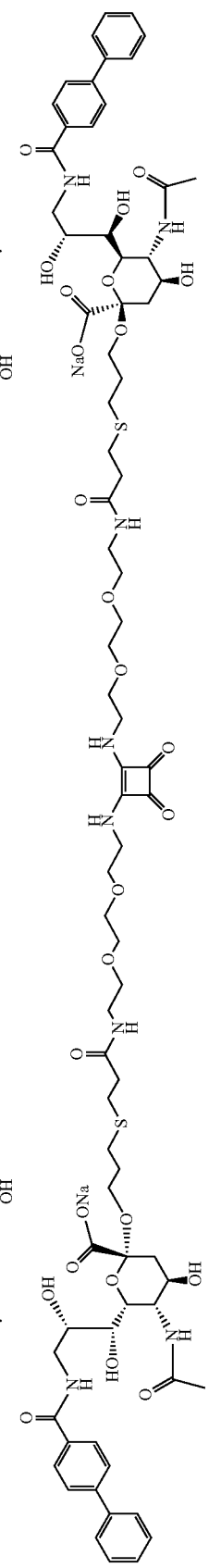
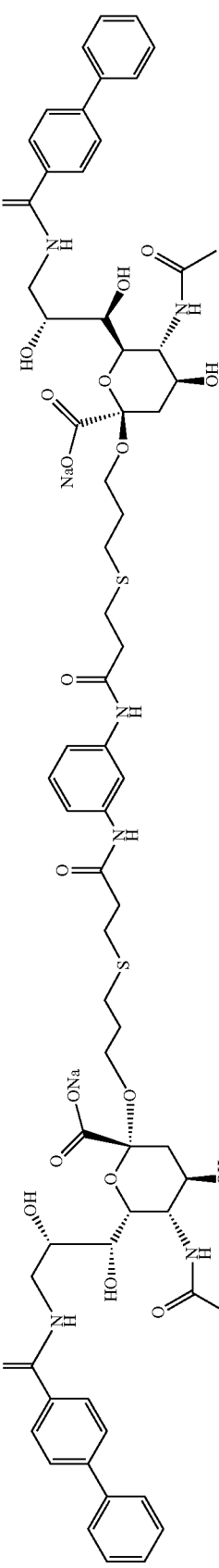
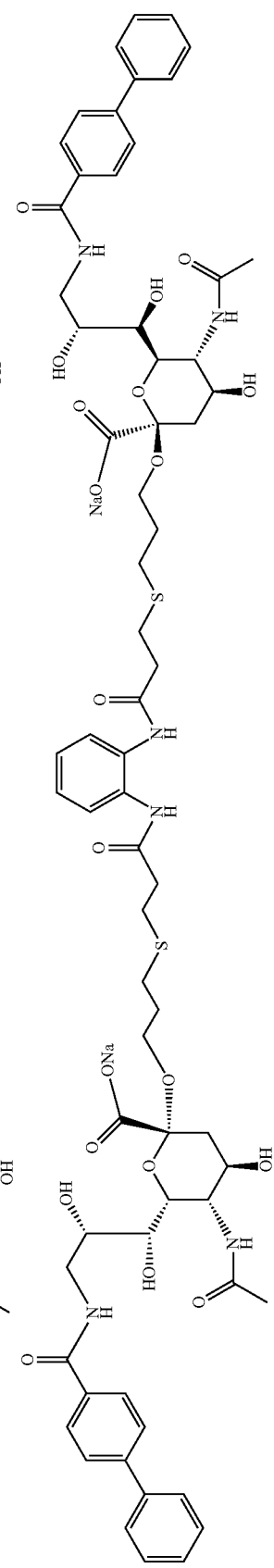

221
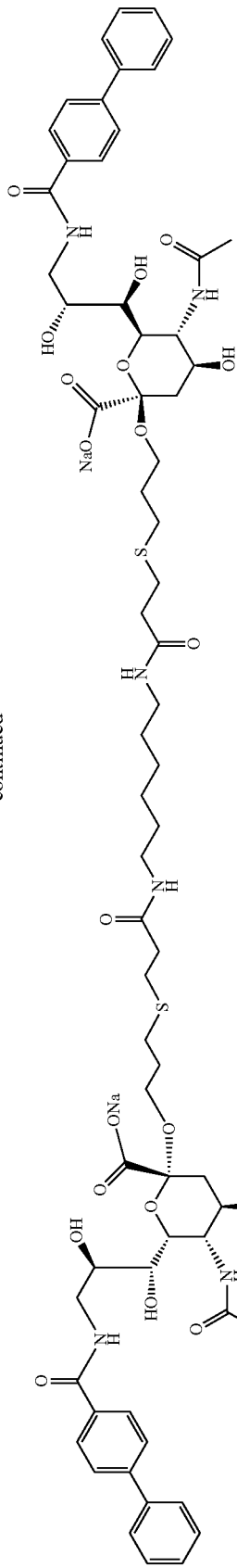
222
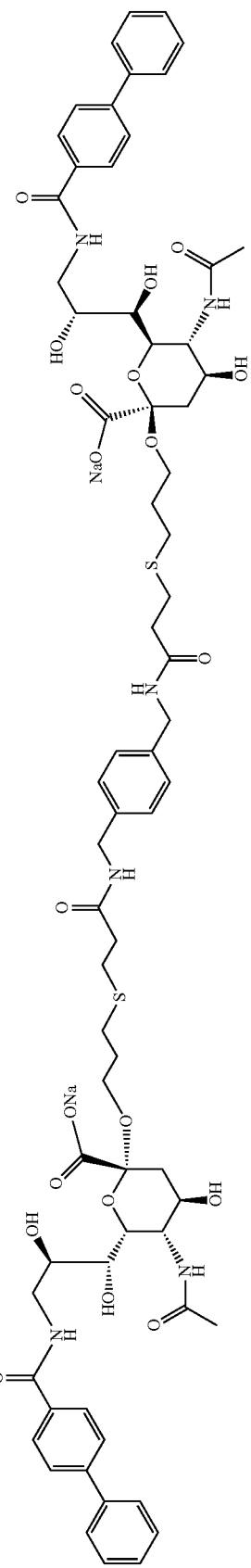
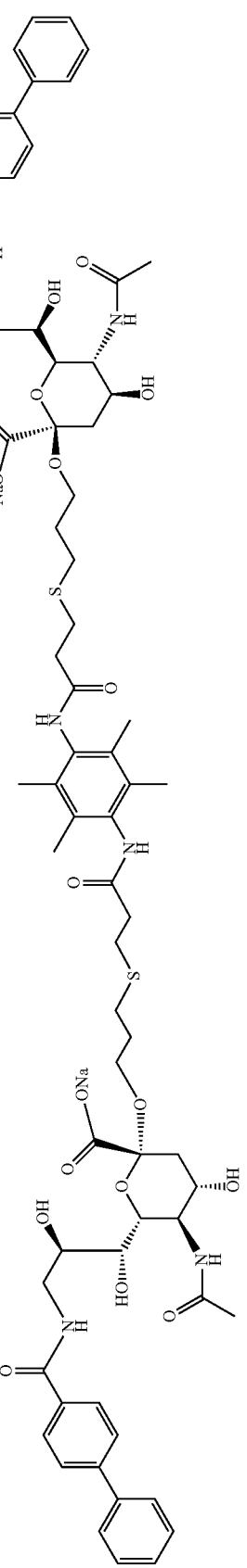

223
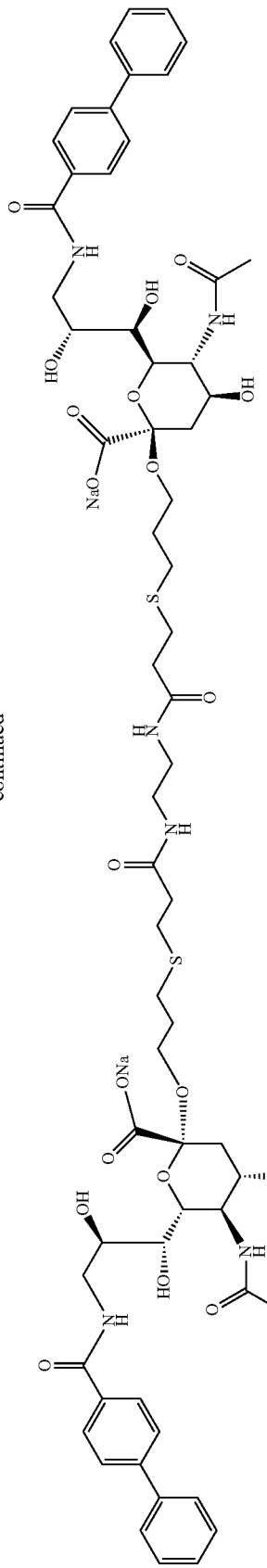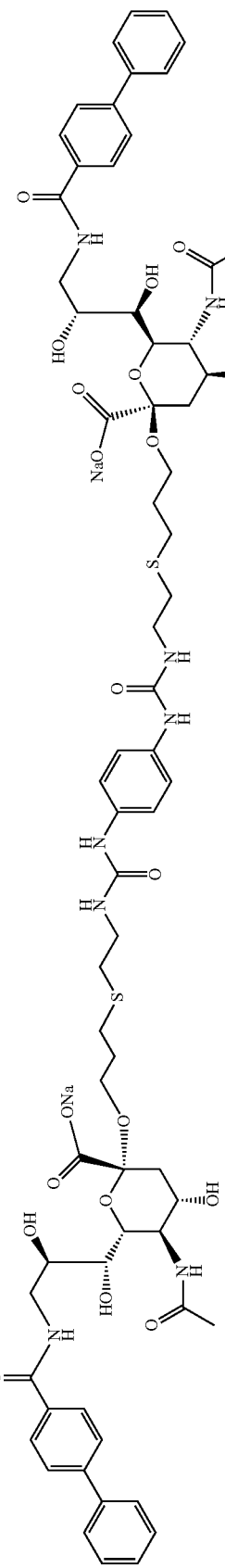
224
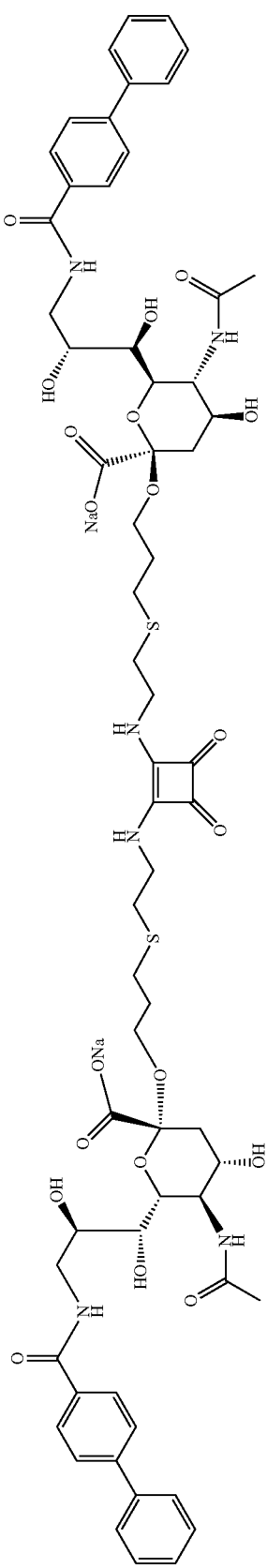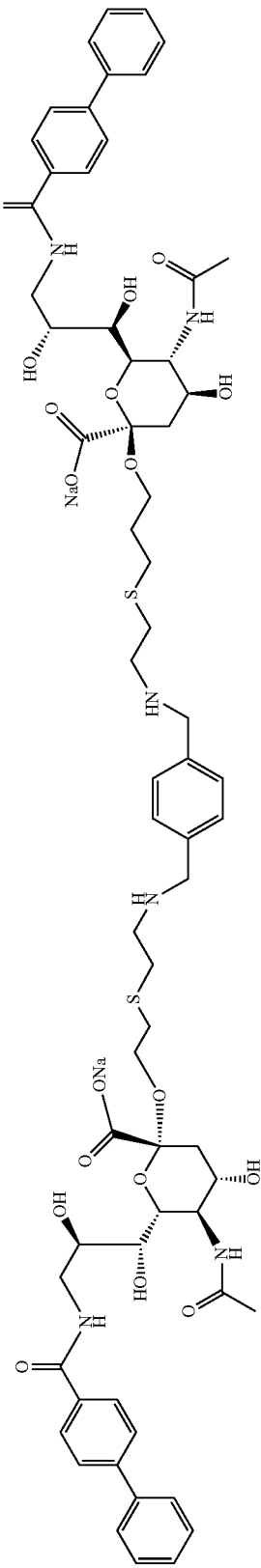

225 226
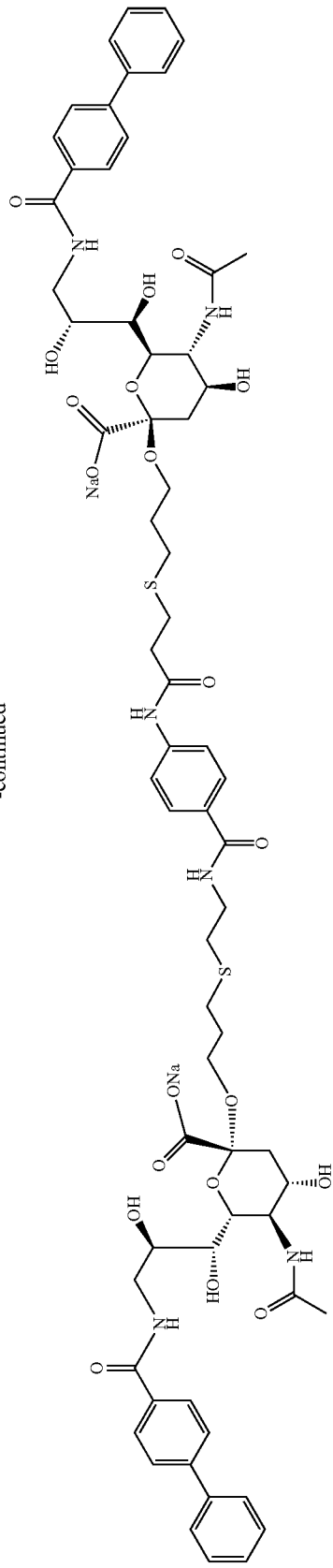
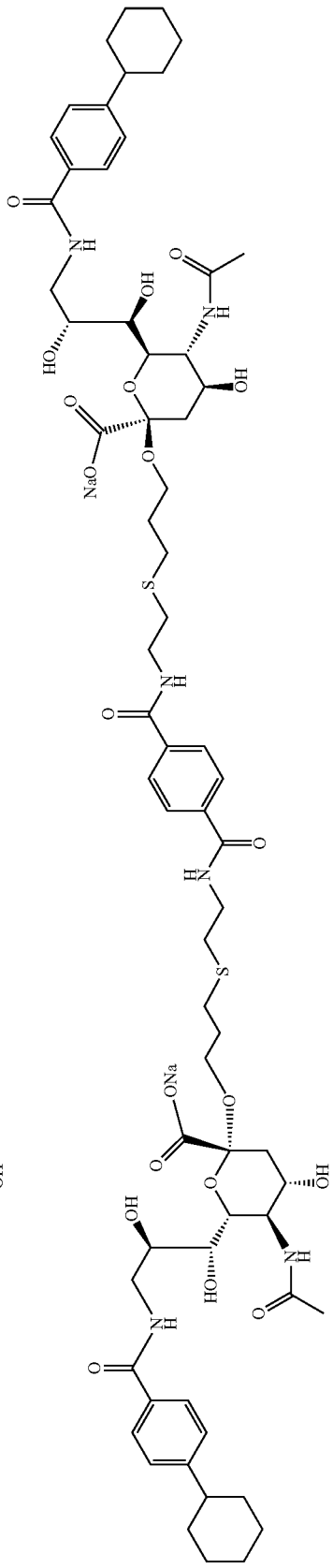
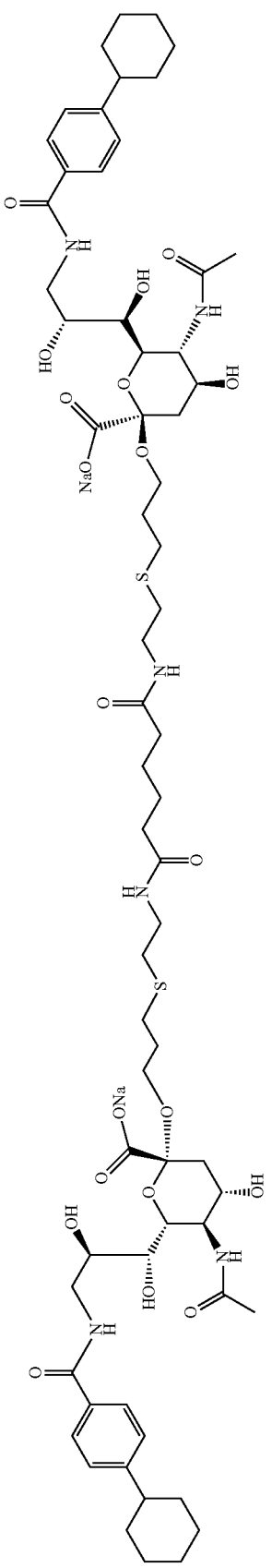

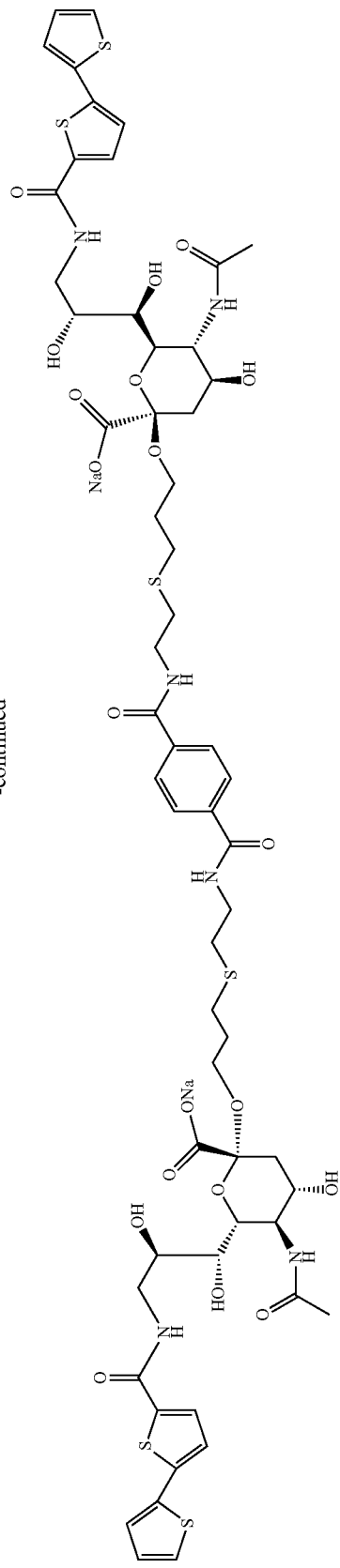
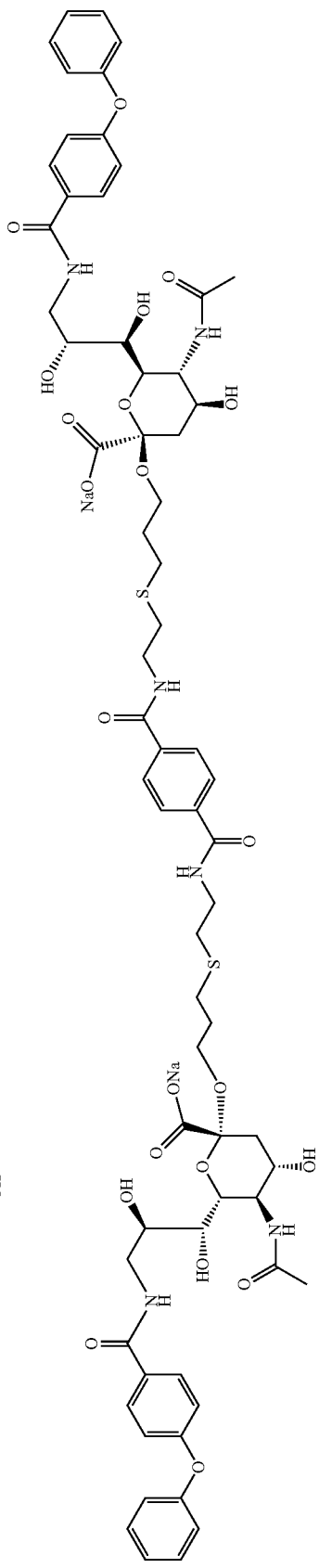
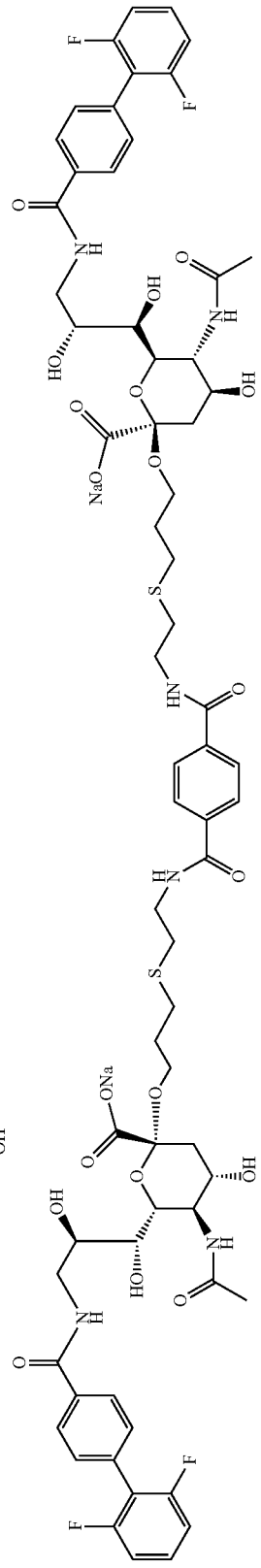

229
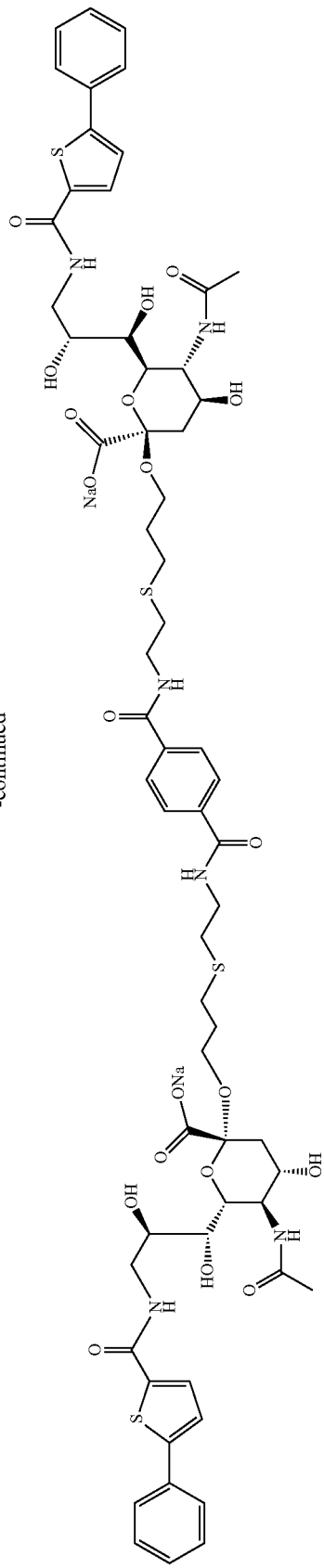
230
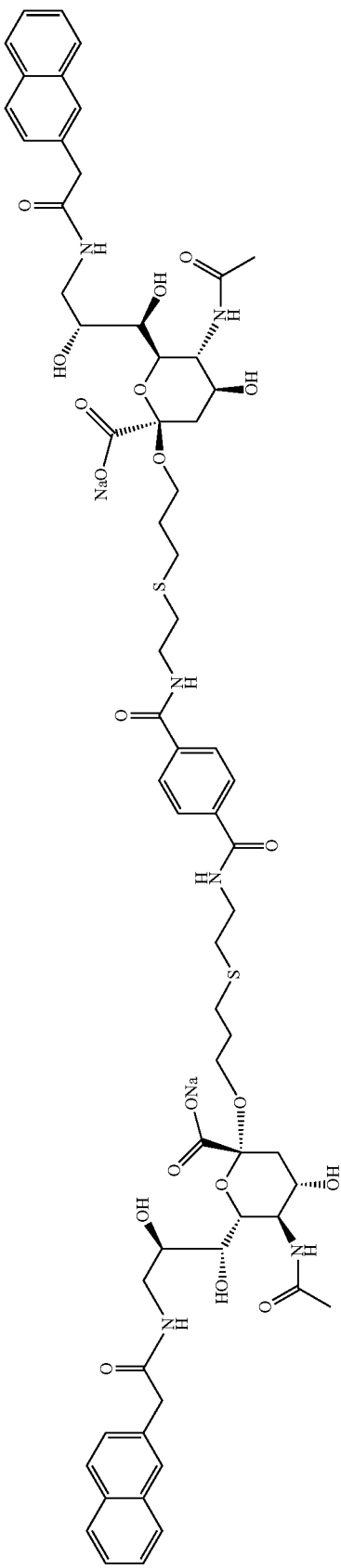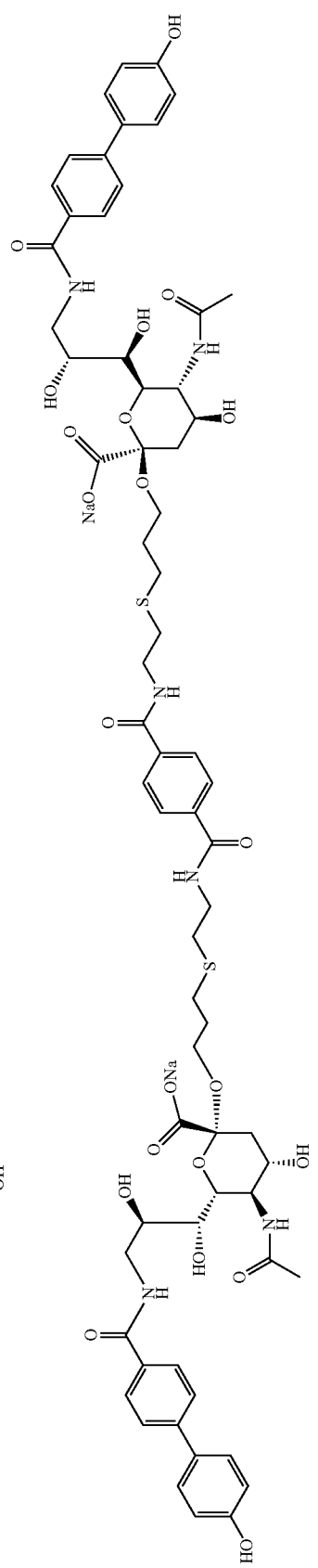

231 232
-continued
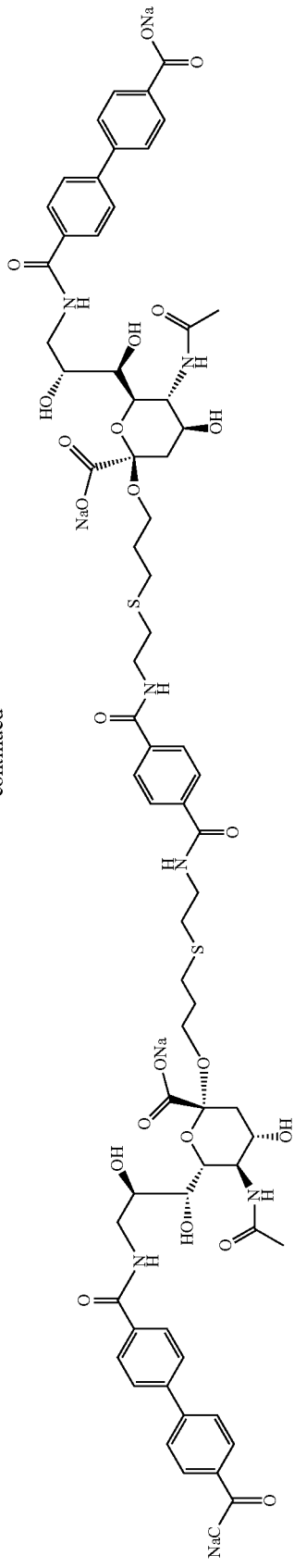
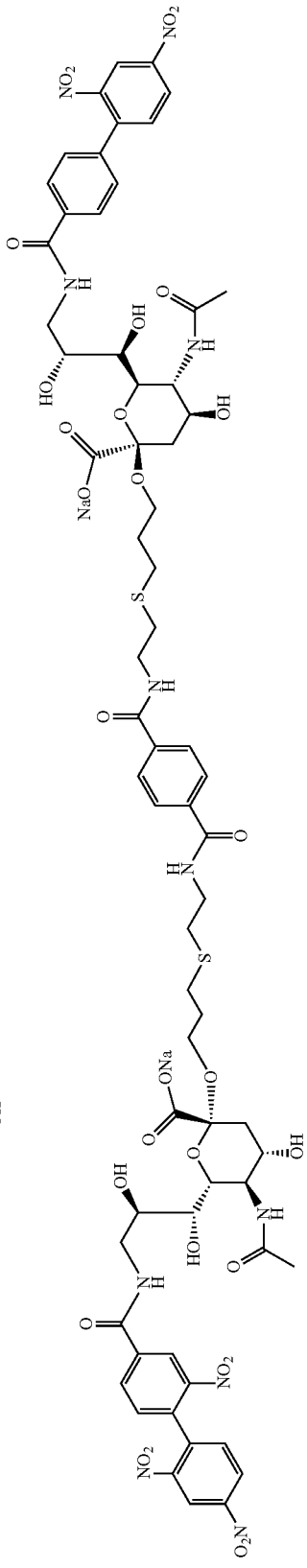
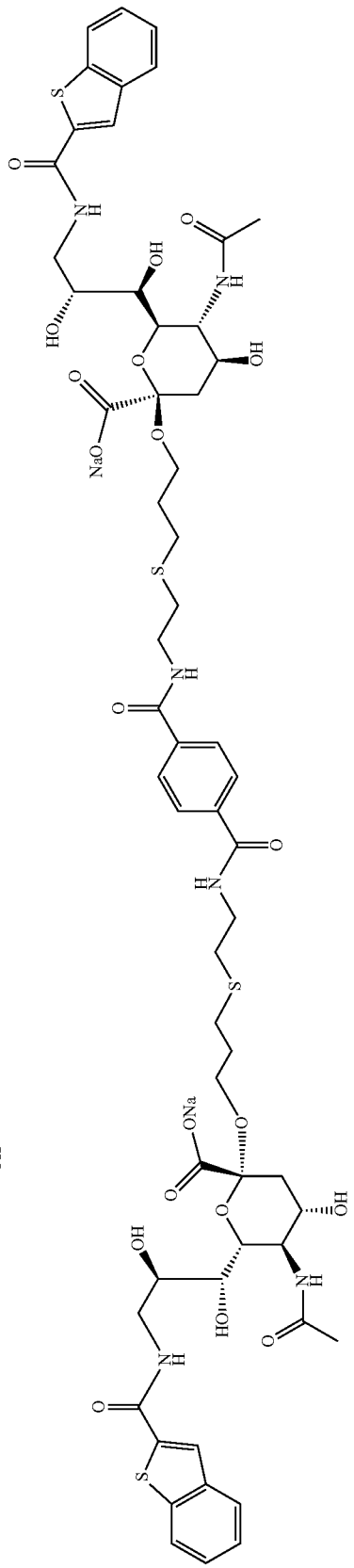

233
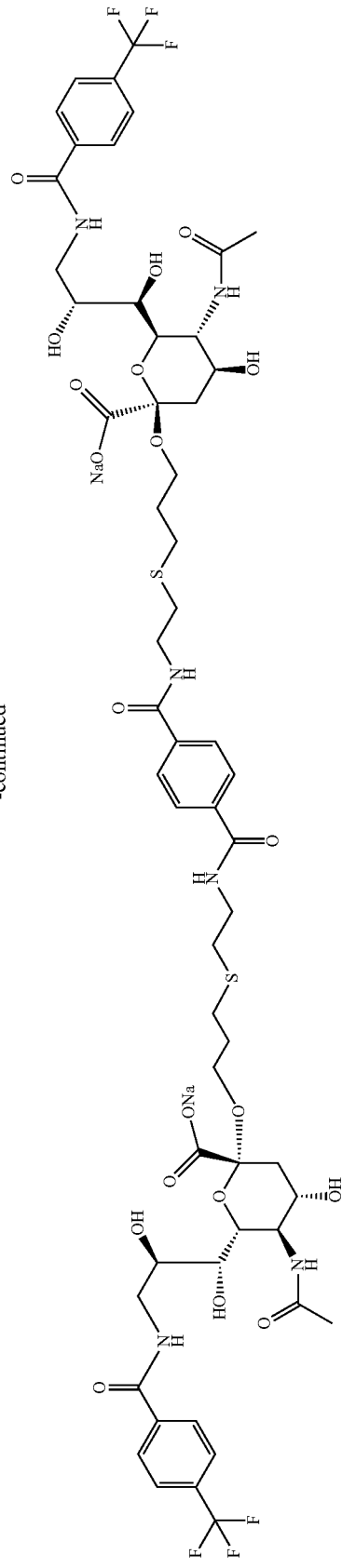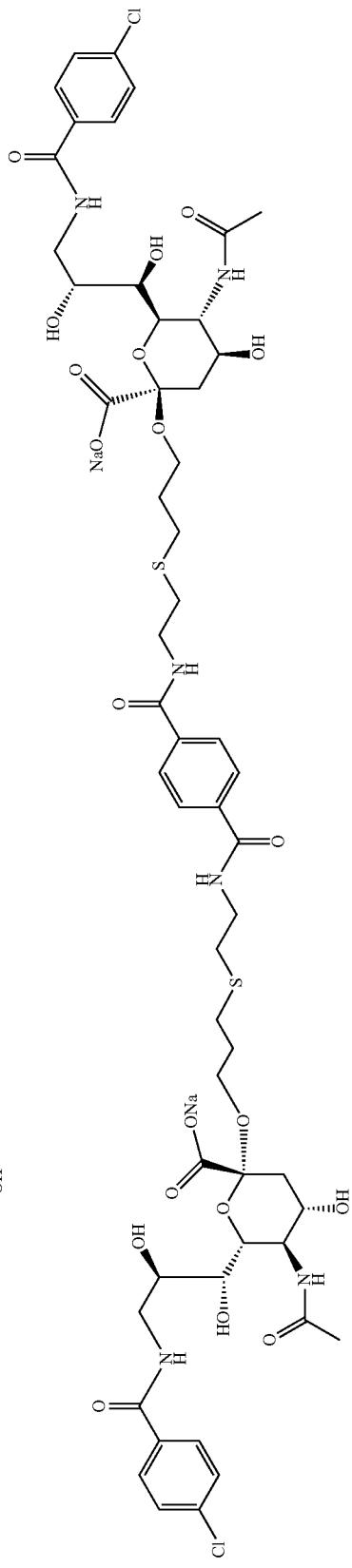
234
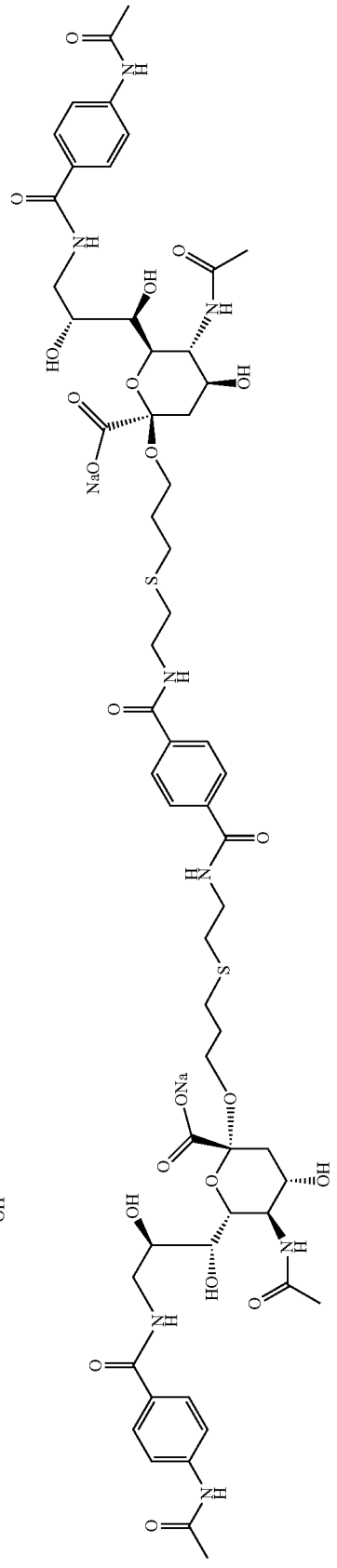

235
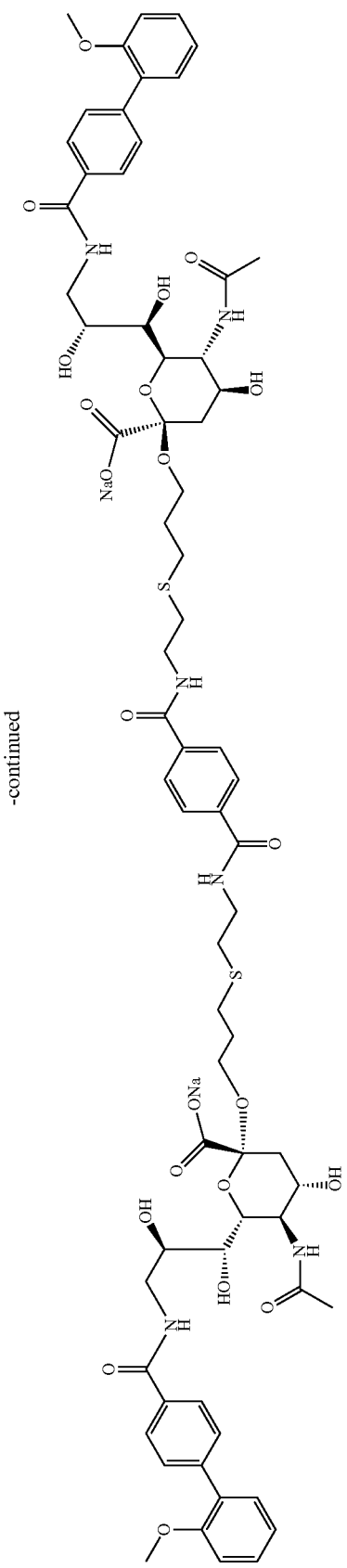
236
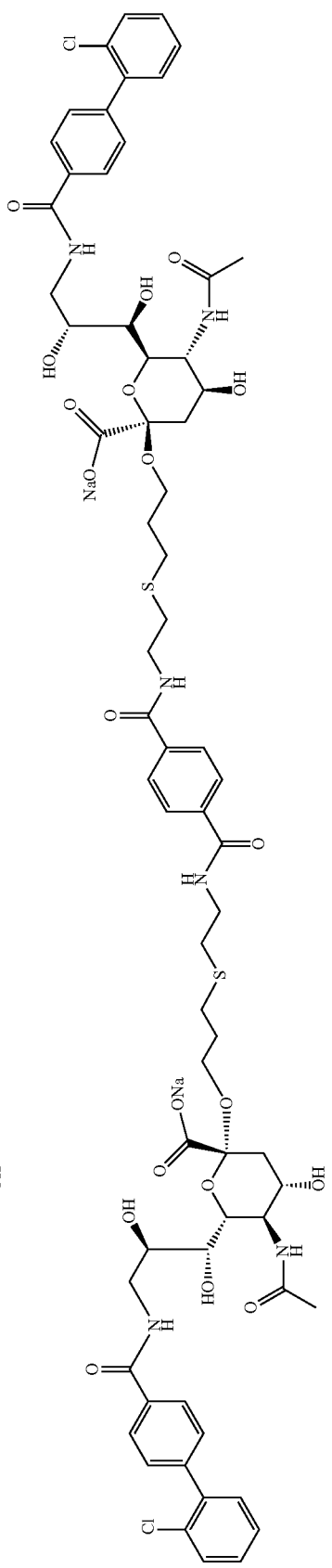
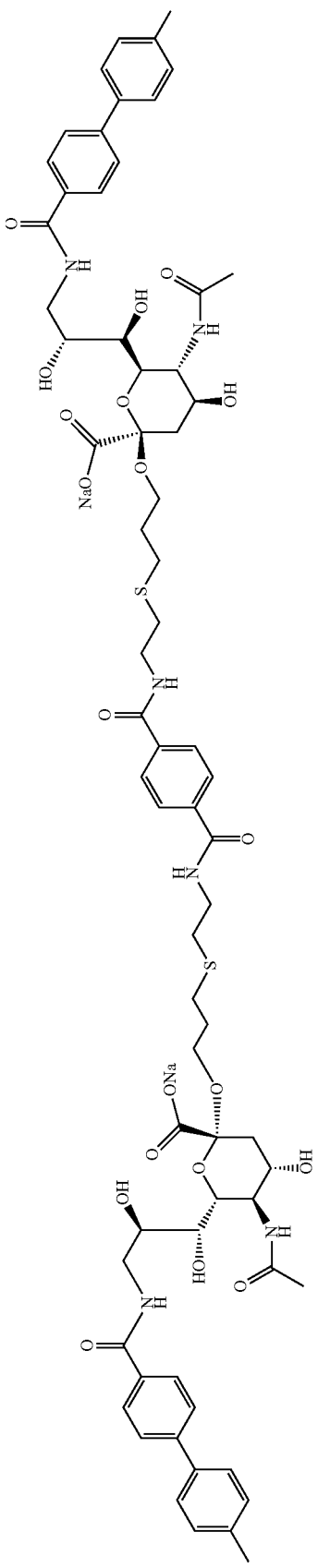

-continued
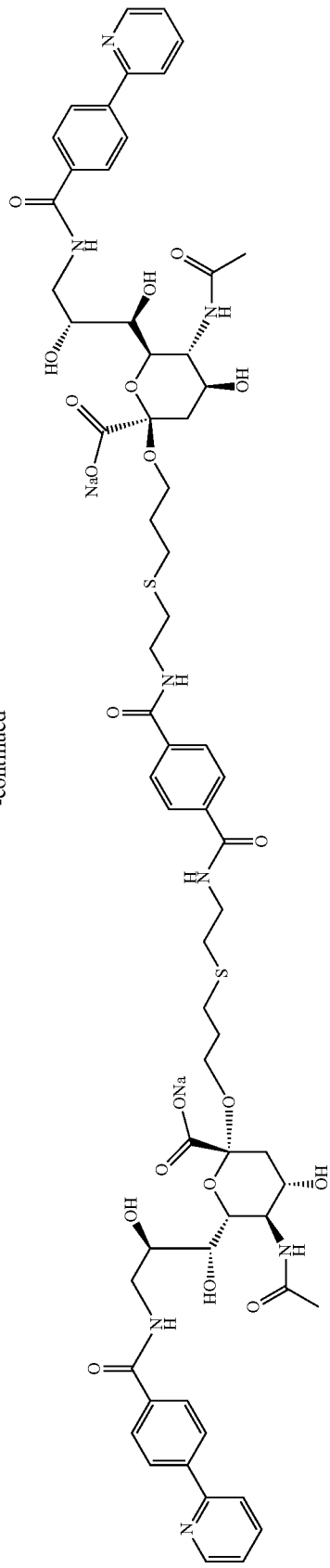
237
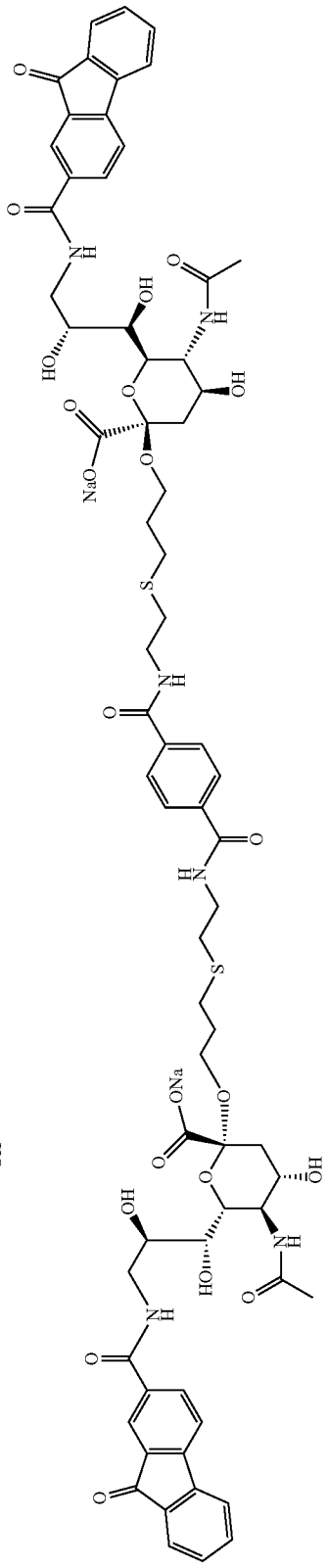
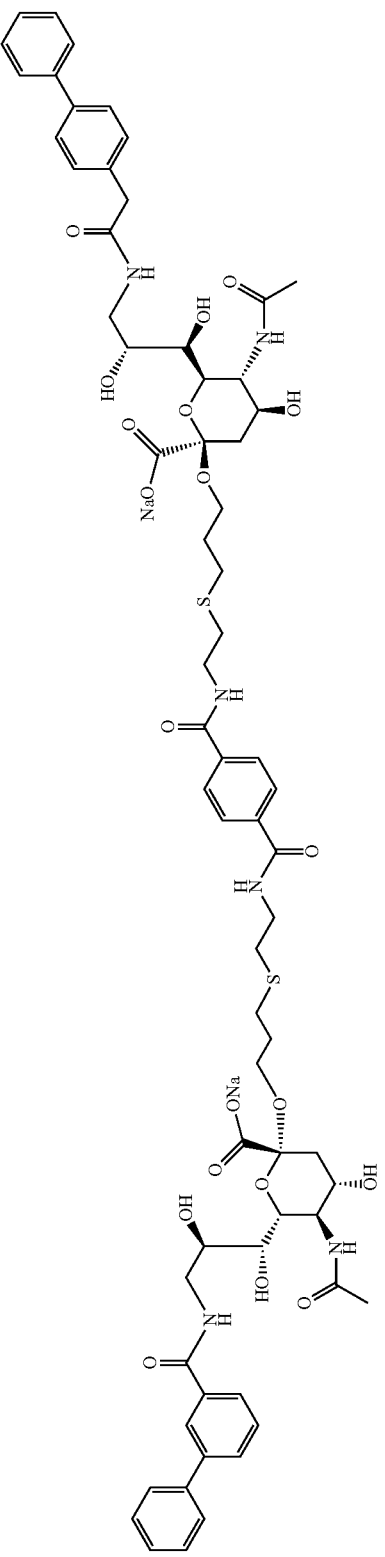
238

239
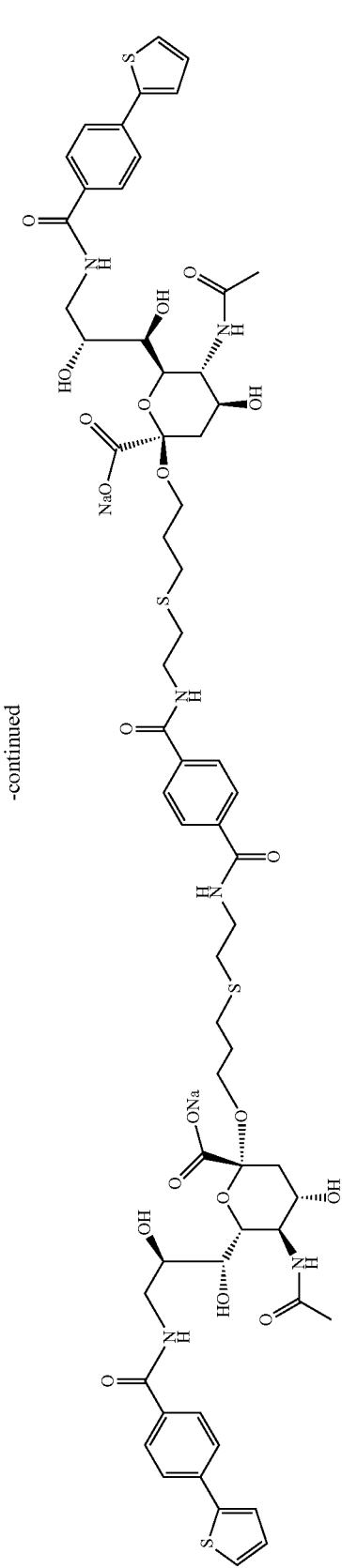 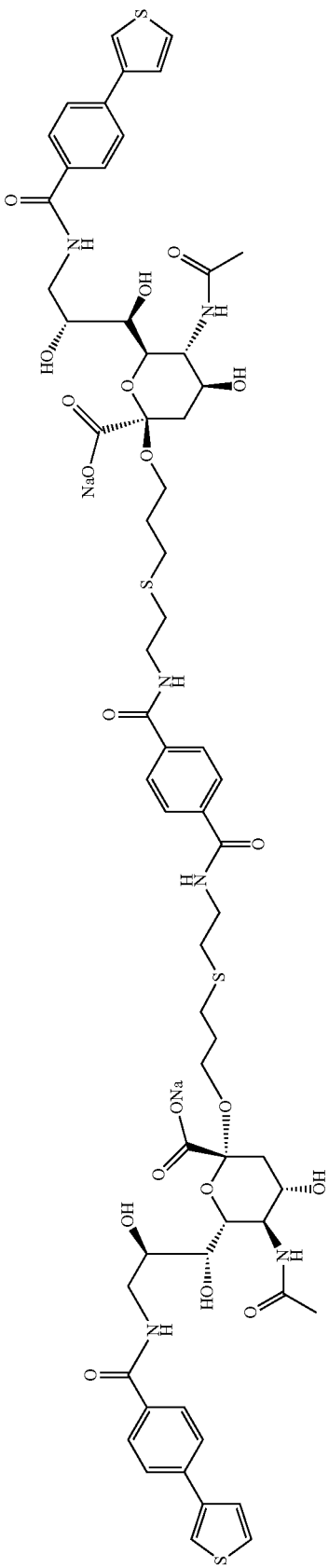
240
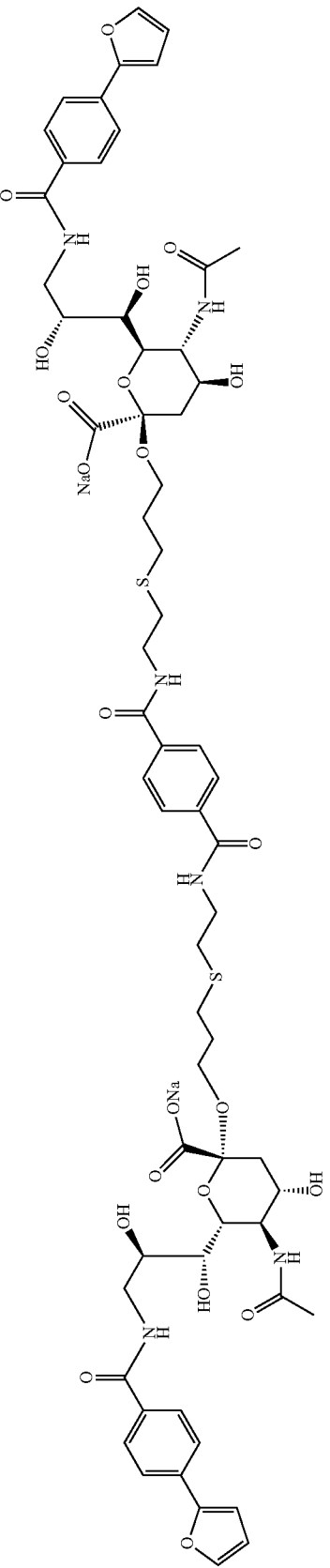

-continued
241
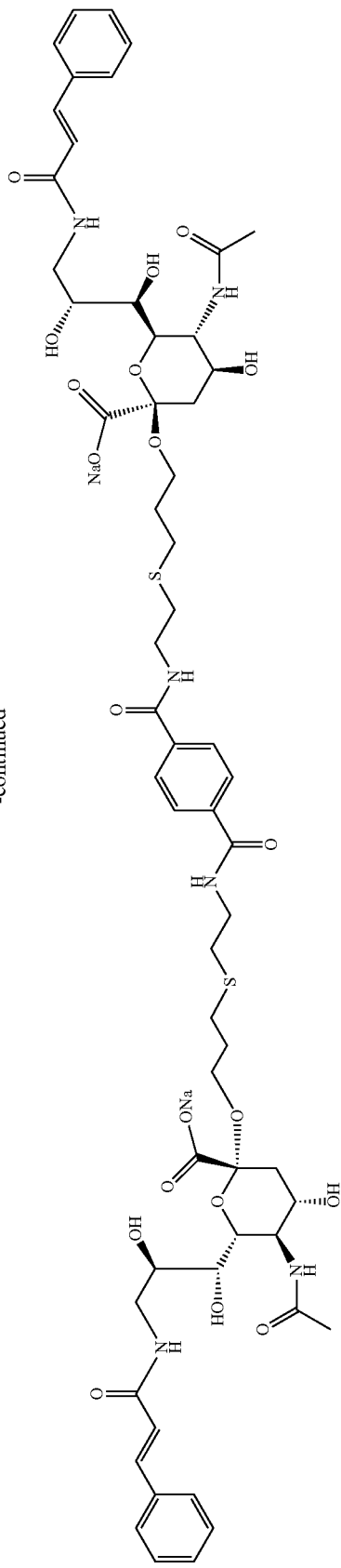
242
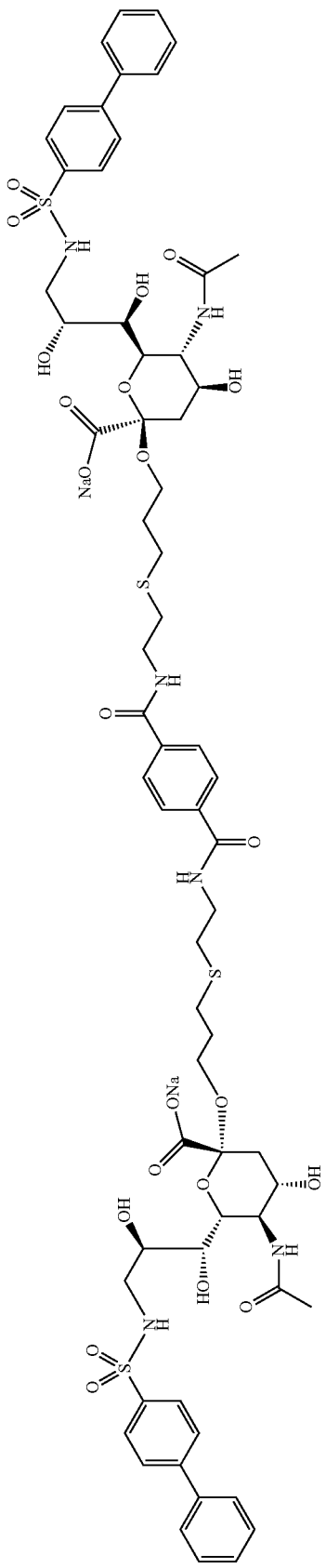
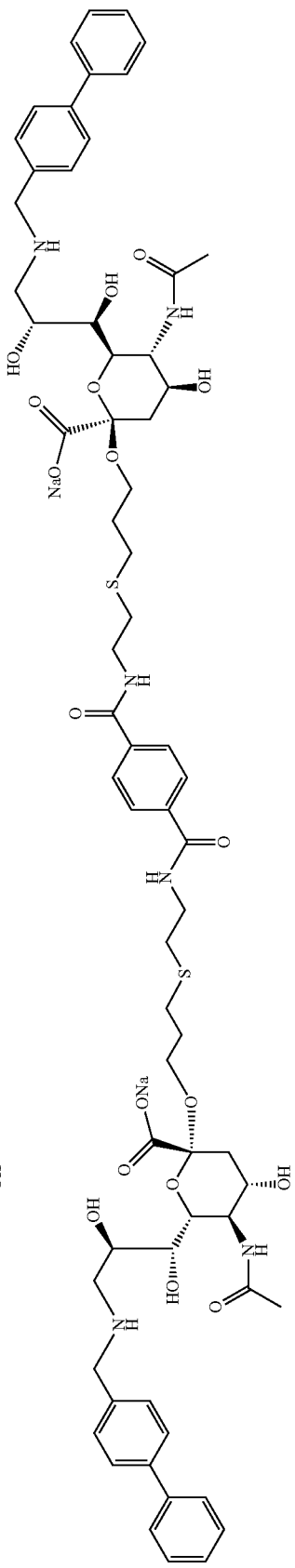

243
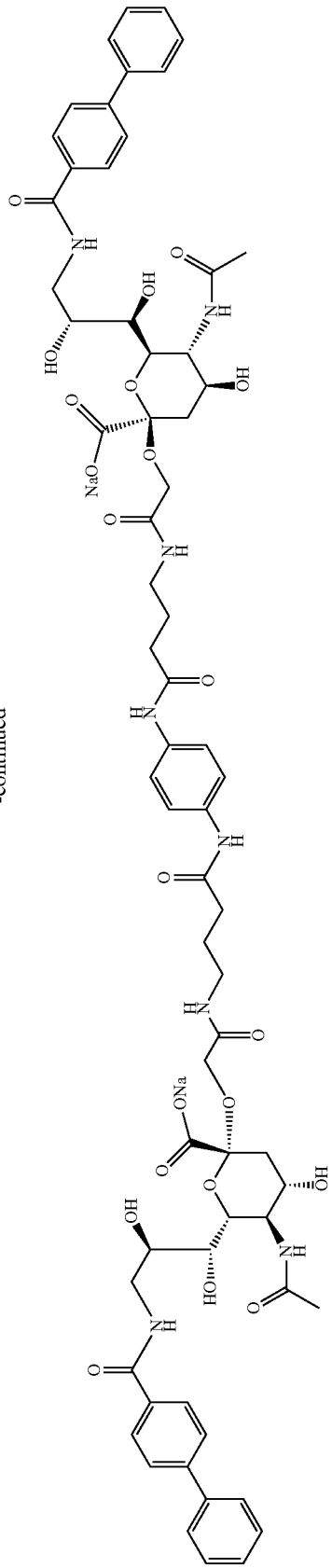
244
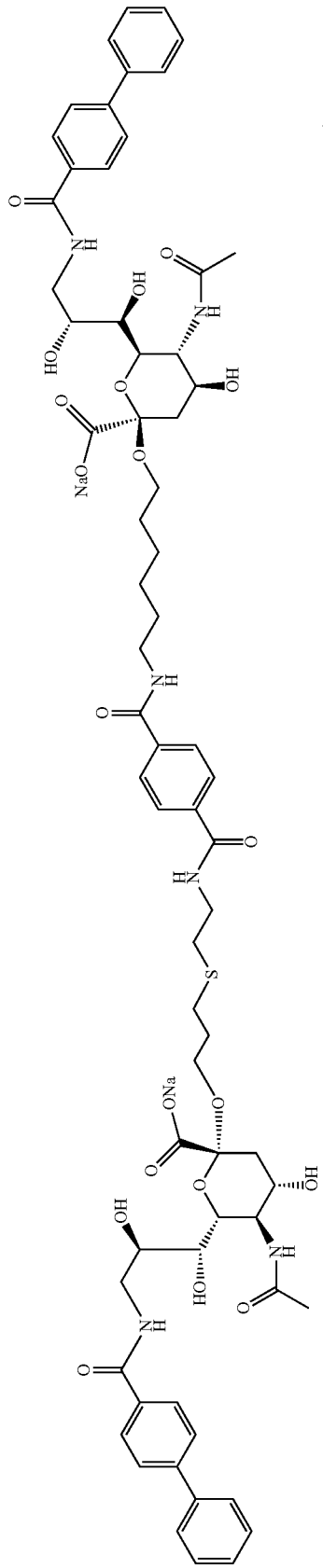
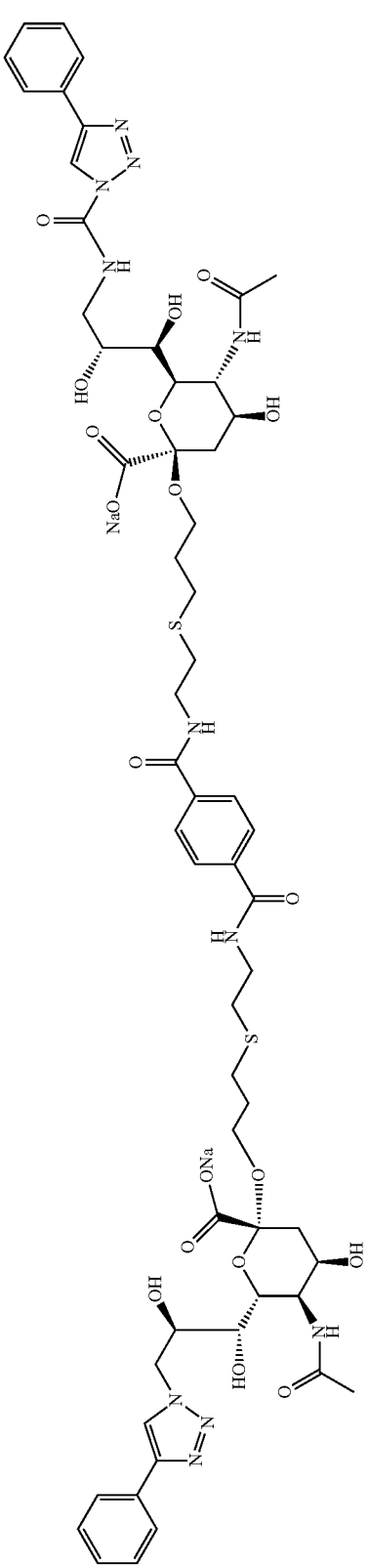

245
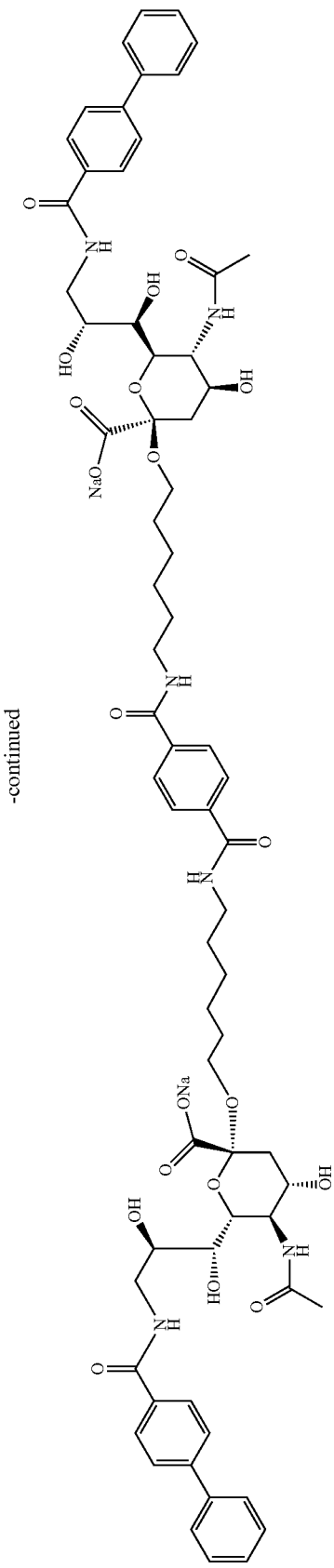
246
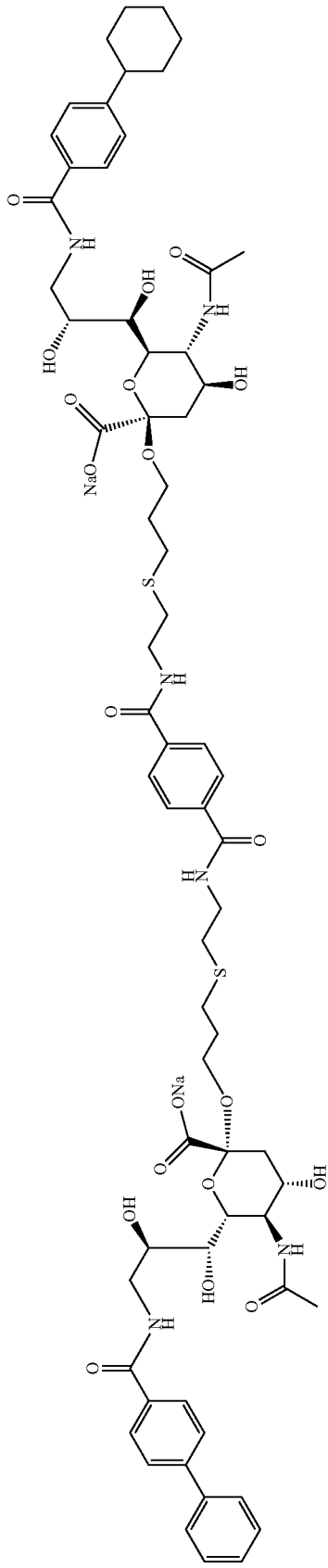
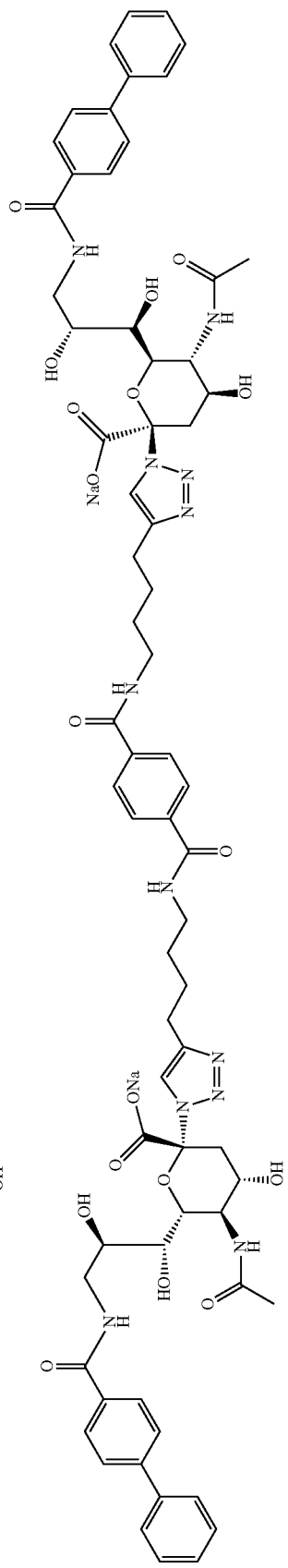

247
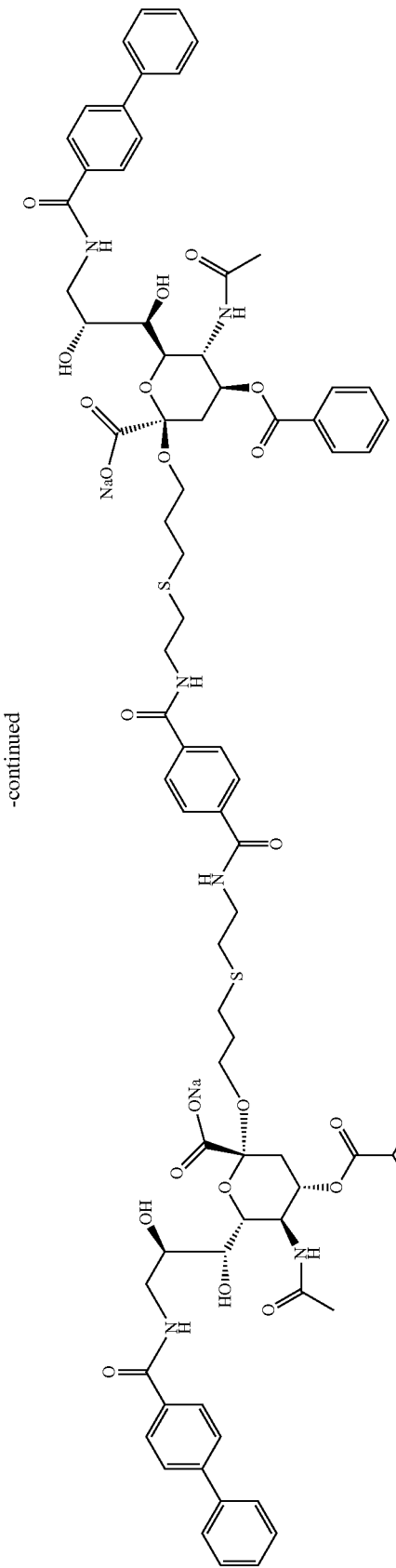
248
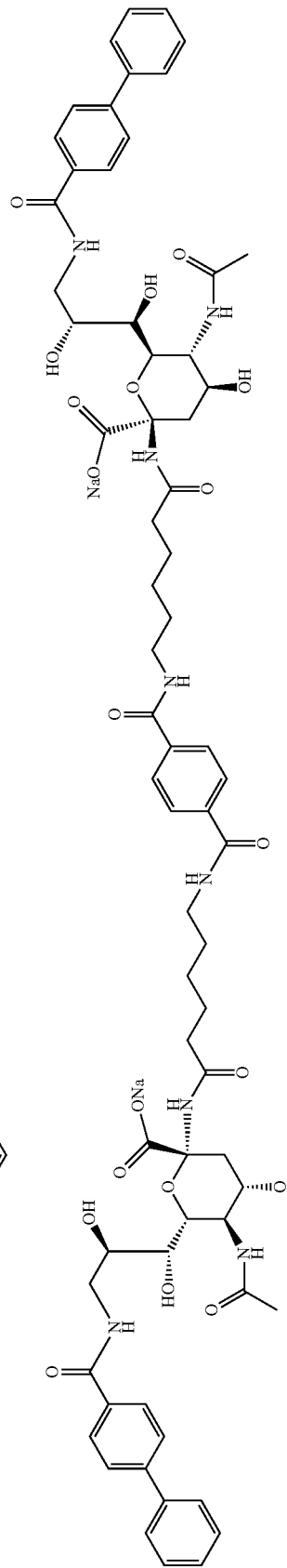
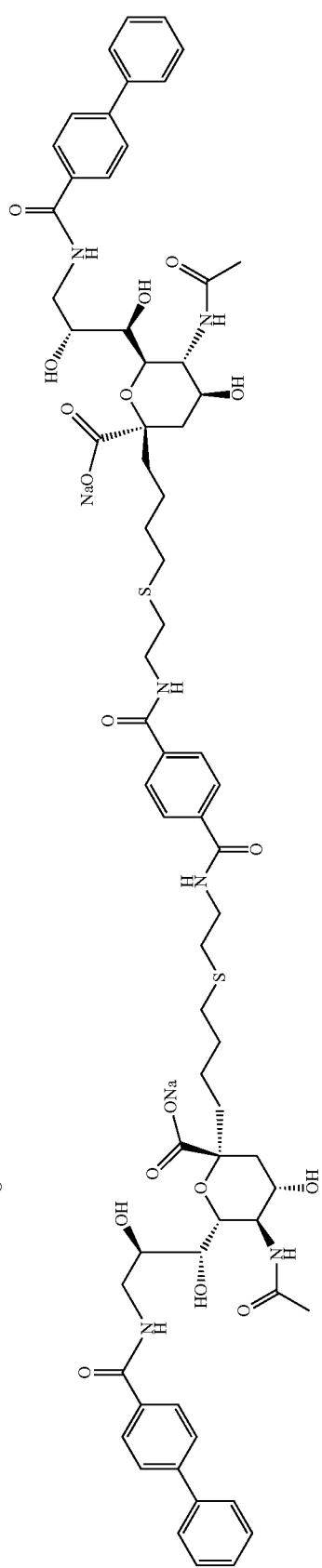

249
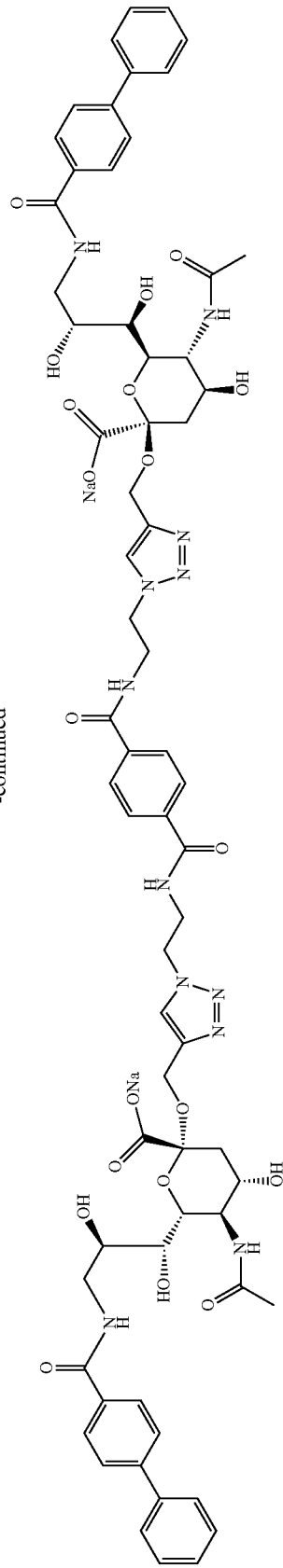
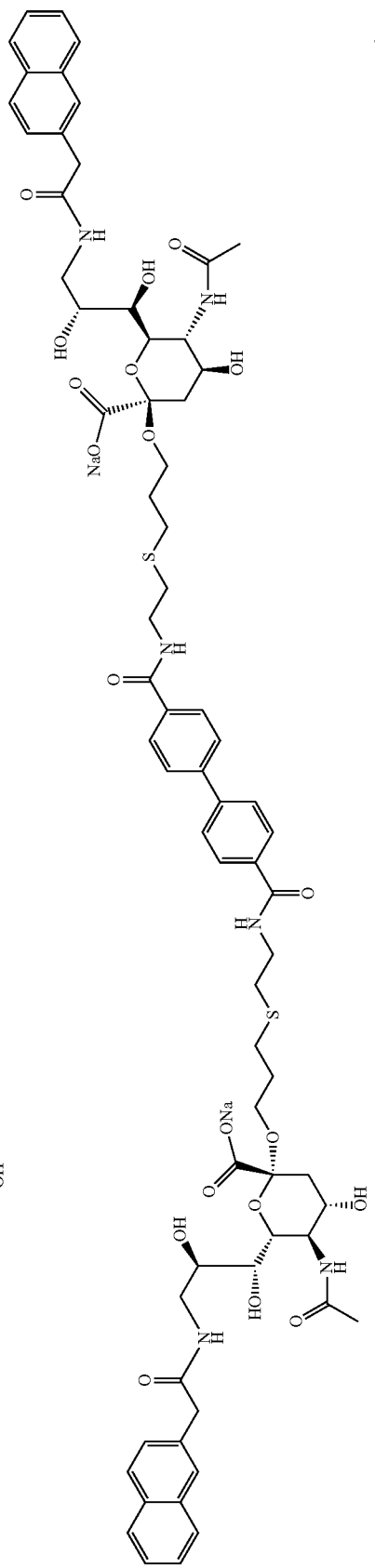
250
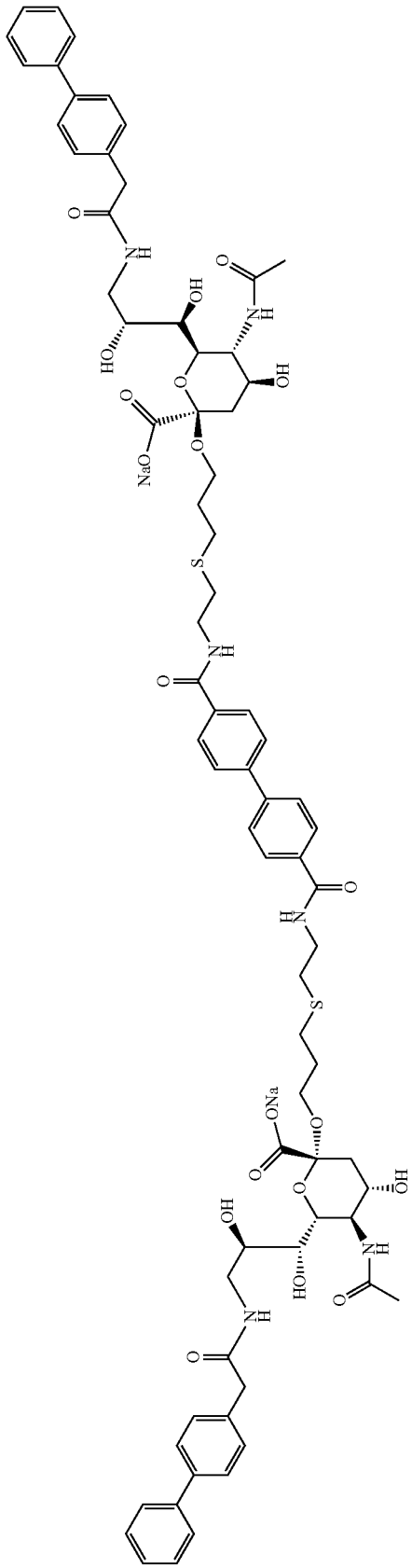

251 252
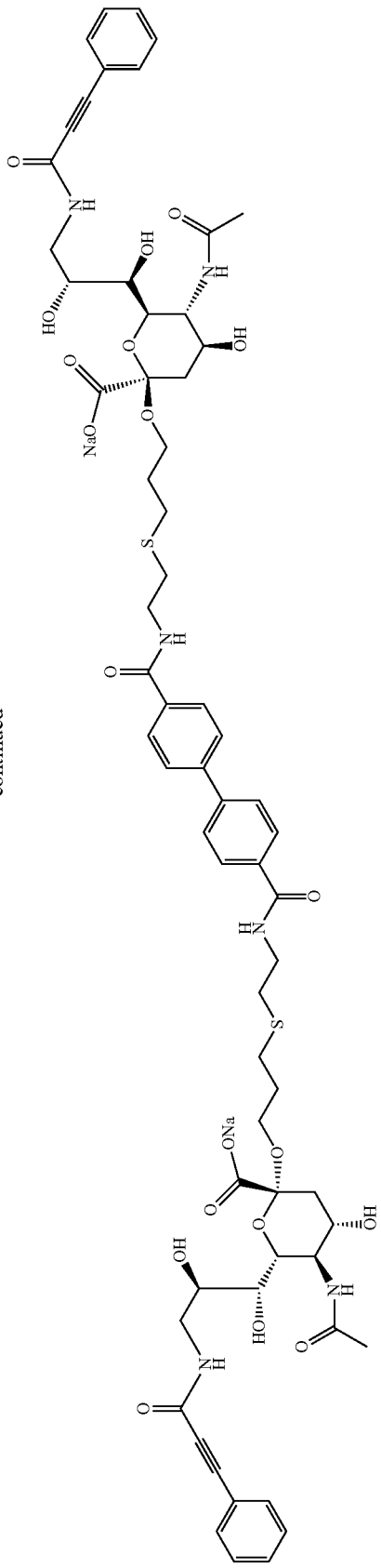
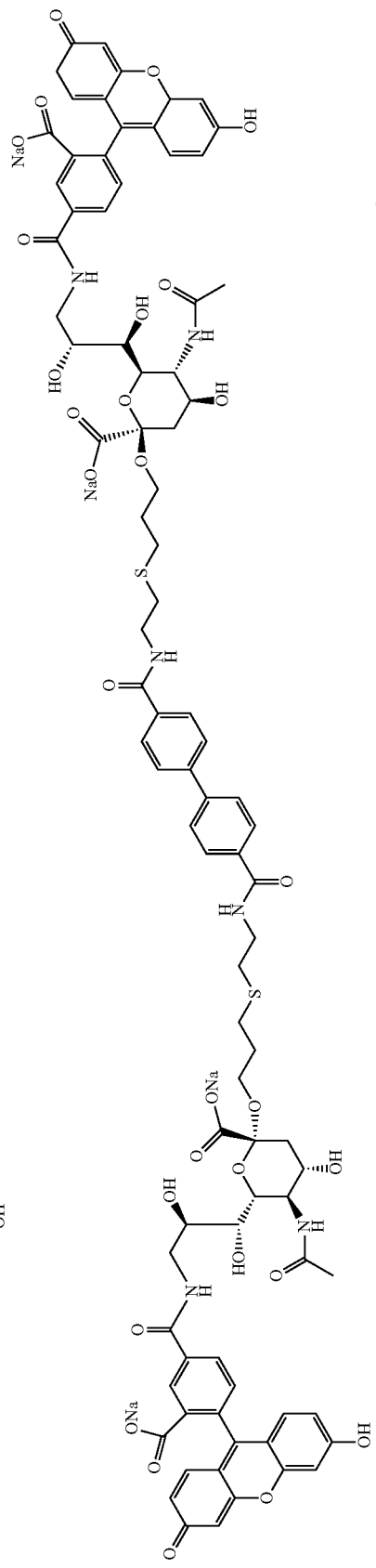
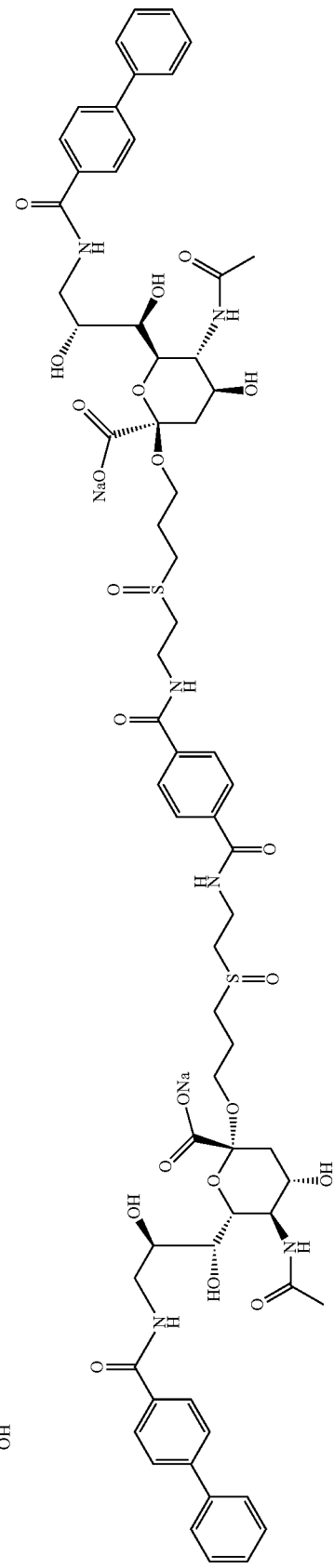

-continued
253 254
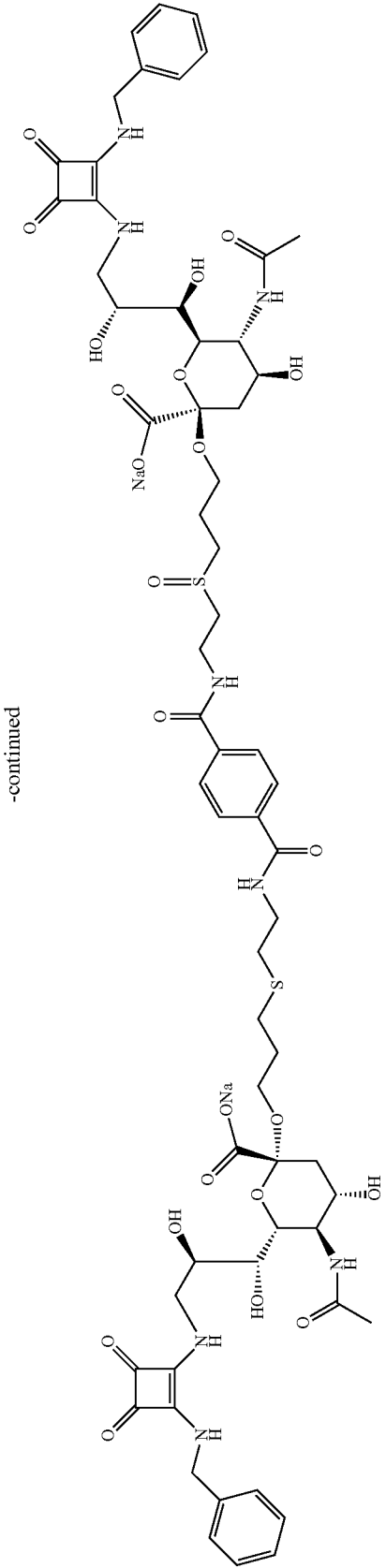
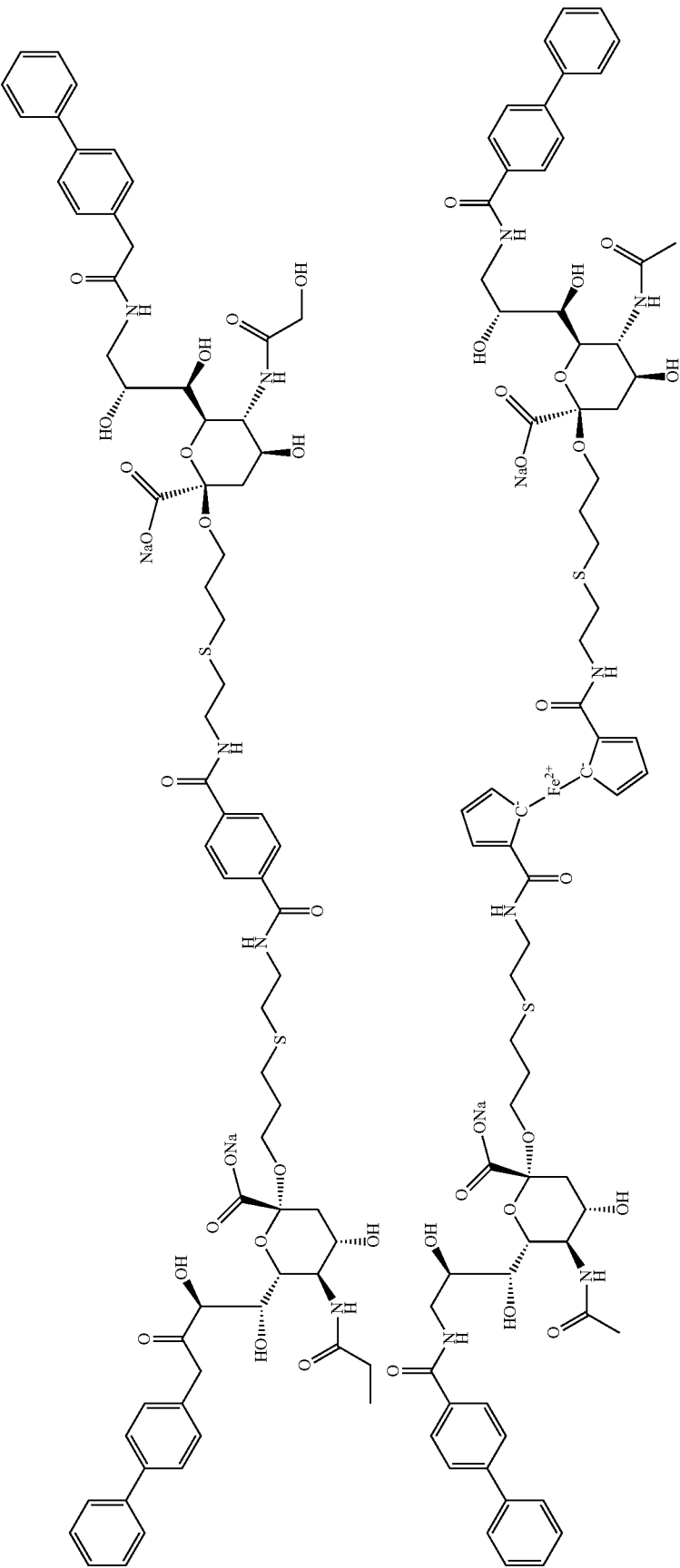

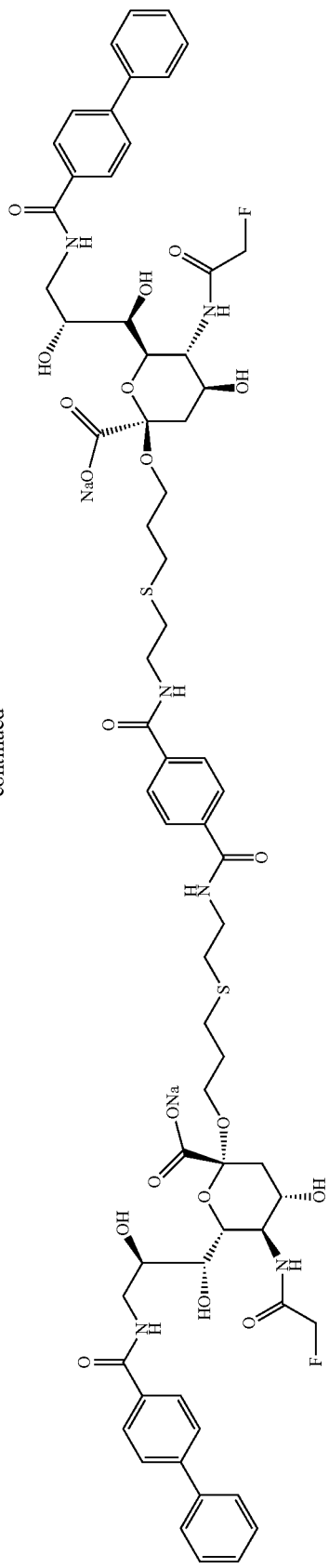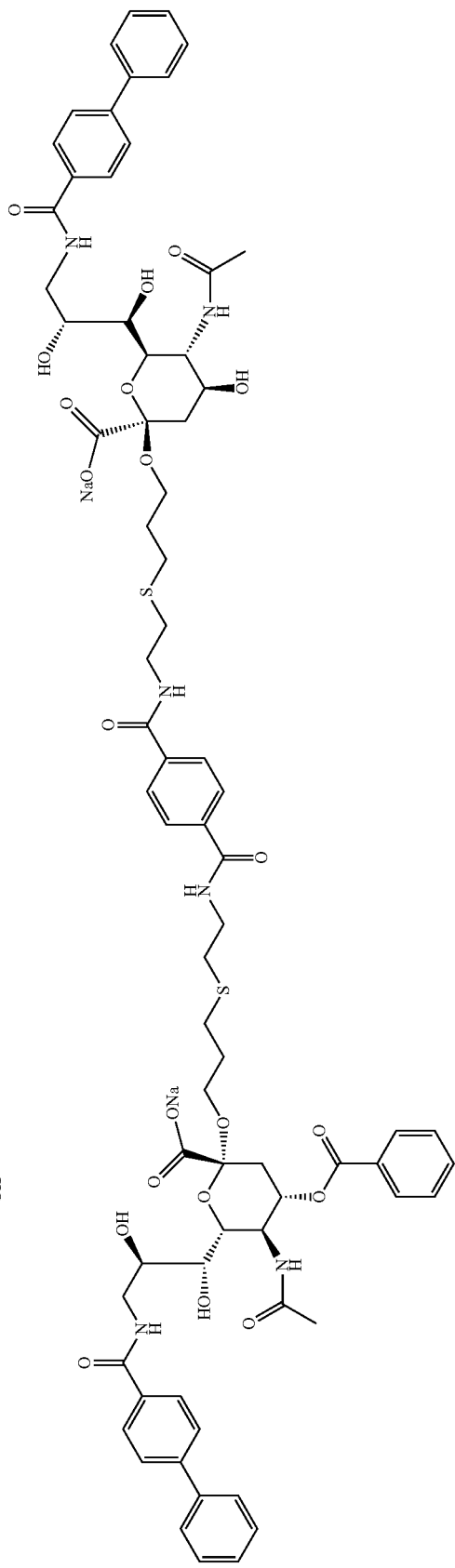

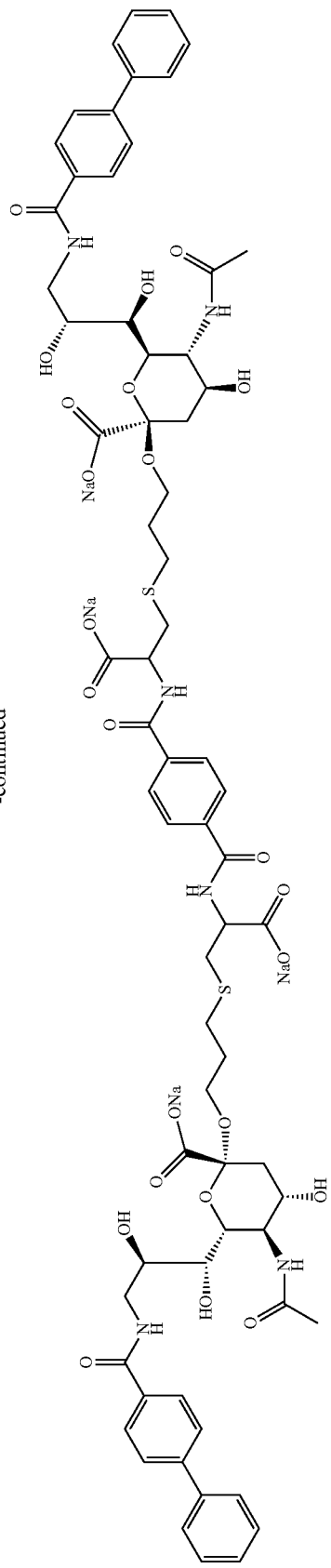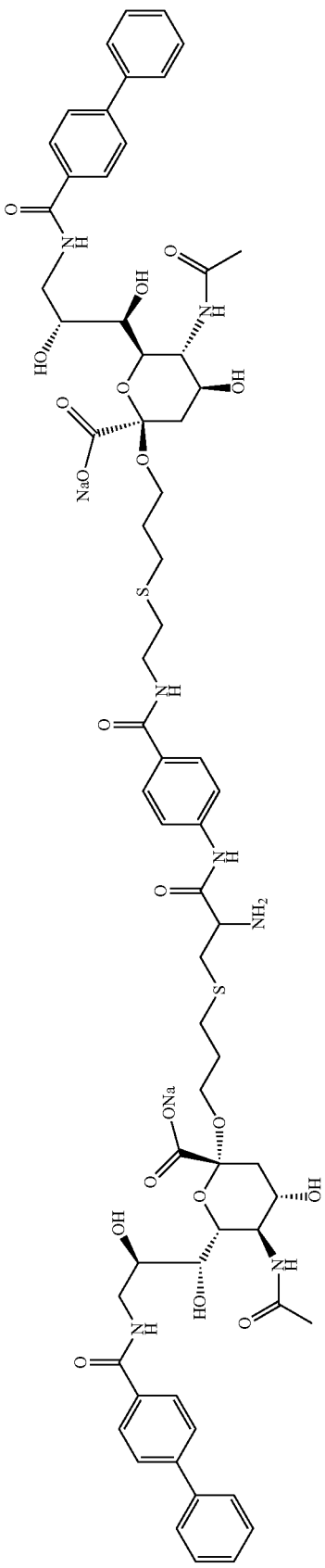

9. A pharmaceutical preparation comprising at least one sialic acid derivative of the formula (I) according to claim 1, or a pharmacologically tolerated salt thereof, and a pharmacologically tolerated carrier.

10. A sialic acid derivative of the formula (I) according to claim 1, or a pharmacologically tolerated salt thereof, as medicament.

11. A sialic acid derivative of the formula (I) according to claim 1, or a pharmacologically tolerated salt thereof, for the treatment of bacterial diseases.

12. A method for the treatment of bacterial, viral, parasitic, autoimmune and immune-deficiency diseases, comprising the step of applying a therapeutically effective amount of a sialic acid derivative of the formula (I) according to claim 1.

* * * * *